US005529780A

United States Patent [19]
Paoletti et al.

[11] Patent Number: 5,529,780
[45] Date of Patent: Jun. 25, 1996

[54] NUCLEOTIDE AND AMINO ACID SEQUENCES OF CANINE HERPESVIRUS GB AND GC

[75] Inventors: Enzo Paoletti, Delmar; Keith J. Limbach, Troy, both of N.Y.

[73] Assignee: Virogenetics Corporation, Troy, N.Y.

[21] Appl. No.: 220,151

[22] Filed: Mar. 30, 1994

[51] Int. Cl.[6] ........................ A61K 39/245; C12P 21/02; C12N 7/01; C12N 15/38

[52] U.S. Cl. .................... 424/199.1; 435/69.1; 435/69.3; 435/172.3; 435/235.1; 435/236; 435/237; 435/320.1; 424/184.1; 424/229.1; 424/232.1; 536/23.72; 536/24.1

[58] Field of Search ................................ 435/69.1, 69.3, 435/172.3, 235.1, 236, 240.1, 320.1; 424/184.1, 199.1, 229.1, 232.1, 205.1, 232.1; 536/23.72, 24.1

[56] References Cited

PUBLICATIONS

Rota et al, Arch Virol (1990) 115:139–145, "Homology Between Feline Herpesvirus–1 and Canine Herpesvirus".
Balachandran, N., S. Bacchetti, and W. E. Rawls, Infect. Immun. 37, 1132–1137 (1982).
Behbehani, A. M., Microbiological Reviews 47, 455–509 (1983).
Ben–Porat, T., J. DeMarchi, J. Pendrys, R. A. Veach, and A. S. Kaplan, J. Virol. 57, 191–196 (1986).
Ben–Porat, T. and A. S. Kaplan, In: The Herpesviruses, vol. 3, ed. B. Roizman (Plenum Publishing Corp., New York) pp. 105–173 (1985).
Ben–Porat, T., F. J. Rixon, and M. L. Blankenship Virology 95, 285–294 (1979).
Bergoin, M., and Dales, S., In Comparative Virology, eds. K. Maramorosch and E. Kurstak, (Academic Press, NY) pp. 169–205 (1971).
Berman, P. W., D. Dowbenko, L. A. Lasky, and C. C. Simonsen, Science 222, 524–527 (1983).
Bertholet, C., Drillien, R., and Wittek, R., Proc. Natl. Acad. Sci. USA 82, 2096–2100 (1985).
Boursnell, M. E. G., P. F. Green, J. I. A. Campbell, A. Deuter, R. W. Peters, F. M. Tomley, A. C. R. Samson, P. Chambers, P. T. Emmerson, and M. M. Binns, J. Gen. Virol. 71, 621–628 (1900a).
Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).
Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).
Buller, R. M. L., G. L. Smith, Cremer, K., Notkins, A. L., and Moss, B., Nature 317, 813–815 (1985).
Buller, R. M. L., Chakrabarti, S., Cooper, J. A., Twardzik, D. R., and Moss, B., J. Virol. 62, 866–874 (1988).
Bzik, D. J., B. A. Fox, N. A. DeLuca, and S. Person, Virology 133, 301–307 (1984).
Cadoz, M., A. Strady, B. Meignier, J. Taylor, J. Tartaglia, E. Paoletti and S. Plotkin, The Lancet, 339, 1429 (1992).
Cantin, E. M., R. Eberle, J. L. Baldick, B. Moss, D. E. Willey, A. L. Notkins, and H. Openshaw, Proc. Natl. Acad. Sci. USA 84, 5908–5912 (1987).
Chambers, P., N. S. Millar, and P. T. Emmerson, J. Gen. Virol. 67, 2685–2694 (1986).
Chan, W., Immunol. 49, 343–352 (1983).
Child, S. J., Palumbo, G. J., Buller, R. M. L., and Hruby, D. E. Virology 174, 625–629 (1990).
Clewell, D. B., J. Bacteriol. 110, 667–676 (1972).
Clewell, D. B. and D. R. Helinski, Proc. Natl. Acad. Sci. USA 62, 1159–1166 (1969).
Colinas, R. J., R. C. Condit and E. Paoletti, Virus Research 18, 49–70 (1990).
Compton, T., In: Cell Biology of Virus Entry, Replication, and Pathogenesis, eds. Compans, R. W., A. Helenius, and M. B. A. Oldstone (Alan R. Liss, Inc.) pp. 45–56 (1989).
Cooney E. L., Corrier A. C., Greenberg, P. D., et al., Lancet 337, 567–572 (1991).
Cranage, M. P., T. Kouzarides, A. T. Bankier, S. Satchwell, K. Weston, P. Tomlinson, B. Barrell, H. Hart, S. E. Bell, A. C. Minson and G. L. Smith, EMBO J. 5, 3057–3063 (1986).
Cremer, K. J., M. Mackett, C. Wohlenberg, A. L. Notkins, and B. Moss, Science 228, 737–740 (1985).
Davis, W., B., J. A. Taylor, and J. E. Oakes, J. Infect. Dis. 140, 534–540 (1979).
Davison, A. J., and J. E. Scott, J. gen. Virol. 67, 1759–1816 (1986).
Drillien, R., F. Koehren and A. Kirn, Virology 111, 488–499 (1981).
Eberle, R., and R. J. Courtney, J. Virol. 35, 902–917 (1980).
Edbauer, C., R. Weinberg, J. Taylor, A. Rey–SeneLonge, J. F. Bouquet, P. Desmettre, and E. Paolette, Virology 179, 901–904 (1990).
Espion, D., S. de Henau, C. Letellier, C.–D. Wemers, R. Brasseur, J. F. Young, M. Gross, M. Rosenberg, G. Meulemans and A. Burny, Arch. Virol. 95, 79–95 (1987).
Etinger H. M., Altenburger W., Vaccine 9, 470–472 (1991).

(List continued on next page.)

*Primary Examiner*—Christine M. Nucker
*Assistant Examiner*—Laurie Scheiner
*Attorney, Agent, or Firm*—Curtis, Morris & Safford

[57] ABSTRACT

Disclosed and claimed are nucleotides for genes encoding the canine herpesvirus (CHV) gB, gC and gD homologues. These genes encode polypeptides of 879, 459 and 345 amino acids, respectively, which are also disclosed. The nucleotides can be expressed in any suitable vector system, allowing for production of the polypeptides. Additionally, the vector system containing any or any combination of the nucleotides can be employed in an antigenic, immunological or vaccine composition, such as a poxvirus vector system, e.g., a CHV-vaccinia or avipox virus recombinant, as can the products from expression, i.e., the gB, gC and gD glycoproteins. Antibodies elicited by the glycoproteins or from expression of the vector containing the nucleotide are also useful. Methods for making and using the composition are also disclosed and claimed.

18 Claims, 51 Drawing Sheets

OTHER PUBLICATIONS

Fargeaud, D., C. Benoit Jeannin, F. Kato and G. Chappuis, Arch. Virol. 80, 69–82 (1984).

Fenner, F., Virology 5, 502–529 (1958).

Flexner, C., Hugen A., and Moss, B., Nature 330, 259–262 (1987).

Frame, M. C., H. S. Marsden, and D. J. McGeoch, J. gen. Virol. 67, 745–751 (1986).

Frink, R. J., M. R. Eisenberg, G. Cohen, and E. K. Wagner, J. Virol. 45, 634–647 (1983).

Funahashi, S., T. Sato and H. Shida, J. Gen. Virol. 69, 35≧47 (1988).

Garten, W., Kohama, T., and H–D. Klenk, J. Gen. Virol. 51, 207–211 (1980).

Ghendon, Y. Z., and Chernos, V. I., Acta Virol. 8, 359–368 (1964).

Gillard, S., Spehner, D., Drillien, R., and Kirn, A., Proc. Natl. Acad. Sci. USA 83, 5573–5577 (1986).

Glorioso, J., C. H. Schroder, G. Kumel, M. Szczesiul, and M. Levine, J. Virol. 50, 805–812 (1984).

Glorioso, J., U. Kees, G. Kumel, H. Kirchner, and P. Krammer, J. Immunol. 135, 575–582 (1985).

Goebel, S. J., Johnson, G. P., Perkus, M. E., Davis, S. W., Winslow, J. P., Paoletti, E., Virology, 179, 247–266 (1990a).

Goebel, S. J., G. P. Johnson, M. E. Perkus, S. W. E. Davis, J. P. Winslow, E. Paoletti, Virology 179, 517–563 (1990b).

Goldstein, D. J. and S. K. Weller, Virology 166, 41–51 (1988).

Gretch, D. R., B. Kari, L. Rasmussen, R. C. Gehrz, and M. F. Stinski, J. Virol. 62, 875–881 (1988).

Guo, P., Goebel, S., Davis, S., Perkus, M. E., Languet, B., Desmettre, P., Allen, G., and Paoletti, E., J. Virol. 63, 4189–4198 (1989).

Guo et al., J. Virol. 64, 2399–2406 (1990).

Hampl, H., T. Ben–Porat, L. Ehrlicher, K–O. Habermehl, and A. S. Kaplan, J. Virol. 52, 583–590 (1984).

Homma, M., and M. Ohuchi, J. Virol. 12, 1457–1465 (1973).

Hruby, D. E., R. A. Maki, D. B. Miller and L. A. Ball, Proc. Natl. Acad. Sci. USA 80, 3411–3415 (1983).

Hruby, D. E. and L. A. Ball, J. Virol. 43, 403–409 (1982).

Ichihashi, Y. and Dales, S., Virology 46, 533–543 (1971).

Ishii, H., Y. Kobayashi, M. Kuroki and Y. Kodama, J. gen. Virol. 69, 1411–1414 (1988).

Jacobson, J. G., D. A. Leib, D. J. Goldstein, C. L. Bogard, P. A. Schaffer, S. K. Weller and D. M. Coen, Virology 173, 276–283 (1989).

Jamieson, A. T., G. A. Gentry and J. H. Subak–Sharpe, J. Gen. Virol. 24, 465–480 (1974).

Kato, S., M. Takahashi, S. Kameyama and J. Kamahora, Biken's 2, 353–363 (1959).

Keller, P. M., A. J. Davison, R. S. Lowe, C. D. Bennett, and R. W. Ellis, Virology 152, 181–191 (1986).

Kieff, E., and D. Liebowitz, In: Virology, Second Edition, eds. Fields B. N. et al. (Raven Press, Ltd., New York) pp. 1889–1920 (1990).

Kieny, M. P., Lathe, R., Drillien, T., Spehner, D., Skory, S., Schmitt, D., Wiktor, T., Koprowski, H., and Lecocq, J. P., Nature (London) 312, 163–166 (1984).

Konishi et al., Virology 190, 454–458 (1992)

Kost, T. A., E. V. Jones, K. M. Smith, A. P. Reed, A. L. Brown and T. J. Miller, Virology 171, 365–376 (1989).

Kotwal, G. J., A. W. Hugin and B. Moss, Virology 171, 579–587 (1989a).

Kotwal, G. J. and B. Moss, J. Virol. 63, 600–606 (1989b).

Kotwal, G. J., S. N. Isaacs, R. McKenzie, M. M. Frank and B. Moss, Science 250, 827–830 (1990).

Kotwal, G. J. and Moss, B., Nature (Lond.) 335, 176–178 (1988).

Kozak, M., Cell 44, 283–292 (1986).

Lai, A. C.–K. and B. G.–T. Pogo, Virus Res. 12, 239–250 (1989).

Lasky, L. A., D. Dowbenko, C. C. Simonsen, and P. W. Berman, Bio–Technology 2, 527–532 (1984).

Lawrence, W. C., R. C. D'Urso, C. A. Kundel, J. C. Whitbeck and L. J. Bello, J. Virol. 60, 405–414 (1986).

Le, L., R. Brasseur, C. Wemers, G. Meulemans, and A. Burny, Virus Genes 1, 333–350 (1988).

Longnecker, R., S. Chatterjee, R. Whitley, and B. Roizman, Proc. Natl. Acad. Sci. USA 84, 4303–4307 (1987).

Mandecki, W., Proc. Natl. Acad. Sci. USA 83, 7177–7182 (1986).

Marchioli, C. C., R. J. Yancey, Jr., R. C. Wardley, D. R. Thomsen and L. E. Post, Am. J. Vet. Res. 48, 1577–1583 (1987).

Marchioli, C., R. J. Yancey, Jr., J. G. Timmins, L. E. Post, B. R. Young, and D. A. Povendo, Am. J. Vet. Res. 49, 860–864 (1988).

Marchioli, C. C., R. J. Yancey, Jr., E. A. Petrovskis, J. G. Timmins, and L. E. Post, J. Virol. 61, 3977–3982 (1987).

Matthews, R. E. F., Intervirology 17, 42–44 (1982).

McGeoch, D. J., M. A. Dalrymple, A. J. Davison, A. Dolan, M. C. Frame, D. McNab, L. J. Perry, J. E. Scott, and P. Taylor, J. gen. Virol. 69, 1531–1574 (1988).

McGinnes, L. W. and T. G. Morrison, Virus Research 5, 343–356 (1986).

McLaughlin–Taylor, E., D. E. Willey, E. M. Cantin, R. Eberle, B. Moss, and H. Openshaw, J. Gen. Virol. 69, 1731–1734 (1988).

Merz, D. C., A. Scheid, and P. Choppin, J. Exper. Med. 151, 275–288 (1980).

Misra, V., R. M. Blumenthal and L. A. Babiuk, J. Virol. 40, 367—378 (1981).

Morgan, A. J., M. Mackett, S. Finerty, J. R. Arrand, F. T. Scullion and M. A. Epstein, J. Med. Virol. 25, 189–195 (1988).

Moss, B., E. Winters and J. A. Cooper, J. Virol. 40, 387–395 (1981).

Nagai, Y., H. D. Klenk, and R. Rott, Virology 72, 494–508 (1976).

Nagai, Y., T. Yoshida, M. Hamaguchi, H. Naruse, M. Iinuma, K. Maeno, and T. Matsumoto, Microbiol. Immunol. 24, 173–177 (1980).

Norrby, E., and Y. Gollmar, Infect. and Immun. 11, 231–239 (1975).

Oakes, J. E., and H. Rosemond–Hornbeak, Infect. Immun. 21, 489–495 (1978).

Ogawa, R., N. Yanagida, S. Saeki, S. Saito, S. Ohkawa, H. Gotoh, K. Kodama, K. Kamagawa, K. Sawaguchi and Y. Iritani, Vaccine 8, 486–490 (1990).

Paez, E., S. Dallo and M. Esteban, Proc. Natl. Acad. Sci. USA 82, 3365–3369 (1985).

Palumbo, G. J., Pickup, D. J., Frederickson, T. N., McIntyre, L. J., and Buller, R. M. L., Virology 172, 262–273 (1989).

Panicali, D., S. W. Davis, S. R. Mercer, and E. Paoletti, J. Virol. 37, 1000–1010 (1981).

Panicali, D. and E. Paoletti, Proc. Natl. Acad. Sci. USA 79, 4927–4931 (1982).

Paolette, E., B. R. Lipinskas, C. Samsonoff, S. Mercer, and D. Panicali, Proc. Natl. Acad. Sci. USA 81, 193–197 (1984).

Papp–Vid, G., and J. B. Derbyshire, Can. J. Comp. Med. 43, 231–233 (1979).

Patel, D. D. and Pickup, D. J., EMBO 6, 3787–3794 (1987).

Patel, D. D., Ray, C. A., Drucker, R. P., and Pickup, D. J., Proc. Natl. Acad. Sci. USA 85, 9431–9435 (1988).

Pellett, P. E., M. D. Biggin, B. L. Barrell, and B. Roizman, J. Virol. 56, 807–813 (1985).

Perkus, M. E., K. Limbach, and E. Paoletti, J. Virol. 63, 3829–3836 (1989).

Perkus, M. E., A. Piccini, B. R. Lipinskas, and E. Paoletti, Science 229, 981–984 (1985).

Perkus, M. E., Goebel, S. J., Davis, S. W., Johnson, G. P., Limbach, K., Norton, E. K., and Paoletti, E., Virology 179, 276–286 (1990).

Perkus, M. E., D. Panicali, S. Mercer and E. Paoletti, Virology 152, 285–297 (1986).

Perkus, M. E., S. J. Goebel, S. W. Davis, G. P. Johnson, E. K. Norton and E. Paoletti, Virology 180, 406–410 (1991).

Petrovskis, E. A., J. G. Timmins, M. A. Armentrout, C. C. Marchioli, R. J. Yancey, Jr., and L. E. Post, J. Virol. 59, 216–223 (1986).

Petrovskis, E. A., J. G. Timmins and L. E. Post, J. Virol. 60, 185–193 (1986).

Piccini, A., M. E. Perkus, and E. Paoletti, Methods in Enzymology 153, 545–563 (1987).

Pickup, D. J., B. S. Ink, W. Hu, C. A. Ray and W. K. Joklik, Proc. Natl. Acad. Sci. USA 83, 7698–7702 (1986).

Pickup, D. J., B. S. Ink, B. L. Parsons, W. Hu and W. K. Joklik, Proc. Natl. Acad. Sci. USA 81, 6817–6821 (1984).

Proudfoot, N. J. & Brownlee, G. G., Nature 163, 211–214 (1976).

Reed, L. J. and Muench, H., Am. J. Hyg. 27, 493≧497 (1938).

Richman, D. D., A. Buckmaster, S. Bell, C. Hodgman and A. C. Minson, J. Virol. 57, 647–655 (1986).

Riggio, M. P., A. A. Cullinane, and D. E. Onions, J. Virol. 63, 1123–1133 (1989).

Riviere, M., Tartaglia, J., Perkus, M. E., Norton, E. K., Bongermino, C. M., Lacoste, F., Duret, C., Desmettre, P. & Paoletti, E., Journal of Virology 66, 3424–3434 (1992).

Robbins, A. K., R. J. Watson, M. E. Whealy, W. W. Hays, and L. W. Enquist, J. Virol. 58, 339–347 (1986).

Robbins, A. K., D. J. Dorney, M. W. Wathen, M. E. Whealey, C. Gold, R. J. Watson, L. E. Holland, S. D. Weed, M. Levine, J. C. Glorioso, and L. W. Enquist, J. Virol. 61, 2691–2701 (1987).

Roizman, B. and A. E. Sears, In: Virology, eds. Fields, B. N. and D. M. Knipe (Raven Press, Ltd., New York) pp. 1795–1841 (1990).

Rooney, J. F., C. Wohlenberg, K. J. Cremer, B. Moss, and A. L. Notkins, J. Virol. 62, 1530–1534 (1988).

Rosenthal, K. L., J. R. Smiley, S. South, and D. C. Johnson, J, Virol. 61, 2438–2447 (1987).

Ross, L., Sanderson, M., Scott, S., Binns, M., Doel, T. & Milne, B., Journal of General Virology 70, 1789–1804 (1989).

Rota, P. A., R. K. Maes, and W. T. Ruyechan, Virology 154, 168–179 (1986).

Rubenstein, A. S. and A. S. Kaplan, Virology 66, 385–392 (1975).

Sanger, F., S. Nicklen, and A. Coulson, Proc. Natl. Acad. Sci. USA 74, 5463–5467 (1977).

Schmidtt, J. F. C. and H. G. Stunnenberg, J. Virol. 62, 1889–1897 (1988).

Seligmann, E. B., In Laboratory Techniques in Rabies, eds. M. M. Kaplan and H. Koprowski, (World Health Organization, Geneva) pp. 279–285 (1973).

Shapira, S. K., Chou, J., Richaud, F. V. and Casadaban, M. J., Gene 25, 71–82 (1983).

Shida, H., Virology 150, 451–462 (1986).

Shida, H., T. Tochikura, T. Sato, T. Konno, K. Hirayoshi, M. Seki, Y. Ito, M. Hatanaka, Y. Hinuma, M. Sugimoto, F. Takahashi–Nishimaki, T. Maruyama, K. Miki, K. Suzuki, M. Morita, H. Sashiyama and M. Hayami, EMBO 6, 3379–3384 (1987).

Shida, H., Hinuma, Y., Hatanaka, M., Morita, M., Kidokoro, M., Suzuki, K., Maruyama, T., Takahashi–Nishimaki, F., Sugimoto, M., Katamura, R., Miyazawa, T., and M., J. Virol. 62, 4474–4480 (1988).

Shimizu, M., K. Satou, and N. Nishioka, Arch. Virol. 104, 169–174 (1989).

Sinclair, R., R. F. Cook, and J. A. Mumford, J. gen. Virol. 70, 455–459 (1989).

Slabaugh, M., N. Roseman, R. Davis and C. Mathews, J. Virol. 62, 519–527 (1988).

Smith, J. S., P. A. Yager and G. M. Baer, in Laboratory Techniques in Rabies, eds. M. M. Kaplan and H. Koprowski (WHO Geneva) pp. 354–357 (1973).

Spear, P. G., In: The Basis for Serodiagnosis and Vaccines, Immunochemistry of Viruses, vol. 2, eds. M. H. V. Van Regenmortel and A. R. Neurath (New York), pp. 425–443 (1985a).

Spear, P. G., In: The Herpesvirus, vol. 3, ed. B. Roizman (New York), pp. 315–356 (1985b).

Stanberry, L. R., S. Kit and M. G. Myers, J. Virol. 55, 322–328 (1985).

Stevely, W. S., J. Virol. 22, 232–234 (1977).

Stokes, A., G. P. Allen, L. A. Pullen, and P. K. Murray, J. Gen. Virol. 70, 1173–1183 (1989).

Sullivan, V. and G. L. Smith, J. Gen. Virol. 68, 2587–2598 (1987).

Sullivan, V. and G. L. Smith, J. Gen. Virol. 69, 859–867 (1988).

Swain, M. A., R. W. Pedt, and D. A. Galloway, J. Virol 53, 561–569 (1985).

Tabor, S., and C. C. Richardson, Proc. Natl. Acad. Sci. USA 84, 4767–4771 (1987).

Tartaglia, J. & E. Paoletti, In Immunochemistry of Viruses, II. The Basis for Serodiagnoss and Vaccines. M. H. V. van Regenmortel & A. R. Neurath, Eds. 125–151. Elsevier Science Publishers, Amsterdam (1990).

Tartaglia, J., Perkus, M. E., Taylor, J., Norton, E. K., Audonnet, J.–C., Cox, W. I., Davis, S. W., Van Der Hoeven, J., Meignier, B., Riviere, M., Languet, B., Paoletti, E., Virology 188, 217–232 (1992).

Taylor, J., C. Trimarchi, R. Weinberg, B. Languet, F. Guillemin, P. Desmettre and E. Paoletti, Vaccine 9, 190–193 (1991b).

Taylor, J., Weinberg, R., Kawaoka, Y., Webster, R. G., and Paoletti, E., Vaccine 6, 504–508 (1988a).

Taylor, J., R. Weinberg, B. Lanquet, P. Desmetttre, and E. Paoletti, Vaccine 6, 497–503 (1988b).

Taylor, J., R. Weinberg, J. Tartaglia, C. Richardson, G. Alkhatib, D. Briedis, M. Appel, E. Norton & E. Paoletti, Virology 187, 321–328 (1992).

Taylor, G., E. J. Stott, G. Wertz and A. Ball, J. Gen. Virol. 72, 125–130 (1991a).

Taylor, J., Edbauer, C., Rey–Senelonge, A., Bouquet, J.–F., Norton, E., Goebel, S., Desmettre, P., Paoletti, E., J. Virol, 64, 1441–1450 (1990).

Wachsman, M., L. Aurelian, J. C. R. Hunter, M. E. Perkus, and E. Paoletti, Bioscience Reports 8, 323–334 (1988).

Wachsman, M., J. H. Luo, L. Aurelian, M. E. Perkus, and E. Paoletti, J. Gen. Virol. 70, 2513–2520 (1989).

Wachsman, M., L. Aurelian, C. C. Smith, B. R. Lipinskas, M. E. Perkus, and E. Paoletti, J. Infect. Dis. 155, 1188–1197 (1987).

Wathen, M. W. and L. M. K. Wathen, J. Virol. 58, 173–178 (1986).

Wathen, M. W. and L. M. K. Wathen, J. Virol. 51, 57–62 (1984).

Wathen, L. M. K., K. B. Platt, M. W. Wathen, R. A. Van Deusen, C. A. Whetstone, and E. C. Pirtle, Virus Res. 4, 19–29 (1985).

Weir, J. P., M. Bennett, E. M. Allen, K. L. Elkins, S. Martin, and B. T. Rouse, J. gen. Virol. 70, 2587–2594 (1989).

Weir, J. P. and B. Moss, J. Virol. 46, 530–537 (1983).

Whalley, J. M., G. R. Robertson, N. A. Scott, G. C. Hudson, C. W. Bell, and L. M. Woodworth, J. gen. Virol. 70, 383–394 (1989).

Whealy, M. E., A. K. Robbins and L. W. Enquist, J. Virol. 63, 4055–4059 (1989).

Whitbeck, J. C., L. Z. Bello, and W. C. Lawrence, J. Virol. 62, 3319–3327 (1988).

Wittmann, G. and H.–J. Rziha, In: Herpesvirus Diseases of Cattle, Horses and Pigs, ed. G. Wittmann (Kluwer Academic Publishers) pp. 230–325 (1989).

Zarling, J. M., P. A. Moran, R. L. Burke, C. Pachl, P. W. Berman, and L. A. Lasky, J. Immunol. 136, 4669–4673 (1986a).

Zarling, J. M., P. A. Moran, L. A. Lasky, and B. Moss, J. Virol. 59, 506–509 (1986b).

Zezulak, K. M., and P. G. Spear, J. Virol. 49, 741–747 (1984).

Zhou, J., L. Crawford, L. McLean, X. Sun, M. Stanley, N. Almond and G. L. Smith, J. Gen. Virol. 71, 2185–2190 (1990).

FIG. IA

| | | | |
|---|---|---|---|
| TTTTCTGGAT | TTCAGCTATG | TCCTTCGGGA | 30 |
| GTTTATATAA | CTTATGAAGA | AAACTGTCCT | 60 |
| TTGGTAGCAG | TTTTACAAAG | CGGTGTAAAT | 90 |
| TGCGAAATTG | GACCAACTAC | AACTGTAATA | 120 |
| TACGACAGTG | ATATTTTTC | TCTTCTTTAT | 150 |
| ACCGTTCTTC | AAAAATTGGC | TCCTGGTGTT | 180 |
| AATATAGAAA | TTTGATAAGT | ATGTTTTCAT<br>M  F  S> | 210<br>3 |
| TGTATCTATA<br>L  Y  L  Y | TATTTTTTT<br>I  F  F | ATTATTTATA<br>I  I  Y> | 240<br>13 |
| CTTTAATAAT<br>T  L  I  I | ATGTGATCCA<br>C  D  P | ACAACACCGG<br>T  T  P> | 270<br>23 |
| AAAGTACTAT<br>E  S  T  I | TAATCCATTA<br>N  P  L | AATCATCACA<br>N  H  H> | 300<br>33 |
| ATTTATCAAC<br>N  L  S  T | ACCTAAACCT<br>P  K  P | ACTTCGGATG<br>T  S  D> | 330<br>43 |
| ATATTCGTGA<br>D  I  R  E | AATTTTACGT<br>I  L  R | GAATCCCAAA<br>E  S  Q> | 360<br>53 |
| TTGAATCTGA<br>I  E  S  D | TGATACATCA<br>D  T  S | ACATTTTACA<br>T  F  Y> | 390<br>63 |
| TGTGCCCACC<br>M  C  P  P | ACCATCGGGA<br>P  S  G | TCAACATTGG<br>S  T  L> | 420<br>73 |
| TGCGTTTGGA<br>V  R  L  E | GCCACCTAGA<br>P  P  R | GCATGTCCTA<br>A  C  P> | 450<br>83 |
| ACTATAAACT<br>N  Y  K  L | TGGTAAAAAT<br>G  K  N | TTTACAGAAG<br>F  T  E> | 480<br>93 |

FIG. 1B

| | | | |
|---|---|---|---|
| GAATTGCTGT | AATATTTAAG | GAAAATATTT | 510 |
| G I A V | I F K | E N I> | 103 |
| CTCCTTATAA | ATTTAAAGCT | AATATATACT | 540 |
| S P Y K | F K A | N I Y> | 113 |
| ACAAAAATAT | TATTATCACC | ACTGTATGGT | 570 |
| Y K N I | I I T | T V W> | 123 |
| CTGGAAGCAC | ATATGCAGTA | ATTACTAATA | 600 |
| S G S T | Y A V | I T N> | 133 |
| GATATACAGA | TCGTGTACCT | ATAGGTGTTC | 630 |
| R Y T D | R V P | I G V> | 143 |
| CTGAAATTAC | AGAGTTGATT | GATAGAAGAG | 660 |
| P E I T | E L I | D R R> | 153 |
| GTATGTGTTT | ATCAAAAGCT | GATTATATTC | 690 |
| G M C L | S K A | D Y I> | 163 |
| GTAATAATTA | TGAATTTACC | GCATTTGATA | 720 |
| R N N Y | E F T | A F D> | 173 |
| AGGATGAAGA | CCCCAGAGAA | GTTCATTTAA | 750 |
| K D E D | P R E | V H L> | 183 |
| AGCCTTCAAA | GTTTAATACA | CCAGGATCCC | 780 |
| K P S K | F N T | P G S> | 193 |
| GTGGATGGCA | TACAGTTAAT | GATACTTACA | 810 |
| R G W H | T V N | D T Y> | 203 |
| CAAAAATTGG | GGGTTCTGGA | TTTTATCATT | 840 |
| T K I G | G S G | F Y H> | 213 |
| CTGGAACATC | TGTAAATTGT | ATAGTTGAAG | 870 |
| S G T S | V N C | I V E> | 223 |
| AAGTTGATGC | CAGATCTGTT | TATCCATATG | 900 |
| E V D A | R S V | Y P Y> | 233 |

FIG. 1C

| | | | | |
|---|---|---|---|---|
| ATTCATTTGC | TATCTCCACC | GGGGATATAA | 930 | |
| D S F A | I S T | G D I> | 243 | |
| TTCATATGTC | CCCTTTTTTT | GGATTACGAG | 960 | |
| I H M S | P F F | G L R> | 253 | |
| ATGGTGCTCA | TACTGAATAT | ATTAGTTATT | 990 | |
| D G A H | T E Y | I S Y> | 263 | |
| CAACTGATAG | ATTTCAACAA | ATAGAAGGTT | 1020 | |
| S T D R | F Q Q | I E G> | 273 | |
| ATTATCCTAT | CGACTTAGAT | ACTAGACTAC | 1050 | |
| Y Y P I | D L D | T R L> | 283 | |
| AGCTTGGTGC | ACCAGTTTCT | AGGAATTTTT | 1080 | |
| Q L G A | P V S | R N F> | 293 | |
| TAACAACACA | ACACGTTACT | GTTGCTTGGA | 1110 | |
| L T T Q | H V T | V A W> | 303 | |
| ATTGGGTTCC | AAAAATTCGT | GAAGTGTGTA | 1140 | |
| N W V P | K I R | E V C> | 313 | |
| CTTTGGCTAA | ATGGCGTGAA | ATTGATGAAA | 1170 | |
| T L A K | W R E | I D E> | 323 | |
| TTATTCGTGA | TGAGTATAAG | GGATCTTACA | 1200 | |
| I I R D | E Y K | G S Y> | 333 | |
| GATTTACAGC | AAAATCAATA | TCTGCAACAT | 1230 | |
| R F T A | K S I | S A T> | 343 | |
| TTATTTCTGA | TACTACTCAA | TTTGATATTG | 1260 | |
| F I S D | T T Q | F D I> | 353 | |
| ATCGTGTAAA | GTTAAGTGAT | TGTGCCAAAC | 1290 | |
| D R V K | L S D | C A K> | 363 | |
| GTGAAGCCAT | AGAAGCTATT | GATAAGATCT | 1320 | |
| R E A I | E A I | D K I> | 373 | |

FIG. 1D

| | | | |
|---|---|---|---|
| ACAAAAAAAA | ATATAATAAA | ACTCATATTC | 1350 |
| Y K K K | Y N K | T H I> | 383 |
| AAACAGGAGA | ATTGGAAACA | TACTTGGCTA | 1380 |
| Q T G E | L E T | Y L A> | 393 |
| GAGGGGGATT | TATTATAGCA | TTTAGACCAA | 1410 |
| R G G F | I I A | F R P> | 403 |
| TGATTAGTAA | TGAGTTAGCA | AAATTGTATA | 1440 |
| M I S N | E L A | K L Y> | 413 |
| TAAATGAGTT | AGTAAGATCT | AATCGTACGG | 1470 |
| I N E L | V R S | N R T> | 423 |
| TTGATTTGAA | ATCTCTTTTA | AATCCATCTG | 1500 |
| V D L K | S L L | N P S> | 433 |
| TAAGAGGGGG | GGCTAGAAAG | AGAAGATCAG | 1530 |
| V R G G | A R K | R R S> | 443 |
| TAGAGGAAAA | TAAAAGATCA | AAACGTAATA | 1560 |
| V E E N | K R S | K R N> | 453 |
| TTGAAGGTGG | TATTGAAAAT | GTAAATAATT | 1590 |
| I E G G | I E N | V N N> | 463 |
| CAACAATAAT | TAAGACAACT | TCATCTGTTC | 1620 |
| S T I I | K T T | S S V> | 473 |
| ATTTTGCTAT | GCTTCAGTTT | GCCTATGATC | 1650 |
| H F A M | L Q F | A Y D> | 483 |
| ATATTCAATC | ACATGTTAAT | GAAATGCTTA | 1680 |
| H I Q S | H V N | E M L> | 493 |
| GTAGAATTGC | AACTGCATGG | TGTAATCTTC | 1710 |
| S R I A | T A W | C N L> | 503 |
| AAAATAAAGA | GAGAACCCTT | TGGAATGAAG | 1740 |
| Q N K E | R T L | W N E> | 513 |

FIG. 1E

| | | | | |
|---|---|---|---|---|
| TTATGAAACT | TAATCCAACT | AGTGTGGCTT | 1770 | |
| V M K L | N P T | S V A> | | 523 |
| CGGTTGCTAT | GGATCAAAGA | GTTTCAGCAC | 1800 | |
| S V A M | D Q R | V S A> | | 533 |
| GAATGTTAGG | GGATGTTCTT | GCAGTTACTC | 1830 | |
| R M L G | D V L | A V T> | | 543 |
| AATGTGTTAA | TATATCAGGT | TCTAGTGTTT | 1860 | |
| Q C V N | I S G | S S V> | | 553 |
| TTATTCAAAA | TTCCATGCGT | GTTTTAGGGT | 1890 | |
| F I Q N | S M R | V L G> | | 563 |
| CAACAACTAC | ATGTTACAGT | CGTCCTCTTA | 1920 | |
| S T T T | C Y S | R P L> | | 573 |
| TATCATTTAA | AGCACTAGAA | AACTCAACTA | 1950 | |
| I S F K | A L E | N S T> | | 583 |
| ACTATATTGA | AGGACAACTT | GGGGAAAATA | 1980 | |
| N Y I E | G Q L | G E N> | | 593 |
| ATGAACTATT | AGTAGAACGA | AAGCTAATTG | 2010 | |
| N E L L | V E R | K L I> | | 603 |
| AACCATGTAC | AGCTAACCAT | AAAAGATATT | 2040 | |
| E P C T | A N H | K R Y> | | 613 |
| TTAAATTTGG | TGCAGATTAT | GTATATTTTG | 2070 | |
| F K F G | A D Y | V Y F> | | 623 |
| AAAACTATGC | ATATGTTCGA | AAGGTACCTC | 2100 | |
| E N Y A | Y V R | K V P> | | 633 |
| TTAATGAAAT | TGAAATGATC | AGTGCATATG | 2130 | |
| L N E I | E M I | S A Y> | | 643 |
| TAGATCTTAA | TATTACATTA | CTTGAGGATC | 2160 | |
| V D L N | I T L | L E D> | | 653 |

FIG. 1F

| | | | |
|---|---|---|---|
| GTGAATTTTT | ACCACTAGAG | GTATATACTC | 2190 |
| R E F L | P L E | V Y T> | 663 |
| GAGCAGAGTT | AGAAGATACA | GGACTATTGG | 2220 |
| R A E L | E D T | G L L> | 673 |
| ACTATAGTGA | GATTCAACGT | AGAAATCAAC | 2250 |
| D Y S E | I Q R | R N Q> | 683 |
| TACATGCACT | TAAGTTTTAT | GATATTGACA | 2280 |
| L H A L | K F Y | D I D> | 693 |
| GTGTTGTAAA | AGTTGATAAT | AATGTTGTAA | 2310 |
| S V V K | V D N | N V V> | 703 |
| TTATGAGGGG | CATTGCAAAT | TTTTTCCAAG | 2340 |
| I M R G | I A N | F F Q> | 713 |
| GACTTGGAGA | TGTTGGAGCG | GGATTTGGAA | 2370 |
| G L G D | V G A | G F G> | 723 |
| AAGTTGTTTT | GGGTGCTGCA | AATGCTGTTA | 2400 |
| K V V L | G A A | N A V> | 733 |
| TTGCAACTGT | TTCTGGAGTG | TCCTCGTTTC | 2430 |
| I A T V | S G V | S S F> | 743 |
| TTAATAACCC | ATTTGGGGCG | CTAGCCGTTG | 2460 |
| L N N P | F G A | L A V> | 753 |
| GATTGCTGAT | TTTAGCTGGA | CTATTTGCAG | 2490 |
| G L L I | L A G | L F A> | 763 |
| CGTTTTTGGC | TTATAGATAT | GTTTCTAAAC | 2520 |
| A F L A | Y R Y | V S K> | 773 |
| TTAAGTCAAA | TCCAATGAAA | GCACTATACC | 2550 |
| L K S N | P M K | A L Y> | 783 |
| CAGTAACTAC | AAAAAATTTA | AAAGAAAGTG | 2580 |
| P V T T | K N L | K E S> | 793 |

FIG. 1G

| | | | | |
|---|---|---|---|---|
| TTAAGAATGG | TAATTCTGGA | AATAATAGTG | | 2610 |
| V K N G | N S G | N N S> | | 803 |
| ATGGAGAAGA | AAATGATGAT | AATATCGATG | | 2640 |
| D G E E | N D D | N I D> | | 813 |
| AAGAAAAGCT | TCAACAAGCT | AAAGAAATGA | | 2670 |
| E E K L | Q Q A | K E M> | | 823 |
| TTAAATATAT | GTCTCTAGTT | TCTGCTATGG | | 2700 |
| I K Y M | S L V | S A M> | | 833 |
| AACAGCAGGA | ACATAAAGCT | ATTAAAAAAA | | 2730 |
| E Q Q E | H K A | I K K> | | 843 |
| ATAGTGGCCC | TGCCCTTCTA | GCAAGTCACA | | 2760 |
| N S G P | A L L | A S H> | | 853 |
| TTACAAACCT | ATCTCTTAAA | CATCGTGGTC | | 2790 |
| I T N L | S L K | H R G> | | 863 |
| CAAAATACAA | ACGTTTGAAA | AATGTAAATG | | 2820 |
| P K Y K | R L K | N V N> | | 873 |
| AAAATGAAAG | TAAAGTTTAA | TAAAAAATTT | | 2850 |
| E N E S | K V * | | | 879 |
| AAATATTACG | TAAAATTTTC | TGACTCTGCC | | 2880 |
| CACTTTTTTT | ATAATATAAA | TTTTAGAAAA | | 2910 |
| TTTTACTCAT | TTTATTATCT | TTTATAAACC | | 2940 |
| TCCAACTATT | TATAAAGGAT | AATAAATGGA | | 2970 |
| CATTTCTGCG | GTGCCTGTAT | ATCCTACTAA | | 3000 |

FIG. 3

| FIG. 3A |
|---|
| FIG. 3B |
| FIG. 3C |
| FIG. 3D |
| FIG. 3E |
| FIG. 3F |

FIG. 3A

```
CHV   M------------------------------------------FSLYL--------------------------------YIFFIIYTLIICDPTTPESTINPLNHHM
FHV   MST--RGDLGKRRRGSRWQHSGYFRQRCFFPSLLGIAATGSRHGNGSSGLTRL-------------ARYVSFIWIVLFLVGPRPVEGQSGSTSEQP
EHV1  MSSGCRS-VGGSTWGN-WRGDGGDLRQRRVLSPVCSAPAAGSWIGSQLGNVGNLLATPHPLGKPASSRVGTIVLACLLLFGSCVVRAVPTTPSPPT
PRV   MPAG--GGLWRGPRGHR-PGHHGGAGLGRLWPA--PHHAAAARGAVALALLLALAAAPPCGAAAVTRA-------ASASPTPGTGATPNDV
VZV   M----------------------FVVWALL-----------GLTLGVLVASAAPSSP-GTPGVARDPG--GERGPCHSGAAALGAAPTGDPK
HSV1  MHQG-----APSWGRRW-----FVVWALL-----------------------------------------FVTAVVSVSPSSFYESL-------
HCMV  MES-----------------RIWCLV------------------VCVNLCIVCLGAAVSSSSTSHATS----------------STHNGSHTSR
EBV   MTR------------------RR---------------------VLSVVVLLAALACRLGAQ--T-------------------PEQPAPPATT
       *
      LST-----------PKPTSD-----D-I--REILRESQIESDDTSTF-Y-M  C  PPPSGSTILVRLEPPRA  C  PNYKLGK-NFTEGIAVIFKENISP
      RRTVATPEVGGTPPKPTTDPTDMSD-M--REALRASQIEANGPSTF-Y-M   C  PPPSGSTVVRLEPPRA   C  PDYKLGK-NFTEGIAVIFKENIAP
      STPTSMSTHSHGTVDPTLLPTETPDPL--RLAVRESGILAED-GDF-Y-T   C  PPPTGSTVVRIEPPRT   C  PKFDLGR-NFTEGIAVIFKENIAP
      SAEASLEEIEAFSPGPSEAPDGEYGDLDARTAVRAA---ATERDRF-Y-V   C  PPPSGSTVVRLEPEQA   C  PEYSQGR-NFTEGIAVLFKENIAP
      ------QVEPTQSEDITRSAHLGDGDEIREAIHKSQ-DAETKPTF-Y-V    C  PPPTGSTIVRLEPTRT   C  PDYHLGK-NFTEGIAVVYKENIAA
      PKKNKKPKNPTPPRPAGDNATVAAGHATLREHLRDIKAENTD-ANF-Y-V   C  PPPTGATVVQFEQPRR   C  PTRPEGQ-NYTEGIAVVFKENIAP
      TTSAQTRSVYSQHVTSSEAVSHRANETIYNITLKYGDVVGVNITKYPYRV   C  SMAQGTDLIRFERNII   C  TSMKPINEDLDEGIMVVYKRNIVA
      VQPTATR--------------------QQTSFPFRV                 C  ELSSHGDLFRFSSDIQ   C  PSF-GTRENHTEGLLMVFFKDNIIP
                              .       .                   *                                        100
                                                                                *   **  .  ..   . .   * .**   .
```

FIG. 3B

```
YKFKANIYYKNIIITTVWSGSTYAVITNRYTDRVPIGVPEITELIDRRGM   C  LSKADYIRNNYEFTAFDKDE-DPREVHLKPSKFNTPGSRGWHT
YKFKANIYYKNIIMTTVWSGSSYAVTTNRYTDRVPVKVQEITDLIDRRGM   C  LSKADYVRNNYQFTAFDRDE-DPRELPLKPSKFNTPQSRGWHT
YKFRANVYYKDIVVTRVWKGYSHTSLSDRYNDRVPVSVEEIFGLIDSKGK   C  SSKAEYLRDNIMHHAYHDDE-DEVELDLCRPSLQLRGARAWQT
HKFKAHIYYKNIVIVTTVWSGSTYAAITNRFTDRVPVPVQEITDVIDRRGK  C  VSKAEYVRNNHKVTAFDRDE-NPVEVDLRPSRLNALGTRGWHT
YKFKATVYYKDVIVSTAWAGSSYTQITNRYADRVPIPVSEITDTIDKFGK   C  SSKATYVRNNHKVEAFNEDK-NPQDMPLIASKYNSVGSKAWHT
YKFKATMYYKDVTVSQVWFGHRYSQFMGIFEDRAPVPFEEVIDKINAKGV   C  RSTAKYVRNNLETTAFHRDD-HETDMELKPANAATRTSRGWHT
HTFKVRVYQKVLTFRRSYAYIYTTYLLGSNIEYVAPPMWEI-HHINKFAQ   C  YSSYSRVIGGTVFVAYHRDSYENKTMQLIPDDYSNTHSTRYVT
YSFKVRSYTKIVTNILIYNGWYADSVTNRHEEKFSVDSYET-DQMDTIYQ   C  YNAVKMTKDGLIRVYVDRDGV-NIIVNLKPTGGLANGVRRYAS
 *    *                                         *       *                               .

200
/NDTYTKIGGSGFYH-SGTSVN   C  IVEEVDARSVYPYDSFAISTGDIIHMSPFFGLRDGAHTEYISYS--TDRFQQIEGYYPI-DLDTRLQLGAP
 NETYTKIGAAGFHH-SGTSVN   C  IVEEVDARSVYPYDSFAISTGDVIHMSPFFGLRDGAHVEHTSYS--SDRFQQIEGYYPI-DLDTRLQLGAP
[NDTTSYVGWMPWRHYTSTSVN   C  IVEEVEARSVYPYDSFALSTGDIVYASPFFYGLRAAARIEHNSYA-QERFRQVEGYRPR-DLDSKLQAEEP
 TNDTYTKIGAAGFYH-TGTSVN  C  IVEEVEARSVYPYDSFALSTGDIVYMSPFYGLREGAHGEHIGYA--PGRFQQVEHYYPI-DLDSRLRASES
 TNDTYMVAGTPGTYR-TGTSVN  C  IIEEVEARSIFPYDSFGLSTGDIIYMSPFFGLRDGAYREHSNYA--MDRFHQFEGYRQR-DLDTR-ALLEP
[DLKYNPSRVEAFHRY-GTTVN   C  IVEEVDARSVYPYDEFVLATGDFVYMSPFYGYREGSHTEHTTYA--ADRFKQVDGFYAR-DLTTKARATAP
/KDQWHSRGS-TWLYRETCNLN   C  MLTITTARSKYPYHFFATSTGDVVYISPFY---NGTNRNASYFGENADKFFIFPNYTIVSDFGRPNAAPET
QTELYDAPGWLIWTYRTRTTVN   C  LITDMMAKSNSPFDFFVTTGQTVEMSPFY---DGKNKET--FHERADSFHVRTNYKIV-DYDNRGTNPQG
            *       *       * *                    *.       *                               .
```

FIG. 3C

```
             300                                                                              
VS-RNFLTTQHVTVAWNWVPKIREV  C  TLAKWREIDEIIRDEYK-GSYRFTAKSISATFISDTT-QFDIDRVKLSD  C  AKREAIEAIDKIYKKK
VS-RNFLETPHVTVAWNWTPKCGRV  C  TLAKWREIDEMLRDEYQ-GSYRFTVKTISATFISNTS-QFEINRIRLGD  C  ATKEAAEAIDRIYKSK
VT-KNFITTPHVTVSWNWTEKKVEA  C  TLTKWKEVDELVRDEFR-GSYRFISSTFISNTT-QFKLESAPLTE     C  VSKEAKEAIDSIYKKQ
VT-RNFLRTPHFTVAWDWAPKTRRV  C  SLAKWREAEEMTRDETRDGSFRFTSRALGASFVSDVT-QLDLQRVHLGD  C  VLREASEAIDAIYRRR
AA-RNFLVTPHLTVGHNWKPKRTEV  C  SLVKWREVEDVVRDEYAH-NFRFTMKTLSTTFISETN-EFNLNQIHLSQ  C  VKEEARAIINRIYTTR
TT-RNLLTTPKFTVAJDWVPKRPSV  C  TMTKWQEVDEMLRSEY-GGSFRFSSDAISTTFTNLT-EYPLSRVDLGD   C  IGKDARDAMDRIFARR
HRLVAFLERADSVISWDIQDEKNVT  C  QLTFWEASERTIRSE-AEDSYHFSSAKMTATFLSKKQ-EVNMSDSAL-D  C  VRDEAINKLQQIFNTS
ER-RAFLDKGTYTLSWKL-ENRTAY  C  PLQHWQTFDSTIATE-TGKSIHFVTDEGTSSFVTNTTVGIELPD-AF-K  C  IEEQVNKTMHEKYEAV
    .    .. .    .         *                   *         *            *        *
             400
YNKTHIQTGEL-ETYLARGGFIIAFRPMISNELAKLYINELVRSNRTVDLKSLLNPSVRGGA---RKRRSV------EEN------KRSKRN
YSKTHIQTGTL-ETYLARGGFIIAFRPMISNELAKLYINELARSNRTVDLSALLNPSGETVQ---RTRGSV------PSNQH------HRSRRS
YESTHVFSGDV-EYYLARGGFLIAFRPMIYDLKNLLNLLNPNANNNNNTRRRRSLLSVPEPQPTQDGVHREQILHRLHKR
YNSTHVLAGDRPEVYLARGGFVVAFRPLISNELAQLYARELER----LGLAGVVGPAAPAARARRSPGPAGTPEPPAVNGTGH--
YNSSHVRTGDI-QTYLARGGFVVVFQPLLSNSLARLYLQELVRENTN------HSPQKHPTRNTRSRRSV------PVELRANRT-------
YNATHIKVGQ-PQYYLANGGFLIAYQPLLSNTLAELYVREHLREQS------------------RKPPNPTPPPGASANAS------------
YNQTYEK-YGNVSVFETSGGLVVFWQGIKQKSLVEL-----ERLANRSSLNITH-------------------------RTRRS
-QDRYTKGQEAITYFITSGGLLLAWLPLTPRSLATV-----KNLTELTTPTSSPPSSPPPAPSAARGSTPAAVLRRRR
              .    ..   *                                               .                .
```

FIG. 3D

```
                                                                                    500
-IEGGIENVNNST------IKTTSSVHFAMLQFAYDHIQSHVNEMLSRIATAW C NLQNKERTLWNEVMKLNPTSVASVAMDQRVSARMLGDVL
TIEGGIETVNNAS------LLKTTSSVEFAMIQFAYDIQAHVNEMLSRIATAW C TLQNREHVLWTETLKLNPGGVVSMALERRVSARLLGDAV
AVEATAGTDSSNVTAKQLELIKTTSSIEFAMLQFAYDHIQSHVNEMLSRIATAW C TLQNKERTLWNEMVKINPSAIVSATLDERVAARVLGDVI
-----------------LRITTGSAEFARLQFTYDHIQAEFARLGQRVSAVATAALGQRVSARMLGDVM
-----------------ITTTSSVEFAMLQFTYDHIQEHVNEMLARISSSW C QLQNRERALWSGLFPINPSALASTILDQRVKARILGDVI
-----------------VERIKTTSSIEFARLQFTYNHIQRHVNDMLGRVAIAW C ELQNHELTLWNEARKLNPAIASVTVGRRVSARMLGDVM
TSDNNTIHLS------SMESVH---NLVYAQLQFTYDTLRGYINRALAQIAEAW C VDQRRTLEVFKELSKINPSAILSAIYNKPIAARFMGDVL
DAGNATTPVPPTAPGKSLGTLN---NPATVQIQFAYDSLRRQINRMLGDLARAW C LEQKRQNMVLRELTKINPTTVMSSIYGKAVAAKRLGDVI
                                                                                    600
AVTQ C VNISGS-SVFIQNSMRVLGSTTT C YSRPLISFKALENSTN--YIEGQLGENNELLVERKLIEP C TANHKRYFKFGADYYVFENYA
AVTQ C VNISSG-HVYIQNSMRVTGSSTT C YSRPLVSFRALNDS-E--YIEGQLGENDDLLVERKLIEP C TVNNKRYFKFGADYVYFEDYA
AITH C AKIEG--NVYLQNSMRSMDSNT- C YSRPPVTFTITKNANNRGSIEGQLGEENEIFTERKLIEP C ALNQKRYFKFGKEYYVYENYI
AISR C VEVRGG--VYVQNSMRVPGERGT C YSRPLVTF----EHNGTGVIEGQLGEQLGDDNELLISRDLIEP C TGNHRRYFKLGSGYVYEDYN
SVSN C PELGSDTRIILQNSMRVSGSTTR C YSRPLISIVSLN---GSGTVEGQLGTDNELIMSRDLLEP C VANHKRYFLFGHHYVYYEDYR
AVST C VPVAAD-NVIVQNSMRISSRPGA C YSRPLVSFRY----EDQGPLVEGQLGENNELRLTRDAIEP C TVGHRRYFTFGGGYVFEEYA
GLAS C VTIN-QTSVKVLRDMNVKESPGR C YSRPVVIFNFANSSY---VQYGQLGEDNEILLGNHRTEE C QLPSLKIFIAGNSAYEYVDYL
SVSQ C VPVN-QATVTLRKSMRVPGSETM C YSRPLVSFSFINDTK---TYEGQLGTDNEIFLTKKMTEV C QATSQYYFQSGNEIHVYNDYH
```

FIG. 3E

```
                                                                                          700                                                         800
YVRKVPLNEIEMISAYVDLNITLLEDREFLPLEVYTRAELEDTGLLDYSEIQRRNQLHALKFYDIDSVVK----VDNNVVIMRGIANFFQGLGDVGA
YVRKVPLSEIELISAYVDLNLTLLEDREFLPLEVYTRAELEDTGLLDYSEIQRRNQLHALKFYDIDSIVR----VDNNLVIMRGMANFFQGLGDVGA
FVRKVPPTEIEVISTYVELNLTLLEDREFLPLEVYTRAELEDTGLLDYSEIQRRNQLHALRFYDIDSVVN----VDNTAVIMQGIASFFKGLGKVGE
YVRMVEVPET--ISTRVTLNETLLEDREFLPLEVYTREELADTGLLDYSEIQRRNQLHALKFYDIDRVVK----VDHNVVLLRGIANFFQGLGDVGA
YVREIAVHDVGMISTYVDLNETLLKDREFMPLQVYTRDELRDTGLLDYSEIQRRNQMHSLRFYDIDKVVQ----YDSGTAIMQGMAQFFQGLGTAGQ
(SHQLSRADITTVSTFIDLNITMLEDHEFVPLEVYTRHEIKDSGLLDYTEVQRRNQLHDLRFADIDTVIH----ADANAAMFAGLGAFFEGMGDLGR
FKRMIDLSSISTVDSMIALDIDPLENTDFRVLELYSQKELRSSNVFDLEEIMREFNSYKQRV----KYVEDKVVDPLPPYLKGLDDLMSGLGAAGK
HFKTIELDGIATLQTFISLNTSLIENIDFASLELYSRDEQRASNVFDLEGIFREYNFQAQNIAGLRKDLDNAVSNGRNQFVDGLGELMDSLGSVGQ
  ..  :  . .   .. .   .      .  *        .  *.*. .          .                          *    *

GFGKVVLGAANAVIATVSGVSSFLNNPFGALAVGLLILAGLFAAFLAYRYVSKLKSNPMKALYP--VTTKNLKE-------SVKNGNSGNNSD
GFGKVVLGAASAVISTVSGVSSFLNNPFGALAVGLLILAGIVAAFLAYRYISRLRANPMKALYP--VTRNLKQ-------TAKSPASTAGGD
AVGTLVLGEAGAVVSTVSGIASFLNNPFGGLAIGLLVIAGLVAAFLAVAFFAYRYVMQIRSNPMKALYP--ITTKALKN-------KAKTS---YGQN
AVGKVVLGATGAVISAVGGMVSFLSNPFGALAIGILVLAGLLVLAGLVLAGLVAAFFAYRHISRLRRNPMKALYP--VTTKTLKE----------
AVGHVVLGATGALLSTVHGFTTFLSNPFGALAVGLLVLAGLVAAFFAYRYVLKLKTSPMKALYP--LITKGLKQLPEGMDPFAEKPNATDTPIEEI
AVGKVVMGLVGGVSVSAVGGVVSFMSNPFGALAVGLVLAGLAAAFFAFRYVMRLQSNPMKALYP--LTTKELKN-------PTNPDASGE
AVGVAIGAVGAVASVVEGVATFLKNPFGAFTIILVAIAVVIITYLIYTRQRRLCTQPLQNLFPYLVSADGTTVTSGSTKDTSLQAPPSYEESVYN
SITNLVSTVGGLFSSLVSGFISFFKNPFGGMLILVLVAGVILVAGVVILVISLTRRTRQMSQQPVQMLYP-----------GIDELAQQHASG---
   .   ::   .   .  . *  ****. *. *      :     *.*    . * *       *        *                *
```

FIG. 3F

```
GEENDDN------IDEEKLQQAKEMIKYMSLVSAMEQQEHKAIKKNSGPALLASHITNLSLK----HRGPKYKRLKNVNENESK----V
SDPGVDD------FDEEKLMQAREMIKYMSLVSAMEQQEHKAMKKNKGPAILTSHLTNMALR----RRGPKYQRLNNLDSGDDTETNLV
EEDDGSD------FDEAKLEEAREMIKYMSMVSALEKQEKKAIKKNSGVGLIASNVSKLALR----RRGPKYTRLQQNDTMEN--EKMV
DGVDEGD------VDEAKLDQARDMIRYMSIVSALEQQEHKARKKNSGPALLASRVGAMATR----RR--HYQRL------ESEDPDAL
GDSQNTEPSVNSGFDPDKFREAQEMIKYMTLVSAAERQESKARKKNKTSALLTSRLTGLALR----NR-RGYSRVR-----TENVTGV
GEEGGD------FDEAKLAEAREMIRYMALVSAMERTEHKAKKGTSR-LLSAKVTDMVMRK---RRNTNYTQVPNKD--GDADEDDL
SGRKGPGPPSSDASTAAPPYTNEQAYQMLLALARLDAEQR--AQQNGTDSLDGQTGTQDKGQKPNLLDRLRHRKNGYRHLKDSDEEENV
---EGPG------INPISKTELQAIMLALHEQNQEQKRAAQRAAGPSVASRALQAARDRFPGLRRRYHDPETAAALLG-EAETEF
```

FIG. 4A

| | | | |
|---|---|---|---|
| CGAGCCCTAA | TTATTGGTTT | GTATATGACT | 30 |
| GTTGGAATTT | GTTACATTTT | TATTAAAACA | 60 |
| ATAAATTAAA | TTTTTTAAAC | TATATTACGG | 90 |
| TTGTGTGTGT | TTTAAGTTTT | AAATAAAGCA | 120 |
| ATATTCGAA | TTCACATTTA | TCAAAACAT | 150 |
| TAAAACCCAA | CACAAAAAAA | TTTCTATAAT | 180 |
| CATTAAGGTA | ATAAGTCAAA | ATGAGTTTTA | 210 |
| | |   M  S  F> | 3 |
| AAAATTTTA | TCTAATATAT | GTAATTATAA | 240 |
| K  N  F  Y | L  I  Y | V  I  I> | 13 |
| TTTTTATAAA | CTCGATAATA | ACTTCGGCAT | 270 |
| I  F  I  N | S  I  I | T  S  A> | 23 |
| CTACATCCAA | ACCTTCAACA | CCTACCATAA | 300 |
| S  T  S  K | P  S  T | P  T  I> | 33 |
| TTCCAACTTC | AGCAAATGAA | TCACCTGCTT | 330 |
| I  P  T  S | A  N  E | S  P  A> | 43 |
| CCATAGATAC | AACTATAACA | AAACCTATAT | 360 |
| S  I  D  T | T  I  T | K  P  I> | 53 |
| CTACAGAGGC | AAATAATTTA | AAATCAGTAA | 390 |
| S  T  E  A | N  N  L | K  S  V> | 63 |
| GTACCTCAAT | TAAACCACCT | AAAAACTTAA | 420 |
| S  T  S  I | K  P  P | K  N  L> | 73 |
| AAAAAAATT | ACTTAAATCT | AAATGTAGAG | 450 |
| K  K  K  L | L  K  S | K  C  R> | 83 |
| ATAATGTTAT | TTATAGGCCA | TATTTTAGTC | 480 |
| D  N  V  I | Y  R  P | Y  F  S> | 93 |
| AATTAGAAAT | TAACTGTACT | ATAACTAAAA | 510 |
| Q  L  E  I | N  C  T | I  T  K> | 103 |

| | | | |
|---|---|---|---|
| AGCAAAATTT | AAGTAATCCT | TTAATTGAGT | 540 |
| K  Q  N  L | S  N  P | L  I  E> | 113 |
| TATGGTTTAA | AGAACTTTCT | ACATATAATA | 570 |
| L  W  F  K | E  L  S | T  Y  N> | 123 |
| AAACCAATGA | AAATGTTGAA | AGTTTAAAAA | 600 |
| K  T  N  E | N  V  E | S  L  K> | 133 |
| CAGATATATC | AAAAAATATT | TTATTATTTT | 630 |
| T  D  I  S | K  N  I | L  L  F> | 143 |
| CGACAAAAAA | TAATAGTGAT | AACTTTATA | 660 |
| S  T  K  N | N  S  D | N  F  Y> | 153 |
| ATGATTTTTT | ATTAGGTATA | CAAAATCAAC | 690 |
| N  D  F  L | L  G  I | Q  N  Q> | 163 |
| CAGTAAATTA | TAAACTTTAC | GGTTCCCAAT | 720 |
| P  V  N  Y | K  L  Y | G  S  Q> | 173 |
| TTTATGATAA | TGGAAACATA | TTACTAAATA | 750 |
| F  Y  D  N | G  N  I | L  L  N> | 183 |
| TAAAGTCGGT | TGACTTTAAA | ACCTCTGGAA | 780 |
| I  K  S  V | D  F  K | T  S  G> | 193 |
| TATATACTTG | GAAACTATAT | AATTCAAATA | 810 |
| I  Y  T  W | K  L  Y | N  S  N> | 203 |
| ATGAAAGTAT | TTTTGAAACT | TTTAAAATTC | 840 |
| N  E  S  I | F  E  T | F  K  I> | 213 |
| AAGTATATGC | ATATCATTCC | CCAAATGTAA | 870 |
| Q  V  Y  A | Y  H  S | P  N  V> | 223 |
| ACTTAAAATC | AAACCCAAGT | TTATATAATG | 900 |
| N  L  K  S | N  P  S | L  Y  N> | 233 |
| AAAACTACAG | CGCTATTTGT | ACAATAGCAA | 930 |
| E  N  Y  S | A  I  C | T  I  A> | 243 |
| ATTACTTTCC | ATTGGAATCT | ACGGAAATAT | 960 |
| N  Y  F  P | L  E  S | T  E  I> | 253 |

FIG. 4C

| | | | | |
|---|---|---|---|---|
| TTTGGTTTAA<br>F  W  F  N | CGATGGACAA<br>   D  G  Q | CCTATTGATA<br>   P  I  D> | 990<br>263 | |
| AAAAATATAT<br>K  K  Y  I | AGATGAAACT<br>   D  E  T | TATAGTGTAT<br>   Y  S  V> | 1020<br>273 | |
| GGATTGACGG<br>W  I  D  G | TCTTATAACA<br>   L  I  T | CGCACTTCAA<br>   R  T  S> | 1050<br>283 | |
| TATTATCCCT<br>I  L  S  L | TCCCTTTTCC<br>   P  F  S | GAAGCCATGG<br>   E  A  M> | 1080<br>293 | |
| AAAGCCCCCC<br>E  S  P  P | CAATTTGCGA<br>   N  L  R | TGTAATGTTG<br>   C  N  V> | 1110<br>303 | |
| AATGGTATAA<br>E  W  Y  K | AAATTCAAAG<br>   N  S  K | GCATCAAAAA<br>   A  S  K> | 1140<br>313 | |
| AATTTTCAAA<br>K  F  S  N | TACCGTTATT<br>   T  V  I | CCAAAAGTTT<br>   P  K  V> | 1170<br>323 | |
| ACTATAAACC<br>Y  Y  K  P | TTTTATATCT<br>   F  I  S | ATAAAATTTG<br>   I  K  F> | 1200<br>333 | |
| ATAATGGTTT<br>D  N  G  L | AGCTATTTGT<br>   A  I  C | GATGCTAAAT<br>   D  A  K> | 1230<br>343 | |
| GTGTTTCCCG<br>C  V  S  R | TGAAAATAAT<br>   E  N  N | AAATTACAAT<br>   K  L  Q> | 1260<br>353 | |
| GGTTAGTTAA<br>W  L  V  K | AGATATACCT<br>   D  I  P | ATAAATGGTG<br>   I  N  G> | 1290<br>363 | |
| ATGATATTAT<br>D  D  I  I | AAGCGGCCCC<br>   S  G  P | TGTTTAAACC<br>   C  L  N> | 1320<br>373 | |
| ACCCTGGTTT<br>H  P  G  L | GGTCAATATT<br>   V  N  I | CAAAATAAAA<br>   Q  N  K> | 1350<br>383 | |
| TAGATATATC<br>I  D  I  S | GGATTATGAT<br>   D  Y  D | GAACCTGTTA<br>   E  P  V> | 1380<br>393 | |

FIG. 4D

| | | | |
|---|---|---|---|
| CCTATAAATG | TTCAATTATT | GGTTATCCAA | 1410 |
| T Y K C | S I I | G Y P> | 403 |
| TAATTTTTCC | CAACTTTTAT | GATGAAAAGG | 1440 |
| I I F P | N F Y | D E K> | 413 |
| TGTTTGATGC | ATCGGATGAA | AATGTTAGTA | 1470 |
| V F D A | S D E | N V S> | 423 |
| AATCGATGTT | AATAAGTATT | ACCACAATAA | 1500 |
| K S M L | I S I | T T I> | 433 |
| TTGGTGGAGC | CATTTTTGTT | ATAGTATTGA | 1530 |
| I G G A | I F V | I V L> | 443 |
| TTTTTATAAC | AGCTTTATGT | TTTTATTGTT | 1560 |
| I F I T | A L C | F Y C> | 453 |
| CAAAAAATAA | TAAGATCTAA | TATCAATATT | 1590 |
| S K N N | K I * | | 459 |
| TACGTAAATG | GATTATATAA | TGTTATATTC | 1620 |
| GTGTTATTAT | GATTTATAAG | TTCATCAAAT | 1650 |
| TTAAAAATTT | GTATAGTATT | AAGATTTTTA | 1680 |
| ATAGGGGTAT | CGTTTAATAT | GGCTCAGTTA | 1710 |
| | M | A Q L | 4 |
| GTTTTAACTG | ATATTCCCCT | CGAAGATGTG | 1740 |
| V L T D | I P L | E D V | 14 |
| GAAAATAAAA | ATACTTCATC | CGACGAAGAA | 1770 |
| E N K N | T S S | D E E | 24 |
| ACAACTAACT | TAAACCAGAA | AAAATCAACA | 1800 |
| T T N L | N Q K | K S T | 34 |
| TGTCAATGTT | TATGTGTTAC | CCTTGGATTT | 1830 |
| C Q C L | C V T | L G F | 44 |
| TTTGCAGCTG | GAATTTTATT | AACCATAGCT | 1860 |
| F A A G | I L L | T I A | 54 |

FIG. 4E

```
GCAATAATTT    TTACTTTTAT    TTTTACAGTA    1890
 A  I  I  F    T  F  I       F  T  V       64

CCATTAGAAA    TGCTTGGATC    TATTAATTGT    1920
 P  L  E  M    L  G  S       I  N  C       74

CCTCCATCTA    CATTTGGTAT    TGATAATGTT    1950
 P  P  S  T    F  G  I       D  N  V       84

TGTATCGAAC    CAATAAAAAA    ATCTATTAAT    1980
 C  I  E  P    I  K  K       S  I  N       94

TCTTATTCAG    AATTATCTAA    AATATGTTAT    2010
 S  Y  S  E    L  S  K       I  C  Y      104

GATAGATTGT    CAAATCCGAT    AAATCAGAGT    2040
 D  R  L  S    N  P  I       N  Q  S      114

ACTATTAACT    CCTTATTAAC    TGTTTTAAAT    2070
 T  I  N  S    L  L  T       V  L  N      124

ATGTTTGCAG    ATAAAAACTA    TGAAAATGTT    2100
 M  F  A  D    K  N  Y       E  N  V      134

TATAATTGTA    ATACAATGAG    TGAAAAAACA    2130
 Y  N  C  N    T  M  S       E  K  T      144

TGTAATTCAT    CAATAGCTAT    TTGTCAAACT    2160
 C  N  S  S    I  A  I       C  Q  T      154

AATCATCCAC    TAAGTTCATT    GGGAAATTTT    2190
 N  H  P  L    S  S  L       G  N  F      164

GTTATTAAAA    TTAGAAAAAT    TTTTGGGTTT    2220
 V  I  K  I    R  K  I       F  G  F      174

AAATAATAAA    TAAAATAAAT    AAACATTACT    2250
 K  *                                     175

TTTTGTTTTT    GTCTTTATTA    AACAGTTGTA    2280
```

FIG. 6

| FIG. 6A |
|---------|
| FIG. 6B |
| FIG. 6C |
| FIG. 6D |

FIG. 6A

```
CHV   MS-FK---NFYLIYVIIIFI----------------------------NSIITSASTSKPSTPTIIPTSANES----
FHV   MRRYRMGRGIYLLYICLLYTLYLQFGTSSTTAVSIENSDNSTAEMLSSTSMSATTPISQPTSPFTTPTRRSTNIATS
EHV1  MWLPNLVRFVAVAYLICAGAILTYASG--------ASASSSQSTPATPTHTTPNLTTAHG
HSV1  MAPGRVGLAVVLWSLL---WLGAGVSGGSETASTGPTIAGAVTNASEAPTSGSPGSAASPEVTPTSTPNPNHVT
                *                                        :   .

------PASIDTTITKP---------------ISTEANNLKSVSTSIKPPKNLKKKL---LKSK
      SSTTQASQPTSTLLTLTRSSTTIATSPSTTQAATFIGSSTDSNTILLKTTKKPKRKKNKNNGARFKLD
      AGSDNTTNANGTESTHSHETT-------------------IT
      QNKTTPTEPASPPTT-PKPTSTPKSPPTSTP------DPKPKNTTPAKSGRPTK------PPGPVW
                                                *
```

FIG. 6B

```
         *  .                      .     *                                       *  .   *  .*    *
IYRPYFSQLEIN C TITKKQHLSNPL-IELWFKELSTYNKTN-E-NVESLKTDI-SK-NILLFSTKNNSDNFYN-
IYRPYFSPLQLN C TLPTEPHITNPL-IELWFKELSTYNKTN-E-NVESLKTDI-SK-NILLFSTKNNSDNFYN-
ISVPYYKSVDMN C TTSVGVNYSE--YRLEIYLNQRTPFSGTPPG-DEENYINHATKDQTLLLFSTAERKKSRRG
LAR-YGSRVQIR C RFRNSTRME---FRLQIWRYSMGPSPPIAPAPDLEEVLTNITAPPGGLLVY---DSAPNLTD
         *  .                 .  *                            **
                                                        200
-DFLLGI-QNQPVNYKLYGSQFYDNGN--ILLNIKSVDFKTSGIYTWKLYNSN----NESIFETFKIQVYAYHSPNV
GDATLGILQSRIPDYTLYNIPIQHTEA--MSLGIKSVESATSGVYTWRVYGGDG-LNKTVLGQVNVSVVAYHPPSV
GQ--LGVIPDRLPKRQLFNLPLHTEGGTKFPLTIKSVDWRTAGIYVWSLYAKNG----ILVNSTSVTVSTYNAPLL
PHVLWAEGAGPGADPPLYSV---TGPLPTQRLIIGEVTPATQGMY----YLAWGRMDSPHEYGTWVRVRMFRPPSL
    *  . *      *             *  **  *    *  *. .*  *          *        *
```

FIG. 6C

```
NLKSNPSLYNENYSAI  C  TIANYFPLESTEIFWFNDGQPID-KKYIDETYSVWIDGLITRTSILSLPFSEAMESP
NLTPRASLFNKTFEAV  C  AVANYFP-RSTKLTWYLDGKPIE-RQYISDTASVWIDGLITRSSVLAIPTTETDSEK
DLSVHPSLKGENYRAT  C  VVASYFPHSSVKLRWYKNAREVDFTKYVTNASSVWDGLITRISTVSIPVDPEEEYT
TLQPHAVMEGQPFKAT  C  TAAAYYPRNPVEFVWFEDDHQVFNPGQIDTQTHEHPDGFTTVSTVTSEAVGGQVP-P
              *     *      *              *    *            **.*    .   ...

300
PNLR  C  NVEWYKNSKASKKFSNTVIPKVYYKPFISIKFDNGLAI  C  DAK  C  VSRENNKLQWLVKDI----PIN
PDIR  C  DLEWHESPVSYKRFTKSVAPDVYYPPTVSVTFADTRAI  C  DVK  C  VPRDGISLMWKIGNYHLPKAMS
PSLR  C  SIDWYRDEVSFARIAKAGTPSVFVAPTVSVSVEDGDAV  C  TAK  C  VPSTGVFVSWSVND-HLP-GVP
RTFT  C  QMTWHRDSVTFSRRNATGLALVLPRPTITMEFGVRIVV  C  TAG  C  VP-EGVTFAWFLGDDPSPAAKS
   *      *                  *                *        *
```

FIG. 6D

```
                                                      400
GDDIISGP C   LNHPGLVNIQNKIDISDYDEPVTYK   C   SIIGYPIIFPNFYDEKVFDASD-ENVSKSMLISITTI
ADILITGP C   IERPGLVNIQSMCDISETDGPVSYT   C   QTIGYPPILPGFYDTQVYDASP-EIVSESMLVSVVAV
SQDMTTGV C   PSHSGLVNMQSRRPLSEENGEREYS   C   IIEGYPDGLPMFSDTVVYDASP-IVEDRPVLTSIIAV
A-VTAQES C   -DHPGLATVRSTLPIS--YDYSEYI   C   RLTGYPAGIPVLEHHGSHQPPPRDPTERQVIEAIEWV
       *    .  **. . ..  . .    *             *** .       . .....   .        .

IGGAIFVIVLIFITALCFYCSKNNK------I
ILGAVLITVFIFITALCLYYSHPRR------L
TCGAAALALVVLITAVCFYCSKPSQAPYKKSDF
GIGIGVLAAGVLVVTAIVYVVRTSQSR-QRHRR
  *          .           ...  .
```

| GATATTTAAT | AAAACTATTA | TGAAACTTCT | 30 |
| TATAACTTAT | TTGTTTTTAT | TAAATGGGTT | 60 |
| GGGTTGGTTT | TAAAATTACA | TACGTGTATT | 90 |
| AAGAATTAAC | ATCATAAGG | ACACACCCAT | 120 |
| GAAAAACATT | TAAATTCTAT | TAATTTGAAC | 150 |
| GGATTAAACA | TTTTCTCATT | TTAAGAGTTG | 180 |
| CTACGACTTT | TGATAGTAAA | ATGATTAAAC | 210 |
|            |            | M  I  K>   | 03 |
| TTCTATTTAT | CTTATTTTAT | TTTAACCCAA | 240 |
| L  L  F  I | L  F  Y    | F  N  P>   | 13 |
| TAACTGGATA | TAAATGGGTA | GACCCTCCTC | 270 |
| I  T  G  Y | K  W  V    | D  P  P>   | 23 |
| GTAGGTATAA | TTACACCGTT | TTAAGAATGA | 300 |
| R  R  Y  N | Y  T  V    | L  R  M>   | 33 |
| TTCCAGATAT | TCCAAATCCA | ATGGATCCTT | 330 |
| I  P  D  I | P  N  P    | M  D  P>   | 43 |
| CTAAAACGC  | TGAAGTTCGG | TATGTAACTT | 360 |
| S  K  N  A | E  V  R    | Y  V  T>   | 53 |
| CTACTGACCC | ATGTGATATG | GTTGCTTTGA | 390 |
| S  T  D  P | C  D  M    | V  A  L>   | 63 |
| TTTCTAATCC | AAATATAGAA | TCTACAATTA | 420 |
| I  S  N  P | N  I  E    | S  T  I>   | 73 |
| AAACGATTCA | ATTTGTGCAA | AAGAAAAAT  | 450 |
| K  T  I  Q | F  V  Q    | K  K  K>   | 83 |
| TTTACAATGC | ATCTCTTAGT | TGGTTTAAAG | 480 |
| F  Y  N  A | S  L  S    | W  F  K>   | 93 |
| TTGGAGATGA | TTGTACATAT | CCAATATATT | 510 |
| V  G  D  D | C  T  Y    | P  I  Y>   | 103 |

FIG. 7B

| | | | | |
|---|---|---|---|---|
| TAATTCAATA | TTTTGATTGT | GATCCTCAAA | 540 | |
| L I Q Y | F D C | D P Q> | 113 | |
| GAGAATTTGG | CATATGTTTA | AAAAGATCTC | 570 | |
| R E F G | I C L | K R S> | 123 | |
| CAGATTTTTG | GAAACCATCG | TTAGTTGGTT | 600 | |
| P D F W | K P S | L V G> | 133 | |
| ACACATTTTT | AACTGATGAT | GAATTGGGAT | 630 | |
| Y T F L | T D D | E L G> | 143 | |
| TAGTTTTAGC | TGCCCCCGCT | CCATTTAATC | 660 | |
| L V L A | A P A | P F N> | 153 | |
| AAGGTCAATA | TAGACGGGTT | ATTCAAATTG | 690 | |
| Q G Q Y | R R V | I Q I> | 163 | |
| AAAATGAAGT | TTTTTATACT | GATTTATGG | 720 | |
| E N E V | F Y T | D F M> | 173 | |
| TTCAATTACC | ACGAGAAACT | TGTTATTTTT | 750 | |
| V Q L P | R E T | C Y F> | 183 | |
| CTAAAGAAGA | TAAATTTGAA | CCAACTTTTA | 780 | |
| S K E D | K F E | P T F> | 193 | |
| TGGAATGGTG | TAAGGAATCT | AGATCTGTAG | 810 | |
| M E W C | K E S | R S V> | 203 | |
| GAGCATCAAA | AGTTGACGAT | GAACTTTTT | 840 | |
| G A S K | V D D | E L F> | 213 | |
| ATCTAAATAG | AGCTGGTCCC | CAAACCCTGC | 870 | |
| Y L N R | A G P | Q T L> | 223 | |
| TTAAATATTA | TGTTATTAAA | GATTTTTATA | 900 | |
| L K Y Y | V I K | D F Y> | 233 | |
| GACTTAACGG | TAGAGAACCT | CCAATAAAAT | 930 | |
| R L N G | R E P | P I K> | 243 | |
| TTAAAGAAGC | TCTTAGATAC | GATATACCAT | 960 | |
| F K E A | L R Y | D I P> | 253 | |

FIG. 7C

| | | | |
|---|---|---|---|
| ATAAAGTGAA | TGATAAATTT | GATGATGAAT | 990 |
| Y K V N | D K F | D D E> | 263 |
| TACCATCGAG | GCCACATATT | AGTAATACTA | 1020 |
| L P S R | P H I | S N T> | 273 |
| TTAATAAAAC | TATTAAAGAA | ATTGTAAATC | 1050 |
| I N K T | I K E | I V N> | 283 |
| TTGAAGATTA | TTTTAAAAAT | ACAAATGTTA | 1080 |
| L E D Y | F K N | T N V> | 293 |
| TAGATACTAC | TACCCCAACA | CCAATAAATA | 1090 |
| I D T T | T P T | P I N> | 303 |
| ATACCCCAAA | AAATATAACC | GTGGGAATTG | 1140 |
| N T P K | N I T | V G I> | 313 |
| TTATAATTAT | ATTAATAATA | CTATTTATAA | 1170 |
| V I I I | L I I | L F I> | 323 |
| TTGGATTTTT | TGTTTATAAA | AGACAAAAAA | 1200 |
| I G F F | V Y K | R Q K> | 333 |
| TATATAATAA | TTATAAAAAA | TTAACAACAA | 1230 |
| I Y N N | Y K K | L T T> | 343 |
| ATGTTTAGCC | TTTATAAATT | AATTTACAGA | 1260 |
| N V * | | | 345 |
| ATAAACAACT | GGGCGGTCTT | TTGTTTAATA | 1290 |
| AAAATTCATG | TACCTACAAC | TTTTATTCAC | 1320 |

```
CHV    MI-KLLF------------------------------------------------ILF-------YF---
FHV    MMTRLHF--------------------------------------WW---C------------------
EH/1   MPAVLLVLYVNPPPSVCILTQKLSLGLYNQWRVCRSVPPPWYVFFNKRSMSTFKLMMDGRLVFAMAIAILSVVLSCGT
HSV1   MGGA-------------------------AARLGAV-----------ILF------VVIVGLHGVRGKYALADASLKM----AD
         *

----NPITGYK--WVDPPRRYNYTVLRMIPDIPNPM----DPSKNAEVRYVTSTDP  C  DMVALISNPNIESTIKTI
       SLTTPKTTTVYVKGFNIPPLRYHYTQARIVPKIPQAM----DPKITAEVRYVTSMDS  C  GMVALISEPDIDATIRTI
       CEKAKRAVRGRQDRPKEFPPPRYNYTILTRYNATALASPFINDQVKNVDLRIVTATRP C  EMIALIAKTNIDSILKEL
       PNRFRGKDLPVLDQLTDPPGVRRVYHI----QAGLPNPF--QPPSLPITVYRRVERA  C  RSVLLNAPSEAPQIVRGA
         * *..*                          *.  .  .            :     *    :.:        .
```

FIG. 9B

```
QFVQKKFYNASLSWFKVGDD C TYPIYLIQYFD C DPQREFGI C LKRSPDFWKPSLVGYTFLTDDELGLVLAAP
QLSQKKT-YNATISWFKVTQG C EYPMFLMDMRL C DPKREFGI C ALRSPSYWLEPLTKYMFLTDDELGLIMMAP
AAAQKT--YSARLTWFKIMPT C ATPIHDVSYMK C NPKLSFAM C DERSDILWQASLITMAAETDDELGLVLAAP
SEDVRKQPYNLTIAWFRMGGN C AIPITVMEYTE C SYNKSLGA C PIRTQPRWN-YYDSFSAVSEDNLGFLMHAP
 .. *.     * **               .*             *            . .**       .  .* **

APFNQGQYRRVIQIENEVFYTDFMVQL-PRET C YFSKEDKFEPTFMEW C KESRSVGASKVDDELFYLNRAGPQT
AQFNQGQYRRVVITIDGSMFYTDFMVQL-SPTP C WFAKPDRYEEILHEW C RNVKTIGLDGARDYHYYWVPYNPQP
AHSASGLYRRVIEIDGRRIYTDFSVTI-PSER C PIAFELNFGN--PDR C KTPEQYSRGEVFTRRFLGEFNFPQG
AFETAGTYLRLVKINDWTEITQFILEHRAKGS C KYTLPLRIPPSA--- C LSPQAYQQGVTVDSIGMLPRFIPEN
*         .  * *.. *          .*            *            *                 *.
```

FIG. 9C

```
-LKYYVIKDFYRLNGREPPIKFKEALRYDIPYKVNDK--FDDELPSRPHISNTINKTIKE-------IVNLEDYFKNT
HHKA-VLLYWYRTHGREPPVRFQEAIRYDRPAIPSGS------EDSKRSNDSRG-ESSGPN------WIDIENYTPKN
EHMTWV-KFWFVYDGGNLPVQFYEAQAFARPVPPDNHPGFDSVESEITQNKTDPKPGQADPKPNQPFKWPSIKHLVPRL
RT--VAVYSLKIAGWHGPRAPYTSTLLPPELPETPNATQPELAPEDPEDSALLEDPVGTVAPQIPPNWH--------
    *    *         *
300
NVIDTTTPINNTPKN------ITVGIVIIILILFIIG--FFVYK-RQKIYNNYKKL----TTNV---------
NVPIIISDDDVPTAPPKGMNNQSVVIPAIVLSCLIIALILGVIYYILRVKRSRSTAYQQLPIHTTHHP------
DEVDEVI-EPVTKPPKTSKSNSTFVGISVGLGIAGLVLVGVILYVCLRRKKELKVCTERLD--SPTLDL-----
--IPSIQDAATPYHPPATPNNMGLIAGAVGGSLLAALVICGIVYW-MRRRTRKAPKRIRLPHIREDDQPSSHQPLFY
              *
```

```
   1    TGAATGTTAA   ATGTTATACT   TTGGATGAAG
  31    CTATAAATAT   GCATTGGAAA   AATAATCCAT
  61    TTAAAGAAAG   GATTCAAATA   CTACAAAACC
  91    TAAGCGATAA   TATGTTAACT   AAGCTTATTC
 121    TTAACGACGC   TTTAAATATA   CACAAATAAA
 151    CATAATTTTT   GTATAACCTA   ACAAATAACT
 181    AAAACATAAA   AATAATAAAA   GGAAATGTAA
 211    TATCGTAATT   ATTTTACTCA   GGAATGGGGT
 241    TAAATATTTA   TATCACGTGT   ATATCTATAC
 271    TGTTATCGTA   TACACTTTAC   AATTACTATT
 301    ACGAATATGC   AAGAGATAAT   AAGATTACGT
 331    ATTTAAGAGA   ATCTTGTCAT   GATAATTGGG
 361    TACGACATAG   TGATAAATGC   TATTTCGCAT
 391    CGTTACATAA   AGTCAGTTGG   AAAGATGGAT
 421    TTGACAGATG   TAACTTAATA   GGTGCAAAAA
 451    TGTTAAATAA   CAGCATTCTA   TCGGAAGATA
 481    GGATACCAGT   TATATTATAC   AAAAATCACT
 511    GGTTGGATAA   AACAGATTCT   GCAATATTCG
 541    TAAAAGATGA   AGATTACTGC   GAATTTGTAA
 571    ACTATGACAA   TAAAAGCCA    TTTATCTCAA
 601    CGACATCGTG   TAATTCTTCC   ATGTTTTATG
 631    TATGTGTTTC   AGATATTATG   AGATTACTAT
 661    AAACTTTTTG   TATACTTATA   TTCCGTAAAC
 691    TATATTAATC   ATGAAGAAAA   TGAAAAAGTA
 721    TAGAAGCTGT   TCACGAGCGG   TTGTTGAAAA
 751    CAACAAAATT   ATACATTCAA   GATGGCTTAC
 781    ATATACGTCT   GTGAGGCTAT   CATGGATAAT
 811    GACAATGCAT   CTCTAAATAG   GTTTTTGGAC
 841    AATGGATTCG   ACCCTAACAC   GGAATATGGT
 871    ACTCTACAAT   CTCCTCTTGA   AATGGCTGTA
 901    ATGTTCAAGA   ATACCGAGGC   TATAAAAATC
 931    TTGATGAGGT   ATGGAGCTAA   ACCTGTAGTT
 961    ACTGAATGCA   CAACTTCTTG   TCTGCATGAT
 991    GCGGTGTTGA   GAGACGACTA   CAAAATAGTG
1021    AAAGATCTGT   TGAAGAATAA   CTATGTAAAC
1051    AATGTTCTTT   ACAGCGGAGG   CTTTACTCCT
1081    TTGTGTTTGG   CAGCTTACCT   TAACAAAGTT
1111    AATTTGGTTA   AACTTCTATT   GGCTCATTCG
1141    GCGGATGTAG   ATATTTCAAA   CACGGATCGG
1171    TTAACTCCTC   TACATATAGC   CGTATCAAAT
1201    AAAAATTTAA   CAATGGTTAA   ACTTCTATTG
1231    AACAAAGGTG   CTGATACTGA   CTTGCTGGAT
1261    AACATGGAC    GTACTCCTTT   AATGATCGCT
1291    GTACAATCTG   GAAATATTGA   AATATGTAGC
```

FIG. 17B

```
1321    ACACTACTTA    AAAAAAATAA    AATGTCCAGA
1351    ACTGGGAAAA    ATTGATCTTG    CCAGCTGTAA
1381    TTCATGGTAG    AAAAGAAGTG    CTCAGGCTAC
1411    TTTTCAACAA    AGGAGCAGAT    GTAAACTACA
1441    TCTTTGAAAG    AAATGGAAAA    TCATATACTG
1471    TTTTGGAATT    GATTAAAGAA    AGTTACTCTG
1501    AGACACAAAA    GAGGTAGCTG    AAGTGGTACT
1531    CTCAAAATGC    AGAACGATGA    CTGCGAAGCA
1561    AGAAGTAGAG    AAATAACACT    TTATGACTTT
1591    CTTAGTTGTA    GAAAGATAG     AGATATAATG
1621    ATGGTCATAA    ATAACTCTGA    TATTGCAAGT
1651    AAATGCAATA    ATAAGTTAGA    TTTATTTAAA
1681    AGGATAGTTA    AAAATAGAAA    AAAAGAGTTA
1711    ATTTGTAGGG    TTAAAATAAT    ACATAAGATC
1741    TTAAAATTTA    TAAATACGCA    TAATAATAAA
1771    AATAGATTAT    ACTTATTACC    TTCAGAGATA
1801    AAATTTAAGA    TATTTACTTA    TTTAACTTAT
1831    AAAGATCTAA    AATGCATAAT    TTCTAAATAA
1861    TGAAAAAAAA    GTACATCATG    AGCAACGCGT
1891    TAGTATATTT    TACAATGGAG    ATTAACGCTC
1921    TATACCGTTC    TATGTTTATT    GATTCAGATG
1951    ATGTTTAGA     AAAGAAAGTT    ATTGAATATG
1981    AAAACTTTAA    TGAAGATGAA    GATGACGACG
2211    ATGATTATTG    TTGTAAATCT    GTTTAGATG
2041    AAGAAGATGA    CGCGCTAAAG    TATACTATGG
2071    TTACAAAGTA    TAAGTCTATA    CTACTAATGG
2101    CGACTTGTGC    AAGAAGGTAT    AGTATAGTGA
2131    AAATGTTGTT    AGATTATGAT    TATGAAAAAC
2161    CAAATAAATC    AGATCCATAT    CTAAAGGTAT
2191    CTCCTTTGCA    CATAATTTCA    TCTATTCCTA
2221    GTTTAGAATA    CTTTTCATTA    TATTTGTTTA
2251    CAGCTGAAGA    CGAAAAAAAT    ATATCGATAA
2281    TAGAAGATTA    TGTTAACTCT    GCTAATAAGA
2311    TGAAATTGAA    TGAGTCTGTG    ATAATAGCTA
2341    TAATCAGAGA    AGTTCTAAAA    GGAAATAAAA
2371    ATCTAACTGA    TCAGGATATA    AAAACATTGG
2401    CTGATGAAAT    CAACAAGGAG    GAACTGAATA
2431    TAGCTAAACT    ATTGTTAGAT    AGAGGGGCCA
2461    AAGTAAATTA    CAAGGATGTT    TACGGTTCTT
2491    CAGCTCTCCA    TAGAGCTGCT    ATTGGTAGGA
2521    AACAGGATAT    GATAAAGCTG    TTAATCGATC
2551    ATGGAGCTGA    TGTAAACTCT    TTAACTATTG
2581    CTAAAGATAA    TCTTATTAAA    AAAAAATAAT
2611    ATCACGTTTA    GTAATATTAA    AATATATTAA
```

FIG. 17C

| | | | |
|---|---|---|---|
| 2641 | TAACTCTATT | ACTAATAACT | CCAGTGGATA |
| 2671 | TGAACATAAT | ACGAAGTTTA | TACATTCTCA |
| 2701 | TCAAAATCTT | ATTGACATCA | AGTTAGATTG |
| 2731 | TGAAAATGAG | ATTATGAAAT | TAAGGAATAC |
| 2761 | AAAAATAGGA | TGTAAGAACT | TACTAGAATG |
| 2791 | TTTTATCAAT | AATGATATGA | ATACAGTATC |
| 2821 | TAGGGCTATA | AACAATGAAA | CGATTAAAAA |
| 2851 | TTATAAAAT | CATTTCCCTA | TATATAATAC |
| 2881 | GCTCATAGAA | AAATTCATTT | CTGAAAGTAT |
| 2911 | ACTAAGACAC | GAATTATTGG | ATGGAGTTAT |
| 2941 | AAATTCTTTT | CAAGGATTCA | ATAATAAATT |
| 2971 | GCCTTACGAG | ATTCAGTACA | TTATACTGGA |
| 3001 | GAATCTTAAT | AACCATGAAC | TAAAAAAAAT |
| 3031 | TTAGATAAT | ATACATTAAA | AAGGTAAATA |
| 3061 | GATCATCTGT | TATTATAAGC | AAAGATGCTT |
| 3091 | GTTGCCAATA | ATATACAACA | GGTATTTGTT |
| 3121 | TTTATTTTA | ACTACATATT | TGATGTTCAT |
| 3151 | TCTCTTTATA | TAGTATACAC | AGAAAATTCA |
| 3181 | TAATCCACTT | AGAATTTCTA | GTTATCTAG |

|      |            |            |            |
|-----:|------------|------------|------------|
|    1 | GATATCTGTG | GTCTATATAT | ACTACACCCT |
|   31 | ACCGATATTA | ACCAACGAGT | TTCTCACAAG |
|   61 | AAAACTTGTT | TAGTAGATAG | AGATTCTTTG |
|   91 | ATTGTGTTTA | AAAGAAGTAC | CAGTAAAAAG |
|  121 | TGTGGCATAT | GCATAGAAGA | AATAAACAAA |
|  151 | AAACATATTT | CCGAACAGTA | TTTTGGAATT |
|  181 | CTCCCAAGTT | GTAAACATAT | TTTTTGCCTA |
|  211 | TCATGTATAA | GACGTTGGGC | AGATACTACC |
|  241 | AGAAATACAG | ATACTGAAAA | TACGTGTCCT |
|  271 | GAATGTAGAA | TAGTTTTTCC | TTTCATAATA |
|  301 | CCCAGTAGGT | ATTGGATAGA | TAATAAATAT |
|  331 | GATAAAAAAA | TATTATATAA | TAGATATAAG |
|  361 | AAAATGATTT | TTACAAAAAT | ACCTATAAGA |
|  391 | ACAATAAAAA | TATAATTACA | TTTACGGAAA |
|  421 | ATAGCTGGTT | TTAGTTTACC | AACTTAGAGT |
|  451 | AATTATCATA | TTGAATCTAT | ATTGTTTTTT |
|  481 | AGTTATATAA | AAACATGATT | AGCCCCCAAT |
|  511 | CGGATGAAAA | TATAAAGAT  | GTTGAGAATT |
|  541 | TCGAATACAA | CAAAAGAGG  | AATCGTACGT |
|  571 | TGTCCATATC | CAAACATATA | AATAAAAATT |
|  601 | CAAAAGTAGT | ATTATACTGG | ATGTTTAGAG |
|  631 | ATCAACGTGT | ACAAGATAAT | TGGGCTTTAA |
|  661 | TTTACGCACA | ACGATTAGCG | TTAAAACTCA |
|  691 | AAATACCTCT | AAGAATATGC | TTTTGTGTCG |
|  721 | TGCCAAAATT | TCACACTACT | ACTTCTAGAC |
|  751 | ACTTTATGTT | TTTAATATCC | GGTCTTAAAG |
|  781 | AAGTCGCGGA | AGAATGTAAA | AGACTATGTA |
|  811 | TAGGGTTTTC | ATTGATATAT | GGCGTACCAA |
|  841 | AAGTAATAAT | TCCGTGTATA | GTAAAAAAT  |
|  871 | ACAGAGTCGG | AGTAATCATA | ACGGATTTCT |
|  901 | TTCCATTACG | TGTTCCCGAA | AGATTAATGA |
|  931 | AACAGACTGT | AATATCTCTT | CCAGATAACA |
|  961 | TACCTTTTAT | ACAAGTAGAC | GCTCATAATA |
|  991 | TAGTACCTTG | TTGGGAAGCT | TCTGATAAAG |
| 1021 | AAGAATACGG | TGCACGAACT | TTAAGAAAAA |
| 1051 | AGATATTTGA | TAAATTATAT | GAATATATGA |
| 1081 | CAGAATTTCC | TGTTGTTCGT | AAACATCCAT |
| 1111 | ACGGTCCATT | TTCTATATCT | ATTGCAAAAC |
| 1141 | CCAAAAATAT | ATCATTAGAC | AAGACGGTAT |
| 1171 | TACCCGTAAA | ATGGGCAACG | CCTGGAACAA |
| 1201 | AAGCTGGAAT | AATTGTTTTA | AAAGAATTTA |
| 1231 | TAAAAACAG  | ATTACCGTCA | TACGACGCGG |
| 1261 | ATCATAACAA | TCCTACGTGT | GACGCTTTGA |
| 1291 | GTAACTTATC | TCCGTGGCTA | CATTTTGGTC |

FIG. 20B

```
1321    ATGTATCCGC    ACAACGTGTT    GCCTTAGAAG
1351    TATTAAAATG    TATACGAGAA    AGCAAAAAAA
1381    ACGTTGAAAC    GTTTATAGAT    GAAATAATTG
1411    TAAGAAGAGA    ACTATCGGAT    AATTTTTGTT
1441    ACTATAACAA    ACATTATGAT    AGTATCCAGT
1471    CTACTCATTC    ATGGGTTAGA    AAAACATTAG
1501    AAGATCACAT    TAATGATCCT    AGAAAGTATA
1531    TATATTCCAT    TAAACAACTC    GAAAAGCGG
1561    AAACTCATGA    TCCTCTATGG    AACGCGTCAC
1591    AAATGCAGAT    GGTGAGAGAA    GGAAAAATGC
1621    ATAGTTTTTT    ACGAATGTAT    TGGGCTAAGA
1651    AGATACTTGA    ATGGACTAGA    ACACCTGAAG
1681    ACGCTTGAG     TTATAGTATC    TATTTGAACA
1711    ACAAGTACGA    ACTAGACGGC    ACGGATCCTA
1741    ACGGATACGT    AGGTTGTATG    TGGTCTATTT
1771    GCGGATTACA    CGATAGAGCG    TGGAAAGCAA
1801    GACCGATATT    TGGAAAGATA    AGATATATGA
1831    ATTATGAGAG    TTCTAAGAAG    AAATTTGATG
1861    TTGCTGTATT    TATACAGAAA    TACAATTAAG
1891    ATAAATAATA    TACAGCATTG    TAACCATCGT
1921    CATCCGTTAT    ACGGGAATA     ATATTACCAT
1951    ACAGTATTAT    TAAATTTCT     TACGAAGAAT
1981    ATAGATCGGT    ATTTATCGTT    AGTTTATTTT
2011    ACATTATTA     ATTAAACATG    TCTACTATTA
2041    CCTGTTATGG    AAATGACAAA    TTTAGTTATA
2071    TAATTTATGA    TAAAATTAAG    ATAATAATAA
2101    TGAAATCAAA    TAATTATGTA    AATGCTACTA
2141    GATTATGTGA    ATTACGAGGA    AGAAAGTTTA
2161    CGAACTGGAA    AAAATTAAGT    GAATCTAAAA
2191    TATTAGTCGA    TAATGTAAAA    AAAATAAATG
2221    ATAAAACTAA    CCAGTTAAAA    ACGGATATGA
2251    TTATATACGT    TAAGGATATT    GATCATAAAG
2281    GAAGAGATAC    TTGCGGTTAC    TATGTACACC
2311    AAGATCTGGT    ATCTTCTATA    TCAAATTGGA
2341    TATCTCCGTT    ATTCGCCGTT    AAGGTAAATA
2371    AAATTATTAA    CTATTATATA    TGTAATGAAT
2401    ATGATATACG    ACTTAGCGAA    ATGGAATCTG
2431    ATATGACAGA    AGTAATAGAT    GTAGTTGATA
2461    AATTAGTAGG    AGGATACAAT    GATGAAATAG
2491    CAGAAATAAT    ATATTTGTTT    AATAAATTTA
2521    TAGAAAAATA    TATTGCTAAC    ATATCGTTAT
2551    CAACTGAATT    ATCTAGTATA    TTAAATAATT
2581    TTATAAATTT    TATAAATTTT    AATAAAAAAT
2611    ACAATAACGA    CATAAAGATA    TTTAATCTTT
```

FIG. 20C

| | | | |
|---|---|---|---|
| 2641 | AATTCTTGAT | CTGAAAAACA | CATCTATAAA |
| 2671 | ACTAGATAAA | AAGTTATTCG | ATAAAGATAA |
| 2701 | TAATGAATCG | AACGATGAAA | AATTGGAAAC |
| 2731 | AGAAGTTGAT | AAGCTAATTT | TTTTCATCTA |
| 2761 | AATAGTATTA | TTTTATTGAA | GTACGAAGTT |
| 2791 | TTACGTTAGA | TAAATAATAA | AGGTCGATTT |
| 2821 | TTACTTTGTT | AAATATCAAA | TATGTCATTA |
| 2851 | TCTGATAAAG | ATACAAAAAC | ACACGGTGAT |
| 2881 | TATCAACCAT | CTAACGAACA | GATATTACAA |
| 2911 | AAAATACGTC | GGACTATGGA | AAACGAAGCT |
| 2941 | GATAGCCTCA | ATAGAAGAAG | CATTAAAGAA |
| 2971 | ATTGTTGTAG | ATGTTATGAA | GAATTGGGAT |
| 3001 | CATCCTCAAC | GAAGAAATAG | ATAAAGTTCT |
| 3031 | AAACTGGAAA | AATGATACAT | TAAACGATTT |
| 3061 | AGATCATCTA | AATACAGATG | ATAATATTAA |
| 3091 | GGAAATCATA | CAATGTCTGA | TTAGAGAATT |
| 3121 | TGCGTTTAAA | AAGATCAATT | CTATTATGTA |
| 3151 | TAGTTATGCT | ATGGTAAAAC | TCAATTCAGA |
| 3181 | TAACGAACAT | TGAAAGATAA | AATTAAGGAT |
| 3211 | TATTTTATAG | AAACTATTCT | TAAAGACAAA |
| 3241 | CGTGGTTATA | AACAAAAGCC | ATTACCCGGA |
| 3271 | TTGGAAACTA | AAATACTAGA | TAGTATTATA |
| 3301 | AGATTTTAAA | AACATAAAAT | TAATAGGTTT |
| 3331 | TTATAGATTG | ACTTATTATA | TACAATATGG |
| 3361 | ATAAAGATA | TATATCAACT | AGAAAGTTGA |
| 3391 | ATGACGGATT | CTTAATTTTA | TATTATGATT |
| 3421 | CAATAGAAAT | TATTGTCATG | TCGTGTAATC |
| 2451 | ATTTATAAA | TATATCAGCG | TTACTAGCTA |
| 3481 | AGAAAAACAA | GGACTTTAAT | GAATGGCTAA |
| 3501 | AGATAGAATC | ATTTAGAGAA | ATAATAGATA |
| 3541 | CTTTAGATAA | AATTAATTAC | GATCTAGGAC |
| 3571 | AACGATATTG | TGAAGAACTT | ACGGCGCATC |
| 3601 | ACATTCCAGT | GTAATTATTG | AGGTCAAAGC |
| 3631 | TAGTAACTTA | ATAGATGACA | GGACAGCTG |

| | | | |
|---|---|---|---|
| 1 | TGTCTGGACT | AACTGATTTC | ATGGAACAAT |
| 31 | TTTCATCAAA | AATATCAGTT | ATACCTAGTT |
| 61 | CTACAAAGAC | AGAACTTTGA | TGTTATGTTT |
| 91 | GTGTTTGTAT | AGAAAATTTT | GGGATACTAA |
| 121 | CTGATATTTC | TGAATATTTC | TGAATATTTC |
| 151 | ATGTTACTTA | CTTACTCCTA | TCTTAGACGA |
| 181 | TAATAAAATT | CGAGGCGTAA | TATGTTTTC |
| 211 | CAAATATTTG | AAATTCTTAT | ACGTATCGGC |
| 241 | GAAGAAAGT | AACATACTAT | AAGTGTTATG |
| 271 | CAAGTAAGGT | ATGTTAATGA | TATTGGATTT |
| 301 | AATTTCATTG | ACAATACATA | TGTCCAAACA |
| 331 | TTCCACTCGT | AATTATGTAC | GGAACGACTT |
| 361 | TAGTTAAATA | CTTAGTCACA | AAAAACTTAT |
| 391 | GACTGTCATT | ATCTGAAAAC | GGTGATTCCC |
| 421 | ATAAATCAGA | ATACTTAATA | TTAAATAGAA |
| 461 | TGCTCGCTTC | TGGAGGTTTC | CGGATACTAG |
| 481 | ATAACATATC | TTCTGTATTA | TAGTTTAATT |
| 511 | CACTCATTTT | ATTACATAAT | ACAGTAACAT |
| 541 | CTCCCGAAAC | CAATGATGTT | ATATTAGATT |
| 571 | TACTTACATA | CTTCTTGTAA | CTATCATGAA |
| 601 | TACGTTTGTT | ATGATCTATA | AAGAAGATGG |
| 631 | ATGTATATTC | TGTTCTAGAT | AGCAAGTTCT |
| 661 | TTAAGTTATT | CTTTGTCTGT | ATTACTATCA |
| 691 | TCGTCTTCAT | CATCGTCTAA | AGGTAGCATT |
| 721 | ATATAATAAA | TCTAATAGTT | GATTTCTCGA |
| 751 | TCTATCAGTA | CTCGCTTTCA | ATAACATTTT |
| 781 | TACTATAAGC | ATAATAGAAG | GCGGTGATAT |
| 811 | CACTATATTT | TTATCGGGTA | TTCTTTTAGT |
| 841 | AATTAGTTAG | TTCGTAGAAT | TTCGTAGAGA |
| 871 | TAAAAGCCAA | TTTGTTGTTG | ATACTGCTTA |
| 901 | CGTTACTCAT | GTTTCTTGTT | TCTGTTAATT |
| 931 | AACAGGTATA | CCCTTACAAT | AAGTTTAATT |
| 961 | AACTTTTAGG | TTTTTGTGAA | GAACTTTTAG |
| 991 | CTTCTAGTTC | CCTTATCCAT | AATTGGGTCT |
| 1021 | TAGATCTAGA | TTCTTCCCAT | GTATAAGGG |
| 1051 | GGACATACCC | AAAATCTTTA | AATGCTTTGT |
| 1081 | CCGTTTCTAT | AGTAAATGTC | GTACATTCCT |
| 1111 | TAATCAAAGT | ATAAGGATTT | AGTAAAGGCG |
| 1141 | TGTAAGAACA | AATAGGTGAT | AGTAATACTC |
| 1171 | TTAAACCTTT | ATTAATATTA | GCGATAAACC |
| 1201 | TTAAACACCA | TAAAGGAAGA | CATGTATTCC |
| 1231 | GTAGATCCAT | CCCTAATTGA | TTAAAGAAAT |
| 1261 | GCATGTTAAA | ATCATGATAA | TGTTCAGTAG |
| 1291 | GAGAGGTATC | GTAACAGTAA | TACACGTTAT |

FIG. 21B

```
1321    TGCAGAGAGG    ACTATGTTGA    CCATTTTCTA
1351    TCATATTTCT    TGCTGCTAAA    ATATGCATCC
1381    AAGCTACGTT    TCCTGCATAG    ACTCTGCTAT
1411    GAAATACTTT    ATCATCCGCA    TATTTATACA
1441    TTTTCCTGCT    TTTATACGAT    CTTCTGTATA
1471    AAGTTTCTAG    TACTGGACAG    TATTCTCCGA
1501    AAACACCTAA    TGGGCGTAGC    GACAAGTGCA
1531    TAATCTAAGT    CCTATATTAG    ACATAGTACC
1561    GTTAGCTTCT    AGTATATATT    TCTCAGATAA
1591    CTTGTTTACT    AAGAGGATAA    GCCTCTTTAT
1621    GGTTAGATTG    ATAATACGTA    TTCTCGTTTC
1651    CTCTTATCAT    CGCATCTCCG    GAGAAAGTTA
1681    GGACCTACCG    CAGAATAACT    ACTCGTATAT
1711    ACTAAGACTC    TTACGCCGTT    ATACAGACAA
1741    GAATCTACTA    CGTTCTTCGT    TCCGTTGATA
1771    TTAACGTCCA    TTATAGAGTC    GTTAGTAAAC
1801    TTACCCGCTA    CATCATTTAT    CGAAGCAATA
1831    TGAATGACCA    CATCTGCTGA    TCTAAGCGCT
1861    TCGTCCAAAG    TACTTTTATT    TCTAACATCT
1891    CCAATCACGG    GAACTATCTT    TATTATATTA
1921    CATTTTTCTA    CAAGATCTAG    TAACCATTGG
1951    TCGATTCTAA    TATCGTAAAC    ACGAACTTCT
1981    TTTTAAAGAG    GATTCGAACA    AGATAAGATT
2011    ATTTATAATG    TGTCTACCTA    AAAATCCACA
2041    CCCTCCGGTT    ACCACGTATA    CTAGTGTACG
2071    CATTTTGAGT    ATTAACTATA    TAAGACCAAA
2101    ATTATATTTT    CATTTCTGT     TATATTATAC
2131    TATATAATAA    AAACAAATAA    ATATACGAAT
2161    ATTATAAGAA    ATTTAGAACA    CGTTATTAAA
2191    GTATTGCCTT    TTTTATTAAC    GGCGTGTTCT
2221    TGTAATTGCC    GTTTAGAATA    GTCTTTATTT
2251    ACTTAGATA     ACTCTTCTAT    CATAACCGTC
2281    TCCTTATTCC    AATCTTCTTC    AGAAGTACAT
2311    GAGTACTTAC    CGAAGTTTAT    CATCATAGAG
2341    ATTATATATG    AAGAAA
```

NUCLEOTIDE AND AMINO ACID SEQUENCES OF CANINE HERPESVIRUS GB AND GC

RELATED APPLICATIONS

Reference is made to copending application Ser. No. 08/124,668, filed Sep. 21, 1993 as a divisional of copending application Ser. No. 07/502,834, filed Apr. 14, 1990, which in turn is a continuation-in-part of application Ser. No. 07/394,488, filed Aug. 16, 1989, which in turn is a continuation-in-part of application Ser. No. 07/339,004, filed Apr. 17, 1989. Reference is also made to copending application Ser. No. 08/105,483, filed Aug. 12, 1993 as a continuation of application Ser. No. 07/847,951, filed Mar. 6, 1992, which in turn is a continuation-in-part of application Ser. No. 07/713,967, filed Jun. 11, 1991 which in turn is a continuation-in-part of application Ser. No. 07/666,056, filed Mar. 7, 1991. Each of the above-mentioned applications are hereby incorporated herein by reference.

FIELD OF THE INVENTION

This invention relates to canine herpesvirus (CHV), nucleotides or isolated nucleic acids encoding the CHV gB, gC and gD glycoproteins, and the amino acid sequences thereof, vectors, such as a recombinant poxvirus, e.g., vaccinia and avipox virus recombinants, containing the CHV gB, gC and/or gD coding or expressing the same, glycoproteins therefrom, vaccines, immunological or antigenic compositions from the nucleotide (such as from vectors, for instance, recombinant poxvirus, e.g., vaccinia or avipox virus recombinants containing the CHV, gB, gC and/or gD coding and expressing glycoprotein(s) therefrom), or, from the glycoproteins, for instance, from expression of the nucleotides in a vector system, and, to methods employing the nucleotides, glycoproteins, and compositions.

Several publications are cited in the following text, with full citation of each set forth in the section headed References. The publications cited throughout the text are hereby incorporated herein by reference.

BACKGROUND OF THE INVENTION

Canine herpesvirus (CHV) causes a fatal, hemorrhagic disease in neonatal puppies and a self-limiting, usually subclinical, upper respiratory tract infection in adult dogs (Appel, 1987). Little is known about the genomic structure of CHV. The genome has not been mapped and no nucleotide sequence has been published. In particular, genes encoding immunologically pertinent proteins have not been identified.

Herpesvirus glycoproteins mediate essential viral functions such as cellular attachment and penetration, cell to cell spread of the virus and, importantly, determine the pathogenicity profile of infection. Herpesvirus glycoproteins are critical components in the interaction with the host immune system (Spear, 1985a; Spear 1985b). Herpesvirus glycoproteins are antigens recognized by both the humoral and cellular immune systems and, have been shown to evoke protective immune responses in vaccinated hosts (Wachsman et al., 1987; Marchioli et al., 1987; Eberle et al., 1980; Papp-Vid et al., 1979).

During a herpesvirus infection, the majority of the immune response is directed against viral envelope glycoproteins. These antigens have been shown to elicit both humoral and cellular immune responses. Several reports have indicated that in other herpesvirus systems immunization with the herpesvirus gB, gC and/or gD glycoproteins can induce a protective immune response.

The well characterized glycoproteins of herpes simplex virus include gB, gC, gD, gE, gG, gH, gI, gJ, gK, gL and gM (Spear, 1985a; Spear 1985b; Ackermann et al., 1986; Frink et al. 1983; Frame et al., 1986; Longnecker et al., 1987; Richman et al., 1986; Swain et al., 1985; Zezulak, 1984; Roizman and Sears, 1990; Hutchinson et al., 1992a; Hutchinson et al., 1992b; Baines and Roizman, 1993). A number of studies have indicated the importance of herpes simplex virus glycoproteins in eliciting immune responses. Hence, it has been reported that gB and gD can elicit important immune responses (Berman et al., 1983; Cantin et al., 1987; Cremer et al., 1985; Lasky et al., 1984; Martin et al., 1987a; Martin et al., 1987b; Paoletti et al., 1984; Perkus et al., 1985; Rooney et al., 1988; Wachsman et al., 1987; Zarling et al., 1986a; Zarling et al., 1986b). gC can stimulate class I restricted cytotoxic lymphocytes (Glorioso et al., 1985; Rosenthal et al., 1987) whereas gD can stimulate class II cytotoxic T cell responses (Martin et al., 1987a; Martin et al,. 1987b; Wachsman et al., 1987; Zarling et al., 1986a; Zarling 1986b). gG was shown to be a target for complement-dependent antibody directed virus neutralizations(Sullivan et al., 1987; Sullivan et al., 1988). A number of glycoproteins from other herpesviruses have also been shown to elicit important immune responses.

Both subtypes of equine herpesvirus (EHV) express six abundant glycoproteins (Allen et al., 1986; Allen et al., 1987). The genomic portions of the DNA sequences encoding gp2, gp10, gp13, gp14, gp17/18, and gp21/22a have been determined using lambda gt11 expression vectors and monoclonal antibodies (Allen et al., 1987). Glycoproteins gp13 and gp14 were located in the same locations within the L component of the genome to which the gC and gB homologs, respectively, of herpes simplex virus map (Allen et al., 1987). The envelope glycoproteins are the principal immunogens of herpesviruses involved in eliciting both humoral and cellular host immune responses (Ben-Porat et al., 1986; Cantin et al., 1987; Glorioso et al., 1984; Wachsman et al., 1988; Wachsman et al., 1989) and so are of the highest interest for those attempting to design vaccines.

Recently, the nucleotide sequence of the Kentucky T431 strain of the EHV-1 transcriptional unit encoding gp13 has been reported (Allen et al., 1988). The glycoprotein was shown to be homologous to the herpes simplex virus (HSV) gC-1 and gC-2, to the pseudorabies virus (PRV) gIII and the varicella-zoster virus (VZV) gpV (Allen et al., 1988). EHV-1 gp13 is thus the structural homolog of the herpesvirus gC-like glycoproteins.

The nucleotide sequence of EHV-1 gp14 (Whalley et al., 1989; Riggio et al., 1989) has recently been reported. Analysis of the predicted amino acid sequence of gp14 glycoprotein revealed significant homology to the corresponding glycoprotein of HSV, gB.

Monoclonal antibodies directed against some EHV-1 glycoproteins have been shown to be neutralizing (Sinclair et al., 1989). Passive immunization experiments demonstrated that monoclonal antibodies directed against gp13 or gp14 (Shimizu et al., 1989) or against gp13, gp14 or gp17/18 (Stokes et al., 1989) could protect hamsters against a lethal challenge. Other gB and gC glycoprotein analogs are also involved in protection against diseases caused by alphaherpesviruses (Cantin et al., 1987; Cranage et al., 1986; Glorioso et al., 1984).

Pseudorabies virus (PRV), an alphaherpesvirus, is the causative agent of Aujesky's disease. The PRV genome consists of a 90×10⁶ dalton double stranded DNA (Rubenstein et al., 1975) separated by inverted repeat sequences into unique long ($U_L$) or unique short ($U_S$) segments (Stevely, 1977; Ben-Porat et al., 1979). The PRV genome encodes approximately 100 polypeptides whose expression is regulated in a cascade-like fashion similar to other herpesviruses (Ben-Porat et al., 1985; Hampl et al., 1984).

PRV glycoprotein gp50 is the Herpes simplex virus type 1 (HSV-1) gD analog (Wathen et al., 1984). The DNA open reading frame encodes 402 amino acids (Petrovskis et al., 1986). The mature glycosylated form (50–60 kDa) contains O-linked carbohydrate without N-linked glycosylation (Petrovskis et al., 1986). Swine serum is highly reactive with PRV gp50, suggesting its importance as an immunogen. Monoclonal antibodies to gp50 neutralize PRV in vitro with or without complement (Wathen et al., 1984; Wathen 1985; Eloit et al., 1988) and passively protect mice (Marchioli et al., 1988; Wathen et al., 1985; Eloit et al., 1988) and swine (Marchioli et al., 1988). Vaccinia virus recombinants expressing PRV gp50 induced serum neutralizing antibodies and protected both mice and swine against lethal PRV challenge (Kost et al., 1989; Marchioli et al., 1987; Ishii et al., 1988).

PRV gIII is the HSV-1 gC analog (Robbins et al., 1986). Functional replacement of PRV gIII by HSVgC was not observed (Whealy et al., 1989). Although PRV gIII is nonessential for replication in vitro (Wathen et al., 1986; Robbins et al., 1986), the mature glycosylated form (98 kDa) is an abundant constituent of the PRV envelope. Anti-gpIII monoclonal antibodies neutralize the virus in vitro with or without complement (Hampl et al., 1984; Eloit et al., 1988; Wathen et al., 1986) and can passively protect mice and swine (Marchioli et al., 1988). The PRV glycoprotein gIII can protect mice and swine from lethal PRV challenge after immunization with a Cro/gIII fusion protein expressed in *E. coli* (Robbins, A., R. Watson, L. Enquist, European Patent application 0162738A1) or when expressed in a vaccinia recombinant (Panicali, D., L. Gritz, G. Mazzara, European Patent application 0261940A2).

PRV gpII is the HSV-1 gB homolog (Robbins et al., 1987). Monoclonal antibodies directed against PRV gpII have been shown to neutralize the virus in vitro (Ben-Porat et al., 1986) with or without complement (Wittmann et al., 1989). Moreover, passive immunization studies demonstrated that neutralizing monoclonal antibodies partially protected swine (Marchioli et al., 1988). Immunization with NYVAC (highly attenuated vaccinia virus)-based recombinants expressing pseudorabies virus (PRV) gII (gB) or gp50 (gD) has been shown to protect swine against a virulent PRV challenge (Brockmeier et al., 1993). Furthermore, vaccinia recombinants expressing PRV gII and gp50, or gII, gIII (gC) and gp50 have been shown to elicit a higher level of protection than recombinants expressing gII or gp50 alone, suggesting a potential synergistic effect with these glycoproteins (Riviere et al., 1992).

The herpes simplex virus type 1 (HSV1) genome encodes at least eleven antigenically distinct glycoproteins: gB, gC, gD, gE, gG, gH, gI, gJ, gK, gL and gM (Roizman et al., 1990). Mice immunized with purified HSV1 gB, gC or gD are protected against lethal HSV1 challenge (Chan, 1983). Mice have also been protected against lethal HSV1 or HSV2 challenge by passive immunization with antibodies to total HSV1 (Davis et al., 1979) or HSV2 (Oakes et al., 1978) virus and with antibodies to the individual HSV2 gB, gC, gD or gE glycoproteins (Balachandran et al., 1982).

Vaccinia virus vectors expressing HSV1 gB (McLaughlin-Taylor et al., 1988) and HSV1 gC (Rosenthal et al., 1987) have been shown to induce cytotoxic T-cell responses. In addition, it has been shown that mice immunized with recombinant vaccinia virus expressing either HSV1 gB (Cantin et al., 1987), HSV1 gC (Weir et al., 1989) or HSV1 gD (Paoletti et al., 1984) are protected against a lethal challenge of HSV1. A recombinant vaccinia virus expressing HSV1 gD has also been shown to be protective against HSV2 in a guinea pig model system (Wachsman et al., 1987).

Bovine herpesvirus 1 (BHV1) specifies more than 30 structural polypeptides, 11 of which are glycosylated (Misra et al., 1981). Three of these glycoproteins, gI, gIII and gIV, have been characterized and found to be homologous to the herpes simplex virus (HSV) glycoproteins gB, gC and gD (Lawrence et al., 1986; Zamb, 1987). Immunization with purified bovine herpesvirus type 1 (BHV1) gI (gB), gIII (gC) and/or gIV (gD) has been shown to protect cattle against a BHV1/*Pasteurella haemolytica* challenge (Babiuk et al., 1987).

Feline herpesvirus type-1 (FHV-1) has been shown to contain at least 23 different proteins (Meas et al., 1984; Fargeaud et al., 1984). Of these, at least five are glycosylated (Fargeaud et al., 1984; Compton, 1989) with reported molecular masses ranging from 120 kDa to 60 kDa. The FHV-1 glycoproteins have been shown to be immunogenic (Meas et al., 1984; Compton, 1989). Like several other alphaherpesviruses, FHV-1 appears to have a homolog of glycoprotein B (gB) of HSV-1 (Maeda et al., 1992). The FHV-1 gB glycoprotein is a 134 kDa complex which is dissociated with B-mercaptoethanol into two glycoproteins of 66 kDa and 60 kDa. The FHV-1 DNA genome is approximately 134 Kb in size (Rota et al., 1986).

Epstein Barr Virus (EBV), a human B lymphotropic herpesvirus, is a member of the genus lymphocryptovirus which belongs to the subfamily gammaherpesvirus (Roizman et al., 1990). Since the EBV genome was completely sequenced (Baer et al., 1984) as the genomes of VZV (Davison et al., 1986), HSV1 (McGeoch et al., 1988), MCHV (Chee et al., 1990) and EHV1 (Telford et al., 1992) numerous homologies between these different herpesviruses have been described (Kieff et al., 1990).

Human cytomegalovirus (HCMV) is a member of the betaherpesvirinae subfamily (family Herpesviridae). Three immunologically distinct families of glycoproteins associated with the HCMV envelope have been described (Gretch et al., 1988): gCI (gp55 and gp93–130); gCII (gp47–52); and gCIII (gp85–145). The gene coding for gCI is homologous to HSVI gB.

In addition, immunization with a fowlpox recombinant expressing Marek's disease virus (MDV) gB has been shown to protect chickens against a virulent MDV challenge (Nazarian et al., 1992).

The results of these studies indicate that an immune response against gB, gC and/or gD glycoproteins can protect target species animals against a herpesvirus challenge and, that the provision of nucleotides for CHV gB, gC and gD glycoproteins is a valuable advance over the current state of the art as it allows for the provision of the glycoproteins and, antigenic, immunological or vaccine compositions from the vector systems or from the glycoproteins. Further, the glycoproteins from expression of the nucleotides can be used to elicit antibodies which can be further used in antibody binding diagnostic assays, kits or tests for ascertaining the presence or absence in a sample such as sera of the glycoprotein(s) and therefore the presence or absence of CHV or of an immune or antigenic response (to either CHV or to the glycoproteins). Thus, many utilities flow from the provision of the nucleotides for CHV gB, gC and gD glycoproteins.

Various vector systems exist for the expression of exogenous DNA, such as the phage, e.g., lambda, and *E. coli* systems (Allen et al., 1987; Robbins, EPA 0162738A1; Panicali, EPA 0261940A2, each of which is expressly incorporated herein by reference).

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the vital genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. $TK^-$ vaccinia virus is also capable of replication in vivo at the site of inoculation in a variety of hosts by a variety of routes.

It has been shown for herpes simplex virus type 2 that intravaginal inoculation of guinea pigs with $TK^-$ virus resulted in significantly lower virus titers in the spinal cord than did inoculation with $TK^+$ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of $TK^-$ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmitt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982b) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

Thus, heretofore, the nucleotide and amino acid sequences for the CHV gB, gC and gD glycoproteins, have not been taught or suggested and, providing these sequences would be of great value. Further, vaccine, antigenic or immunological compositions from the nucleotides for the CHV gB, gC and gD glycoproteins (such as from vector systems containing such nucleotides) as well as from the glycoproteins themselves (such as from expression by the vector systems) have not heretofore been taught or suggested and, these nucleotides, vector systems, glycoproteins and compositions would be of great value.

OBJECTS AND SUMMARY OF THE INVENTION

It is therefore an object of the invention to provide nucleotides or isolated nucleic acids coding for CHV gB, gC and gD.

It is a further object of the invention to provide vectors containing nucleotides or isolated nucleic acids coding for CHV gB, gC and/or gD.

It is another object of the invention to provide CHV gB, gC and/or gD glycoproteins, especially from expression of nucleotides or isolated nucleic acids therefor in a vector system.

It is an additional object of the invention to provide antigenic, vaccine or immunological compositions from the CHV gB, gC and/or gD nucleotides or isolated nucleic acids or a vector containing them or, from the glycoproteins themselves, such as by way of expression by the vector.

It is yet another object of this invention to provide modified recombinant viruses, which viruses have enhanced safety, and to provide a method of making such recombinant viruses.

It is an additional object of this invention to provide a recombinant poxvirus antigenic, vaccine or immunological composition having an increased level of safety compared to known recombinant poxvirus antigenic, vaccine or immunological compositions.

It is a further object of this invention to provide a modified vector for expressing a gene product in a host, wherein the vector is modified so that it has attenuated virulence in the host.

It is another object of this invention to provide a method for expressing a gene product, such as CHV gB, gC and/or gD, in a cell cultured in vitro using a modified recombinant virus or modified vector having an increased level of safety.

These and other objects and advantages of the present invention will become more readily apparent after consideration of the following.

The present invention involves the elucidation of the CHV gB, gC and gD nucleotides, glycoproteins therefrom and, antigenic, vaccine or immunological compositions employing the nucleotide sequences and the glycoproteins.

Accordingly, the present invention provides a nucleotide or isolated nucleic acid coding for canine herpesvirus gB glycoprotein.

The present invention provides a nucleotide or isolated nucleic acid coding for canine herpesvirus gC glycoprotein.

The present invention provides a nucleotide or isolated nucleic acid coding for canine herpesvirus gD glycoprotein.

The nucleotides are preferably DNA. The nucleotides or isolated nucleic acids preferably have the DNA sequences as set forth in FIGS. 1, 4 and 7.

The present invention also provides canine herpesvirus glycoprotein gB.

The present invention provides canine herpesvirus glycoprotein gC.

The present invention provides canine herpesvirus glycoprotein gD.

The present invention further provides a vector containing the nucleotide or isolated nucleic acid for canine herpesvirus gB, gC and/or gD. Preferably the vector is a recombinant poxvirus such as a recombinant vaccinia or avipox virus, more preferably the vaccinia or avipox virus is attenuated such as NYVAC, ALVAC or TROVAC.

Thus, in one preferred aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes a CHV antigenic protein, e.g., CHV gC, gB, and gD or any combination thereof.

In a still further preferred aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for a CHV gB, gC and gD, or any combination thereof. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992).

The present invention still further provides an antigenic, vaccine or immunological composition for inducing an antigenic or immunological response in a host, such as a canine, comprising a suitable vector containing the nucleotide(s) or isolated nucleic acid(s) for canine herpesvirus gB, gC and/or gD and a suitable carrier; or, canine herpesvirus gB, gC and/or gD glycoprotein(s), such as from expression thereof in a vector containing the nucleotide(s) of the invention, and a suitable carrier.

The present invention yet further provides methods employing the inventive nucleotide(s) or isolated nucleic acid(s), glycoprotein(s), composition(s).

Thus, the invention provides a method for preparing canine herpesvirus gB, gC and/or gD comprising inserting the nucleotide(s) or isolated nucleic acid(s) therefor into a suitable vector, cultivating the vector, and, collecting the glycoprotein from the vector. The vector can be a poxvirus, such as vaccinia or avipox virus, a phage such as lambda, or E. coli or any other suitable virus or bacterial vector. The cultivating can be infecting cells susceptible to viral infection by the virus vector or, growing colonies of the bacterial vector system, such as by plate or broth methods. And, collecting can be by separating the glycoprotein(s) from the viral-infected cells or from the bacterial cells.

Thus, in a preferred aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., CHV gB, gC and gD, or any combination thereof.

Likewise, the invention provides a method for inoculating or for stimulating an antigenic or immunological response in a host such as a canine against canine herpesvirus comprising administering the inventive antigenic, vaccine or immunological composition to the host, e.g., canine. Additionally, the invention includes an antibody elicited by the expression of the inventive nucleotide(s). The antibody can be generated into a monoclonal antibody by known techniques and, the antibody or the monoclonal antibody can be employed in a binding diagnostic assay, test or kit to determine the presence or absence of CHV gB, gC and/or gD in a sample such as sera and therefore the presence or absence of CHV or, of an antibody or immune response to CHV or to glycoproteins thereof.

These and other embodiments within the present invention are described or are obvious from the following detailed description.

BRIEF DESCRIPTION OF DRAWINGS

The following detailed description, given by way of example, but not intended to limit the invention solely to the specific embodiments described, may best be understood in conjunction with the accompanying drawings, in which:

FIG. 1 shows the nucleotide sequence and predicted amino acid sequence of the CHV gB homologue (SEQ ID NOS:1, 2);

FIGS. 3A to 3F show the amino acid homology of 8 gB homologues (SEQ ID NOS:3–10);

FIG. 4 shows the nucleotide sequence and predicted amino acid sequence of the CHV gC homologue and ORF2 (SEQ ID NOS:11–13);

FIG. 6 shows the amino acid homology of 4 gC homologues (SEQ ID NOS:14–17);

FIG. 7 shows the nucleotide sequence and predicted amino acid sequence of the CHV gD homologue; SEQ ID NOS:18–19)

FIG. 9 shows amino acid homology of 4 gD homologues (SEQ ID NOS:20–23);

FIG. 17 shows the DNA sequence (SEQ ID NO:59) of a canarypox PvuII fragment containing the C5 ORF.

FIG. 20 shows the nucleotide sequence (SEQ ID NO:69) of a fragment of TROVAC DNA containing an F8 ORF;

FIG. 21 shows the DNA sequence (SEQ ID NO:72) of a 2356 base pair fragment of TROVAC DNA containing the F7 ORF.

DETAILED DESCRIPTION

Figure 2:
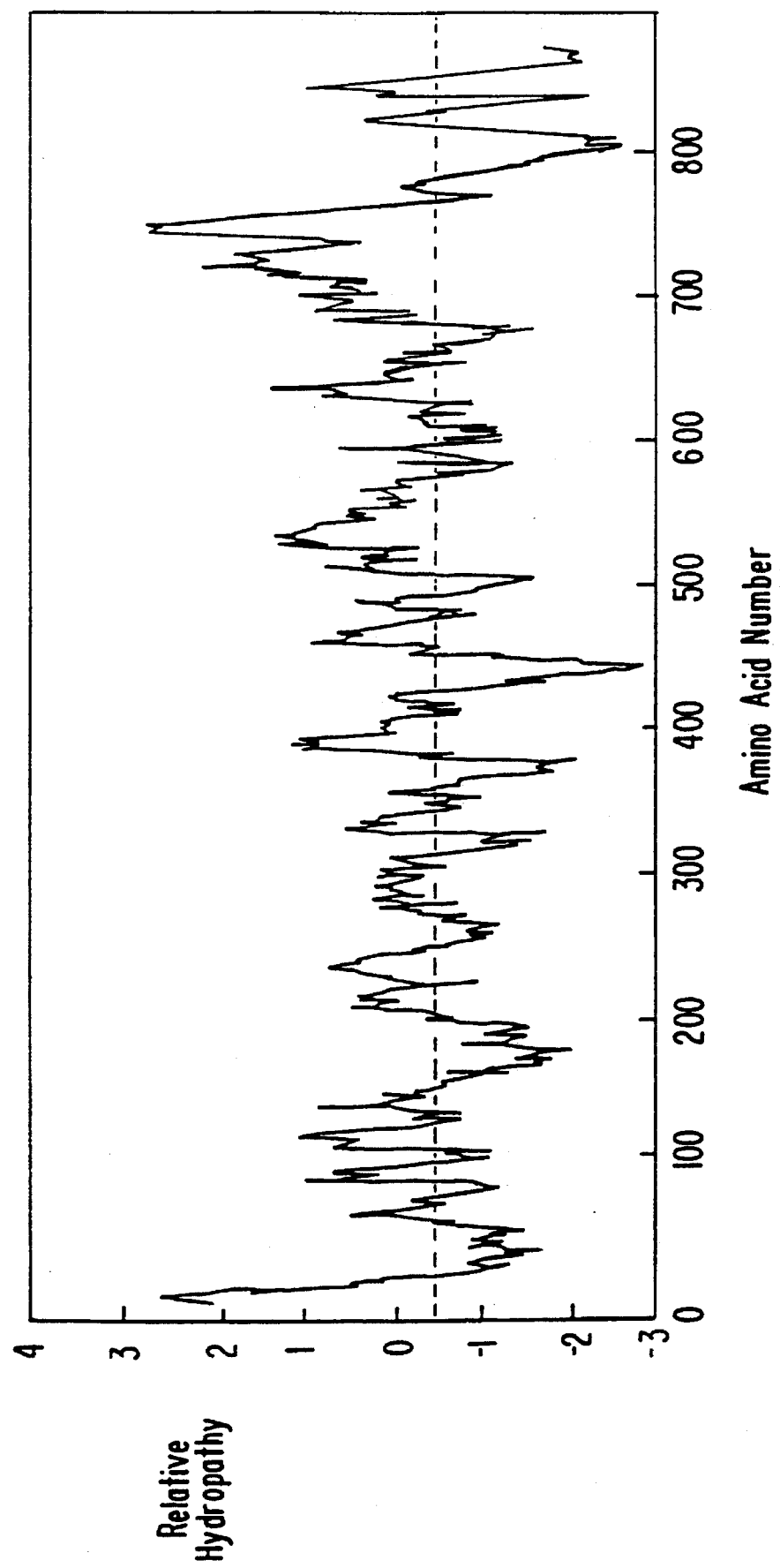
FIG. 2 shows the hydropathicity analysis of the CHV gB homologue.

This invention provides nucleotides coding for the CHV gB, gC and gD genes. These genes encode polypeptides of 879, 459 and 345 amino acids, respectively. Comparison of the predicted amino acid sequence of these glycoproteins with the gB, gC and gD amino acid sequences of other herpesviruses indicates that CHV is an alphaherpesvirus; a conclusion that is consistent with the previous classification of this virus according to biological properties. This analysis also revealed that the homology among gB homologues is greater than the homology among gC or gD homologues, suggesting that the structural and functional constraints on gB may be greater than those on gC or gD.

Alignment of homologous gB, gC and gD polypeptides revealed that the vast majority of cysteine residues are perfectly conserved. These results suggest that these cysteine residues, due to their ability to form disulfide bonds, are important in maintaining the structural and functional integrity of the gB, gC and gD glycoproteins. In fact, in HSV1 gD, it has been shown that cysteine 1 forms a disulfide bond with cysteine 5, cysteine 2 forms a disulfide bond with cysteine 6 and cysteine 3 forms a disulfide bond with cysteine 4 (Long et al., 1992). Furthermore, it has been shown that a mutation of any of these residues has a profound effect on the conformation, processing and function of the resulting glycoprotein (Wilcox et al., 1988; Long et al., 1990). Therefore, the conservation of cysteine residues in the glycoproteins of the invention may also have structural significance.

The high degree of homology among the gC, gD and, in particular, gB homologues also suggests that these glycoproteins have common functions. In fact, it has been shown that the BHV1 gB homologue can rescue a gB⁻ PRV virus, indicating that these 2 glycoproteins are functionally equivalent (Kopp & Mettenleiter, 1992).

Alignment of the gB, gC and gD amino acid sequences also revealed that potential N-linked glycosylation sites are somewhat conserved. N-linked glycosylation is thought to play a role in a variety of functions, such as maintenance of protein conformation and protection against proteolytic degradation. The biological significance of N-linked carbohydrates on herpesvirus glycoproteins, however, is not completely understood. For example, tunicamycin treatment of HSV1 infected cells has been shown to inhibit the production of infectious virions (Pizer et al., 1980). In addition, endoglycosidase treatment of HSV1 virions has been shown to decrease infectivity (Kuhn et al., 1988). On the other hand, N-linked glycosylation of HSV1 gD does not appear to be absolutely essential, since mutagenesis of the glycosylation sites on this glycoprotein does not affect infectivity (Sodora et al., 1991). Therefore, although the glycosylation sites on the gB, gC and gD glycoproteins are relatively well conserved, proper glycosylation of each of these polypeptides may not be absolutely essential.

The G+C content of herpesviruses varies from 33%–75% (Roizman, 1982). It has been suggested that this extensive variability is due to a nonselective mutational bias based on the presence (or absence) of virally encoded or induced enzymes involved in nucleotide metabolism (Honess, 1984). For example, VZV and herpesvirus saimiri (HVS) both have relatively low G+C contents (46% and 46%, respectively) and both encode an enzyme, thymidylate synthetase, which is involved in TTP synthesis (Davison & Scott, 1986; Honess et al., 1986). HSV1, HCMV and EBV, on the other hand, have relatively high G+C contents (68%, 57% and 60%, respectively) and do not appear to encode a thymidylate synthetase (Honess et al., 1986). CHV has been determined by DNA density analysis to have the lowest G+C content of any herpesvirus, 33% (Plummer et al., 1969; Roizman, 1982); a value which is consistent with the relatively low G+C content of the nucleotides of the invention (29%). Without wishing it to be bound by the theory that CHV does not encode an enzyme involved in nucleotide metabolism, from the present invention the ORF located immediately downstream from the CHV gC gene is not homologous to VZV thymidylate synthetase. Therefore, if CHV contains a thymidylate synthetase gene, it is not found at the same genomic location as VZV.

Newborn pups exposed to CHV usually die without forming CHV-specific neutralizing antibodies. Also, the maternal antibodies or treatment with immune serum from seropositive dogs can protect pups from a fatal CHV infection (Carmichael, 1970). Therefore, serum neutralizing antibodies can protect pups against a fatal CHV infection. Likewise, serum neutralizing antibodies can protect adult dogs from the self-limiting subclinical, upper respiratory tract infection.

Three CHV glycoproteins, gp145/112, gp80 and gp47, are known to elicit CHV neutralizing antibodies (Xuan et al., 1991). The genes encoding these glycoproteins have not been identified. Without wishing to be bound by any one theory, it is possible, however, that these antigens are encoded by the gB, gC and gD genes of this invention. Since several reports have indicated that an immune response against gB, gC and/or gD can provide protection of target species animals against a herpesvirus challenge (Babiuk et al., 1987; Nazarian et al., 1992; Riviere et al., 1992; Brockmeier et al., 1993), the CHV gB, gC and gD genes of this invention provide efficacious CHV glycoproteins, immunological or vaccine compositions and methods of using the same.

In particular, the nucleotides of this invention can be inserted into any suitable vector system for expression. For instance, the nucleotide(s) can be inserted into any suitable bacterial vector system such as the *E. coli* system, employing known methods (see, e.g., Robbins, EPA 0162738A1; Panicali, EPA 0261940A2).

The nucleotide(s) can be inserted into any suitable phage or viral vector system such as lambda, poxvirus, herpesvirus (see Roizman, U.S. Pat. No. 4,769,331, incorporated herein by reference), baculovirus, polio virus (see Kitson et al., J. Virol. 65, 3068–3075, 1991, incorporated herein by reference), and adenovirus (see Grunhaus et al., 1992, "Adenovirus as cloning vectors," Seminars in Virology (Vol. 3) p. 237–52, 1993; Ballay et al., EMBO Journal, vol. 4, p. 3861–65; Graham, Tibtech 8, 85–87, April, 1990; Prevec et al., J. Gen. Virol. 70, 429–434, each of which is incorporated herein by reference) systems employing known methods.

The preferred vector system is a poxvirus vector system, especially an avipox vaccinia virus system wherein recombination is as in U.S. Pat. Nos. 4,769,330, 4,772,848, 4,603,112, 5,100,587 and 5,179,993. However, an attenuated poxvirus system is even more preferred.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L–K1L) vP804; and (6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH") (U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

After growing the bacteria or infecting cells with the recombinant virus, the glycoprotein(s) are collected by known techniques such as chromatography (see Robbins, EPA 0162738A1; Panicali, EPA 0261940A2).

The collected glycoprotein(s) can then be employed in a vaccine, antigenic or immunological composition which also contains a suitable carrier.

Alternatively, the viral vector system, especially the preferred poxvirus vector system, can be employed in a vaccine, antigenic or immunological composition which also contains a suitable carrier. The CHV recombinant poxvirus in the composition expresses the CHV glycoprotein in vivo after administration or inoculation.

The antigenic, immunological or vaccine composition of the invention (either containing glycoprotein(s) expressed from a vector system containing the inventive nucleotide(s) or containing a suitable vector system such as the CHV recombinant poxvirus is administered to pups in the same fashion as maternal antibodies or immune serum from seropositive dogs (Carmichael, 1970). Seronegative dogs are administered the composition in the same fashion as other antigenic, vaccine or immunological compositions are administered. One skilled in the veterinary arts can determine dosage from this disclosure without undue experimentation, taking into consideration such factors as the age, weight, breed, sex and general health of the particular dog or pup.

Additionally, the inventive recombinant poxvirus and the expression products therefrom stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of particular CHV gB, gC and/or gD antigen(s) and therefrom the presence or absence of the virus or, to determine whether an immune response to the virus or antigen(s) has simply been stimulated.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

The following non-limiting Examples are given by way of illustration only and are not to be considered a limitation of this invention.

EXAMPLES

METHODS AND MATERIALS:

Preparation of genomic CHV DNA. CHV (obtained from L. Carmichael, Cornell University) was propagated on Madin-Darby canine kidney (MDCK) cells (ATCC CCL34). Viral DNA was isolated by standard methodology (Tartaglia et al., 1990).

DNA hybridization.

CHV genomic DNA was digested with restriction enzymes, run on agarose gels and transferred to Gene-Screen membranes (New England Nuclear) under conditions recommended by the manufacturers. Hybridizations were performed at 44° C., 53° C. or 59° C. in 1M NaCl, 1% SDS and 10% dextran sulfate. The hybridization probe included a 1800 bp BamHI-XbaI fragment, containing an internal segment of the feline herpesvirus (FHV) gB gene, a 950 bp BamHI-EcoRI fragment, containing the 3'-end of the FHV gC gene and a 970 bp BamHI-HindIII fragment, containing the 3'-end of the FHV gD gene (Audonnet, unpublished results).

Cloning and DNA sequencing.

CHV genomic fragments were subcloned into pBluescriptSK (Stratagene). Plasmid DNA was prepared and manipulated using standard techniques. Nucleotide sequencing was performed on double-stranded plasmid templates, using the modified T7 enzyme, Sequenase (U.S. Biochemical Corporation), and standard protocols recommended by the manufacturer. M13 forward and reverse primers were used to obtain initial sequence, and custom primers, prepared with a Biosearch 8700 or an Applied Biosystems 380B oligonucleotide synthesizer, were used for subsequent reactions.

DNA and amino acid sequence analyses.

DNA and amino acid sequence analyses were performed with PC/GENE (IntelliGenetics, Incorporated), ALIGN Plus (Scientific and Educational Software) and IBI-Pustell (International Biotechnologies, Incorporated) software packages. Homology searches were conducted on the SWISS-PROT (Release 20 or 23) (IntelliGenetics, Incorporated) database, using the FASTA program (Pearson & Lipman, 1988).

DNA Cloning and Synthesis.

Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection.

The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scale from a chicken. The virus was attenuated by approximately 50 serial passages in chicken embryohated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC vital vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

IDENTIFICATION AND SEQUENCING OF THE CHV gB GENE

Hybridization of CHV genomic DNA at relatively low stringency with a radiolabelled probe containing the feline herpesvirus (FHV) gB, gC and gD genes (Audonnet, unpublished results) identified one complimentary sequence. A 6 kb XbaI fragment containing this sequence was cloned and the nucleotide sequence of the hybridizing region was determined. The sequence of the nucleotide coding the CHV gB gene is shown in FIG. 1 together with the predicted amino acid expression (gB glycoprotein) therefrom. The putative transmembrane regions and potential TATA, CAAT and polyadenylation signal sequences are underlined. Nucleotides and predicted amino acid residues are numbered to the right of the sequence.

An open reading frame (ORF) starting at position 201 and ending at position 2840 was identified. The translation product (predicted) of this ORF is 879 amino acids long. Comparison of this amino acid sequence with the SWISS-PROT (Release 20) database revealed significant homology with the gB glycoprotein of numerous herpesviruses. Additional analyses revealed that the CHV gene product (predicted) was more homologous to the gB glycoprotein of alpha-herpesviruses, such as herpes simplex virus type 1 (HSV1), than beta- or gamma-herpesviruses, such as human cytomegalovirus (HCMV) or Epstein-Barr virus (EBV). These analyses and the results thereof are shown in Table 1 below. These results indicate that CHV should be classified as an alphaherpesvirus; a conclusion that is consistent with the previous classification of this virus according to biological properties (Carmichael et al., 1965; Roizman, 1982).

TABLE 1

HOMOLOGY BETWEEN THE PREDICTED AMINO ACID SEQUENCES OF 10 HERPESVIRUS gB GLYCOPROTEINS

|      | FHV | EHV1 | PRV | BHV1 | VZV | MDV | HSV1 | HCMV | EBV |
|------|-----|------|-----|------|-----|-----|------|------|-----|
| CHV  | 78  | 61   | 61  | 59   | 55  | 52  | 50   | 29   | 27  |
| FHV  |     | 57   | 59  | 58   | 51  | 48  | 48   | 27   | 27  |
| EHV1 |     |      | 52  | 52   | 47  | 45  | 44   | 27   | 26  |
| PRV  |     |      |     | 63   | 52  | 48  | 50   | 29   | 29  |
| BHV1 |     |      |     |      | 52  | 46  | 48   | 28   | 28  |
| VZV  |     |      |     |      |     | 49  | 48   | 30   | 28  |
| MDV  |     |      |     |      |     |     | 48   | 30   | 29  |
| HSV1 |     |      |     |      |     |     |      | 28   | 29  |
| HCMV |     |      |     |      |     |     |      |      | 32  |

Values in Table 1 were obtained using the ALIGN Plus program and are expressed as percent homology. The entire gB amino acid sequence was used. The alignment parameters were: mismatch penalty=2, open gap penalty=4, extended gap penalty=1. References: FHV (Maeda et al., 1992), EHV1 (Whalley et al., 1989), PRV (Robbins et al., 1987), BHV1 (Whitbeck et al., 1988), VZV (Keller et al., 1986), MDV (Ross et al., 1989), HSV1 (Bzik et al., 1984), HCMV (Kouzarides et al., 1987) and EBV (Pellett et al., 1985).

Example 2

ANALYSIS OF THE CHV gB NUCLEOTIDE SEQUENCE

The 5'- and 3'-noncoding regions of the CHV gB gene contain numerous RNA polymerase II regulatory sequence motifs, such as TATA box, CAAT box and polyadenylation signal sequences (Corden et al., 1980; Proudfoot & Brownlee, 1976) (FIG. 1). Potential TATA box sequences are found at positions 34, 36, 119 and 148, approximately 165 bp, 160 bp, 80 bp and 50 bp upstream from the CHV gB initiation codon. Potential CAAT box sequences (ATTG) are found at positions 89, 97 and 165, approximately 110 bp, 100 bp and 35 bp upstream from the gB initiation codon. Potential polyadenylation signal sequences (AATAAA) are found at positions 2839 and 2961, approximately 0 bp and 120 bp downstream from the CHV gB termination codon.

The nucleotide sequence surrounding the initiation codon has been shown to affect the efficiency of translation initiation (Kozak, 1986). In particular, the sequence, [A/G]NN ATGG, has been found to be most efficient. Therefore, relative to Kozak's rules, the nucleotide sequence surrounding the CHV gB initiation codon (AGTATGT) is favorable at position −3, but not at position +4 (FIG. 1). The fact that the CHV gB gene does not follow Kozak's rules is not unusual. The FHV (Maeda et al., 1992), PRV (Robbins et al., 1987), varicellazoster virus (VZV) (Keller et al., 1986), MDV (Ross et al., 1989) and HSV1 (Bzik et al., 1984) gB genes also contain a pyrimidine at position +4.

Example 3

ANALYSIS OF THE PREDICTED CHV gB AMINO ACID SEQUENCE

The deduced amino acid sequence of the CHV gB homologue is presented in FIG. 1. Hydropathicity analysis of this amino acid sequence is shown in FIG. 2. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gB homologue.

Hydropathicity analysis of this amino acid sequence revealed the presence of 2 prominent hydrophobic peaks. The first peak, located at the N-terminus, without wishing to be bound by any one theory, represents a potential signal sequence. N-terminal signal sequences initiate transport across the endoplasmic reticulum membrane and can be critical for the proper post-translational modification and targeting of glycoproteins (Blobel, 1980). Signal sequences vary in length from about 15–30 residues and usually consist of a basic N-terminal region, a central hydrophobic region and a short, relatively polar C-terminal region. In addition, the cleavage site usually conforms to the −3, −1 rule, where the residue at position −1 is small (Ala, Ser, Gly, Cys, Thr or Gln) and the residue at position −3 is not aromatic (Phe, His, Tyr or Trp), charged (Asp, Glu, Lys or Arg) or large and polar (Ash or Gln), and residues −3 through +1 are not Pro (yon Heijne, 1986). Although analysis with PSIGNAL, a PC/GENE program designed to detect eukaryotic signal sequences, does not identify the N-terminal end of CHV gB as a potential signal sequence, this region does have elements consistent with typical signal sequences; namely a hydrophobic core (residues 2–17) and a relatively polar C-terminal region (FIG. 1). The fact that PSIGNAL does not detect a signal sequence in the N-terminal region of CHV gB is not unique. This algorithm also does not detect a signal sequence in the N-terminal region of the VZV gB homologue.

The second, very broad, hydrophobic peak(s) (FIG. 2), with predicted membrane-spanning segments between amino acid residues 725 and 741 and 746–750 and 766–772 (using the method of Klein et al. (1985)), without wishing to be bound by any one theory, functions as a membrane anchor region. It has been hypothesized that the transmembrane domain of HSV1 gB, as well as other gB homologues, transverses the membrane 3 times (Pellett et al., 1985). Hydropathicity analysis of CHV gB reveals the presence of at least 2 distinct hydrophobic peaks. Therefore, CHV gB and HSV1 gB have similar transmembrane structures.

Alignment of the CHV gB amino acid sequence with similar sequences from other herpesviruses revealed extensive homology throughout the entire sequence, with the exception of the N-terminus, a region surrounding the putative cleavage site (see below) and a region near the C-terminus. FIGS. 3A and 3B show the amino acid homology of 8 gB homologues. The amino acid sequences of the CHV, FHV, EHV1, PRV, HSV1, VZV, HCMV and EBV gB homologues (for references from which the sequences were obtained, see text below Table 1) were aligned using the PC/GENE CLUSTAL program. Gaps, indicated by dashes, were introduced to maximize homology. Aligned residues which are identical in all 8 sequences are indicated by an asterisk (*). Aligned residues which are identical in the majority of sequences are indicated by a period (.). Conserved cysteine residues are boxed. Potential N-linked glycosylation sites are shaded. Putative proteolytic cleavage sites are underlined.

This alignment also revealed that the vast majority of cysteine residues are perfectly conserved. For example, CHV gB contains 11 cysteine residues, 10 of which are perfectly conserved in all alpha-, beta- and gamma-herpesviruses. In fact, the only cysteine residue in CHV gB that is not conserved is found near the N-terminus and may be located in the putative signal sequence. These results show that the gB glycoproteins have relatively similar tertiary structures.

Alignment of the gB amino acid sequences also revealed that the potential N-linked glycosylation sites are relatively well conserved (FIGS. 3A and 3B). N-linked oligosaccharides can be added to Asn residues that have the sequence Asn-X-Ser or Asn-X-Thr, where X is not Pro (Bause, 1983). CHV gB contains 13 potential N-linked glycosylation sites. Three of these sites, however, are situated in the putative cytoplasmic domain and, therefore, may not be glycosylated. The location of the potential N-linked glycosylation sites is relatively well conserved in the majority of gB glycoproteins (FIGS. 3A and 3B).

The gB glycoprotein of most herpesviruses is cleaved internally during maturation, with the subsequent peptides being held together by disulfide bonds. The VZV gB homologue (gpII), for example, is cleaved between Arg and Ser residues, resulting in 2 glycoproteins of approximately 60 kd (Keller et al., 1986). The gB glycoproteins of FHV (Maeda et al., 1992), equine herpesvirus type 1 (EHV1) (Whalley et al., 1989), PRV (Robbins et al., 1987), BHV1 (Whitbeck et al., 1988), MDV (Ross et al., 1989) and HCMV (Kouzarides et al., 1987) are also cleaved. Furthermore, a sequence, Arg-X-Arg-Arg/Lys-Ser/Ala, similar to the sequence at the VZV cleavage site, Arg-Thr-Arg-Arg-Ser, is present at virtually the same location in each of these gB glycoproteins. Conversely, this sequence is not found in the HSV1 (Bzik et al., 1984) and EBV (Pellett et al., 1985) gB glycoproteins, which are not cleaved. The significance of this cleavage event is unknown. It does not appear, however, to be essential for replication, in vitro, since strains of BHV1 (Blewett & Misra, 1991) and HCMV (Spaete et al., 1990) that have been mutated at the cleavage site, and therefore encode an uncleaved gB glycoprotein, are still infectious. Without wishing to be bound by the theory that CHV gB is cleaved internally, proteolytically, the sequence, Arg-Lys-Arg-Arg-Ser, is present at the same location in CHV as in VZV, FHV, EHV1, PRV, BHV1, MDV and HCMV.

Example 4

IDENTIFICATION AND SEQUENCING OF THE CHV gC GENE

CHV genomic fragments were randomly cloned into pBluescriptSK. The nucleotide sequence of the termini of these fragments was determined and the predicted amino acid sequence of potential ORFs were analyzed for homology against the SWISS-PROT (Release 20) amino acid database. Using this methodology, a 12 kb XbaI fragment encoding an ORF with homology to herpesvirus gC glycoproteins was identified. The nucleotide sequence of this ORF is presented in FIG. 4. FIG. 4 shows the nucleotide sequence and predicted amino acid sequence of the CHV gC homologue and ORF2. The putative transmembrane region and potential TATA, CAAT and polyadenylation signal sequences are underlined. Nucleotides and predicted amino acid residues are numbered to the right of the sequence. The putative CHV gC gene starts at position 201 and ends at position 1580. The predicted translation product is 459 amino acids long. Comparison of this amino acid sequence with the sequence of gC glycoproteins from other herpesviruses is shown in Table 2, below, and revealed extensive homology, indicating that this ORF encodes the CHV gC homologue (Table 2).

TABLE 2

HOMOLOGY BETWEEN THE PREDICTED AMINO ACID SEQUENCES OF 9 HERPESVIRUS gC GLYCOPROTEINS

|      | FHV | EHV1 | EHV4 | PRV | BHV1 | VZV | MDV | HSV1 |
|------|-----|------|------|-----|------|-----|-----|------|
| CHV  | 44  | 32   | 34   | 27  | 27   | 29  | 27  | 25   |
| FHV  |     | 32   | 33   | 29  | 31   | 28  | 25  | 23   |
| EHV1 |     |      | 81   | 31  | 32   | 30  | 27  | 27   |
| EHV4 |     |      |      | 32  | 31   | 31  | 25  | 27   |
| PRV  |     |      |      |     | 37   | 27  | 25  | 29   |
| BHV1 |     |      |      |     |      | 29  | 25  | 27   |
| VZV  |     |      |      |     |      |     | 22  | 22   |
| MDV  |     |      |      |     |      |     |     | 23   |

Values in Table 2 were obtained using the ALIGN Plus program and are expressed as percent homology. The entire gC amino acid sequence was used. See Table 1 for alignment parameters. References: FHV (Audonnet, unpublished results), EHV1 (Allen & Coogle, 1988), EHV4 (Nicolson & Onions, 1990), PRV (Robbins et al., 1986), BHV1 (Fitzpatrick et al., 1989), VZV (Davison & Scott, 1986), MDV (Ihara et al., 1989) and HSV1 (McGeoch et al., 1988).

Example 5

ANALYSIS OF THE CHV gC NUCLEOTIDE SEQUENCE

Potential TATA box sequences (TATA) are found at positions 22 and 81, approximately 180 bp and 120 bp upstream from the CHV gC initiation codon (FIG. 4). An additional TATA sequence is found at position 175. Due to its proximity to the gC initiation codon, however, this sequence may not be a potential TATA box sequence. Potential CAAT box sequences (CAAT and ATTG) are found at positions 13, 59 and 119, approximately 190 bp, 140 bp and 80 bp upstream from the gC initiation codon. A potential polyadenylation signal sequence (AATAAA) is found at position 1744, approximately 165 bp downstream from the CHV gC termination codon and 45 bp within ORF2 (see below). Other potential polyadenylation signal-like sequences are also found in the gC 3'-noncoding region.

Like the CHV gB gene, the nucleotide sequence surrounding the CHV gC initiation codon (AAAATGA) is favorable with respect to Kozak's rules at position −3, but not at position +4 (FIG. 4). The FHV (Audonnet, unpublished results), EHV1 (Allen & Coogle, 1988) and VZV (Davison & Scott, 1986) gC genes also contain an unfavorable nucleotide at position +4.

Example 6

ANALYSIS OF THE CHV gC AMINO ACID SEQUENCE PREDICTED

Figure 5:
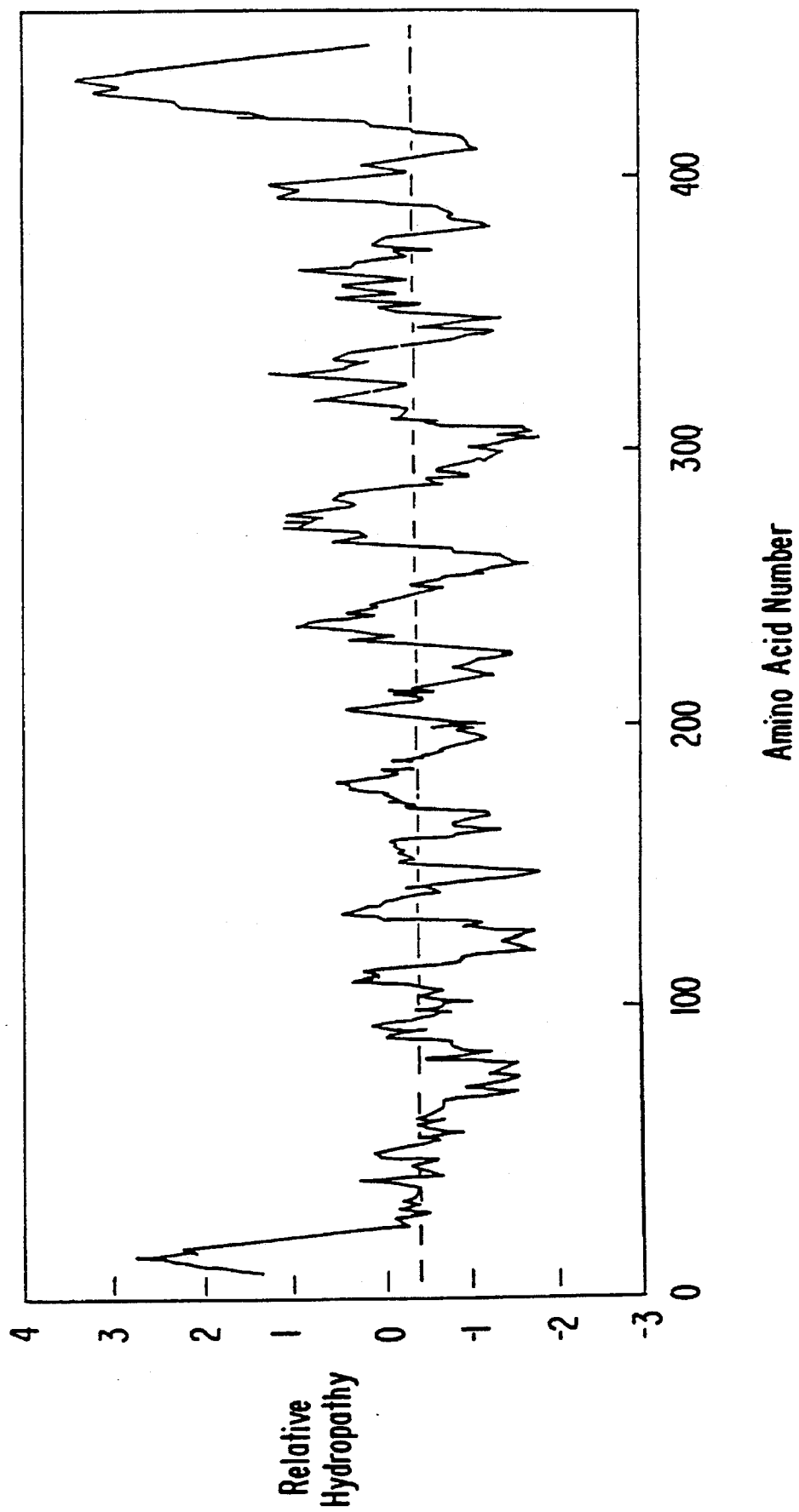
FIG. 5 shows the hydropathicity analysis of the CHV gC homologue.

The deduced amino acid sequence of the CHV gC homologue is presented in FIG. 4. FIG. 5 shows the hydropathicity analysis of the CHV gC homologue. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gC homologue.

Hydropathicity analysis of the predicted CHV gC amino acid sequence revealed the presence of 2 prominent hydrophobic peaks (FIG. 5). The first peak, located at the N-terminus, without wishing to be bound by any one theory, represents a potential signal sequence. Although analysis with PSIGNAL does not identify the N-terminal end of this polypeptide as a potential signal sequence, this region does have a basic N-terminal region, a hydrophobic core (residues 6–20) and a relatively polar C-terminal region (FIG. 4). The second hydrophobic peak, with a predicted membrane-spanning segment between residues 424–433 and 449–456 (using the method of Klein et al. (1985)), without wishing to be bound by any one theory, functions as a membrane anchor region. FIG. 6 shows the amino acid homology of 4 gC homologues. The amino acid sequences of the CHV, FHV, EHV1 and HSV1 gC homologues (for references see Table 2) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded.

Alignment of the CHV gC amino acid sequence with homologous sequences from other herpesviruses revealed a moderate level of homology throughout the entire sequence, with the exception of the N-terminus (FIG. 6). This alignment also revealed that the majority of cysteine residues are perfectly conserved. For example, CHV gC contains 10 cysteine residues, 8 of which are perfectly conserved in all alpha-herpesviruses. In fact, the only cysteine residues in CHV gC that are not conserved are located in the putative transmembrane or intracellular domains. These results show that the gC glycoproteins have relatively similar tertiary structures. Alignment with other gC sequences also revealed the relative conservation of potential N-linked glycosylation sites.

Example 7

IDENTIFICATION AND SEQUENCING OF ORF2

Nucleotide sequence analysis of the region downstream from the CHV gC gene revealed the presence of a second ORF (FIG. 4). This ORF (ORF2) starts at position 1699 and ends at position 2226. The predicted translation product is 175 amino acids long. Table 3, below, shows the comparison of this amino acid sequence with the SWISS-PROT (Release 23) database revealed significant homology with the ORFs located downstream from other alpha-herpesvirus gC genes. The homology scores for the ORF2 homologues shows that in CHV, FHV, EHV1, equine herpesvirus type 4 (EHV4), MDV, herpesvirus of turkey (HVT) and possibly HSV1, the ORF located downstream from the gC gene represents a highly divergent, but evolutionarily related, gene family. Conversely, the ORF (gene 13) located next to the VZV gC gene does not exhibit significant homology with any of the other comparably positioned ORFs. Furthermore, gene 13 is oriented on the genome in the opposite direction relative to all the other ORF2-like genes (Davison & Scott, 1986). These results are consistent with the proposed functions of the proteins encoded by these 2 groups of genes; VZV gene 13 encodes a thymidylate synthetase (Davison and Scott, 1986), whereas the HSV1 ORF2-like gene (UL45) encodes a putative virion protein (Telford et al., 1992). Therefore, the ORFs located next to the gC gene in CHV, FHV, EHV1, EHV4, MDV, HVT and possibly HSV1 encode proteins that are structurally and functionally unrelated to the protein encoded downstream from the VZV gC homologue.

TABLE 3

HOMOLOGY BETWEEN THE PREDICTED AMINO ACID SEQUENCES OF THE ORFS LOCATED ADJACENT TO THE gC GENE IN 8 HERPESVIRUSES

|  | FHV | EHV1 | EHV4 | MDV | HTV | HSV1 | VZV |
|---|---|---|---|---|---|---|---|
| CHV | 197(22) | 211(22) | 219(21) | 62(4) | 105(13) | 53(4) | 31(0) |
| FHV |  | 177(24) | 167(18) | 69(4) | 66(4) | 40(1) | 52(1) |
| EHV1 |  |  | 470(50) | 95(8) | 104(9) | 79(7) | 58(3) |
| EHV4 |  |  |  | 132(8) | 130(11) | 60(5) | 30(0) |
| MDV |  |  |  |  | 767(75) | 83(6) | 28(0) |
| HTV |  |  |  |  |  | 91(7) | 33(0) |
| HSV1 |  |  |  |  |  |  | 49(2) |

Values in Table 3 were obtained using the FASTA and RDF2 programs (Pearson & Lipman, 1988). A ktup of 1 was used. Values in parentheses represent the number of standard deviations between the FASTA score and the mean of the scores obtained from 100 randomly permutated versions of the potentially related sequence. References: FHV (Audonnet, unpublished results), EHV1 (Telford et al., 1992), EHV4 (Nicolson & Onions, 1990), MDV (Ihara et al., 1989), HVT (Kato et al., 1989), HSV1 (McGeoch et al., 1988) and VZV (Davison & Scott, 1986).

Example 8

ANALYSIS OF THE CHV ORF2 NUCLEOTIDE SEQUENCE

Potential TATA box sequences (TATA) are found at positions 1604, 1606, 1635 and 1662, approximately 95, 93, 65 and 35 bp upstream from the ORF2 initiation codon and approximately 24, 26, 55 and 80 bp downstream from the gC gene termination codon (FIG. 4). A potential CAAT box sequence (CAAT) is found at position 1584, approximately 115 bp upstream from the initiation codon. Potential polyadenylation signal sequences (AATAAA) are found at overlapping positions 2225, 2229, 2234 and 2238, approximately 0–15 bp downstream from the ORF2 termination codon. The nucleotide sequence surrounding the ORF2 initiation codon (AATATGG) is favorable with respect to Kozak's rules at positions −3 and +4.

Example 9

IDENTIFICATION AND SEQUENCING OF THE CHV gD GENE

Employing the same methodology used to map the CHV gC homologue, a 7 kb PstI fragment encoding an ORF with homology to herpesvirus gD glycoproteins was identified. FIG. 7 shows the nucleotide sequence and predicted amino acid sequence of the CHV gD homologue. The putative signal sequence, transmembrane region and potential polyadenylation signal sequences are underlined. Nucleotides and predicted amino acid residues are numbered to the right of the sequence. The CHV gD gene starts at position 201 and ends at position 1238. The translation product (predicted) is 345 amino acids long. Table 4, below, provides comparison of this amino acid sequence with the sequence of other gD glycoproteins and, revealed extensive homology, indicating that this ORF encodes the CHV gD homologue.

TABLE 4

Homology between the predicted amino acid sequences of 6 herpesvirus gD glycoproteins

|  | FHV | EHV1 | PRV | BHV1 | HSV1 |
| --- | --- | --- | --- | --- | --- |
| CHV | 45 | 35 | 27 | 34 | 21 |
| FHV |  | 31 | 30 | 34 | 24 |
| EHV1 |  |  | 26 | 27 | 21 |
| PRV |  |  |  | 37 | 27 |
| BHV1 |  |  |  |  | 24 |

Values in Table 4 were obtained using the ALIGN Plus program and are expressed as percent homology. The entire gD amino acid sequence was used. See Table 1 for alignment parameters. References: FHV (Audonnet, unpublished results), EHV1 (Flowers et al., 1991), PRV (Petrovskis et al., 1986), BHV1 (Tikoo et al., 1990) and HSV1 (Lasky & Dowbenko, 1984).

Example 10

ANALYSIS OF THE CHV gD NUCLEOTIDE SEQUENCE

No TATA or CAAT/ATTG sequences were identified immediately upstream from the CHV gD gene (FIG. 7). Numerous potential TATA box-like sequences, however, were found. Potential polyadenylation signal sequences (AATAAA) were found at positions 1260 and 1287, approximately 25 bp and 50 bp downstream from the CHV gD termination codon. Like the CHV gB and gC genes, the nucleotide sequence surrounding the CHV gD initiation codon (AAAATGA) is favorable with respect to Kozak's rules at position −3, but not at position +4 (FIG. 7). The FHV (Audonnet, unpublished results), EHV1 (Audonnet et al., 1990; Flowers et al., 1991), PRV (Petrovskis et al., 1986) and BHV1 (Tikoo et al., 1990) gD genes also contain an unfavorable nucleotide at position +4.

Example 11

ANALYSIS OF THE PREDICTED CHV gD AMINO SEQUENCE

Figure 8:
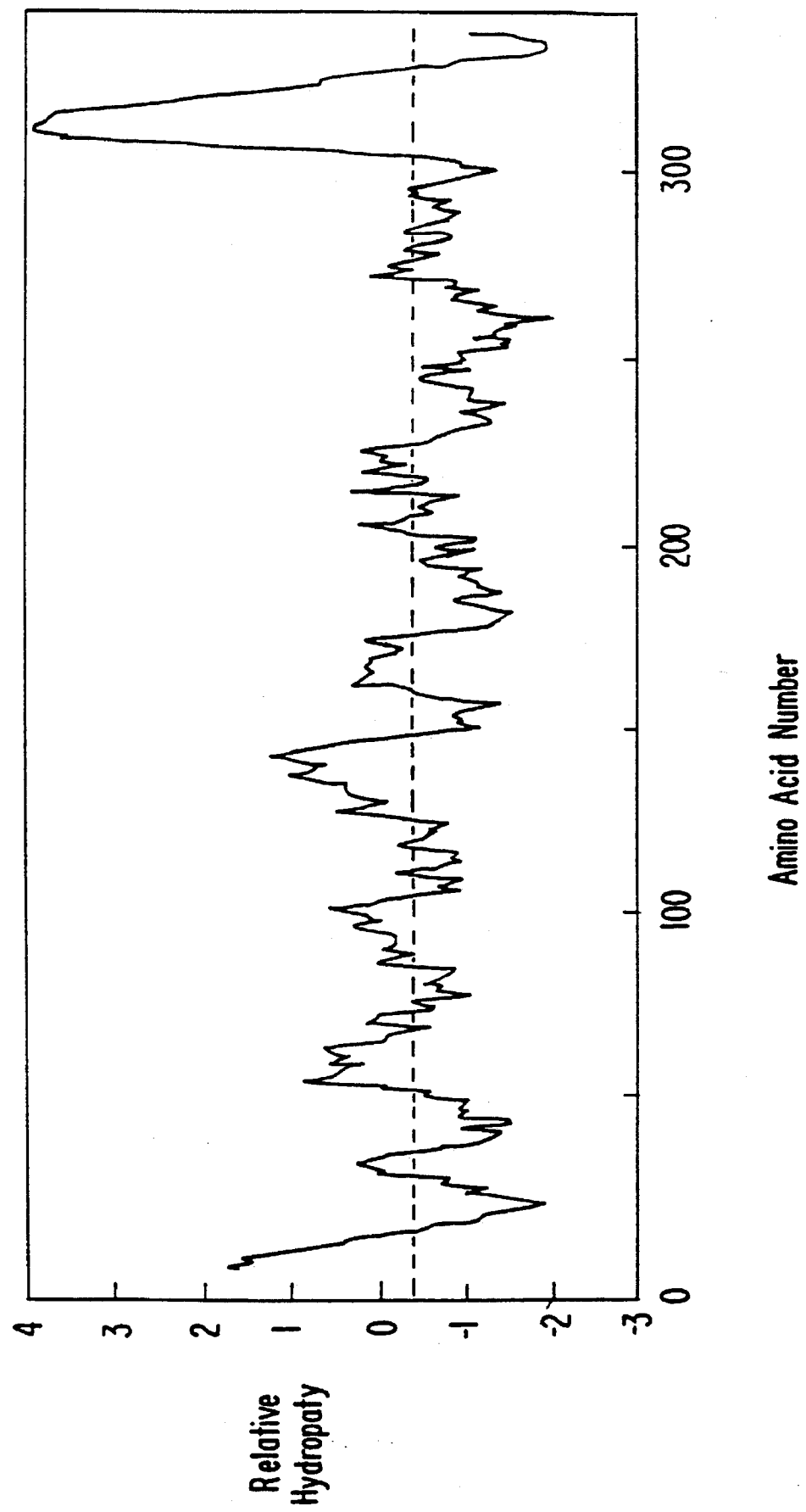
FIG. 8 shows the hydropathicity analysis of the CHV gD homologue.

The deduced amino acid sequence of the CHV gD homologue is presented in FIG. 7. FIG. 8 shows the hydropathicity analysis of the CHV gD homologue. The profile was obtained with the PC/GENE SOAP program, using the method of Kyte & Doolittle (1982) and an interval of 11 amino acids. The vertical axis represents relative hydropathicity, where positive values are hydrophobic and negative values are hydrophilic. The horizontal axis represents the amino acid number of the CHV gD homologue.

Hydropathicity analysis of the predicted CHV gD amino acid sequence revealed the presence of 2 prominent hydrophobic peaks (FIG. 8). The first peak, located at the N-terminus, without wishing to be bound by any one theory, represents a potential signal sequence. In fact, PSIGNAL identified a potential cleavage site between positions 16 and 17. The second hydrophobic peak, with a predicted membrane-spanning segment between residues 304–311 and 327–332 (using the method of Klein et al. (1985)), without wishing to be bound by any one theory, functions as a membrane anchor region.

FIG. 9 shows amino acid homology of 4 gD homologues. The amino acid sequences of the CHV, FHV, EHV1 and HSV1 gD homologues (for references see Table 4) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded. Alignment of the CHV gD amino acid sequence with homologous sequences from other herpesviruses revealed a moderate level of homology throughout the entire sequence, with the exception of the N-terminus (FIG. 9). This alignment also revealed that the vast majority of cysteine residues are perfectly conserved. For example, CHV gD contains 6 cysteine residues, all of which are perfectly conserved in all alphaherpesviruses. These results show that the gD glycoproteins have relatively similar tertiary structures. This alignment also revealed that the potential N-linked glycosylation sites are well conserved. Without wishing to be bound by any theory that the CHV gD glycosylation sites are utilized, it is known that all of the potential HSV1 gD glycosylation sites are used (Sodora et al., 1991).

Example 12

GENOMIC ORGANIZATION

The gB, gC and gD genes were not mapped to specific locations on the CHV genome. Nucleotide sequence analyses of the regions flanking these genes, however, indicates that the genomic organization of CHV is similar to other alpha-herpesviruses. For example, the ORF located immediately upstream from the CHV gB gene has homology with gene 30 of VZV (Davison & Scott, 1986) and UL28 of HSV1 (McGeoch et al., 1988), both of which are located immediately upstream from the gB homologue in those viruses. ORF2, located immediately downstream from the CHV gC gene, has homology with the ORFs located immediately downstream from the gC homologue in FHV (Audonnet, unpublished results), EHV1 (Telford et al., 1992), EHV4 (Nicolson & Onions, 1990), HVT (Kato et al., 1988) and perhaps HSV1 (McGeoch et al., 1988. Additionally, the ORF located immediately downstream from the CHV gD gene has homology to the gI gene of EHV1 (Audonnet et al., 1990) and the gp63 gene of PRV (Petrovskis et al., 1986), both of which are located immediately downstream from the gD homologue in those viruses (data not shown).

Example 13

CONSTRUCTION OF PLASMID pSD460 FOR DELETION OF THYMIDINE KINASE GENE (J2R)

Figure 10:
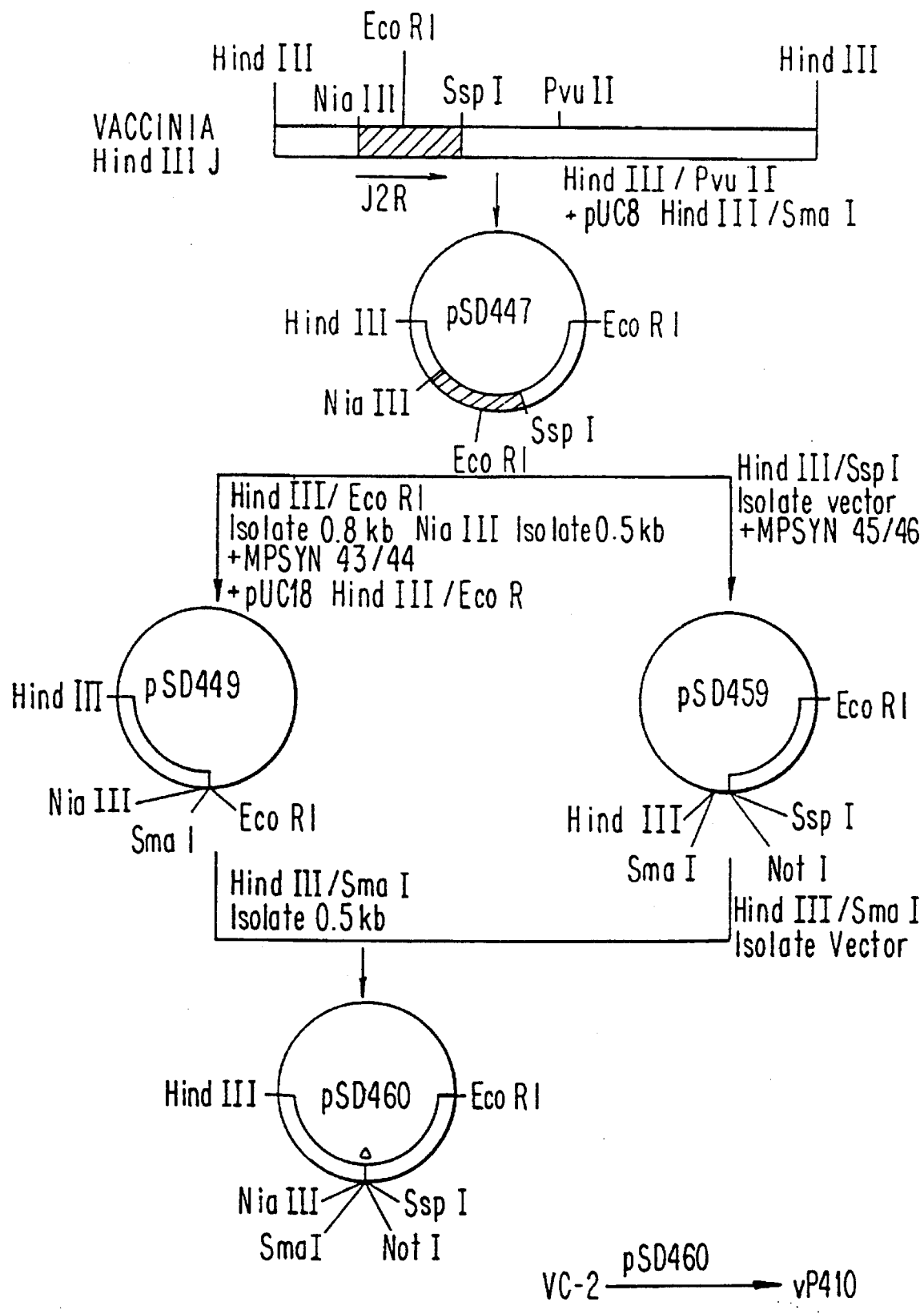
FIG. 10 schematically shows a method for the construction of plasmid pSD460 for deletion of thymidine kinase gene and generation of recombinant vaccinia virus vP410.

Referring now to FIG. 10, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 10.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:24/SEQ ID NO:25)

```
                              SmaI
MPSYN43  5'       TAATTAACTAGCTACCCGGG           3'
MPSYN44  3' GTACATTAATTGATCGATGGGCCCTTAA         5'
         NlaIII                        EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:26/SEQ ID NO:27)

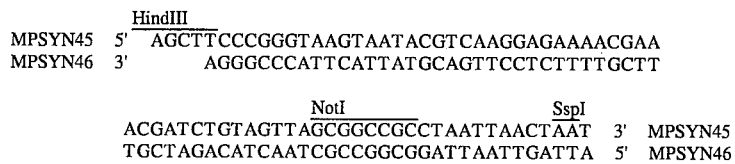

```
                              NotI                  SspI
            ACGATCTGTAGTTAGCGGCCGCCTAATTAACTAAT    3'  MPSYN45
            TGCTAGACATCAATCGCCGGCGGATTAATTGATTA    5'  MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:25) as template and the complementary 20 mer oligonucleotide MPSYN47 (SEQ ID NO:28) (5' TTAGTTAATTAGGCGGCCGC 3') as primer. Recombinant virus vP410 was identified by plaque hybridization.

Example 14

CONSTRUCTION OF PLASMID pSD486 FOR DELETION OF HEMORRHAGIC REGION (B13R+B14R)

Figure 11:
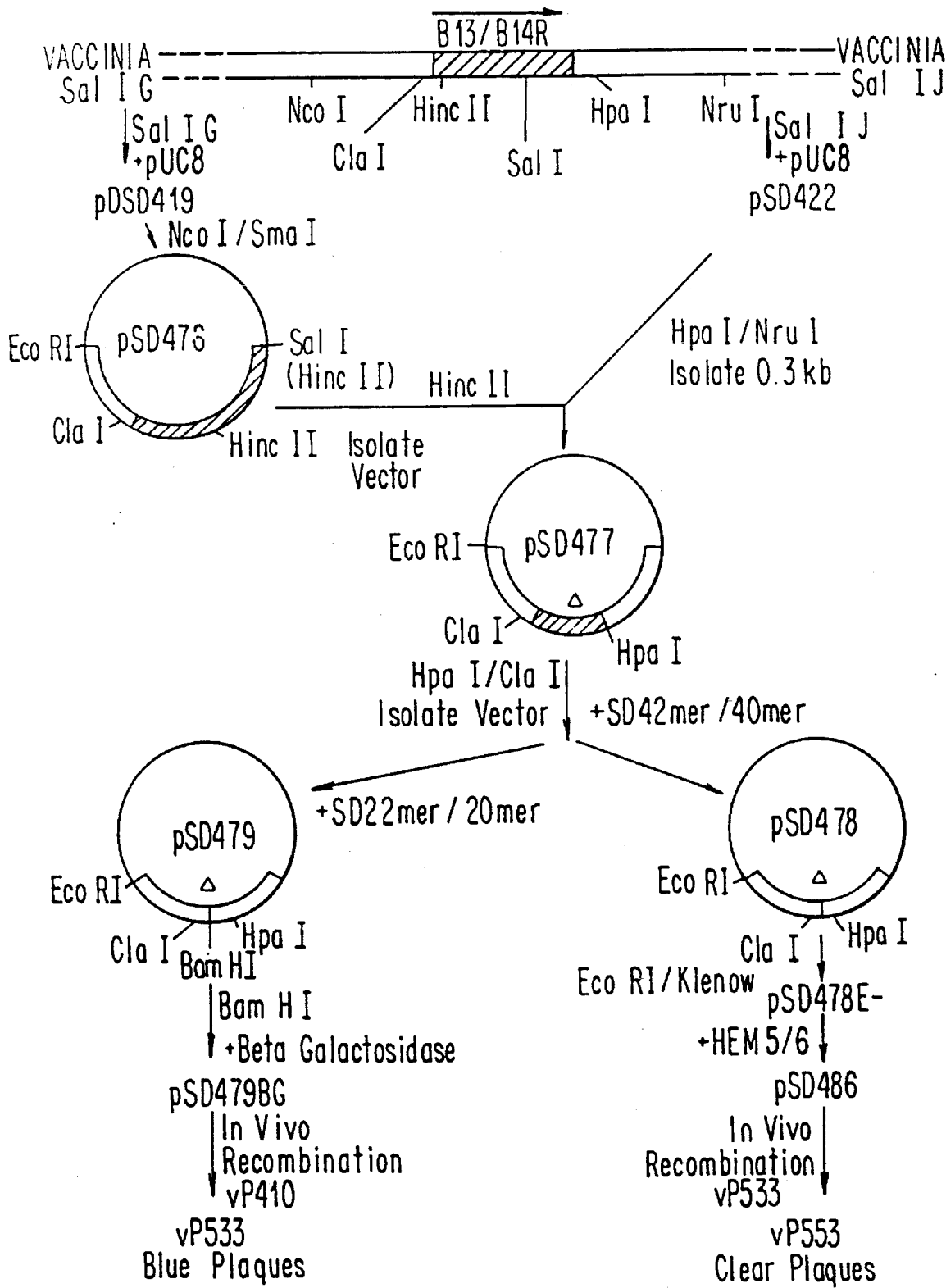
FIG. 11 schematically shows a method for the construction of plasmid pSD486 for deletion of hemorrhagic region and generation of recombinant vaccinia virus vP553.

Referring now to FIG. 11, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R-B14R (pos. 172,549–173,552), pSD419 was used as the source for the left flanking arm and pSD422 was used as the source of the right flanking arm. The direction of transcription for the u region is indicated by an arrow in FIG. 11.

To remove unwanted sequences from pSD419, sequences to the left of the NcoI site (pos. 172,253) were removed by digestion of pSD419 with NcoI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:29/SEQ ID NO:30)

```
                  ClaI         BamHI  HpaI
SD22mer  5'  CGATTACTATGAAGGATCCGTT  3'
SD20mer  3'      TAATGATACTTCCTAGGCAA  5'
``` generating pSD479. pSD479 contains an initiation codon (underlined) followed by a BamHI site. To place *E. coli* Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:31/SEQ ID NO:32)

pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:35/SEQ ID NO:36)

```
              NdeI
ATI3  5' TATGAGTAACTTAACTCTTTTGTTAATTAAAAGTATATTCAAAAAATAAGT
ATI4  3'     ACTCATTGAATTGAGAAAACAATTAATTTTCATATAAGTTTTTATTCA

BglII    EcoRI  HpaI
     TATATAAATAGATCTGAATTCGTT  3'  ATI3
     ATATATTTATCTAGACTTAAGCAA  5'  ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the

```
          ClaI         SacI        XhoI         HpaI
SD42mer  5' CGATTACTAGATCTGAGCTCCCCGGGCTCGAGGGATCCGTT  3'
SD40mer  3'     TAATGATCTAGACTCGAGGGGCCCGAGCTCCCTAGGCAA  5'
               BglII         SmaI         BamHI
``` generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6 (SEQ ID NO:33/SEQ ID NO:34)

```
         BamHI  EcoRI  HpaI
HEM5  5' GATCCGAATTCTAGCT  3'
HEM6  3'     GCTTAAGATCGA  5'
``` generating plasmid pSD486. pSD486 was used as donor plasmid for recombination with recombinant vaccinia virus vP533, generating vP553, which was isolated as a clear plaque in the presence of X-gal.

Example 15

CONSTRUCTION OF PLASMID pMP494Δ FOR DELETION OF ATI REGION (A26L)

Figure 12:
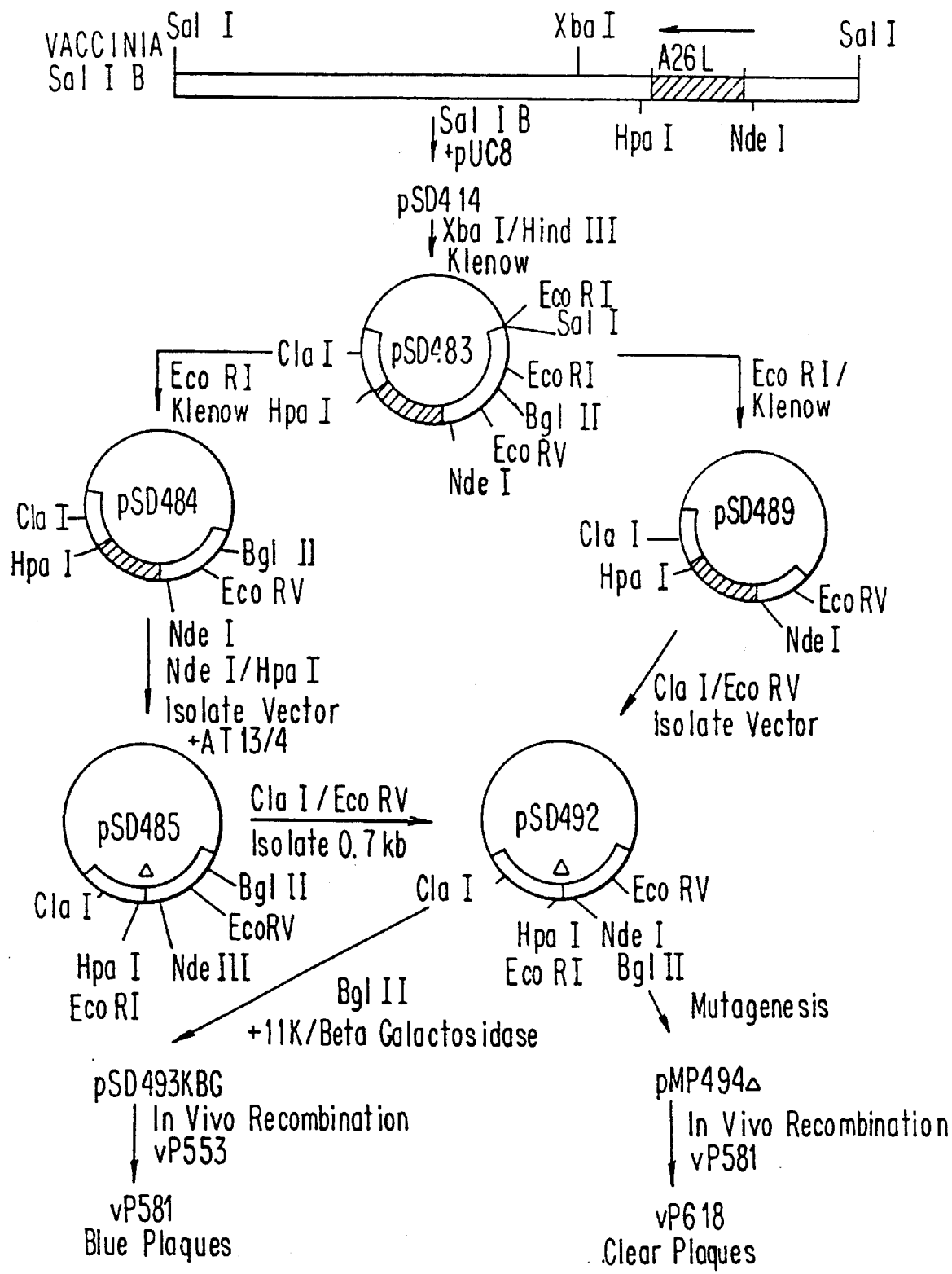
FIG. 12 schematically shows a method for the construction of plasmid pMP494Δ for deletion of ATI region and generation of recombinant vaccinia virus vP618.

Referring now to FIG. 12, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid polylinker region of pSD492 are unique.

A 3.3 kb BglII cassette containing the *E. coli* Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:37) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 16

CONSTRUCTION OF PLASMID pSD467 FOR DELETION OF HEMAGGLUTININ GENE (A56R)

Figure 13:
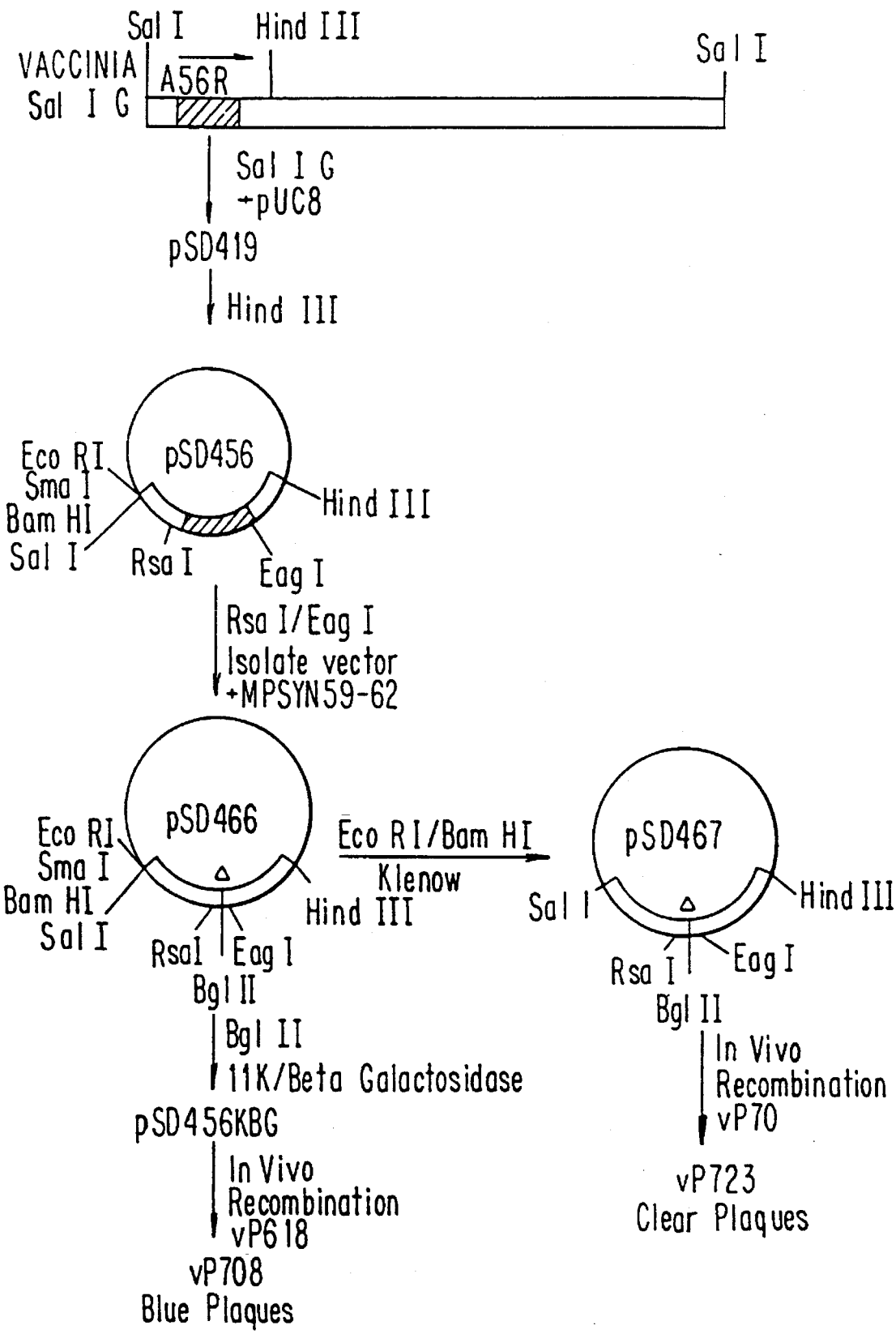
FIG. 13 schematically shows a method for the construction of plasmid pSD467 for deletion of hemagglutinin gene and generation of recombinant vaccinia virus vP723.

Referring now to FIG. 13, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 13. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:38), MPSYN62 (SEQ ID NO:39), MPSYN60 (SEQ ID NO:40), and MPSYN61 (SEQ ID NO:41)

```
                RsaI
MPSYN59  5' ACACGAATGATTTTCTAAAGTATTTGGAAAGTTTTATAGGT-
MPSYN62  3' TGTGCTTACTAAAAGATTTCATAAACCTTTCAAAATATCCA-

MPSYN59     AGTTGATAGAACAAAATACATAATTT   3'
MPSYN62     TCAACTATCT   5'

MPSYN60  5'                        TGTAAAAATAAATCACTTTTTATA-
MPSYN61  3' TGTTTTATGTATTAAAACATTTTTATTTAGTGAAAAATAT-

BglII    SmaI    PstI    EagI
MPSYN60     CTAAGATCTCCCGGGCTGCAGC    3'
MPSYN61     GATTCTAGAGGGCCCGACGTCGCCGG  5'
``` reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 13.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

Example 17

CONSTRUCTION OF PLASMID pMPCSK1Δ FOR DELETION OF OPEN READING FRAMES [C7L–K1L]

Figure 14:
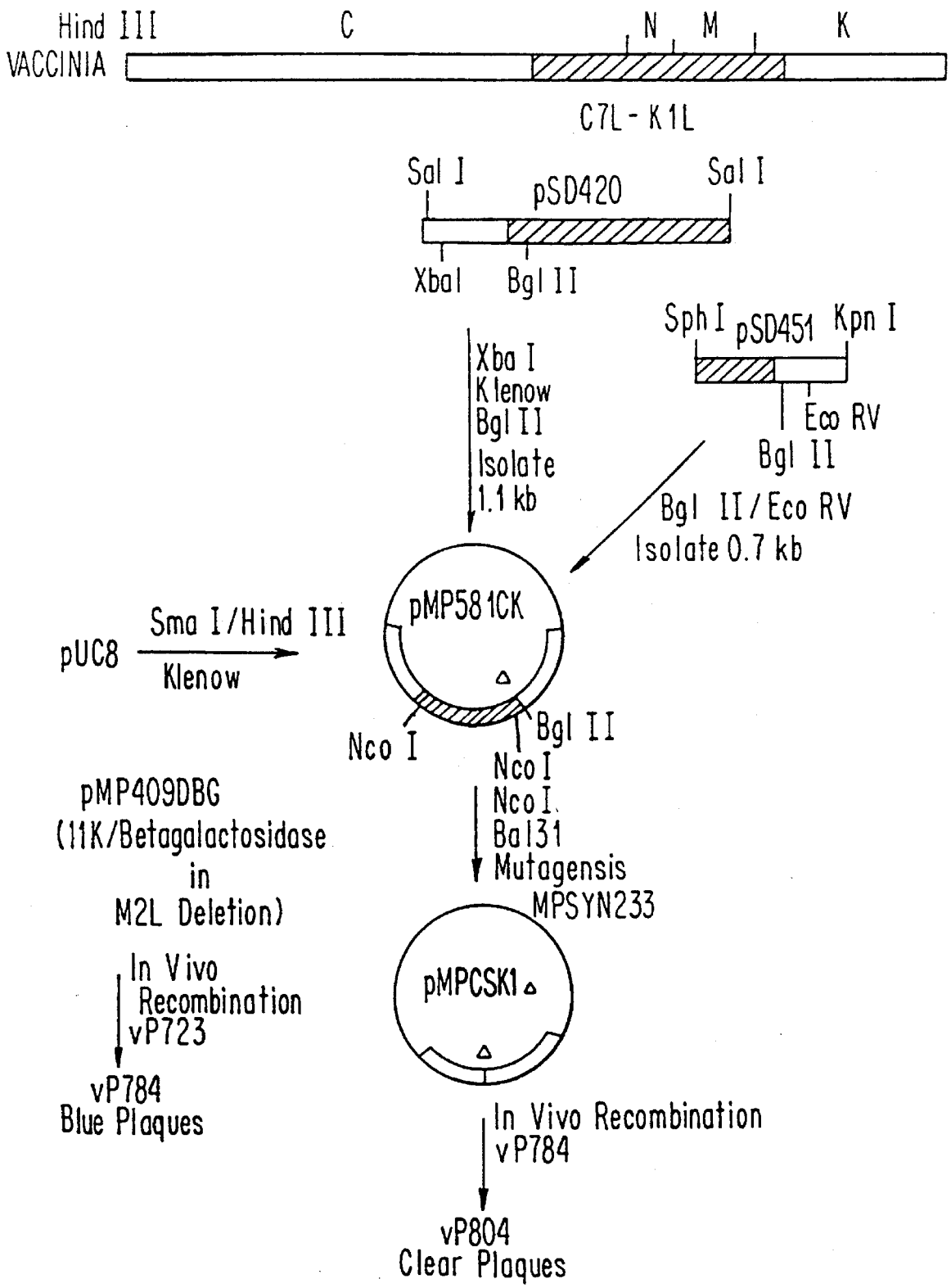
FIG. 14 schematically shows a method for the construction of plasmid pMPCK1Δ for deletion of gene cluster [C7L–K1L] and generation of recombinant vaccinia virus vP804.

Referring now to FIG. 14, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
                                              BglII
MPSYN82  (SEQ ID NO: 42)  5'  TTTCTGTATATTTGCACCAATTTAGATCTT-
                              ACTCAAAATATGTAACAATA  3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628)

followed by blunt ending with Klenow fragment of *E. coli* polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 14.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:43)  5'-TGTCATTTAACACTATACTCATATTAAT AAAAATAATATTTATT-3'.

The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

was digested with BamHI (pos. 65,381) and HpaI (pos. 67,001) and blunt ended using Klenow fragment of *E. coli* polymerase. This 4.8 kb vector fragment was ligated with a 3.2 kb SmaI cassette containing the *E. coli* Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 15.

To construct a vector plasmid to accept the left vaccinia flanking arm, pUC8 was cut with BamHI/EcoRI and ligated with annealed synthetic oligonucleotides 518A1/518A2 (SEQ ID NO:44/SEQ ID NO:45)

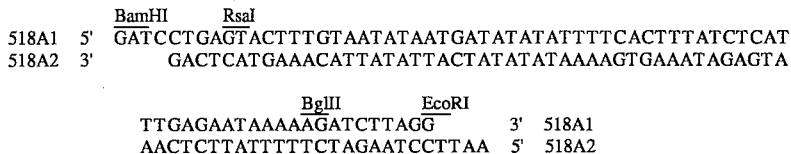

forming plasmid pSD531. pSD531 was cut with RsaI (partial) and BamHI and a 2.7 kb vector fragment isolated. pSD518 was cut with BglII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:46/SEQ ID NO:47)

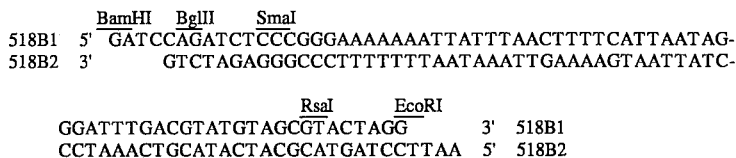

Example 18

CONSTRUCTION OF PLASMID pSD548 FOR DELETION OF LARGE SUBUNIT, RIBONUCLEOTIDE REDUCTASE (I4L)

Figure 15:
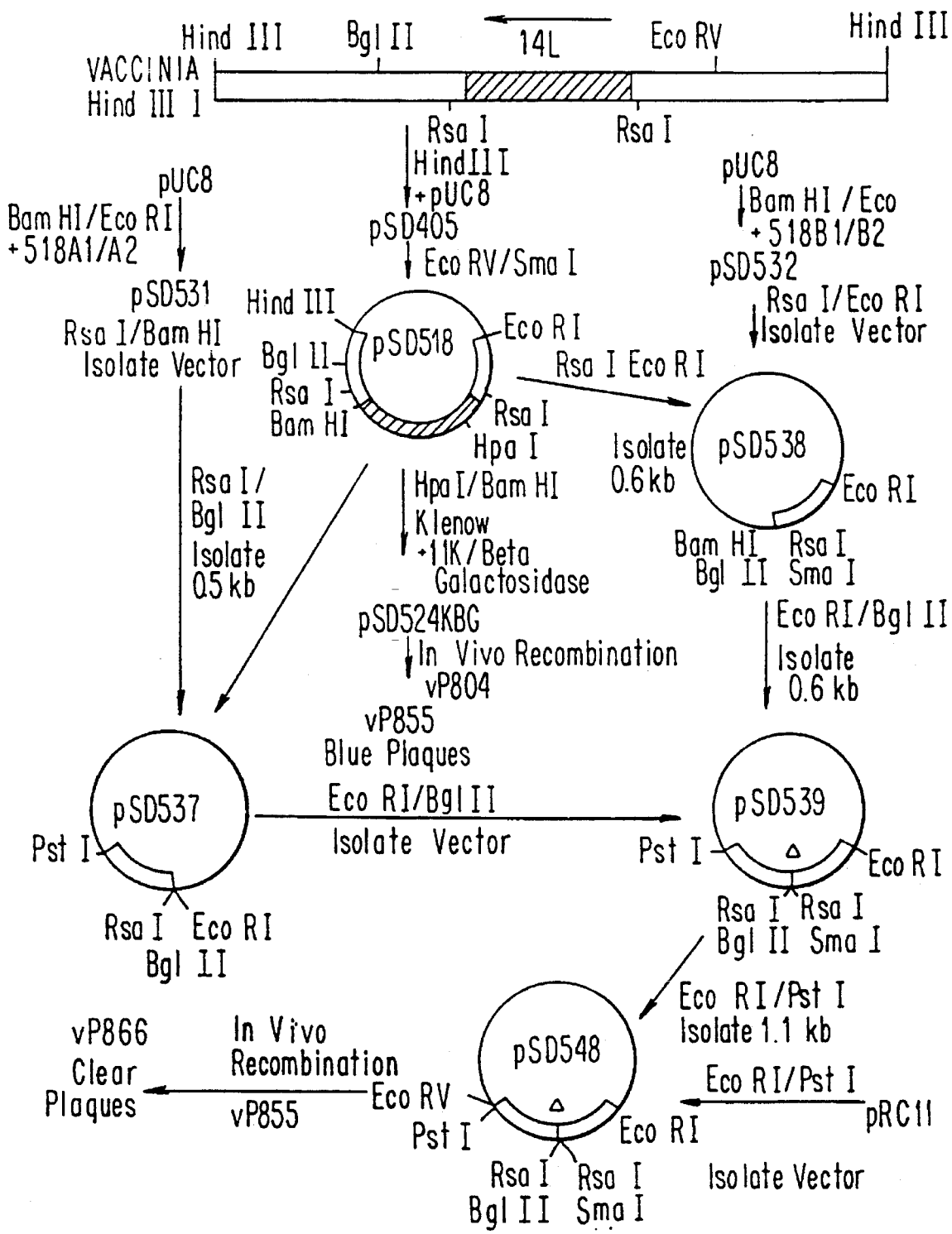
FIG. 15 schematically shows a method for the construction of plasmid pSD548 for deletion of large subunit, ribonucleotide reductase and generation of recombinant vaccinia virus vP866 (NYVAC)

Referring now to FIG. 15, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65, 059. Direction of transcription for I4L is indicated by an arrow in FIG. 15. To obtain a vector plasmid fragment deleted for a portion of the I4L coding sequences, pSD518 forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 15. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 19

INSERTION OF A RABIES GLYCOPROTEIN G GENE INTO NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 10) except for the presence of a polylinker region.

Figure 16:
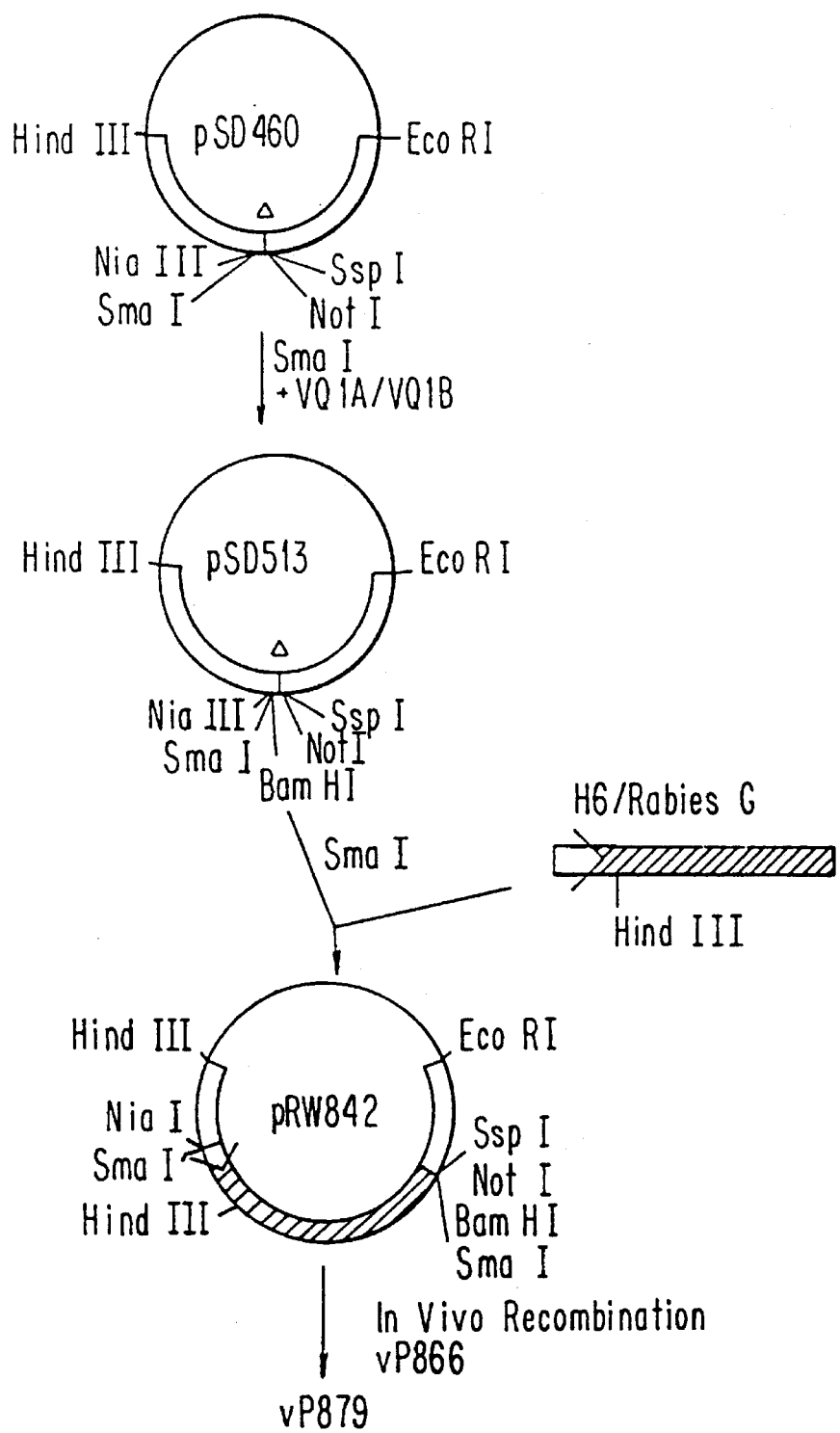
FIG. 16 schematically shows a method for the construction of plasmid pRW842 for insertion of rabies glycoprotein G gene into the TK deletion locus and generation of recombinant vaccinia virus vP879.

Referring now to FIG. 16, the polylinker region was inserted by cutting pSD460 with SmaI and ligating the plasmid vector with annealed synthetic oligonucleotides VQ1A/VQ1B (SEQ ID NO:48/SEQ ID NO:49)

```
         SmaI    BglII    XhoI    PstI     NarI    BamHI
VQ1A  5'  GGGAGATCTCTCGAGCTGCAGGGCGCCGGATCCTTTTTCT  3'
VQ1B  3'  CCCTCTAGAGAGCTCGACGTCCCGCGGCCTAGGAAAAAGA  5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 20

CONSTRUCTION OF TROVAC-NDV EXPRESSING THE FUSION AND HEMAGGLUTININ-NEURAMINIDASE GLYCOPROTEINS OF NEWCASTLE DISEASE VIRUS

This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.
Cells and Viruses.

The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.
Construction of a Cassette for NDV-F.

A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al., 1989; Perkus et al., 1989) was inserted into pCE13 by digesting pCE13 with SalI, filling in the sticky ends with Klenow fragment of E. coli DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:50) and CE76 (SEQ ID NO:51) to generate pCE47.

CE75: CGATATCCGTTAAGTTTGTATCGTAATGGGCTCCAGATCTTCTACCAGGATCCCGGTAC
CE76: CGGGATCCTGGTAGAAGATCTGGAGCCCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:52) and CE43 (SEQ ID NO:53) were then inserted to form pCE29.

CE42:  AATTCGAGCTCCCCGGG
CE43:  CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII-NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:54) and CE167 (SEQ ID NO:55) to generate pCE58.

CE166:  CTTTTTATAAAAAGTTAACTACGTAG
CE167:  GATCCTACGTAGTTAACTTTTTATAAAAAGAGCT

A perfect 3' end for NDV-F was obtained by using the polymerase chain reaction (PCR) with pCE54 as template and oligonucleotides CE182 (SEQ ID NO:56) and CE183 (SEQ ID NO:57) as primers.

CE182:  CTTAACTCAGCTGACTATCC
CE183:  TACGTAGTTAACTTTTTATAAAAATCATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.
Construction of Cassette for NDV-HN.

Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:58) and CE163 (SEQ ID NO:59) into the EcoRI site of pRW830 to form pCE59, the final cassette for NDV-HN.

CE162:
AATTCAGGATCGTTCCTTTACTAGTTGAGATTCTCAAGGATGATGGGATTTAATTTT
TATAAGCTTG

CE163:
AATTCAAGCTTATAAAAATTAAATCCCATCATCCTTGAGAATCTCAACTAGTAAAGG
AACGATCCTG

Construction of FPV Insertion Vector.

Plasmid pRW731-15 contains a 10kb PvuII-PvuII fragment cloned from genomic DNA. The nucleotide sequence was determined on both strands for a 3660 bp PvuII-EcoRV fragment. The limits of an open reading frame designated here as F8 were determined. Plasmid pRW761 is a sub-clone of pRW731-15 containing a 2430 bp EcoRV-EcoRV fragment. The F8 ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:60) and JCA018 (SEQ ID NO:61).

JCA017: 5'

CTAGACACTTTATGTTTTTTAATATCCGGTCTTAAAAGCTTCCCGGGGATCCTTATA
CGGGGAATAAT

JCA018: 5'

ATTATTCCCCGTATAAGGATCCCCCGGGAAGCTTTTAAGACCGGATATTAAAAAACA
TAAAGTGT

The plasmid resulting from this ligation was designated pJCA002.

Construction of Double Insertion Vector for NDV F and HN.

The H6 promoted NDV-HN sequence was inserted into the H6 promoted NDV-F cassette by cloning a HindIII fragment from pCE59 that had been filled in with Klenow fragment of E. coli DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+. Plasmid pJCA021 was then digested with NdeI and BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV.

Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence.

Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation.

Immunoprecipitation reactions were performed as described (Taylor et al., 1990) using a polyclonal anti-NDV serum obtained from SPAFAS Inc., Storrs, Conn.

The stock virus was screened by in situ plaque hybridization to confirm that the F8 ORF was deleted. The correct insertion of the NDV genes into the TROVAC genome and the deletion of the F8 ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO:39) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycosylated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975). Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 21

CONSTRUCTION OF ALVAC RECOMBINANTS EXPRESSING RABIES VIRUS GLYCOPROTEIN G

This example describes the development of ALVAC, a canarypox virus vector and, of a canarypox-rabies recombinant designated as ALVAC-RG (vCP65) and its safety and efficacy.

Cells and Viruses.

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector.

An 880 bp canarypox PvuII fragment was cloned between the PvuII sites of pUC9 to form pRW764.5. The sequence of this fragment is shown in FIG. 17 (SEQ ID NO:62) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:63) GCTTCCCGGGAATTCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO: 64):

ACTCTCAAAAGCTTCCCGGGAATTCTAGCTAGCTAGTTTTTATAAA

RW146 (SEQ ID NO: 65):

GATCTTTATAAAAACTAGCTAGCTAGAATTCCCGGGAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene.

Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. sequences of oligonucleotides A through E ((SEQ ID NO:66)–(SEQ ID NO:70)) are:

A (SEQ ID NO: 66):  CTGAAATTATTTCATTATCGCGATATCCGTTAA
                   GTTTGTATCGTAATGGTTCCTCAGGCTCTCCTGTTTGT

B (SEQ ID NO: 67):  CATTACGATACAAACTTAACGGATATCGCGATAA TGAAATAATTTCAG

C (SEQ ID NO: 68):  ACCCCTTCTGGTTTTTCCGTTGTGTTTTGGGAAA
                   TTCCCTATTTACACGATCCCAGACAAGCTTAGATCTCAG

D (SEQ ID NO: 69):  CTGAGATCTAAGCTTGTCTGGGATCGTGTAAATA
                   GGGAATTTCCCAAAACA

E (SEQ ID NO: 70):  CAACGGAAAAACCAGAAGGGGTACAAACAGGAGA GCCTGAGGAAC

The diagram of annealed oligonucleotides A through E is as follows:

```
            A                    C
   ─────────────────────:─────────────────
   ─────────────:────────────────:────────
            B              E         D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:71): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG.

Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 18A and 18B). The correct insertion of the rabies G gene into the ALVAC genome without subsequent mutation was confirmed by sequence analysis.

Immunofluorescence.

During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation.

Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment.

In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell lines:

(1) Primary chick embryo fibroblast (CEF) cells produced from 11 day old white leghorn embryos;

(2) Vero cells—a continuous line of African Green monkey kidney cells (ATCC # CCL81); and (3) MRC-5 cells—a diploid cell line derived from human fetal lung tissue (ATCC # CCL171).

The initial inoculation was performed at an m.o.i. of 0.1 pfu per cell using three 60 mm dishes of each cell line containing $2 \times 10^6$ cells per dish. One dish was inoculated in the presence of 40 μg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 μg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell line was inoculated undiluted onto three dishes of the same cell line (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 5 and 6.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 5 and 6 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell line was inoculated onto a permissive CEF monolayer and harvested at cytopathic effect (CPE) or at 7 days if no CPE was evident. The results of this experiment are shown in Table 7. Even after amplification through a permissive cell line, virus was only detected in MRC-5 and Vero cells for two additional passages. These results indicated that under the conditions used, there was no adaptation of either virus to growth in Vero or MRC-5 cells.

Inoculation of Macaques.

Four HIV seropositive macaques were initially inoculated with ALVAC-RG as described in Table 8. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees.

Two adult male chimpanzees (50 to 65 kg weight range) were inoculated intramuscularly or subcutaneously with $1 \times 10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice.

Groups of mice were inoculated with 50 to 100 μl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats.

Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys.

Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 μl instilled on the surface of the right eye without scarification; (2) 100 μl as several droplets in the mouth; (3) 100 μl in each of two intradermal injection sites in the shaven skin of the external face of the right arm; and (4) 100 μl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG.

In order to determine whether efficient expression of a foreign gene could be obtained in non-arian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;

(b) MRC-5, human embryonic lung, ATCC # CCL 171;

(c) WISH human amnion, ATCC # CCL 25;

(d) Detroit-532, human foreskin, Downs's syndrome, ATCC # CCL 54; and (e) Primary CEF cells.

Chicken embryo fibroblast cells produced from 11 day old white leghorn embryos were included as a positive control. All inoculations were performed on preformed monolayers of $2 \times 10^6$ cells as discussed below.

A. Methods for DNA analysis.

Three dishes of each cell line were inoculated at 5 pfu/cell of the virus under test, allowing one extra dish of each cell line un-inoculated. One dish was incubated in the presence of 40 μg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2 \times 10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 μg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene.

Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield.

The results of titration for yield at 72 hours after inoculation at 0.1 pfu per cell are shown in Table 9. The results indicate that while a productive infection can be attained in the avian cells, no increase in virus yield can be detected by this method in the four non-avian cell systems.

Analysis of Viral DNA Accumulation.

In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which vital DNA replication was measured by 3H-thymidine incorporation support the results obtained with Vero and MRC-5 cells.

Analysis of Rabies Gene Expression.

To determine if any viral gene expression, particularly that of the inserted foreign gene, was occurring in the human cell lines even in the absence of viral DNA replication, immunoprecipitation experiments were performed on $^{35}$S-methionine labelled lysates of arian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable vital progeny produced. In the Vero cells, although some level of ALVAC-RG specific DNA accumulation was observed, no vital progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID50 per ml were serially diluted and 50 to 100 µl of dilutions inoculated into the footpad of four to six week old mice. Mice were challenged 14 days later by the intracranial route with 300 µl of the CVS strain of rabies virus containing from 15 to 43 mouse $LD_{50}$ as determined by lethality titration in a control group of mice. Potency, expressed as the $PD_{50}$ (Protective dose 50%), was calculated at 14 days post-challenge. The results of the experiment are shown in Table 10. The results indicated that ALVAC-RG was consistently able to protect mice against rabies virus challenge with a $PD_{50}$ value ranging from 3.33 to 4.56 with a mean value of 3.73 (STD 0.48). As an extension of this study, male mice were inoculated intracranially with 50 µl of virus containing 6.0 $\log_{10}$ $TCID_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ $TCID_{50}$ subcutaneously and five animals received 7.7 $\log_{10}$ $TCID_{50}$ by the same route. Animals were bled for analysis for anti-rabies antibody. Animals receiving no inoculation or 6.7 $\log_{10}$ $TCID_{50}$ of ALVAC-RG were challenged at 29 days post-vaccination with 3.7 $\log_{10}$ mouse $LD_{50}$ (dogs, in the temporal muscle) or 4.3 $\log_{10}$ mouse $LD_{50}$ (cats, in the neck) of the NYGS rabies virus challenge strain. The results of the experiment are shown in Table 11.

No adverse reactions to inoculation were seen in either cats or dogs with either dose of inoculum virus. Four of 5 dogs immunized with 6.7 $\log_{10}$ $TCID_{50}$ had antibody titers on day 14 post-vaccination and all dogs had titers at 29 days. All dogs were protected from a challenge which killed three out of four controls. In cats, three of five cats receiving 6.7 $\log_{10}$ $TCID_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ $TCID_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intramuscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 12.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An amnanestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 13, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 14.

No adverse reactivity to inoculation was noted by either intramuscular or subcutaneous routes. Both chimpanzees responded to primary inoculation by 14 days and a strongly rising response was detected following re-vaccination.

TABLE 5

Sequential Passage of ALVAC in Avian and non-Avian Cells.

|  |  | CEF | Vero | MRC-5 |
|---|---|---|---|---|
| Pass 1 |  |  |  |  |
| Sample | to[a] | 2.4 | 3.0 | 2.6 |
|  | t7[b] | 7.0 | 1.4 | 0.4 |
|  | t7A[c] | 1.2 | 1.2 | 0.4 |
| Pass 2 |  |  |  |  |
| Sample | to | 5.0 | 0.4 | N.D.[d] |
|  | t7 | 7.3 | 0.4 | N.D. |
|  | t7A | 3.9 | N.D. | N.D. |
| Pass 3 |  |  |  |  |
| Sample | to | 5.4 | 0.4 | N.D. |
|  | t7 | 7.4 | N.D. | N.D. |

TABLE 5-continued

Sequential Passage of ALVAC in Avian and non-Avian Cells.

|  |  | CEF | Vero | MRC-5 |
|---|---|---|---|---|
|  | t7A | 3.8 | N.D. | N.D. |
| Pass 4 |  |  |  |  |
| Sample | to | 5.2 | N.D. | N.D. |
|  | t7 | 7.1 | N.D. | N.D. |
|  | t7A | 3.9 | N.D. | N.D. |

[a]: This sample was harvested at zero time and represents the residual input virus. The titer is expressed as $\log_{10}$ pfu per ml.
[b]: This sample was harvested at 7 days post-infection.
[c]: This sample was inoculated in the presence of 40 µg/ml of Cytosine arabinoside and harvested at 7 days post infection.
[d]: Not detectable

TABLE 6

Sequential Passage of ALVAC-RG in Avian and non-Avian Cells

|  |  | CEF | Vero | MRC-5 |
|---|---|---|---|---|
| Pass 1 |  |  |  |  |
| Sample | to[a] | 3.0 | 2.9 | 2.9 |
|  | t7[b] | 7.1 | 1.0 | 1.4 |
|  | t7A[c] | 1.8 | 1.4 | 1.2 |
| Pass 2 |  |  |  |  |
| Sample | to | 5.1 | 0.4 | 0.4 |
|  | t7 | 7.1 | N.D.[d] | N.D. |
|  | t7A | 3.8 | N.D. | N.D. |
| Pass 3 |  |  |  |  |
| Sample | to | 5.1 | 0.4 | N.D. |
|  | t7 | 7.2 | N.D. | N.D. |
|  | t7A | 3.6 | N.D. | N.D. |
| Pass 4 |  |  |  |  |
| Sample | to | 5.1 | N.D. | N.D. |
|  | t7 | 7.0 | N.D. | N.D. |
|  | t7A | 4.0 | N.D. | N.D. |

[a]: This sample was harvested at zero time and represents the residual input virus. The titer is expressed as $\log_{10}$ pfu per ml.
[b]: This sample was harvested at 7 days post-infection.
[c]: This sample was inoculated in the presence of 40 µg/ml of Cytosine arabinoside and harvested at 7 days post infection.
[d]: Not detectable.

TABLE 7

Amplification of residual virus by passage in CEF cells

|  |  | CEF | Vero | MRC-5 |
|---|---|---|---|---|
| a) ALVAC |  |  |  |  |
| Pass | 2[a] | 7.0[b] | 6.0 | 5.2 |
|  | 3 | 7.5 | 4.1 | 4.9 |
|  | 4 | 7.5 | N.D.[c] | N.D. |
|  | 5 | 7.1 | N.D. | N.D. |
| b) ALVAC-RG |  |  |  |  |
| Pass | 2[a] | 7.2 | 5.5 | 5.5 |
|  | 3 | 7.2 | 5.0 | 5.1 |
|  | 4 | 7.2 | N.D. | N.D. |
|  | 5 | 7.2 | N.D. | N.D. |

[a]: Pass 2 represents the amplification in CEF cells of the 7 day sample from Pass 1.
[b]: Titer expressed as $\log_{10}$ pfu per ml
[c]: Not Detectable

TABLE 8

Schedule of inoculation of rhesus macaques with ALVAC-RG (vCP65)

| Animal | | Inoculation |
|---|---|---|
| 176L | Primary: | $1 \times 10^8$ pfu of vCP65 orally in TANG |
| | Secondary: | $1 \times 10^7$ pfu of vCP65 plus $1 \times 10^7$ pfu of vCP82[a] by SC route |
| 185L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP65 by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP65 orally |

[a]: vCP82 is a canarypox virus recombinant expressing the measles virus fusion and hemagglutinin genes.

TABLE 9

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]: Titer expressed as $\log_{10}$ pfu per ml
[b]: Culture incubated in the presence of 40 µg/ml of Cytosine arabinoside

TABLE 10

Potency of ALVAC-RG as tested in mice

| Test | Challenge Dose[a] | $PD_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]: Expressed as mouse $LD_{50}$
[b]: Expressed as $\log_{10} TCID_{50}$

TABLE 11

Efficacy of ALVAC-RG in dogs and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | |
| N.T. | | | | |

[a]: Antibody at day 29 post inoculation expressed as the geometric mean titer in International Units.
[b]: Expressed as a ratio of survivors over animals challenged

TABLE 12

Anti-rabies serological response of Squirrel monkeys inoculated with canarypox recombinants

| Monkey # | Previous Exposure | Rabies serum-neutralizing antibody[a] | | | | | |
|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]: As determined by RFFI test on days indicated and expressed in International Units
[b]: Day −196 represents serum from day 28 after primary vaccination
[c]: Animals received 5.0 $\log_{10}$ $TCID_{50}$ of ALVAC
[d]: Animals received 5.0 $\log_{10}$ $TCID_{50}$ of vCP37
[e]: Animals received 5.0 $\log_{10}$ $TCID_{50}$ of ALVAC-RG
[f]: Animals received 7.0 $\log_{10}$ $TCID_{50}$ of ALVAC-RG
[g]: Not tested.

TABLE 13

Inoculation of rhesus macaques with ALVAC-RG[a]

| Days post-Inoculation | Route of Primary Inoculation | | | | | | | | | | |
|---|---|---|---|---|---|---|---|---|---|---|---|
| | or/Tang | | SC | SC | SC | IM | SC | IM | SC | IM | OR |
| | 176L[b] | 185L | 177L | 186L | 178L | 182L | 179L | 183L | 180L | 184L | 187L[b] |
| −84 | — | — | | | | | | | | | |
| −9 | — | — | — | — | — | — | | | | | |
| 3 | — | — | — | — | | | | | | | |
| 6 | — | — | ± | ± | | | | | | | |
| 11 | — | — | 16[d] | 128 | | | | | | | |
| 19 | — | — | 32 | 128 | — | | — | | | | |
| 35 | — | — | 32 | 512 | | | | | | | |
| 59 | — | — | 64 | 256 | | | | | | | |
| 75 | — | — | 64 | 128 | — | | — | | | | |
| 99[c] | — | — | 64 | 256 | — | — | — | — | — | — | — |
| 2 | — | — | 32 | 256 | — | — | — | — | — | — | |
| 6 | — | — | 512 | 512 | — | — | — | — | — | — | |
| 15 | 16 | 16 | 512 | 512 | 64 | 32 | 64 | 128 | 32 | — | — |
| 29 | 16 | 32 | 256 | 256 | 64 | 64 | 32 | 128 | 32 | — | — |
| 55 | | 32 | | | | 32 | | 32 | 16 | — | |
| 57 | 16 | | 128 | 128 | 16 | | 16 | | | — | — |

[a]: See Table 9 for schedule of inoculations.
[b]: Animals 176L and 185L received 8.0 log$_{10}$ pfu by the oral route in 5 ml Tang. Animal 187L received 7.0 log$_{10}$ pfu by oral route not in Tang.
[c]: Days of re-vaccination for animals 176L, 185L, 177L and 186L by S.C. route, and primary vaccination for animals 178L, 182L, 179L, 183L, 180L, 184L and 187L.
[d]: Titers expressed as reciprocal of last dilution showing inhibition of fluorescence in an RFFI test.

TABLE 14

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |
| 20/8 | 64 | 128 |
| 26/12 | 32 | 128 |

[a]: Titer expressed as reciprocal of last dilution showing inhibition of fluorescence in an RFFI test
[b]: Day of re-inoculation Example 22

IMMUNIZATION OF HUMANS USING CANARYPOX EXPRESSING RABIES GLYCOPROTEIN (ALVAC-RG; vCP65)

Figure 18A:
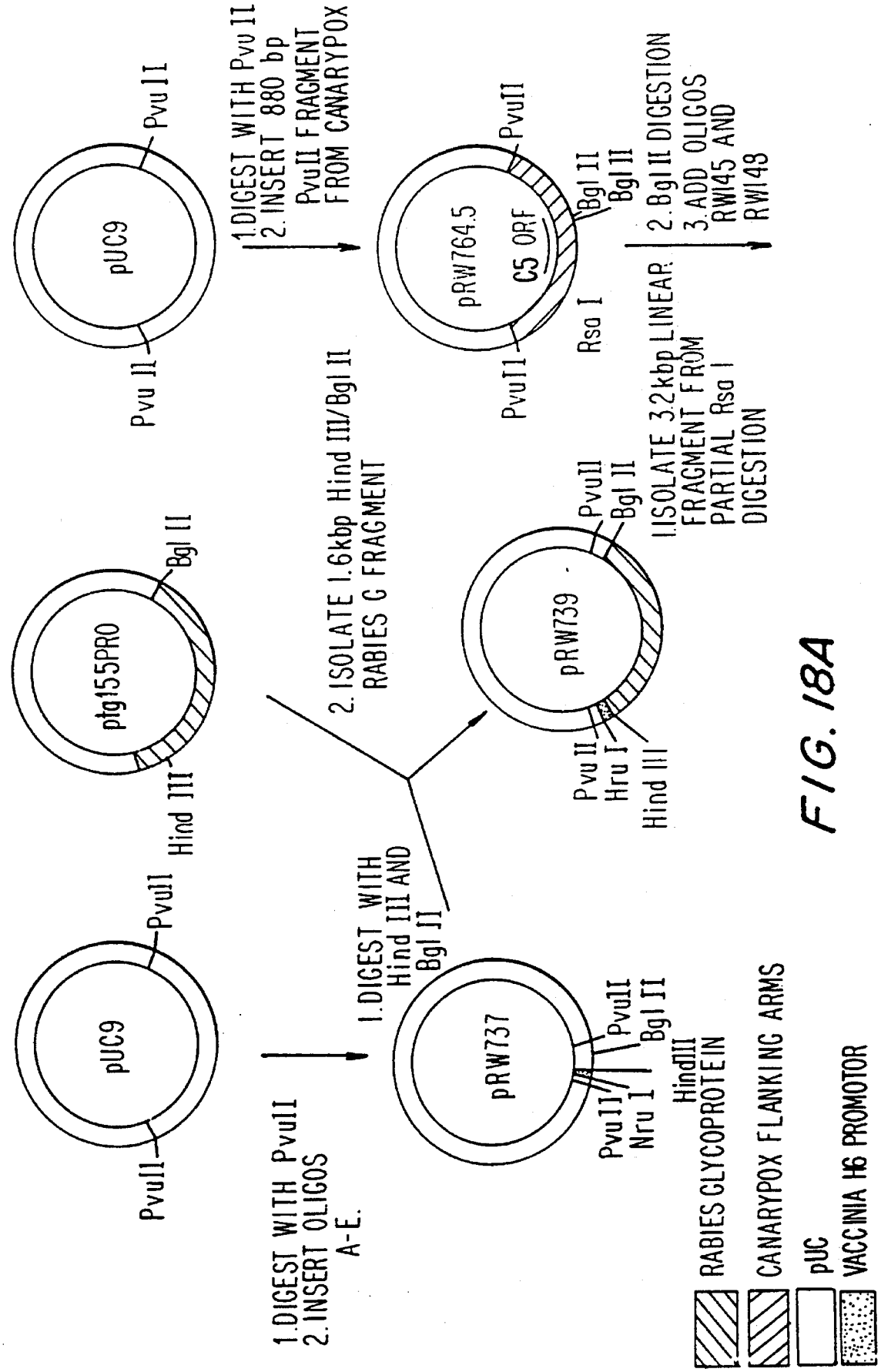
FIGS. 18A and 18B schematically show a method for the construction of recombinant canarypox virus vCP65 (ALVAC-RG)
Figure 18B:
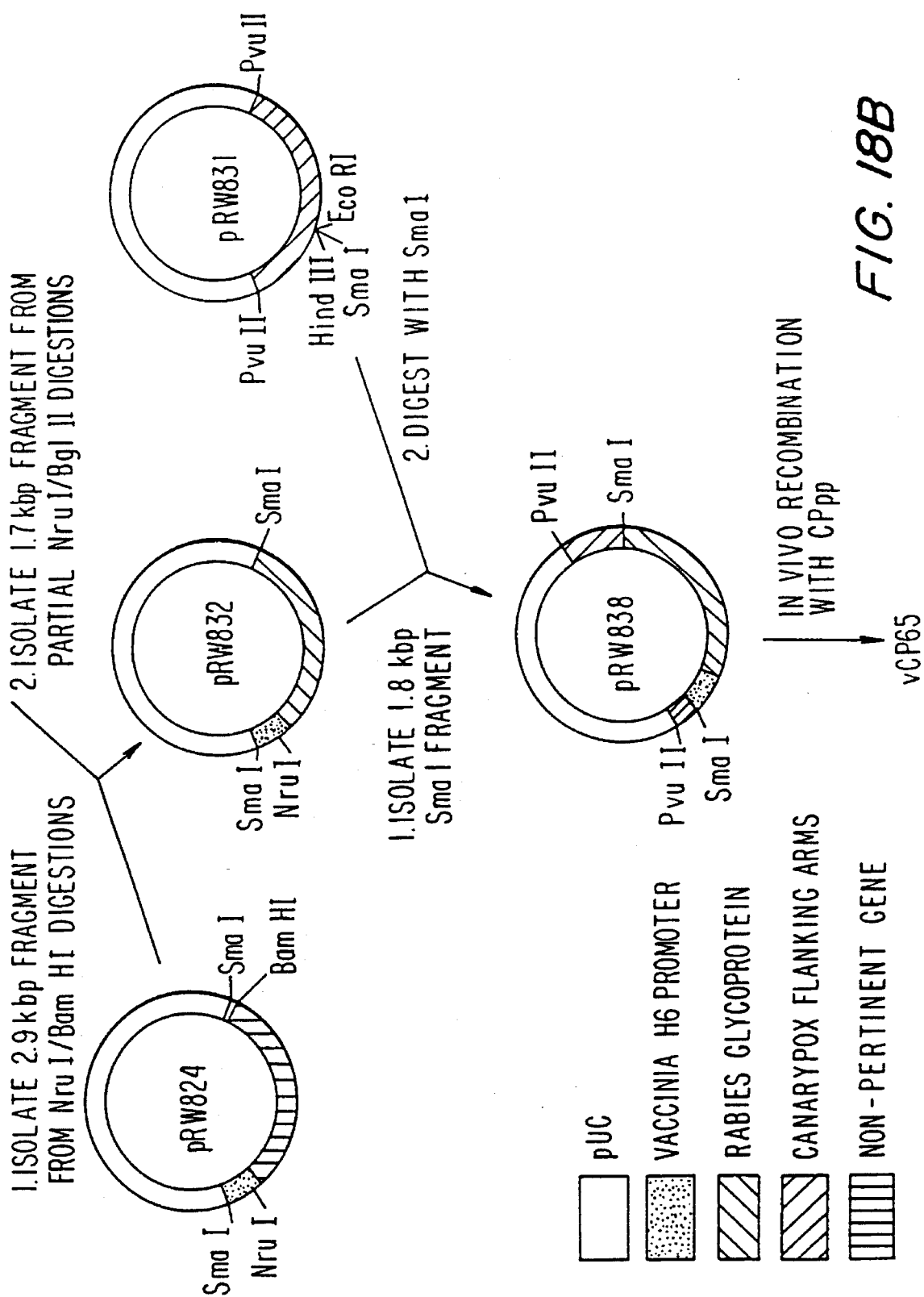

ALVAC-RG (vCP65) was generated as described in Example 21 and FIGS. 18A and 18B. For scaling-up and vaccine manufacturing ALVAC-RG (vCP65) was grown in primary CEF derived from specified pathogen free eggs, Cells were infected at a multiplicity of 0.01 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No undesirable trait was found.

Preclinical data.

Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers.

Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design.

Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC-HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects.

All subjects were monitored for 1 h after injection and re-examined every day for the next five days. They were asked to record local and systemic reactions for the next three weeks and were questioned by telephone two times a week.

Laboratory Investigators.

Blood specimens were obtained before enrollment and two, four and six days after each injection. Analysis included complete blood cell count, liver enzymes and creatine kinase assays.

Antibody assays.

Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith & Yaeger, In Laboratory Techniques on Rabies). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490 nm.

Analysis.

Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 14).

During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses; Neutralizing Antibodies to Rabies (Table 16).

Twenty eight days after the first injection all the HDC recipients had protective titers ($\geq 0.5$ IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 17).

The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection.

The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations.

FIGS. 22A–22D shows graphs of rabies neutralizing antibody titers (Rapid Fluorescent Focus Inhibition Test or RFFIT, IU/ml): Booster effect of HDC and vCP65 ($10^{5.5}$ TCID$_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 22A–22D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)–ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., Lancet 1991, 337:567–72; Etinger et al., Vaccine 9:470–72, 1991).

Thus, this Example clearly demonstrates that a non-replicating poxvirus can serve as an immunizing vector in animals or humans, with all of the advantages that replicating agents confer on the immune response, but without the safety problem created by a fully permissive virus.

TABLE 15

Reactions in the 5 days following vaccination

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 16

Rabies neutralizing antibodies (REFIT; IU/ml) Individual titers and geometric mean titers GMT)

| No. | TCID50/dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| G.M.T. | | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| G.M.T. | | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| G.M.T. | | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| G.M.T. | | <0.1 | <0.1 | 2.96 | 9.0 | 11.5* |

*p = 0.007 student t test

TABLE 17

Canarypox antibodies: ELISA Geometric Mean Titers*

| vCP65 dosage | Days | | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

Example 23

COMPARISON OF THE LD$_{50}$ OF ALVAC AND NYVAC WITH VARIOUS VACCINIA VIRUS STRAINS

Mice.

Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses.

ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated in CEF cells.

Inoculations.

Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population (LD$_{50}$) was determined by the proportional method of Reed and Muench.

Comparison of the LD$_{50}$ of ALVAC and NYVAC with Various Vaccinia Virus Strains for Normal, Young Outbred Mice by the ic Route.

In young, normal mice, the virulence of NYVAC and ALVAC were several orders of magnitude lower than the other vaccinia virus strains tested (Table 18). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses (3.85×10$^8$ PFUs, ALVAC and 3×10$^8$ PFUs, NYVAC) by an undetermined mechanism by this route of inoculation.

Comparison of the LD$_{50}$ of ALVAC and NYVAC with Various Vaccinia Virus Strains for Newborn Outbred Mice by the ic Route.

The relative virulence of 5 poxvirus strains for normal, newborn mice was tested by titration in an intracranial (ic) challenge model system (Table 19). With mortality as the endpoint, LD$_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, 6.3×10$^7$ PFUs, 100% mortality resulted. Mortality rates of 33.3% were observed at 6.3×10$^6$ PFUs. The cause of death, while not actually determined, was not likely of toxicological or traumatic nature since the mean survival time (MST) of mice of the highest dosage group (approximately 6.3 LD$_{50}$) was 6.7±1.5 days. When compared to WR(L) at a challenge dose of 5 LD$_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, 6×10$^8$ and 6×10$^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 LD$_{50}$, survived to day 4.

TABLE 18

Calculated 50% Lethal Dose for mice by various vaccinia virus strains and for canarypox virus (ALVAC) by the ic route.

| POXVIRUS STRAIN | CALCULATED LD$_{50}$ (PFUs) |
| --- | --- |
| WR(L) | 2.5 |
| VC-2 | 1.26 × 10$^4$ |
| WYETH | 5.00 × 10$^4$ |
| NYVAC | 1.58 × 10$^8$ |
| ALVAC | 1.58 × 10$^8$ |

TABLE 19

Calculated 50% Lethal Dose for newborn mice by various vaccinia virus strains and for canarypox virus (ALVAC) by the ic route.

| POXVIRUS STRAIN | CALCULATED LD$_{50}$ (PFUs) |
| --- | --- |
| WR(L) | 0.4 |
| VC-2 | 0.1 |
| WYETH | 1.6 |
| NYVAC | 1.58 × 10$^6$ |
| ALVAC | 1.00 × 10$^7$ |

Example 24

EVALUATION OF NYVAC (vP866) AND NYVAC-RG (vP879)

Immunoprecipitations.

Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trimarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals.

New Zealand White rabbits were obtained from Hare-Marland (Hewitt, N.J.). Three week old male Swiss Webster outbred mice, timed pregnant female Swiss Webster outbred mice, and four week old Swiss Webster nude (nu$^+$nu$^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits.

Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites.

A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice.

Groups of ten mice, or five in the nude mice experiment, were inoculated ip with one of several dilutions of virus in 0.5 ml of sterile PBS. Reference is also made to Example 23.

Cyclophosphamide (CY) Treatment.

Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per µl for untreated mice (n=4) and 4,220 cells per µl for CY-treated control mice (n=5).

Calculation of $LD_{50}$.

The lethal dose required to produce 50% mortality ($LD_{50}$) was determined by the proportional method of Reed and Muench (Reed and Muench 1938).

Potency Testing of NYVAC-RG in Mice.

Four to six week old mice were inoculated in the footpad with 50 to 100 µl of a range of dilutions (2.0–8.0 log$_{10}$ tissue culture infective dose 50% (TCID$_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 LD$_{50}$ of the rabies virus CVS strain (0.03 ml). On day 28, surviving mice were counted and protective does 50% (PD$_{50}$) calculated.

Derivation of NYVAC (vP866).

Figure 19:
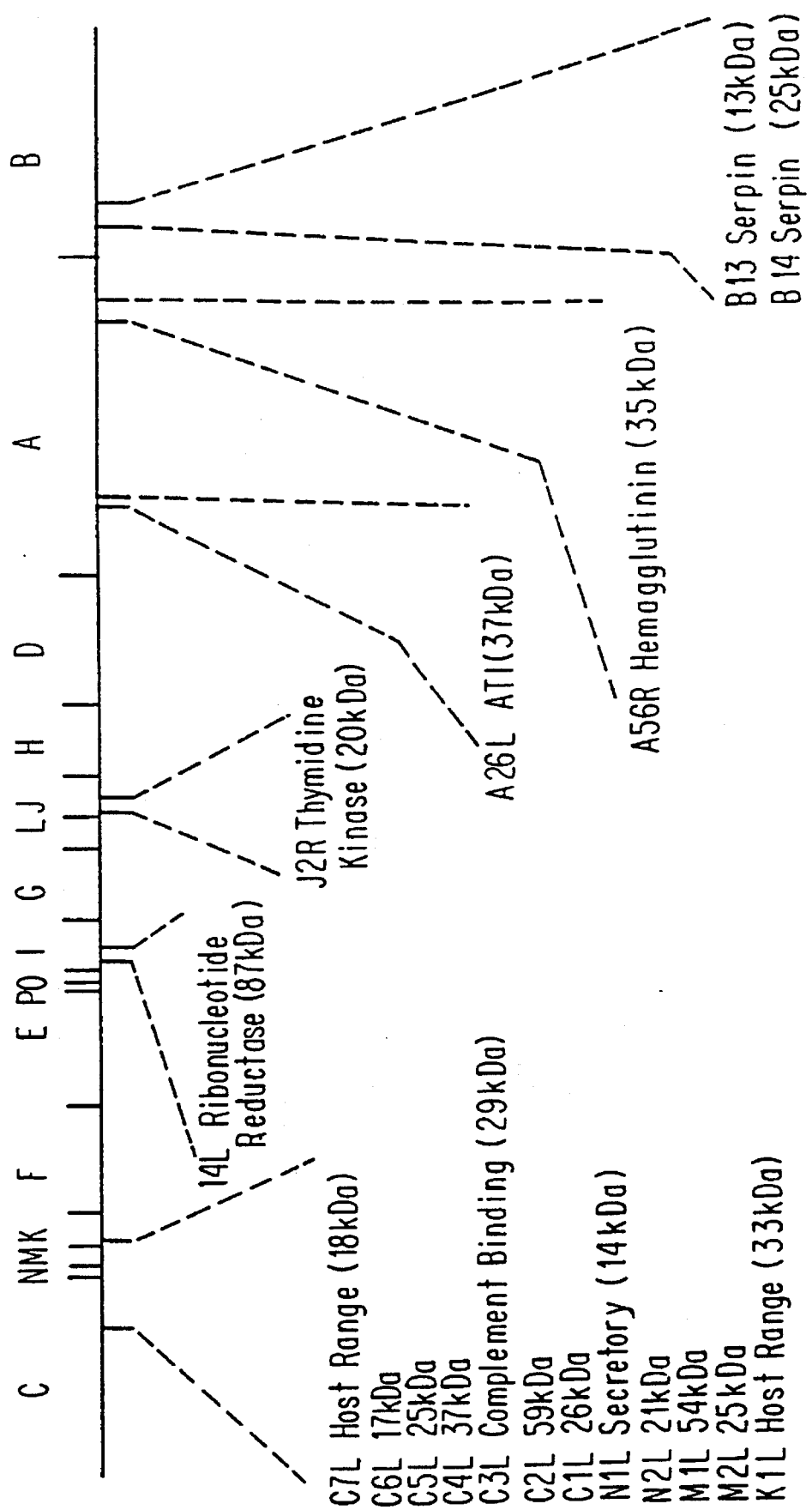
FIG. 19 shows schematically the ORFs deleted to generate NYVAC.
Figure 22A:
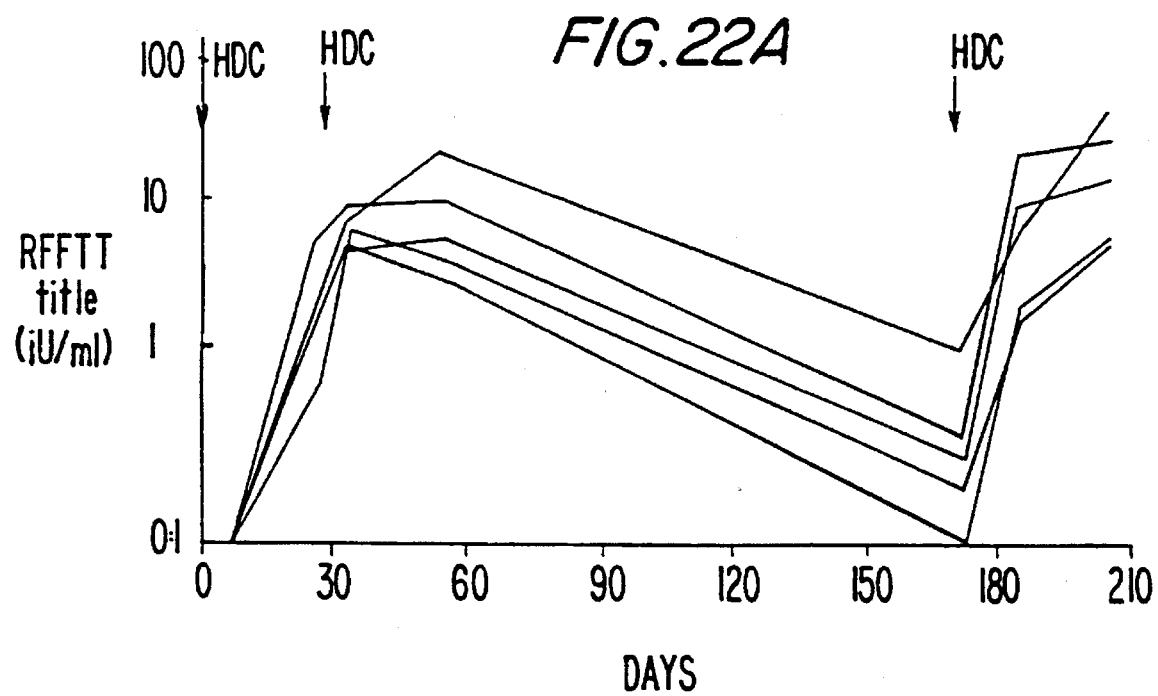
FIGS. 22A to 22D show graphs of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208).
Figure 22C:
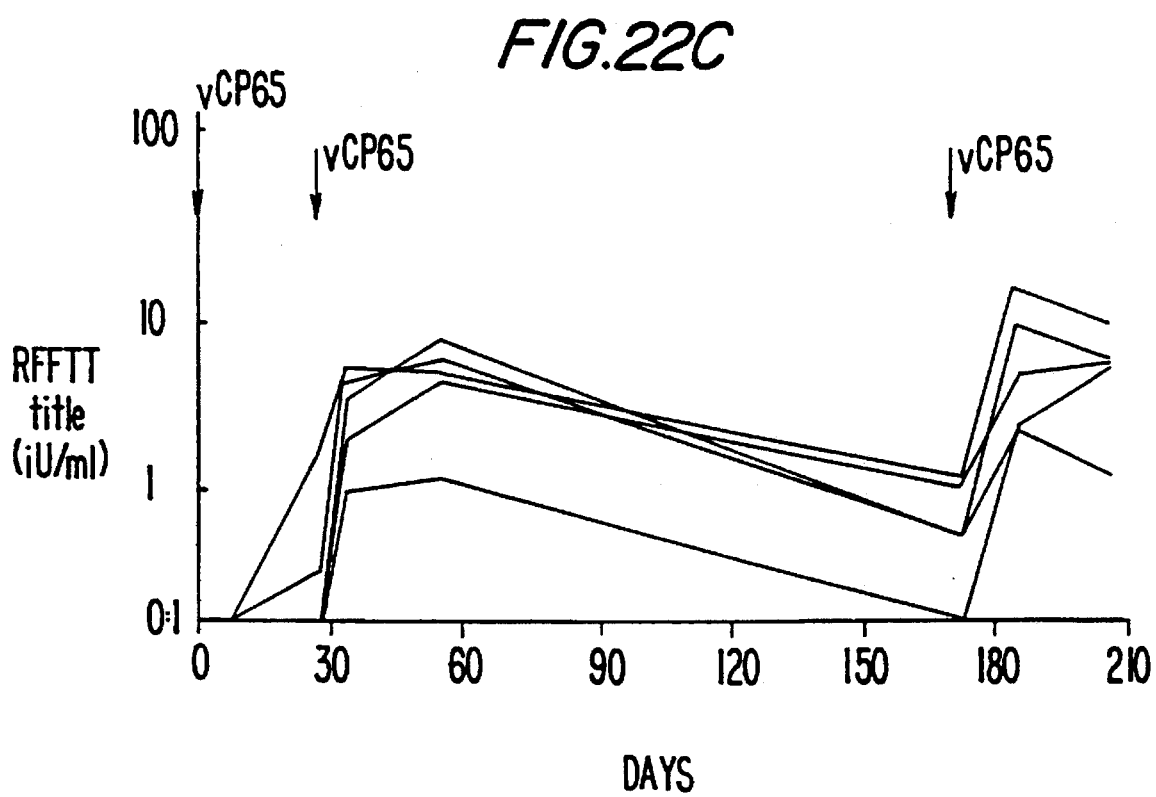
Figure 22B:
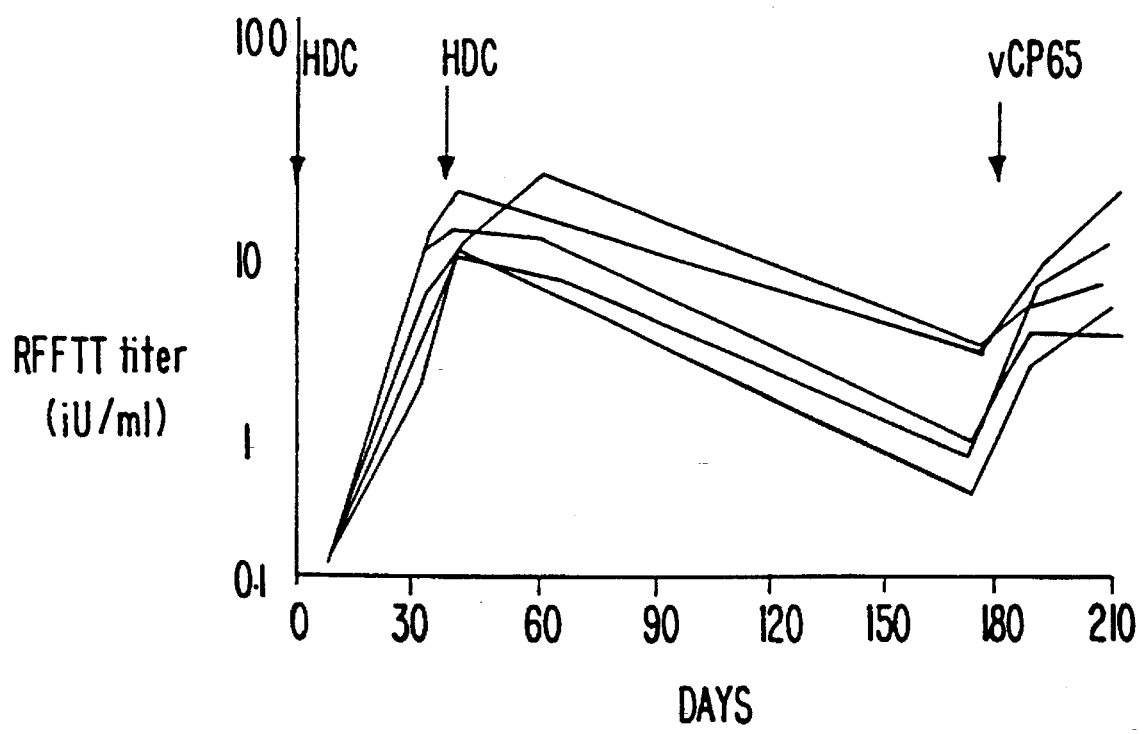
Figure 22D:
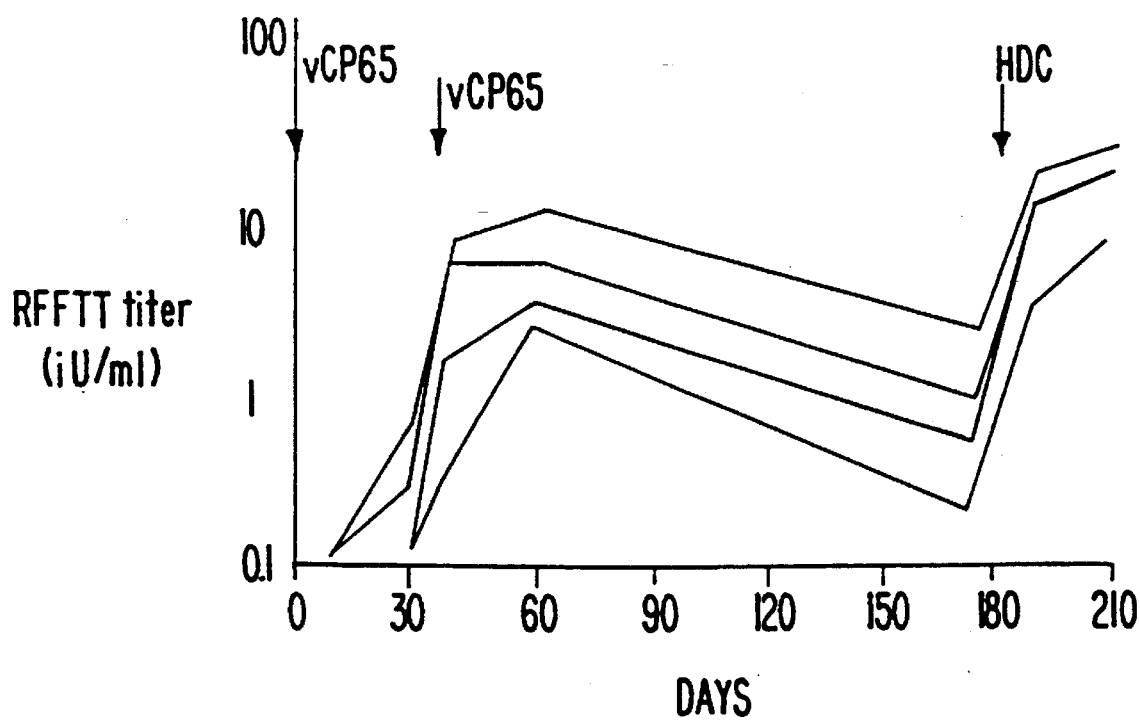

The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 19 schematically depicts the ORFs deleted to generate NYVAC. At the top of FIG. 19 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 13 through 18). Below such deletion locus is listed the ORFs which were deleted from that locus, along with the functions or homologies and molecular weight of their gene products.

Replication Studies of NYVAC and ALVAC on Human Tissue Cell Lines.

In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 20. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contract, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70-151) cells. Replication on these cell lines was significantly reduced when compared to virus yields obtained from NYVAC-infected CEF cells or with parental VC-2 (Table 20). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 20. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells.

In order to determine whether efficient expression of a foreign gene could be obtained in the absence of significant levels of productive viral replication, the same cell lines were inoculated with the NYVAC recombinant expressing the rabies virus glycoprotein (vP879, Example 19) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin.

The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 21). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation.

To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 22). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells. The results are shown in Table 22. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice.

Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 23.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu) on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu showed lesions on toes and tails, developed orchitis, and died. Mice injected with $5 \times 10^6$ pfu or less of WYETH showed no signs of disease or lesions.

As shown in Table 23, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG.

In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 24 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations.

NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 23). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 18–24). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 23, Tables 18, 19, 23). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 21 and 22). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 21 and 22). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of genes in NYVAC prevents lesion occurrence.

Together, the results in this Example and in foregoing Examples, including Example 23, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 20) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 24). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1990). Furthermore, the use of NYVAC as a general laboratory expression vector system may greatly reduce the biological hazards associated with using vaccinia virus.

By the following criteria, the results of this Example and the Examples herein, including Example 23, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 20

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]: Yield of NYVAC at 72 hours post-infection expressed as a percentage of yield of VAC-2 after 72 hours on the same cell line.
[b]: Titer expressed as $LOG_{50}$ pfu per ml.
[c]: Sample was incubated in the presence of 40 μg/ml of cytosine arabinoside.
[d]: Not determined.
*: ATCC #CCL25 Human amnionic cells.

TABLE 21

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]: pfu of indicated vaccinia virus in 0.1 ml PBS inoculated intradermally into one site.
[b]: mean maximum size of lesions (mm²)
[c]: mean time after inoculation for complete healing of lesion.
[d]: no lesions discernable.

TABLE 22

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]: expressed as $\log_{10}$ pfu.

TABLE 23

Virulence studies in immunocompromised mice

| Poxvirus Strain | $LD_{50}$[a] Nude mice | Cyclophosphamide treated mice |
|---|---|---|
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $\geq 5.00 \times 10^{8b}$ |

[a]: Calculated 50% lethal dose (pfu) for nude or cyclophosphamide treated mice by the indicated vaccinia viruses and for ALVAC by intraperitoneal route.
[b]: 5 out of 10 mice died at the highest dose of $5 \times 10^8$ pfu.

TABLE 24

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]: Four to six week old mice were inoculated in the footpad with 50–100 μl of a range of dilutions (2.0–8.0 $\log_{10}$ tissue culture infection dose 50% ($TCID_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% ($LD_{50}$) per mouse. At day 28, surviving mice were counted and a protective dose 50% ($PD_{50}$) was calculated.

Example 25

CONSTRUCTION OF TROVAC RECOMBINANTS EXPRESSING THE HEMAGGLUTININ GLYCOPROTEINS OF AVIAN INFLUENZA VIRUSES

This Example describes the development of fowlpox virus recombinants expressing the hemagglutinin genes of three serotypes of arian influenza virus.

RW178 (SEQ ID NO: 70): 5'  TCATTATCGCGATATCCGTGTTAACTAGCTA
GCTAATTTTTATTCCCGGGATCCTTATCA 3'

RW179 (SEQ ID NO: 71): 5'  GTATAAGGATCCCGGGAATAAAAATTAGCT
AGCTAGTTAACACGGATATCGCGATAATGA 3'

Cells and Viruses.

Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Construction of Fowlpox Insertion Plasmid at F8 Locus.

Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 20 (SEQ ID NO:72). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:60) and JCA018 (SEQ ID NO:61).

JCA017 (SEQ ID NO: 60) 5'  CTAGACACTTTATGTTTTTTAATATCCGGTCTT
AAAAGCTTCCCGGGGATCCTTATATCGGGGAATAAT 3'

JCA018 (SEQ ID NO: 61) 5'  ATTATTCCCCGTATAAGGATCCCCCGGGAA
GCTTTTAAGACCGGATATTAAAAAACATAAAGTGT 3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:73) and RW179 (SEQ ID NO:74) were cut with EcoRV and BamHI and inserted between the EcoRV and BamHI sites of JCA004 to form pRW846.

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus.

The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 21 (SEQ ID NO:75) was determined for a 2356 bp region encompassing the unique HincII site. Analysis of this sequence revealed that the unique HincII site (FIG. 21, underlined) was situated within an ORF encoding a polypeptide of 90 amino acids. The ORF begins with an ATG at position 1531 and terminates at position 898 (positions marked by arrows in FIG. 21).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:76) (5'-GACAATCTAAGTCCTATATTAGAC-3') and F73PB (SEQ ID NO:77) (5'-GGATTTTTAGGTAGACAC-3'). A 270 bp arm (designated as EH) corresponding to the region downstream from the ORF was amplified using oligonucleotides F75PE (SEQ ID NO:78) (5'-TCATCGTCTTCATCATCG-3') and F73PH1 (SEQ ID NO:79) (5'-GTCTTAAACTTATTGTAAGGGTATACCTG-3').

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the E. coli DNA polymerase in the presence of 2 mM dNTPs. This linearized plasmid was ligated with annealed oligonucleotides F7MCSB (SEQ ID NO: 80) (5'-AACGATTAGTTAGTTAC-TAAAAGCTTGCTGCAGCCCGGGTTTTT-TATTAGTTTAGTTAGTC-3') and F7MCSA (SEQ ID NO:81) (5'-GACTAACTAACTAATAAAAAAC-CCGGGCTGCAGCAAGCTTTTTGTAAC-TAACTAATCGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus.

A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recut with HindIII. Plasmid pRW828 now with a 100 bp HindIII-BanII deletion was used as a vector for the synthetic oligonucleotides RW152 (SEQ ID NO:82) and RW153 (SEQ ID NO:83). These oligonucleotides represent the 3' portion of the H6 promoter from the EcoRV site and align the ATG of the promoter with the ATG of the H4 cDNA.

```
RW152  (SEQ ID NO: 82):  5'  GCACGGAACAAAGCTTATCGCGATATCCGTTA
                             AGTTTGTATCGTAATGCTATCAATCACGATTCTGTTCCTGCTCAT
                             AGCAGAGGGCTCATCTCAGAAT  3'
RW153  (SEQ ID NO: 83):  5'  ATTCTGAGATGAGCCCTCTGCTATGAGCAGGA
                             ACAGAATCGTGATTGATAGCATTACGATACAAACTTAACGGATAT
                             CGCGATAAGCTTTGTTCCGTGC  3'
```

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

Construction of Insertion Plasmid for H5 Hemagglutinin at the F8 Locus.

A cDNA clone of avian influenza H5 derived from A/Turkey/Ireland/1378/83 was received in plasmid pTH29 from Dr. R. Webster. Synthetic oligonucleotides RW10 (SEQ ID NO:84) through RW13 (SEQ ID NO:87) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

```
RW10  (SEQ ID NO: 84):  5'  GAAAAATTTAAAGTCGACCGTTTTGTTGAGT
                            TGTTTGCGTGGTAACCAATGCAAATCTGGTC
                            ACT  3'

RW11  (SEQ ID NO: 85):  5'  TCTAGCAAGACTGACTATTGCAAAAAGAAGCA
                            CTATTTCCTCCATTACGATACAAACTTAACG
                            GAT  3'

RW12  (SEQ ID NO: 86):  5'  ATCCGTTAAGTTTGTATCGTAATGGAGGAAA
                            TAGTGCTTCTTTTTGCAATAGTCAGTCTTGCTAGAAGTGACCAGA
                            TTTGCATTGGT  3'

RW13  (SEQ ID NO: 87):  5'  TACCACGCAAACAACTCAACAAAACAGGTCG
                            ACTTTAAATTTTTCTGCA  3'
```

The oligonucleotides were annealed at 95° C. for three minutes followed by slow cooling at room temperature. This results in the following double strand structure with the indicated ends.

| EcoRV | | | | PstI |
|---|---|---|---|---|
| | RW12 | | RW13 | |
| RW11 | | | RW10 | |

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5 3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recut with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting plasmid pRW849 contains the H6 promoted arian influenza virus H5 gene in the de-ORFed F8 locus.

Construction of Insertion Vector for H7 Hemagglutinin at the F7 Locus.

Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:88) and RW166 (SEQ ID NO:89) were annealed, cut with HincII and StyI and inserted between the EcoRV and StyI sites of pRW827 to generate pRW845.

kb resultant fragment was isolated and blunt-ended using the Klenow fragment of the *E. coli* DNA polymerase in the presence of 2 mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants.

Insertion plasmids containing the avian influenza virus HA coding sequences were individually transfected into RW165 (SEQ ID NO: 88):   5'   GTACAGGTCGACAAGCTTCCCGGGTATCGCG
                              ATATCCGTTAAGTTTGTATCGTAATGAATACTCAAATTCTAATAC
                              TCACTCTTGTGGCAGCCATTCACACAAATGCAGACAAAATCTGCC
                              TTGGACATCAT   3'

RW166 (SEQ ID NO: 89):   5'   ATGATGTCCAAGGCAGATTTTGTCTGCATTTG
                              TGTGAATGGCTGCCACAAGAGTGAGTATTAGAATTTGAGTATTA
                              TTACGATACAAACTTAACGGATATCGCGATACCCGGGAAGCTTGT
                              CGACCTGTAC   3'

Oligonucleotides RW165 (SEQ ID NO:88) and RW166 (SEQ ID NO:89) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:90) and RW228 (SEQ ID NO:91). The resulting plasmid was pRW854.

TROVAC infected primary CEF cells by using the calcium phosphate precipitation method previously described (Panicali et al., 1982; Piccini et al., 1987). Positive plaques were selected on the basis of hybridization to HA specific radio-labelled probes and subjected to sequential rounds of plaque purification until a pure population was achieved. One representative plaque was then amplified to produce a stock virus. Plasmid pRW849 was used in an in vitro recombina- RW227 (SEQ ID NO: 90):   5'   ATAACATGCGGTGCACCATTTGTATAT
                              AAGTTAACGAATTCCAATCAAGC   3'

RW228 (SEQ ID NO: 91):   5'   GCTTGACTTGGAATTCGTTAACTTATA
                              TACAAATGGTGCACCGCATGTTAT   3'

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the SmaI site of pF7DO described previously. The non-pertinent sequences were excised by digestion of pRW858 with EcoRV (site 24 bp upstream of the 3'-end of the H6 promoter) and PstI. The 3.5 tion test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence.

In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation.

It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the $HA_2$ cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_o$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 26

CHV gB, gC AND gD NUCLEOTIDES IN VECTOR SYSTEM, EXPRESSION THEREFROM AND USE OF VECTOR SYSTEM AND EXPRESSION PRODUCT

Expression of the CHV gB glycoprotein is accomplished by putting the CHV gB homolog gene under the control of the vaccinia virus I3L promoter. Expression of the CHV gC glycoprotein is accomplished by putting the CHV gC homolog gene under the control of the vaccinia virus H6 promoter. Expression of the CHV gD glycoprotein is accomplished by putting the CHV gD homolog gene under the control of the entomopox virus 42K gene promoter. The gB and gC coding is in the ATI locus and, the gD coding is in the HA locus.

Generation of Donor Plasmid.

The CHV gB coding sequence is PCR-derived. The CHV gB fragment is fused to a PCR-derived fragment containing the I3L promoter element in a plasmid containing the cassette I3L-CHV gB in the ATI deorfed locus. The CHV gC coding is PCR-derived and is fused in the HA deorfed locus in a plasmid.

A donor plasmid is used to insert the I3L-CHV gB—H6-CHV gC double construction in the NYVAC ATI deorfed locus.

In vitro recombination is performed on Vero cells using the donor plasmid and vP866 (NYVAC) as the rescuing virus. Standard protocols were used to identify and purify the recombinant virus (Piccini et al., 1987). The NYVAC-based recombinant containing the CHV gB and gC genes in the ATI deorfed locus is designated NYVAC-CHVgBgC.

Generation of Donor Plasmid.

The CHV gD coding sequence is fused to the 42K promoter and a resulting plasmid therefrom generated for insertion with the NYVAC HA deorfed locus.

In vitro recombination is performed on Vero cells using the CHV gD-42K donor plasmid and recombinant vaccinia virus NYVAC-CHVgBgC (NYVAC background) as the rescuing virus. This is performed with standard procedures (Piccini et al., 1987). The NYVAC-based recombinant containing the CHV gB and gC genes in the ATI deorfed locus and the CHV gD gene in the HA deorfed locus is designated NYVAC-CHVgBgCgD.

Generation of ALVAC donor plasmid.

A plasmid donor plasmid to insert the I3L-CHV gB—H6-CHV gC—42K-CHV gD triple construction in the ALVAC C3 deorfed locus is constructed from the above plasmids.

In vitro recombination is performed on primary chick embryo fibroblasts using the donor plasmid and CPpp (ALVAC) as the rescuing virus. Standard procedures are followed to identify and purify the generated recombinant (Piccini et al., 1987). The ALVAC-based recombinant contains the CHV gB, gC and gD genes in the C3 deorfed locus and is designated ALVAC-CHVgBgCgD.

Analysis confirms expression of the glycoproteins by the recombinants and, the glycoproteins are substantially within the predicted sequences.

The recombinants can be used to stimulate an antibody or immune response in pups and adult dogs against CHV and, so too can the expression products which can be isolated from cells infected by the recombinants. Further, the recombinants or the expression products therefrom can be used to generate antibodies in an animal administered the recombinants or the expression products therefrom and, the antibodies can be further used as described herein.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Ackermann, M., R. Longnecker, B. Roizman, and L. Pereira, Virology 150, 207–220 (1986).
2. Allen, G. P. and M. R. Yeargan, J. Virol. 61, 2454–2461 (1987).

3. Allen, G. P. and J. T. Bryans, In: Progress in Veterinary Microbiology and Immunology, Vol. 2, ed. R. Pandey (Basel), pp. 78–144 (1986).

4. Allen, G. P., and L. D. Coogle, J. Virol. 62, 2850–2858 (1988).

5. Altenburger, W., C.-P. Suter and J. Altenburger, Archives Virol. 105, 15–27 (1989).

6. Appel, M., In Virus Infections of Vertebrates, vol. 1, pp. 5–15. Edited by M. Appel. Amsterdam-Oxford-New York-Tokyo: Elsevier Science Publishers (1987).

7. Audonnet, J.-C., Winslow, J., Allen, G. & Paoletti, E., Journal of General Virology 71, 2969–2978 (1990).

8. Avery, R. J., and J. Niven., Infect. and Immun. 26, 795–801 (1979).

9. Babiuk, L. A., J. L'Italien, S. van Drunen Littel-van den Hurk, T. Zamb, M. J. P. Lawman, G. Hughes, and G. A. Gifford, J. Virol. 159, 57–66 (1987).

10. Baer, R., A. T. Bankier, M. D. Biggin, P. L. Deininger, P. J. Farrell, T. J. Gibson, G. Hatfull, G. S. Hudson, S. C. Satchwell, C. Seguin, P. S. Tuffnell, and B. G. Barrell, Nature 310, 207–211 (1984).

11. Baines, J., and B. Roizman, J. Virol. 67, 1441–1452 (1993).

12. Balachandran, N., S. Bacchetti, and W. E. Rawls, Infect. Immun. 37, 1132–1137 (1982).

13. Bause, E., Biochemical Journal 209, 331–336 (1983).

14. Behbehani, A. M., Microbiological Reviews 47, 455–509 (1983).

15. Ben-Porat, T., J. DeMarchi, J. Pendrys, R. A. Veach, and A. S. Kaplan, J. Virol. 57, 191–196 (1986).

16. Ben-Porat, T. and A. S. Kaplan, In: The Herpesviruses, vol. 3, ed. B. Roizman (Plenum Publishing Corp., New York) pp. 105–173 (1985).

17. Ben-Porat, T., F. J. Rixon, and M. L. Blankenship, Virology 95, 285–294 (1979).

18. Bergoin, M., and Dales, S., In Comparative Virology, eds. K. Maramorosch and E. Kurstak, (Academic Press, New York) pp. 169–205 (1971).

19. Berman, P. W., D. Dowbenko, L. A. Lasky, and C. C. Simonsen, Science 222, 524–527 (1983).

20. Bertholet, C., Drillien, R., and Wittek, R., Proc. Natl. Acad. Sci. U.S.A. 82, 2096–2100 (1985).

21. Blewett, E. & Misra, V., Journal of General Virology 72, 2083–2090 (1991).

22. Blobel, G., Proceedings of the National Academy of Sciences, U.S.A. 77, 1496–1500 (1980).

23. Boursnell, M. E. G., P. F. Green, J. I. A. Campbell, A. Deuter, R. W. Peters., F. M. Tomley, A. C. R. Samson, P. Chambers, P. T. Emmetson, and M. M. Binns, J. Gen. Virol. 71, 621–628 (1990a).

24. Boutsnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23, 305–316 (1990b).

25. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).

26. Brockmeier, S., Lager, K., Tartaglia, J., Riviere, M., Paoletti, E. & Mengeling, W., Veterinary Microbiology 38, 41–58 (1993).

27. Buller, R. M. L., G. L. Smith, Cremer, K., Notkins, A. L., and Moss, B., Nature 317, 813–815 (1985).

28. Buller, R. M. L., Chakrabarti, S., Cooper, J. A., Twardzik, D. R., and Moss, B., J. Virol. 62, 866–874 (1988).

29. Bzik, D. J., B. A. Fox, N. A. DeLuca, and S. Person, Virology 133, 301–307 (1984).

30. Cadoz, M., A. Strady, B. Meignier, J. Taylor, J. Tartaglia, E. Paoletti and S. Plotkin, The Lancet, 339, 1429 (1992).

31. Cantin, E. M., R. Eberle, J. L. Baldick, B. Moss, D. E. Willey, A. L. Notkins, and H. Openshaw, Proc. Natl. Acad. Sci. U.S.A. 84, 5908–5912 (1987).

32. Carmichael, L., Strandberg, J. & Barnes, F., Proceedings of the Society for Experimental Biology and Medicine, 120, 644–650 (1965).

33. Carmichael, L., Journal of the American Veterinary Medical Association 156, 1714–1721 (1970).

34. Chambers, P., N. S. Millar, and P. T. Emmerson, J. Gen. Virol. 67, 2685–2694 (1986).

35. Chan, W., Immunol. 49, 343–352 (1983).

36. Child, S. J., Palumbo, G. J., Buller, R. M. L., and Hruby, D. E. Virology 174, 625–629 (1990).

37. Clewell, D. B., J. Bacteriol. 110, 667–676 (1972).

38. Clewell, D. B. and D. R. Helinski, Proc. Natl. Acad. Sci. U.S.A. 62, 1159–1166 (1969).

39. Colinas, R. J., R. C. Condit and E. Paoletti, Virus Research 18, 49–70 (1990).

40. Compton, T., In: Cell Biology of Virus Entry, Replication, and Pathogenesis, eds. Compans, R. W., A. Helenius, and M. B. A. Oldstone (Alan R. Liss, Inc.) pp. 45–56 (1989).

41. Cooney E. L., Corrier A. C., Greenberg P. D., et al., Lancet 337, 567–572 (1991).

42. Corden, J., Wasylyk, B., Buchwalder, A., Sassone-Corsi, P., Kedinger, C. & Chambon, P., Science 209, 1406–1414 (1980).

43. Cranage, M. P., T. Kouzarides, A. T. Bankier, S. Satchwell, K. Weston, P. Tomlinson, B. Barrell, H. Hart, S. E. Bell, A. C. Minson, and G. L. Smith, EMBO J. 5, 3057–3063 (1986).

44. Cremer, K. J., M. Mackett, C. Wohlenberg, A. L. Notkins, and B. Moss, Science 228, 737–740 (1985).

45. Davis, W. B., J. A. Taylor, and J. E. Oakes, J. Infect. Dis. 140, 534–540 (1979).

46. Davison, A. J., and J. E. Scott, J. gen. Virol. 67, 1759–1816 (1986).

47. Drillien, R., F. Koehren and A. Kirn, Virology 111, 488–499 (1981).

48. Eberle, R., and R. J. Courtney, J. Virol. 35, 902–917 (1980).

49. Edbauer, C., R. Weinberg, J. Taylor, A. Rey-Senelonge, J. F. Bouquet, P. Desmettre, and E. Paoletti, Virology 179, 901–904 (1990).

50. Engelke, D. R., Hoener, P. A., and Collins, F. S., Proc. Natl. Acad. Sci. U.S.A. 85, 544–548 (1988).

51. Espion, D., S. de Henau, C. Letellier, C.-D. Wemers, R. Brasseur, J. F. Young, M. Gross, M. Rosenberg, G. Meulemans and A. Burny, Arch. Virol. 95, 79–95 (1987).

52. Etinger H. M., Altenburger W., Vaccine 9, 470–472 (1991).

53. Fargeaud, D., C. Benoit Jeannin, F. Kato, and G. Chappuis, Arch. Virol. 80, 69–82 (1984).

54. Fenner, F., Virology 5, 502–529 (1958).

55. Fitzpatrick, D. R., Babiuk, L. A. & Zamb, T. J., Virology 173, 46–57 (1989).

56. Flexner, C., Hugen, A., and Moss, B., Nature 330, 259–262 (1987).

57. Flowers, C., Eastman, E. & O'Callaghan, D., Virology 180, 175–184 (1991).

58. Frame, M. C., H. S. Marsden, and D. J. McGeoch, J. gen. Virol. 67, 745–751 (1986).

59. Fries et al., 32nd Interscience Conference on Antimicrobial Agents and Chemotherapy, Anaheim, Calif. (October 1992).

60. Frink, R. J., M. R. Eisenberg, G. Cohen, and E. K. Wagner, J. Virol. 45, 634–647 (1983).
61. Funahashi, S., T. Sato and H. Shida, J. Gen. Virol. 69, 35–47 (1988).
62. Garten, W., Kohama, T., and H.-D. Klenk. J. Gen. Virol. 51, 207–211 (1980).
63. Ghendon, Y. Z., and Chernos, V. I., Acta Virol. 8, 359–368 (1964).
64. Gillard, S., Spehner, D., Drillien, R., and Kirn, A., Proc. Natl. Acad. Sci. U.S.A. 83, 5573–5577 (1986).
65. Glorioso, J., C. H. Schroder, G. Kumel, M. Szczesiul, and M. Levine, J. Virol. 50, 805–812 (1984).
66. Glorioso, J., U. Kees, G. Kumel, H. Kirchner, and P. Krammer, J. Immunol. 135, 575–582 (1985).
67. Goebel, S. J., Johnson, G. P., Perkus, M. E., Davis, S. W., Winslow, J. P., Paoletti, E., Virology 179, 247–266 (1990a).
68. Goebel, S. J., G. P. Johnson, M. E. Perkus, S. W. Davis, J. P. Winslow and E. Paoletti, Virology 179, 517–563 (1990b).
69. Goldstein, D. J. and S. K. Weller, Virology 166, 41–51 (1988).
70. Gretch, D. R., B. Kari, L. Rasmussen, R. C. Gehrz, and M. F. Stinski, J. Virol. 62, 875–881 (1988).
71. Guo, P., Goebel, S., Davis, S., Perkus, M. E., Languet, B., Desmettre, P., Allen, G., and Paoletti, E., J. Virol. 63, 4189–4198 (1989).
72. Guo et al., J. Virol. 64, 2399–2406 (1990).
73. Hampl, H., T. Ben-Porat, L. Ehrlicher, K.-O. Habermehl, and A. S. Kaplan, J. Virol. 52, 583–590 (1984).
74. Homma, M., and M. Ohuchi, J. Virol. 12, 1457–1465 (1973).
75. Honess, R. W., Journal of General Virology 65, 2077–2107 (1984).
76. Honess, R. W., Bodemer, W., Cameron, K. R., Niller, H.-H. & Fleckenstein, B., Proceedings of the National Academy of Sciences, U.S.A. 83, 3604–3608 (1986).
77. Hruby, D. E., R. A. Maki, D. B. Miller and L. A. Ball, Proc. Natl. Acad. Sci. U.S.A. 80, 3411–3415 (1983).
78. Hutchinson, L., Browne, H., Wargents, V., Doris-Poynter, N., Primorac, S., Goldsmith, K., Minson, A., and D. C. Johnson. J. Virol. 66, 2240–2250 (1992).
79. Hutchinson, L., Goldsmith, K., Snoddy, A., Ghash, H., Graham, F. and D. Johnson. J. Virol. 66, 5603–5609 (1992b).
80. Hruby, D. E. and L. A. Ball, J. Virol. 43, 403–409 (1982).
81. Ichihashi, Y. and Dales, S., Virology 46, 533–543 (1971).
82. Ihara, T., Kato, A., Ueda, S., Ishihama, A. & Hirai, K., Virus Genes 3, 127–140 (1989).
83. Ishii, H., Y. Kobayashi, M. Kuroki and Y. Kodama, J. gen. Virol. 69, 1411–1414 (1988).
84. Jacobson, J. G., D. A. Leib, D. J. Goldstein, C. L. Bogard, P. A. Schaffer, S. K. Weller and D. M. Coen, Virology 173, 276–283 (1989).
85. Jamieson, A. T., G. A. Gentry and J. H. Subak-Sharpe, J. Gen. Virol. 24, 465–480 (1974).
86. Kato, A., Sato, I., Ihara, T., Ueda, S., Ishihama, A. & Hirai, K., Gene 84, 399–405 (1989).
87. Kato, S., M. Takahashi, S. Kameyama and J. Kamahora, Biken's 2, 353–363 (1959).
88. Keller, P. M., A. J. Davison, R. S. Lowe, C. D. Bennett, and R. W. Ellis, Virology 152, 181–191 (1986).
89. Kieff, E., and D. Liebowitz, In: Virology, Second Edition, eds. Fields, B. N. et al. (Raven Press, Ltd., New York) pp. 1889–1920 (1990).
90. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
91. Klein, P., Kanehisa, M. & DeLisi, C., Biochimica Biophysica Acta 815, 468–476 (1985).
92. Konishi et al., Virology 190, 454–458 (1992).
93. Kopp, A. & Mettenleiter, T., Journal of Virology 66, 2754–2762 (1992).
94. Kost, T. A., E. V. Jones, K. M. Smith, A. P Reed, A. L. Brown, and T. J. Miller, Virology 171, 365–376 (1989).
95. Kotwal, G. J., A. W. Hugin and B. Moss, Virology 171, 579–587 (1989a).
96. Kotwal, G. J. and B. Moss, J. Virol. 63, 600–606 (1989b).
97. Kotwal, G. J., S. N. Isaacs, R. McKenzie, M. M. Frank and B. Moss, Science 250, 827–830 (1990).
98. Kotwal, G. J. and Moss, B., Nature (Lond.) 335, 176–178 (1988).
99. Kouzarides, T., Bankier, A. T., Satchwell, S. C., Weston, K., Tomlinson, P. & Barrell, B. G., Virology 157, 397–413 (1987).
100. Kozak, M., Cell 44, 283–292 (1986).
101. Kuhn, J., Eing, B., Brossmer, R., Munk, K. & Braun, R., Journal of General Virology 69, 2847–2858 (1988).
102. Lai, A. C.-K. and B. G.-T. Pogo, Virus Res. 12, 239–250 (1989).
103. Lasky, L. A., D. Dowbenko, C. C. Simonsen, and P. W. Berman, Bio-Technology 2, 527–532 (1984).
104. Lawrence, W. C., R. C. D'Urso, C. A. Kundel, J. C. Whitbeck and L. J. Bello, J. Virol. 60, 405–414 (1986).
105. Le, L., R. Brasseur, C. Wemers, G. Meulemans, and A. Burny, Virus Genes 1, 333–350 (1988).
106. Long, D., Cohen, G., Muggeridge, M. & Eisenberg, R., Journal of Virology 64, 5542–5552 (1990).
107. Long, D., Wilcox, W., Abrams, W., Cohen, G. & Eisenberg, R., Journal of Virology 66, 6668–6685 (1992).
108. Longnecker, R., S. Chatterjee, R. Whitley, and B. Roizman, Proc. Natl. Acad. Sci. U.S.A. 84, 4303–4307 (1987).
109. Maeda, K., Horimoto, T., Norimine, J., Kawaguchi, Y., Tomonaga, K., Niikura, M., Kai, C., Takahashi, E. & Mikami, T., Archives of Virology 127, 387–397.
110. Mandecki, W., Proc. Natl. Acad. Sci. U.S.A. 83, 7177–7182 (1986).
111. Maniatis, T., E. F. Fritsch, and J. Sambrook, Molecular Cloning: A Laboratory Manual, (Cold Spring Harbor Laboratory, New York) (1982).
112. Marchioli, C. C., R. J. Yancey, Jr., R. C. Wardley, D. R. Thomsen and L. E. Post, Am. J. Vet. Res. 48, 1577–1583 (1987).
113. Marchioli, C., R. J. Yancey, Jr., J. G. Timmins, L. E. Post, B. R. Young, and D. A. Povendo, Am. J. Vet. Res. 49, 860–864 (1988).
114. Marchioli, C. C., R. J. Yancey, Jr., E. A. Petrovskis, J. G. Timmins, and L. E. Post, J. Virol. 61, 3977–3982 (1987).
115. Matthews, R. E. F., Intervirology 17, 42–44 (1982).
116. McGeoch, D. J., M. A. Dalrymple, A. J. Davison, A. Dolan, M. C. Frame, D. McNab, L. J. Perry, J. E. Scott, and P. Taylor, J. gen. Virol. 69, 1531–1574 (1988).
117. McGinnes, L. W., and T. G. Morrison, Virus Research 5, 343–356 (1986).
118. McLaughlin-Taylor, E., D. E. Willey, E. M. Cantin, R. Eberle, B. Moss, and H. Openshaw, J. gen. Virol. 69, 1731–1734 (1988).
119. Meas, R. K., S. L. Fritsch, L. L. Herr, and P. A. Rota, J. Virol. 51, 259–262 (1984).
120. Merz, D. C., A. Scheid, and P. Choppin, J. Exper. Med. 151, 275–288 (1980).
121. Misra, V., R. M. Blumenthal and L. A. Babiuk, J. Virol. 40, 367–378 (1981).

122. Morgan, A. J., M. Mackett, S. Finerty, J. R. Arrand, F. T. Scullion and M. A. Epstein, J. Med. Virol. 25, 189–195 (1988).
123. Moss, B., E. Winters and J. A. Cooper, J. Virol. 40, 387–395 (1981).
124. Nagai, Y., H. D. Klenk, and R. Rott, Virology 72, 494–508 (1976).
125. Nagai, Y., T. Yoshida, M. Hamaguchi, H. Naruse, M. Iinuma, K. Maeno, and T. Matsumoto, Microbiol. Immunol. 24, 173–177 (1980).
126. Nazerian, K., Lee, L., Yanagida, N. & Ogawa, R., Journal of Virology 66, 1409–1413 (1992).
127. Nicolson, L. & Onions, D. E., Virology 179, 378–387 (1990).
128. Norrby, E., and Y. Gollmar, Infect. and Immun. 11, 231–239 (1975).
129. Oakes, J. E., and H. Rosemond-Hornbeak, Infect. Immun. 21, 489–495 (1978).
130. Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).
131. Paez, E., S. Dallo and M. Esteban, Proc. Natl. Acad. Sci. U.S.A. 82, 3365–3369 (1985).
132. Palumbo, G. J., Pickup, D. J., Fredrickson, T. N., Mcintyre, L. J., and Buller, R. M. L., Virology 172, 262–273 (1989).
133. Panicali, D., S. W. Davis, S. R. Mercer, and E. Paoletti, J. Virol. 37, 1000–1010 (1981).
134. Panicali, D. and E. Paoletti, Proc. Natl. Acad. Sci. U.S.A. 79, 4927–4931 (1982).
135. Panicali, D., Davis, S. W., Mercer, S. R., and Paoletti, E., J. Virol. 37, 1000–1010 (1981).
136. Paoletti, E., B. R. Lipinskas, C. Samsonoff, S. Mercer, and D. Panicali, Proc. Natl. Acad. Sci. U.S.A. 81, 193–197 (1984).
137. Papp-Vid, G., and J. B. Derbyshire, Can. J. Comp. Med. 43, 231–233 (1979).
138. Patel, D. D. and Pickup, D. J., EMBO 6, 3787–3794 (1987).
139. Patel, D. D., Ray, C. A., Drucker, R. P., and Pickup, D. J., Proc. Natl. Acad. Sci. U.S.A. 85, 9431–9435 (1988).
140. Pearson, W. R. & Lipman, D. J., Proceedings of the National Academy of Sciences 85, 2444–2448 (1988).
141. Pellett, P. E., M. D. Biggin, B. L. Barrell, and B. Roizman, J. Virol. 56, 807–813 (1985).
142. Perkus M. E., Piccini A., Lipinskas B. R., et al., Science 229, 981–984 (1985).
143. Perkus, M. E., K. Limbach, and E. Paoletti, J. Virol. 63, 3829–3836 (1989).
144. Perkus, M. E., A. Piccini, B. R. Lipinskas, and E. Paoletti, Science 229, 981–984 (1985).
145. Perkus, M. E., Goebel, S. J., Davis, S. W., Johnson, G. P., Limbach, K., Norton, E. K., and Paoletti, E., Virology 179, 276–286 (1990).
146. Perkus, M. E., D. Panicali, S. Mercer and E. Paoletti, Virology 152, 285–297 (1986).
147. Perkus, M. E., Limbach, K., and Paoletti, E., J. Virol. 63, 3829–3836 (1989).
148. Perkus, M. E., S. J. Goebel, S. W. Davis, G. P. Johnson, E. K. Norton and E. Paoletti, Virology 180, 406–410 (1991).
149. Petrovskis, E. A., J. G. Timmins, M. A. Armentrout, C. C. Marchioli, R. J. Yancey, Jr., and L. E. Post, J. Virol. 59, 216–223 (1986).
150. Petrovskis, E. A., J. G. Timmins, and L. E. Post, J. Virol. 60, 185–193 (1986).
151. Piccini, A., M. E. Perkus, and E. Paoletti, Methods in Enzymology 153, 545–563 (1987).
152. Piccini, A., M. E. Perkus, and E. Paoletti, In: Methods in Enzymology, Vol. 153, eds. Wu, R., and L. Grossman (Academic Press) pp. 545–563 (1987).
153. Pickup, D. J., B. S. Ink, W. Hu, C. A. Ray and W. K. Joklik, Proc. Natl. Acad. Sci. U.S.A. 83, 7698–7702 (1986).
154. Pickup, D. J., B. S. Ink, B. L. Parsons, W. Hu and W. K. Joklik, Proc. Natl. Acad. Sci. U.S.A. 81, 6817–6821 (1984).
155. Pizer, L., Cohen, G. & Eisenberg, R., Journal of Virology 34, 142–153 (1980).
156. Plummer, G., Goodheart, C., Henson, D. & Bowling, C., Virology 39, 134–137 (1969).
157. Proudfoot, N. J. & Brownlee, G. G., Nature 163, 211–214 (1976).
158. Reed, L. J. and Muench, H., Am. J. Hyg. 27, 493–497 (1938).
159. Richman, D. D., A. Buckmaster, S. Bell, C. Hodgman and A. C. Minson, J. Virol. 57, 647–655 (1986).
160. Riggio, M. P., A. A. Cullinane, and D. E. Onions, J. Virol. 63, 1123–1133 (1989).
161. Riviere, M., Tartaglia, J., Perkus, M. E., Norton, E. K., Bongermino, C. M., Lacoste, F., Duret, C., Desmettre, P. & Paoletti, E., Journal of Virology 66, 3424–3434 (1992).
162. Robbins, A. K., R. J. Watson, M. E. Whealy, W. W. Hays, and L. W. Enquist, J. Virol. 58, 339–347 (1986).
163. Robbins, A. K., D. J. Dorney, M. W. Wathen, M. E. Whealey, C. Gold, R. J. Watson, L. E. Holland, S. D. Weed, M. Levine, J. C. Glorioso, and L. W. Enquist, J. Virol. 61, 2691–2701 (1987).
164. Roizman, B. and A. E. Sears, In: Virology, eds. Fields, B. N. and D. M. Knipe (Raven Press, Ltd., New York) pp. 1795–1841 (1990).
165. Roizman, B., In The Herpesviruses, vol. 1, pp. 1–23, Ed. B. Roizman, New York & London: Plenum Press (1982).
166. Rooney, J. F., C. Wohlenberg, K. J. Cremer, B. Moss, and A. L. Notkins, J. Virol. 62, 1530–1534 (1988).
167. Rosenthal, K. L., J. R. Smiley, S. South, and D. C. Johnson, J. Virol. 61, 2438–2447 (1987).
168. Ross, L., Sanderson, M., Scott, S., Binns, M., Doel, T. & Milne, B., Journal of General Virology 70, 1789–1804 (1989).
169. Rota, P. A., R. K. Maes, and W. T. Ruyechan, Virology 154, 168–179 (1986).
170. Rubenstein, A. S. and A. S. Kaplan, Virology 66, 385–392 (1975).
171. Sanger, F., S. Nicklen, and A. Coulson, Proc. Natl. Acad. Sci. U.S.A. 74, 5463–5467 (1977).
172. Schmidtt, J. F. C. and H. G. Stunnenberg, J. Virol. 62, 1889–1897 (1988).
173. Seligmann, E. B., In Laboratory Techniques in Rabies, eds. M. M. Kaplan and H. Koprowski, (World Health Organization, Geneva) pp. 279–285 (1973).
174. Shapira, S. K., Chou, J., Richaud, F. V. and Casadaban, M. J., Gene 25, 71–82 (1983).
175. Shida, H., Virology 150, 451–462 (1986).
176. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
177. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
178. Shimizu, M., K. Satou, and N. Nishioka, Arch. Virol. 104, 169–174 (1989).

179. Sinclair, R., R. F. Cook, and J. A. Mumford, J. gen. Virol. 70, 455–459 (1989).
180. Slabaugh, M., N. Roseman, R. Davis and C. Mathews, J. Virol. 62, 519–527 (1988).
181. Smith, J. S., P. A. Yager and G. M. Baer, In Laboratory Techniques in Rabies, eds. M. M. Kaplan and H. Koprowski (WHO Geneva) pp. 354–357 (1973).
182. Sodora, D., Cohen, G., Muggeridge, M. & Eisenberg, R., Journal of Virology 65, 4424–4431 (1991).
183. Spaete, R., Saxena, A., Scott, P., Long, G., Probert, W., Britt, W., Gibson W., Rasmussen, L. & Pachl, C., Journal of Virology 64, 2922–2931 (1990).
184. Spear, P. G., In: The Basis for Serodiagnosis and Vaccines, Immunochemistry of Viruses, Vol. 2, eds. M. H. V. Van Regenmortel and A. R. Neurath (New York), pp. 425–443 (1985a).
185. Spear, P. G., In: The Herpesvirus, Vol. 3, ed. B. Roizman (New York), pp. 315–356 (1985b).
186. Stanberry, L. R., S. Kit and M. G. Myers, J. Virol. 55, 322–328 (1985).
187. Stevely, W. S., J. Virol. 22, 232–234 (1977).
188. Stokes, A., G. P. Allen, L. A. Pullen, and P. K. Murray, J. gen. Virol. 70, 1173–1183 (1989).
189. Sullivan, V. and G. L. Smith, J. gen. Virol. 68, 2587–2598 (1987).
190. Sullivan, V. and G. L. Smith, J. gen. Virol. 69, 859–867 (1988).
191. Swain, M. A., R. W. Peet, and D. A. Galloway, J. Virol. 53, 561–569 (1985).
192. Tabor, S., and C. C. Richardson, Proc. Natl. Acad. Sci. U.S.A. 84, 4767–4771 (1987).
193. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990).
194. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, W. Koff, F. Wong-Staal & R. C. Kenedy, Eds., Vol. 3, Marcel Dekker, New York (In press) (1993a).
195. Tartaglia, J., Perkus, M. E., Taylor, J., Norton, E. K., Audonnet, J.-C., Cox, W. I., Davis, S. W., Van Der Hoeven, J., Meignier, B., Riviere, M., Languet, B., Paoletti, E., Virology 188, 217–232 (1992).
196. Tartaglia, J., Jarrett, O., Desmettre, P., Paoletti, E. (1993b) J. Virol., in press.
197. Taylor, J., C. Trimarchi, R. Weinberg, B. Languet, F. Guillemin, P. Desmettre and E. Paoletti, Vaccine 9, 190–193 (1991b).
198. Taylor, J., C. Trimarchi, R. Weinberg, B. Languet, F. Guillemin, P. Desmettre & E. Paoletti, Vaccine 9, 190 (1991).
199. Taylor, J., Weinberg, R., Kawaoka, Y., Webster, R. G., and Paoletti, E., Vaccine 6, 504–508 (1988a).
200. Taylor, J., R. Weinberg, B. Lanquet, P. Desmettre, and E. Paoletti, Vaccine 6, 497–503 (1988b).
201. Taylor, J., R. Weinberg, J. Tartaglia, C. Richardson, G. Alkhatib, D. Briedis, M. Appel, E. Norton & E. Paoletti, Virology 187, 321–328 (1992).
202. Taylor, G., E. J. Stott, G. Wertz and A. Ball, J. Gen. Virol. 72, 125–130 (1991a).
203. Taylor, J., Edbauer, C., Rey-Senelonge, A., Bouquet, J.-F., Norton, E., Goebel, S., Desmettre, P., Paoletti, E., J. Virol. 64, 1441–1450 (1990).
204. Telford, E. A., Watson, M. S., McBride, K. & Davison, A. J. (1992). The DNA sequence of equine herpesvirus-1. Virology 189, 304–316.
205. Tikoo, S. K., Fitzpatrick, D. R., Babiuk, L. A. & Zamb, T. J., Journal of Virology 64, 5132–5142 (1990).
206. Toyoda, T., T. Sakaguchi, K. Imai, N. M. Inocencio, B. Gotoh, M. Hamaguchi, and Y. Nagai, Virology 158, 242–247 (1987).
207. Wachsman, M., L. Aurelian, J. C. R. Hunter, M. E. Perkus, and E. Paoletti, Bioscience Reports 8, 323–234 (1988).
208. Wachsman, M., J. H. Luo, L. Aurelian, M. E. Perkus, and E. Paoletti, J. gen. Virol. 70, 2513–2520 (1989).
209. Wachsman, M., L. Aurelian, C. C. Smith, B. R. Lipinskas, M. E. Perkus, and E. Paoletti, J. Infect. Dis. 155, 1188–1197 (1987).
210. Wathen, M. W. and L. M. K. Wathen, J. Virol. 58, 173–178 (1986).
211. Wathen, M. W. and L. M. K. Wathen, J. Virol. 51, 57–62 (1984).
212. Wathen, L. M. K., K. B. Platt, M. W. Wathen, R. A. Van Deusen, C. A. Whetstone, and E. C. Pirtle, Virus Res. 4, 19–29 (1985).
213. Weir, J. P., M. Bennett, E. M. Allen, K. L. Elkins, S. Martin, and B. T. Rouse, J. gen. Virol. 70, 2587–2594 (1989).
214. Weir, J. P. and B. Moss, J. Virol. 46, 530–537 (1983).
215. Whalley, J. M., G. R. Robertson, N. A. Scott, G. C. Hudson, C. W. Bell, and L. M. Woodworth, J. gen. Virol. 70, 383–394 (1989).
216. Whealy, M. E., A. K. Robbins and L. W. Enquist, J. Virol. 63, 4055–4059 (1989).
217. Whitbeck, J. C., L. Z. Bello, and W. C. Lawrence, J. Virol. 62, 3319–3327 (1988).
218. Wilcox, W. C., Long, D., Sodora, D. L., Eisenberg, R. J. & Cohen, G. H., Journal of Virology 62, 1941–1947 (1988).
219. Wittmann, G. and H.-J. Rziha, In: Herpesvirus Diseases of Cattle, Horses and Pigs, ed. G. Wittmann (Kluwer Academic Publishers) pp. 230–325 (1989).
220. Xuan, X., Horimoto, T., Limcumpao, J. A., Takumi, A., Tohya, Y., Takahashi, E. & Mikami, T., Archives of Virology 116, 185–195 (1991).
221. Zamb, T., Abstract No. 330, 68th Annual Meeting of Conference of Research Workers in Animal Disease, 16 and 17 Nov. 1987, Chicago, Ill., U.S.A. (1987).
222. Zarling, J. M., P. A. Moran, R. L. Burke, C. Pachl, P. W. Berman, and L. A. Lasky, J. Immunol. 136, 4669–4673 (1986a).
223. Zarling, J. M., P. A. Moran, L. A. Lasky, and B. Moss, J. Virol. 59, 506–509 (1986b).
224. Zezulak, K. M., and P. G. Spear, J. Virol. 49, 741–747 (1984).
225. Zhou, J., L. Crawford, L. McLean, X. Sun, M. Stanley, N. Almond and G. L. Smith, J. Gen. Virol. 71, 2185–2190 (1990).

What is claimed is:

1. An isolated nucleic acid coding for canine herpesvirus gB, or gC glycoprotein and having a sequence as set forth in SEQ ID NO:1 or SEQ ID NO:11.

2. The isolated nucleic acid of claim 1 which is DNA.

3. The isolated nucleic acid of claim 1 coding for canine herpesvirus gB glycoprotein.

4. The isolated nucleic acid of claim 1 coding for canine herspevirus gC glycoprotein.

5. A vector containing the isolated nucleic acid of claim 2.

6. The vector of claim 5 wherein the vector is a poxvirus.

7. The vector of claim 6 wherein the poxvirus is an avipoxvirus or a vaccinia virus.

8. The vector of claim 7 wherein said avipoxvirus is a canarypox virus.

9. The vector of claim 8 wherein the canarypox virus is a Rentschler vaccine strain which was attenuated through more than 200 serial passages on chick embryo fibroblasts, a master seed therefrom was subjected to four successive plaque purifications under agar, from which a plaque clone was amplified through five additional passages.

10. The vector of claim 7 wherein the poxvirus is a vaccinia virus.

11. The vector of claim 10 wherein deleted therefrom are genetic functions including a C7L–K1L open reading frame, or, a host range region.

12. The vector of claim 11 wherein at least one additional open reading frame is deleted; and, the additional open reading frame is selected from the group consisting of: J2R, B13R+B14R, A26L, A56R, and I4L.

13. The vector of claim 12 wherein J2R, B13R+B14R, A26L, A56R, C7L–K1L and I4L are deleted from the virus.

14. The vector of claim 13 which is a NYVAC recombinant virus.

15. The vector of claim 11 wherein at least one additional region is deleted; and, the additional region is selected from the group consisting of: a thymidine kinase gene, a hemorrhagic region, an A type inclusion body region, a hemagglutinin gene, and a large subunit, ribonucleotide reductase.

16. The vector of claim 15 wherein a thymidine kinase gene, a hemorrhagic region, an A type inclusion body region, a hemagglutinin gene, a host range region, and a large subunit, ribonucleotide reductase are deleted from the virus.

17. A composition for inducing an antigenic or immunological response comprising a vector as claimed in any one of claims 6, 11, 14, 8 or 9 in admixture with a suitable carrier.

18. A method for expressing a gene product in a cell cultured in vitro comprising introducing into the cell a vector as claimed in any one of claims 5, 11, 14, 8 or 9.

* * * * *

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 3000 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TTTTCTGGAT TTCAGCTATG TCCTTCGGGA GTTTATATAA CTTATGAAGA AAACTGTCCT        60
TTGGTAGCAG TTTTACAAAG CGGTGTAAAT TGCGAAATTG GACCAACTAC AACTGTAATA       120
TACGACAGTG ATATTTTTC  TCTTCTTTAT ACCGTTCTTC AAAAATTGGC TCCTGGTGTT       180
AATATAGAAA TTTGATAAGT ATGTTTCAT  TGTATCTATA TATTTTTTT  ATTATTTATA       240
CTTTAATAAT ATGTGATCCA ACAACACCGG AAAGTACTAT TAATCCATTA AATCATCACA       300
ATTTATCAAC ACCTAAACCT ACTTCGGATG ATATTCGTGA AATTTTACGT GAATCCCAAA       360
TTGAATCTGA TGATACATCA ACATTTTACA TGTGCCCACC ACCATCGGGA TCAACATTGG       420
TGCGTTTGGA GCCACCTAGA GCATGTCCTA ACTATAAACT TGGTAAAAAT TTTACAGAAG       480
GAATTGCTGT AATATTTAAG GAAAATATTT CTCCTTATAA ATTTAAAGCT AATATATACT       540
ACAAAAATAT TATTATCACC ACTGTATGGT CTGGAAGCAC ATATGCAGTA ATTACTAATA       600
GATATACAGA TCGTGTACCT ATAGGTGTTC CTGAAATTAC AGAGTTGATT GATAGAAGAG       660
GTATGTGTTT ATCAAAAGCT GATTATATTC GTAATAATTA TGAATTTACC GCATTTGATA       720
AGGATGAAGA CCCCAGAGAA GTTCATTTAA AGCCTTCAAA GTTTAATACA CCAGGATCCC       780
GTGGATGGCA TACAGTTAAT GATACTTACA CAAAAATTGG GGGTTCTGGA TTTTATCATT       840
CTGGAACATC TGTAAATTGT ATAGTTGAAG AAGTTGATGC CAGATCTGTT TATCCATATG       900
ATTCATTTGC TATCTCCACC GGGGATATAA TTCATATGTC CCCTTTTTTT GGATTACGAG       960
ATGGTGCTCA TACTGAATAT ATTAGTTATT CAACTGATAG ATTTCAACAA ATAGAAGGTT      1020
ATTATCCTAT CGACTTAGAT ACTAGACTAC AGCTTGGTGC ACCAGTTTCT AGGAATTTTT      1080
TAACAACACA ACACGTTACT GTTGCTTGGA ATTGGGTTCC AAAAATTCGT GAAGTGTGTA      1140
CTTTGGCTAA ATGGCGTGAA ATTGATGAAA TTATTCGTGA TGAGTATAAG GGATCTTACA      1200
GATTACAGC  AAAATCAATA TCTGCAACAT TTATTTCTGA TACTACTCAA TTTGATATTG      1260
ATCGTGTAAA GTTAAGTGAT TGTGCCAAAC GTGAAGCCAT AGAAGCTATT GATAAGATCT      1320
ACAAAAAAAA ATATAATAAA ACTCATATTC AAACAGGAGA ATTGGAAACA TACTTGGCTA      1380
GAGGGGGATT TATTATAGCA TTTAGACCAA TGATTAGTAA TGAGTTAGCA AAATTGTATA      1440
TAAATGAGTT AGTAAGATCT AATCGTACGG TTGATTTGAA ATCTCTTTTA AATCCATCTG      1500
TAAGAGGGGG GGCTAGAAAG AGAAGATCAG TAGAGGAAAA TAAAAGATCA AAACGTAATA      1560
TTGAAGGTGG TATTGAAAAT GTAAATAATT CAACAATAAT TAAGACAACT TCATCTGTTC      1620
ATTTTGCTAT GCTTCAGTTT GCCTATGATC ATATTCAATC ACATGTTAAT GAAATGCTTA      1680
GTAGAATTGC AACTGCATGG TGTAATCTTC AAAATAAAGA GAGAACCCTT TGGAATGAAG      1740
TTATGAAACT TAATCCAACT AGTGTGGCTT CGGTTGCTAT GGATCAAAGA GTTTCAGCAC      1800
```

| | | | | | |
|---|---|---|---|---|---|
| GAATGTTAGG | GGATGTTCTT | GCAGTTACTC | AATGTGTTAA | TATATCAGGT | TCTAGTGTTT | 1860 |
| TTATTCAAAA | TTCCATGCGT | GTTTTAGGGT | CAACAACTAC | ATGTTACAGT | CGTCCTCTTA | 1920 |
| TATCATTTAA | AGCACTAGAA | AACTCAACTA | ACTATATTGA | AGGACAACTT | GGGGAAAATA | 1980 |
| ATGAACTATT | AGTAGAACGA | AAGCTAATTG | AACCATGTAC | AGCTAACCAT | AAAAGATATT | 2040 |
| TTAAATTTGG | TGCAGATTAT | GTATATTTTG | AAAACTATGC | ATATGTTCGA | AAGGTACCTC | 2100 |
| TTAATGAAAT | TGAAATGATC | AGTGCATATG | TAGATCTTAA | TATTACATTA | CTTGAGGATC | 2160 |
| GTGAATTTTT | ACCACTAGAG | GTATATACTC | GAGCAGAGTT | AGAAGATACA | GGACTATTGG | 2220 |
| ACTATAGTGA | GATTCAACGT | AGAAATCAAC | TACATGCACT | TAAGTTTTAT | GATATTGACA | 2280 |
| GTGTTGTAAA | AGTTGATAAT | AATGTTGTAA | TTATGAGGGG | CATTGCAAAT | TTTTTCCAAG | 2340 |
| GACTTGGAGA | TGTTGGAGCG | GGATTTGGAA | AAGTTGTTTT | GGGTGCTGCA | AATGCTGTTA | 2400 |
| TTGCAACTGT | TTCTGGAGTG | TCCTCGTTTC | TTAATAACCC | ATTTGGGGCG | CTAGCCGTTG | 2460 |
| GATTGCTGAT | TTTAGCTGGA | CTATTTGCAG | CGTTTTTGGC | TTATAGATAT | GTTTCTAAAC | 2520 |
| TTAAGTCAAA | TCCAATGAAA | GCACTATACC | CAGTAACTAC | AAAAAATTTA | AAGAAAGTG | 2580 |
| TTAAGAATGG | TAATTCTGGA | AATAATAGTG | ATGGAGAAGA | AAATGATGAT | AATATCGATG | 2640 |
| AAGAAAAGCT | TCAACAAGCT | AAAGAAATGA | TTAAATATAT | GTCTCTAGTT | TCTGCTATGG | 2700 |
| AACAGCAGGA | ACATAAAGCT | ATTAAAAAAA | ATAGTGGCCC | TGCCCTTCTA | GCAAGTCACA | 2760 |
| TTACAAACCT | ATCTCTTAAA | CATCGTGGTC | CAAAATACAA | ACGTTTGAAA | AATGTAAATG | 2820 |
| AAAATGAAAG | TAAAGTTTAA | TAAAAAATTT | AAATATTACG | TAAAATTTTC | TGACTCTGCC | 2880 |
| CACTTTTTTT | ATAATATAAA | TTTTAGAAAA | TTTTACTCAT | TTTATTATCT | TTTATAAACC | 2940 |
| TCCAACTATT | TATAAAGGAT | AATAAATGGA | CATTTCTGCG | GTGCCTGTAT | ATCCTACTAA | 3000 |

(2) INFORMATION FOR SEQ ID NO:2:

(i) SEQUENCE CHARACTERISTICS:
        (A) LENGTH: 879 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:2:

```
Met Phe Ser Leu Tyr Leu Tyr Ile Phe Phe Ile Ile Tyr Thr Leu Ile
 1               5                  10                  15

Ile Cys Asp Pro Thr Thr Pro Glu Ser Thr Ile Asn Pro Leu Asn His
            20                  25                  30

His Asn Leu Ser Thr Pro Lys Pro Thr Ser Asp Asp Ile Arg Glu Ile
        35                  40                  45

Leu Arg Glu Ser Gln Ile Glu Ser Asp Asp Thr Ser Thr Phe Tyr Met
    50                  55                  60

Cys Pro Pro Pro Ser Gly Ser Thr Leu Val Arg Leu Glu Pro Pro Arg
65                  70                  75                  80

Ala Cys Pro Asn Tyr Lys Leu Gly Lys Asn Phe Thr Glu Gly Ile Ala
                85                  90                  95

Val Ile Phe Lys Glu Asn Ile Ser Pro Tyr Lys Phe Lys Ala Asn Ile
            100                 105                 110

Tyr Tyr Lys Asn Ile Ile Thr Thr Val Trp Ser Gly Ser Thr Tyr
        115                 120                 125

Ala Val Ile Thr Asn Arg Tyr Thr Asp Arg Val Pro Ile Gly Val Pro
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     | 130 |     |     |     | 135 |     |     |     |     | 140 |     |     |     |     |
| Glu | Ile | Thr | Glu | Leu | Ile | Asp | Arg | Arg | Gly | Met | Cys | Leu | Ser | Lys | Ala |
| 145 |     |     |     |     | 150 |     |     |     |     | 155 |     |     |     |     | 160 |
| Asp | Tyr | Ile | Arg | Asn | Asn | Tyr | Glu | Phe | Thr | Ala | Phe | Asp | Lys | Asp | Glu |
|     |     |     |     | 165 |     |     |     |     | 170 |     |     |     |     | 175 |     |
| Asp | Pro | Arg | Glu | Val | His | Leu | Lys | Pro | Ser | Lys | Phe | Asn | Thr | Pro | Gly |
|     |     |     | 180 |     |     |     |     | 185 |     |     |     |     | 190 |     |     |
| Ser | Arg | Gly | Trp | His | Thr | Val | Asn | Asp | Thr | Tyr | Thr | Lys | Ile | Gly | Gly |
|     |     | 195 |     |     |     |     | 200 |     |     |     |     | 205 |     |     |     |
| Ser | Gly | Phe | Tyr | His | Ser | Gly | Thr | Ser | Val | Asn | Cys | Ile | Val | Glu | Glu |
|     | 210 |     |     |     |     | 215 |     |     |     |     | 220 |     |     |     |     |
| Val | Asp | Ala | Arg | Ser | Val | Tyr | Pro | Tyr | Asp | Ser | Phe | Ala | Ile | Ser | Thr |
| 225 |     |     |     |     | 230 |     |     |     |     | 235 |     |     |     |     | 240 |
| Gly | Asp | Ile | Ile | His | Met | Ser | Pro | Phe | Phe | Gly | Leu | Arg | Asp | Gly | Ala |
|     |     |     |     | 245 |     |     |     |     | 250 |     |     |     |     | 255 |     |
| His | Thr | Glu | Tyr | Ile | Ser | Tyr | Ser | Thr | Asp | Arg | Phe | Gln | Gln | Ile | Glu |
|     |     |     | 260 |     |     |     |     | 265 |     |     |     |     | 270 |     |     |
| Gly | Tyr | Tyr | Pro | Ile | Asp | Leu | Asp | Thr | Arg | Leu | Gln | Leu | Gly | Ala | Pro |
|     |     | 275 |     |     |     |     | 280 |     |     |     |     | 285 |     |     |     |
| Val | Ser | Arg | Asn | Phe | Leu | Thr | Thr | Gln | His | Val | Thr | Val | Ala | Trp | Asn |
|     | 290 |     |     |     |     | 295 |     |     |     |     | 300 |     |     |     |     |
| Trp | Val | Pro | Lys | Ile | Arg | Glu | Val | Cys | Thr | Leu | Ala | Lys | Trp | Arg | Glu |
| 305 |     |     |     |     | 310 |     |     |     |     | 315 |     |     |     |     | 320 |
| Ile | Asp | Glu | Ile | Ile | Arg | Asp | Glu | Tyr | Lys | Gly | Ser | Tyr | Arg | Phe | Thr |
|     |     |     |     | 325 |     |     |     |     | 330 |     |     |     |     | 335 |     |
| Ala | Lys | Ser | Ile | Ser | Ala | Thr | Phe | Ile | Ser | Asp | Thr | Thr | Gln | Phe | Asp |
|     |     |     | 340 |     |     |     |     | 345 |     |     |     |     | 350 |     |     |
| Ile | Asp | Arg | Val | Lys | Leu | Ser | Asp | Cys | Ala | Lys | Arg | Glu | Ala | Ile | Glu |
|     |     | 355 |     |     |     |     | 360 |     |     |     |     | 365 |     |     |     |
| Ala | Ile | Asp | Lys | Ile | Tyr | Lys | Lys | Lys | Tyr | Asn | Lys | Thr | His | Ile | Gln |
|     | 370 |     |     |     |     | 375 |     |     |     |     | 380 |     |     |     |     |
| Thr | Gly | Glu | Leu | Glu | Thr | Tyr | Leu | Ala | Arg | Gly | Gly | Phe | Ile | Ile | Ala |
| 385 |     |     |     |     | 390 |     |     |     |     | 395 |     |     |     |     | 400 |
| Phe | Arg | Pro | Met | Ile | Ser | Asn | Glu | Leu | Ala | Lys | Leu | Tyr | Ile | Asn | Glu |
|     |     |     |     | 405 |     |     |     |     | 410 |     |     |     |     | 415 |     |
| Leu | Val | Arg | Ser | Asn | Arg | Thr | Val | Asp | Leu | Lys | Ser | Leu | Leu | Asn | Pro |
|     |     |     | 420 |     |     |     |     | 425 |     |     |     |     | 430 |     |     |
| Ser | Val | Arg | Gly | Gly | Ala | Arg | Lys | Arg | Arg | Ser | Val | Glu | Glu | Asn | Lys |
|     |     | 435 |     |     |     |     | 440 |     |     |     |     | 445 |     |     |     |
| Arg | Ser | Lys | Arg | Asn | Ile | Glu | Gly | Gly | Ile | Glu | Asn | Val | Asn | Asn | Ser |
|     | 450 |     |     |     |     | 455 |     |     |     |     | 460 |     |     |     |     |
| Thr | Ile | Ile | Lys | Thr | Thr | Ser | Ser | Val | His | Phe | Ala | Met | Leu | Gln | Phe |
| 465 |     |     |     |     | 470 |     |     |     |     | 475 |     |     |     |     | 480 |
| Ala | Tyr | Asp | His | Ile | Gln | Ser | His | Val | Asn | Glu | Met | Leu | Ser | Arg | Ile |
|     |     |     |     | 485 |     |     |     |     | 490 |     |     |     |     | 495 |     |
| Ala | Thr | Ala | Trp | Cys | Asn | Leu | Gln | Asn | Lys | Glu | Arg | Thr | Leu | Trp | Asn |
|     |     |     | 500 |     |     |     |     | 505 |     |     |     |     | 510 |     |     |
| Glu | Val | Met | Lys | Leu | Asn | Pro | Thr | Ser | Val | Ala | Ser | Val | Ala | Met | Asp |
|     |     | 515 |     |     |     |     | 520 |     |     |     |     | 525 |     |     |     |
| Gln | Arg | Val | Ser | Ala | Arg | Met | Leu | Gly | Asp | Val | Leu | Ala | Val | Thr | Gln |
|     | 530 |     |     |     |     | 535 |     |     |     |     | 540 |     |     |     |     |
| Cys | Val | Asn | Ile | Ser | Gly | Ser | Ser | Val | Phe | Ile | Gln | Asn | Ser | Met | Arg |
| 545 |     |     |     |     | 550 |     |     |     |     | 555 |     |     |     |     | 560 |

| | | | | | | | | | | | | | | |
|---|---|---|---|---|---|---|---|---|---|---|---|---|---|---|
| Val | Leu | Gly | Ser | Thr 565 | Thr | Thr | Cys | Tyr | Ser 570 | Arg | Pro | Leu | Ile | Ser 575 | Phe |
| Lys | Ala | Leu | Glu | Asn 580 | Ser | Thr | Asn | Tyr 585 | Ile | Glu | Gly | Gln | Leu 590 | Gly | Glu |
| Asn | Asn | Glu 595 | Leu | Leu | Val | Glu | Arg 600 | Lys | Leu | Ile | Glu | Pro 605 | Cys | Thr | Ala |
| Asn | His 610 | Lys | Arg | Tyr | Phe | Lys 615 | Phe | Gly | Ala | Asp | Tyr 620 | Val | Tyr | Phe | Glu |
| Asn 625 | Tyr | Ala | Tyr | Val | Arg 630 | Lys | Val | Pro | Leu | Asn 635 | Glu | Ile | Glu | Met | Ile 640 |
| Ser | Ala | Tyr | Val | Asp 645 | Leu | Asn | Ile | Thr | Leu 650 | Leu | Glu | Asp | Arg | Glu 655 | Phe |
| Leu | Pro | Leu | Glu 660 | Val | Tyr | Thr | Arg | Ala 665 | Glu | Leu | Glu | Asp | Thr 670 | Gly | Leu |
| Leu | Asp | Tyr 675 | Ser | Glu | Ile | Gln | Arg 680 | Arg | Asn | Gln | Leu | His 685 | Ala | Leu | Lys |
| Phe | Tyr 690 | Asp | Ile | Asp | Ser | Val 695 | Val | Lys | Val | Asp | Asn 700 | Asn | Val | Val | Ile |
| Met 705 | Arg | Gly | Ile | Ala | Asn 710 | Phe | Phe | Gln | Gly | Leu 715 | Gly | Asp | Val | Gly | Ala 720 |
| Gly | Phe | Gly | Lys | Val 725 | Val | Leu | Gly | Ala | Ala 730 | Asn | Ala | Val | Ile | Ala 735 | Thr |
| Val | Ser | Gly | Val 740 | Ser | Ser | Phe | Leu | Asn 745 | Asn | Pro | Phe | Gly | Ala 750 | Leu | Ala |
| Val | Gly | Leu 755 | Leu | Ile | Leu | Ala | Gly 760 | Leu | Phe | Ala | Ala | Phe 765 | Leu | Ala | Tyr |
| Arg | Tyr 770 | Val | Ser | Lys | Leu | Lys 775 | Ser | Asn | Pro | Met | Lys 780 | Ala | Leu | Tyr | Pro |
| Val 785 | Thr | Thr | Lys | Asn | Leu 790 | Lys | Glu | Ser | Val | Lys 795 | Asn | Gly | Asn | Ser | Gly 800 |
| Asn | Asn | Ser | Asp | Gly 805 | Glu | Glu | Asn | Asp | Asp 810 | Asn | Ile | Asp | Glu | Glu 815 | Lys |
| Leu | Gln | Gln | Ala 820 | Lys | Glu | Met | Ile | Lys 825 | Tyr | Met | Ser | Leu | Val 830 | Ser | Ala |
| Met | Glu | Gln 835 | Gln | Glu | His | Lys | Ala 840 | Ile | Lys | Lys | Asn | Ser 845 | Gly | Pro | Ala |
| Leu | Leu 850 | Ala | Ser | His | Ile | Thr 855 | Asn | Leu | Ser | Leu | Lys 860 | His | Arg | Gly | Pro |
| Lys 865 | Tyr | Lys | Arg | Leu | Lys 870 | Asn | Val | Asn | Glu | Asn 875 | Glu | Ser | Lys | Val | |

( 2 ) INFORMATION FOR SEQ ID NO:3:

( i ) SEQUENCE CHARACTERISTICS:
        ( A ) LENGTH: 879 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:3:

| | | | | | | | | | | | | | | |
|---|---|---|---|---|---|---|---|---|---|---|---|---|---|---|
| Met 1 | Phe | Ser | Leu | Tyr 5 | Leu | Tyr | Ile | Phe | Phe 10 | Ile | Ile | Tyr | Thr | Leu 15 | Ile |
| Ile | Cys | Asp | Pro 20 | Thr | Thr | Pro | Glu | Ser 25 | Thr | Ile | Asn | Pro | Leu 30 | Asn | His |

| | | | | | | | | | | | | | | |
|---|---|---|---|---|---|---|---|---|---|---|---|---|---|---|
| His | Asn | Leu | Ser | Thr | Pro | Lys | Pro | Thr | Ser | Asp | Asp | Ile | Arg | Glu | Ile |
| | | 35 | | | | 40 | | | | | 45 | | | |
| Leu | Arg | Glu | Ser | Gln | Ile | Glu | Ser | Asp | Asp | Thr | Ser | Thr | Phe | Tyr | Met |
| | 50 | | | | 55 | | | | | 60 | | | | |
| Cys | Pro | Pro | Pro | Ser | Gly | Ser | Thr | Leu | Val | Arg | Leu | Glu | Pro | Pro | Arg |
| 65 | | | | 70 | | | | | 75 | | | | | 80 |
| Ala | Cys | Pro | Asn | Tyr | Lys | Leu | Gly | Lys | Asn | Phe | Thr | Glu | Gly | Ile | Ala |
| | | | | 85 | | | | | 90 | | | | | 95 |
| Val | Ile | Phe | Lys | Glu | Asn | Ile | Ser | Pro | Tyr | Lys | Phe | Lys | Ala | Asn | Ile |
| | | | 100 | | | | | 105 | | | | | 110 | |
| Tyr | Tyr | Lys | Asn | Ile | Ile | Ile | Thr | Thr | Val | Trp | Ser | Gly | Ser | Thr | Tyr |
| | | 115 | | | | | 120 | | | | | 125 | | |
| Ala | Val | Ile | Thr | Asn | Arg | Tyr | Thr | Asp | Arg | Val | Pro | Ile | Gly | Val | Pro |
| | 130 | | | | | 135 | | | | | 140 | | | |
| Glu | Ile | Thr | Glu | Leu | Ile | Asp | Arg | Arg | Gly | Met | Cys | Leu | Ser | Lys | Ala |
| 145 | | | | | 150 | | | | | 155 | | | | | 160 |
| Asp | Tyr | Ile | Arg | Asn | Asn | Tyr | Glu | Phe | Thr | Ala | Phe | Asp | Lys | Asp | Glu |
| | | | | 165 | | | | | 170 | | | | | 175 | |
| Asp | Pro | Arg | Glu | Val | His | Leu | Lys | Pro | Ser | Lys | Phe | Asn | Thr | Pro | Gly |
| | | | 180 | | | | | 185 | | | | | 190 | | |
| Ser | Arg | Gly | Trp | His | Thr | Val | Asn | Asp | Thr | Tyr | Thr | Lys | Ile | Gly | Gly |
| | | 195 | | | | | 200 | | | | | 205 | | | |
| Ser | Gly | Phe | Tyr | His | Ser | Gly | Thr | Ser | Val | Asn | Cys | Ile | Val | Glu | Glu |
| | 210 | | | | | 215 | | | | | 220 | | | | |
| Val | Asp | Ala | Arg | Ser | Val | Tyr | Pro | Tyr | Asp | Ser | Phe | Ala | Ile | Ser | Thr |
| 225 | | | | | 230 | | | | | 235 | | | | | 240 |
| Gly | Asp | Ile | Ile | His | Met | Ser | Pro | Phe | Phe | Gly | Leu | Arg | Asp | Gly | Ala |
| | | | | 245 | | | | | 250 | | | | | 255 | |
| His | Thr | Glu | Tyr | Ile | Ser | Tyr | Ser | Thr | Asp | Arg | Phe | Gln | Gln | Ile | Glu |
| | | | 260 | | | | | 265 | | | | | 270 | | |
| Gly | Tyr | Tyr | Pro | Ile | Asp | Leu | Asp | Thr | Arg | Leu | Gln | Leu | Gly | Ala | Pro |
| | | 275 | | | | | 280 | | | | | 285 | | | |
| Val | Ser | Arg | Asn | Phe | Leu | Thr | Thr | Gln | His | Val | Thr | Val | Ala | Trp | Asn |
| | 290 | | | | | 295 | | | | | 300 | | | | |
| Trp | Val | Pro | Lys | Ile | Arg | Glu | Val | Cys | Thr | Leu | Ala | Lys | Trp | Arg | Glu |
| 305 | | | | | 310 | | | | | 315 | | | | | 320 |
| Ile | Asp | Glu | Ile | Ile | Arg | Asp | Glu | Tyr | Lys | Gly | Ser | Tyr | Arg | Phe | Thr |
| | | | | 325 | | | | | 330 | | | | | 335 | |
| Ala | Lys | Ser | Ile | Ser | Ala | Thr | Phe | Ile | Ser | Asp | Thr | Thr | Gln | Phe | Asp |
| | | | 340 | | | | | 345 | | | | | 350 | | |
| Ile | Asp | Arg | Val | Lys | Leu | Ser | Asp | Cys | Ala | Lys | Arg | Glu | Ala | Ile | Glu |
| | | 355 | | | | | 360 | | | | | 365 | | | |
| Ala | Ile | Asp | Lys | Ile | Tyr | Lys | Lys | Tyr | Asn | Lys | Thr | His | Ile | Gln |
| | 370 | | | | | 375 | | | | | 380 | | | | |
| Thr | Gly | Glu | Leu | Glu | Thr | Tyr | Leu | Ala | Arg | Gly | Gly | Phe | Ile | Ile | Ala |
| 385 | | | | | 390 | | | | | 395 | | | | | 400 |
| Phe | Arg | Pro | Met | Ile | Ser | Asn | Glu | Leu | Ala | Lys | Leu | Tyr | Ile | Asn | Glu |
| | | | | 405 | | | | | 410 | | | | | 415 | |
| Leu | Val | Arg | Ser | Asn | Arg | Thr | Val | Asp | Leu | Lys | Ser | Leu | Leu | Asn | Pro |
| | | | 420 | | | | | 425 | | | | | 430 | | |
| Ser | Val | Arg | Gly | Gly | Ala | Arg | Lys | Arg | Arg | Ser | Val | Glu | Glu | Asn | Lys |
| | | 435 | | | | | 440 | | | | | 445 | | | |
| Arg | Ser | Lys | Arg | Asn | Ile | Glu | Gly | Gly | Ile | Glu | Asn | Val | Asn | Asn | Ser |

```
                450                      455                      460
Thr   Ile   Ile   Lys   Thr   Thr   Ser   Ser   Val   His   Phe   Ala   Met   Leu   Gln   Phe
465                     470                     475                                 480

Ala   Tyr   Asp   His   Ile   Gln   Ser   His   Val   Asn   Glu   Met   Leu   Ser   Arg   Ile
                  485                     490                                 495

Ala   Thr   Ala   Trp   Cys   Asn   Leu   Gln   Asn   Lys   Glu   Arg   Thr   Leu   Trp   Asn
                  500                     505                           510

Glu   Val   Met   Lys   Leu   Asn   Pro   Thr   Ser   Val   Ala   Ser   Val   Ala   Met   Asp
            515                     520                     525

Gln   Arg   Val   Ser   Ala   Arg   Met   Leu   Gly   Asp   Val   Leu   Ala   Val   Thr   Gln
      530                     535                           540

Cys   Val   Asn   Ile   Ser   Gly   Ser   Ser   Val   Phe   Ile   Gln   Asn   Ser   Met   Arg
545                           550                     555                                 560

Val   Leu   Gly   Ser   Thr   Thr   Thr   Cys   Tyr   Ser   Arg   Pro   Leu   Ile   Ser   Phe
                        565                     570                           575

Lys   Ala   Leu   Glu   Asn   Ser   Thr   Asn   Tyr   Ile   Glu   Gly   Gln   Leu   Gly   Glu
                  580                     585                           590

Asn   Asn   Glu   Leu   Leu   Val   Glu   Arg   Lys   Leu   Ile   Glu   Pro   Cys   Thr   Ala
                  595                     600                     605

Asn   His   Lys   Arg   Tyr   Phe   Lys   Phe   Gly   Ala   Asp   Tyr   Val   Tyr   Phe   Glu
      610                     615                           620

Asn   Tyr   Ala   Tyr   Val   Arg   Lys   Val   Pro   Leu   Asn   Glu   Ile   Glu   Met   Ile
625                           630                     635                                 640

Ser   Ala   Tyr   Val   Asp   Leu   Asn   Ile   Thr   Leu   Leu   Glu   Asp   Arg   Glu   Phe
                        645                     650                           655

Leu   Pro   Leu   Glu   Val   Tyr   Thr   Arg   Ala   Glu   Leu   Glu   Asp   Thr   Gly   Leu
                  660                     665                     670

Leu   Asp   Tyr   Ser   Glu   Ile   Gln   Arg   Arg   Asn   Gln   Leu   His   Ala   Leu   Lys
            675                     680                     685

Phe   Tyr   Asp   Ile   Asp   Ser   Val   Val   Lys   Val   Asp   Asn   Asn   Val   Val   Ile
      690                     695                     700

Met   Arg   Gly   Ile   Ala   Asn   Phe   Phe   Gln   Gly   Leu   Gly   Asp   Val   Gly   Ala
705                           710                     715                                 720

Gly   Phe   Gly   Lys   Val   Leu   Gly   Ala   Ala   Asn   Ala   Val   Ile   Ala   Thr
                        725                     730                           735

Val   Ser   Gly   Val   Ser   Ser   Phe   Leu   Asn   Asn   Pro   Phe   Gly   Ala   Leu   Ala
                  740                     745                           750

Val   Gly   Leu   Leu   Ile   Leu   Ala   Gly   Leu   Phe   Ala   Ala   Phe   Leu   Ala   Tyr
            755                     760                     765

Arg   Tyr   Val   Ser   Lys   Leu   Lys   Ser   Asn   Pro   Met   Lys   Ala   Leu   Tyr   Pro
      770                     775                     780

Val   Thr   Thr   Lys   Asn   Leu   Lys   Glu   Ser   Val   Lys   Asn   Gly   Asn   Ser   Gly
785                           790                     795                                 800

Asn   Asn   Ser   Asp   Gly   Glu   Glu   Asn   Asp   Asp   Asn   Ile   Asp   Glu   Glu   Lys
                        805                     810                           815

Leu   Gln   Gln   Ala   Lys   Glu   Met   Ile   Lys   Tyr   Met   Ser   Leu   Val   Ser   Ala
                  820                     825                     830

Met   Glu   Gln   Gln   Glu   His   Lys   Ala   Ile   Lys   Lys   Asn   Ser   Gly   Pro   Ala
            835                     840                     845

Leu   Leu   Ala   Ser   His   Ile   Thr   Asn   Leu   Ser   Leu   Lys   His   Arg   Gly   Pro
      850                     855                           860

Lys   Tyr   Lys   Arg   Leu   Lys   Asn   Val   Asn   Glu   Asn   Glu   Ser   Lys   Val
865                     870                     875
```

( 2 ) INFORMATION FOR SEQ ID NO:4:

( i ) SEQUENCE CHARACTERISTICS:
        ( A ) LENGTH: 1041 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

```
Met Ser Thr Arg Gly Asp Leu Gly Lys Arg Arg Arg Gly Ser Arg Trp
 1               5                  10                  15
Gln Gly His Ser Gly Tyr Phe Arg Gln Arg Cys Phe Phe Pro Ser Leu
                20                  25                  30
Leu Gly Ile Ala Ala Thr Gly Ser Arg His Gly Asn Gly Ser Ser Gly
            35                  40                  45
Leu Thr Arg Leu Ala Arg Tyr Val Ser Phe Ile Trp Ile Val Leu Phe
        50                  55                  60
Leu Val Gly Pro Arg Pro Val Glu Gly Gln Ser Gly Ser Thr Ser Glu
65                  70                  75                  80
Gln Pro Arg Arg Thr Val Ala Thr Pro Glu Val Gly Gly Thr Pro Pro
                85                  90                  95
Lys Pro Thr Thr Asp Pro Thr Asp Met Ser Asp Met Arg Glu Ala Leu
               100                 105                 110
Arg Ala Ser Gln Ile Glu Ala Asn Gly Pro Ser Thr Phe Tyr Met Cys
           115                 120                 125
Pro Pro Pro Ser Gly Ser Thr Val Val Arg Leu Glu Pro Pro Arg Ala
       130                 135                 140
Cys Pro Asp Tyr Lys Leu Gly Lys Asn Phe Thr Glu Gly Ile Ala Val
145                 150                 155                 160
Ile Phe Lys Glu Asn Ile Ala Pro Tyr Lys Phe Lys Ala Asn Ile Tyr
               165                 170                 175
Tyr Lys Asn Ile Ile Met Thr Thr Val Trp Ser Gly Ser Ser Tyr Ala
           180                 185                 190
Val Thr Thr Asn Arg Tyr Thr Asp Arg Val Pro Val Lys Val Gln Glu
       195                 200                 205
Ile Thr Asp Leu Ile Asp Arg Arg Gly Met Cys Leu Ser Lys Ala Asp
   210                 215                 220
Tyr Val Arg Asn Asn Tyr Gln Phe Thr Ala Phe Asp Arg Asp Glu Asp
225                 230                 235                 240
Pro Arg Glu Leu Pro Leu Lys Pro Ser Lys Phe Asn Thr Pro Gln Ser
               245                 250                 255
Arg Gly Trp His Thr Tyr Lys Phe Lys Ala Thr Val Tyr Tyr Lys Asp
           260                 265                 270
Val Ile Val Ser Thr Ala Trp Ala Gly Ser Ser Tyr Thr Gln Ile Thr
       275                 280                 285
Asn Arg Tyr Ala Asp Arg Val Pro Ile Pro Val Ser Glu Ile Thr Asp
   290                 295                 300
Thr Ile Asp Lys Phe Gly Lys Cys Ser Ser Lys Ala Thr Tyr Val Arg
305                 310                 315                 320
Asn Asn His Lys Val Glu Ala Phe Asn Glu Asp Lys Asn Pro Gln Asp
               325                 330                 335
Met Pro Leu Ile Ala Ser Lys Tyr Asn Ser Val Gly Ser Lys Ala Trp
           340                 345                 350
```

```
His Thr Thr Asn Glu Thr Tyr Thr Lys Ile Gly Ala Ala Gly Phe His
    355             360             365
His Ser Gly Thr Ser Val Asn Cys Ile Val Glu Glu Val Asp Ala Arg
    370             375             380
Ser Val Tyr Pro Tyr Asp Ser Phe Ala Ile Ser Thr Gly Asp Val Ile
385             390             395             400
His Met Ser Pro Phe Phe Gly Leu Arg Asp Gly Ala His Val Glu His
                405             410             415
Thr Ser Tyr Ser Ser Asp Arg Phe Gln Gln Ile Glu Gly Tyr Tyr Pro
            420             425             430
Ile Asp Leu Asp Thr Arg Leu Gln Leu Gly Ala Pro Val Ser Arg Asn
        435             440             445
Phe Leu Glu Thr Pro His Val Thr Val Ala Trp Asn Trp Thr Pro Lys
    450             455             460
Cys Gly Arg Val Cys Thr Leu Ala Lys Trp Arg Glu Ile Asp Glu Met
465             470             475             480
Leu Arg Asp Glu Tyr Gln Gly Ser Tyr Arg Phe Thr Val Lys Thr Ile
                485             490             495
Ser Ala Thr Phe Ile Ser Asn Thr Ser Gln Phe Glu Ile Asn Arg Ile
            500             505             510
Arg Leu Gly Asp Cys Ala Thr Lys Glu Ala Glu Ala Ile Asp Arg
        515             520             525
Ile Tyr Lys Ser Lys Tyr Ser Lys Thr His Ile Gln Thr Gly Thr Leu
    530             535             540
Glu Thr Tyr Leu Ala Arg Gly Gly Phe Leu Ile Ala Phe Arg Pro Met
545             550             555             560
Ile Ser Asn Glu Leu Ala Lys Leu Tyr Ile Asn Glu Leu Ala Arg Ser
                565             570             575
Asn Arg Thr Val Asp Leu Ser Ala Leu Leu Asn Pro Ser Gly Glu Thr
            580             585             590
Val Gln Arg Thr Arg Gly Ser Val Pro Ser Asn Gln His His Arg Ser
        595             600             605
Arg Arg Ser Thr Ile Glu Gly Gly Ile Glu Thr Val Asn Asn Ala Ser
    610             615             620
Leu Leu Lys Thr Thr Ser Ser Val Glu Phe Ala Met Ile Gln Phe Ala
625             630             635             640
Tyr Asp Tyr Ile Gln Ala His Val Asn Glu Met Leu Ser Arg Ile Ala
                645             650             655
Thr Ala Trp Cys Thr Leu Gln Asn Arg Glu His Val Leu Trp Thr Glu
            660             665             670
Thr Leu Lys Leu Asn Pro Gly Gly Val Val Ser Met Ala Leu Glu Arg
        675             680             685
Arg Val Ser Ala Arg Leu Leu Gly Asp Ala Val Ala Val Thr Gln Cys
    690             695             700
Val Asn Ile Ser Ser Gly His Val Tyr Ile Gln Asn Ser Met Arg Val
705             710             715             720
Thr Gly Ser Ser Thr Thr Cys Tyr Ser Arg Pro Leu Val Ser Phe Arg
                725             730             735
Ala Leu Asn Asp Ser Glu Tyr Ile Glu Gly Gln Leu Gly Glu Asn Asn
            740             745             750
Asp Leu Leu Val Glu Arg Lys Leu Ile Glu Pro Cys Thr Val Asn Asn
        755             760             765
Lys Arg Tyr Phe Lys Phe Gly Ala Asp Tyr Val Tyr Phe Glu Asp Tyr
```

|     |     |     |     |     | 770 |     |     |     |     | 775 |     |     |     |     | 780 |     |     |
| --- | --- | --- | --- | --- | --- | --- | --- | --- | --- | --- | --- | --- | --- | --- | --- | --- | --- |
| Ala | Tyr | Val | Arg | Lys | Val | Pro | Leu | Ser | Glu | Ile | Glu | Leu | Ile | Ser | Ala |
| 785 |     |     |     |     | 790 |     |     |     | 795 |     |     |     |     |     | 800 |
| Tyr | Val | Asp | Leu | Asn | Leu | Thr | Leu | Leu | Glu | Asp | Arg | Glu | Phe | Leu | Pro |
|     |     |     |     | 805 |     |     |     |     | 810 |     |     |     |     | 815 |     |
| Leu | Glu | Val | Tyr | Thr | Arg | Ala | Glu | Leu | Glu | Asp | Thr | Gly | Leu | Leu | Asp |
|     |     |     | 820 |     |     |     |     | 825 |     |     |     |     | 830 |     |     |
| Tyr | Ser | Glu | Ile | Gln | Arg | Arg | Asn | Gln | Leu | His | Ala | Leu | Lys | Phe | Tyr |
|     |     | 835 |     |     |     |     | 840 |     |     |     |     | 845 |     |     |     |
| Asp | Ile | Asp | Ser | Ile | Val | Arg | Val | Asp | Asn | Asn | Leu | Val | Ile | Met | Arg |
|     | 850 |     |     |     |     | 855 |     |     |     |     | 860 |     |     |     |     |
| Gly | Met | Ala | Asn | Phe | Phe | Gln | Gly | Leu | Gly | Asp | Val | Gly | Ala | Gly | Phe |
| 865 |     |     |     |     | 870 |     |     |     |     | 875 |     |     |     |     | 880 |
| Gly | Lys | Val | Val | Leu | Gly | Ala | Ala | Ser | Ala | Val | Ile | Ser | Thr | Val | Ser |
|     |     |     |     | 885 |     |     |     |     | 890 |     |     |     |     | 895 |     |
| Gly | Val | Ser | Ser | Phe | Leu | Asn | Asn | Pro | Phe | Gly | Ala | Leu | Ala | Val | Gly |
|     |     |     | 900 |     |     |     |     | 905 |     |     |     |     | 910 |     |     |
| Leu | Leu | Ile | Leu | Ala | Gly | Ile | Val | Ala | Ala | Phe | Leu | Ala | Tyr | Arg | Tyr |
|     |     | 915 |     |     |     |     | 920 |     |     |     |     | 925 |     |     |     |
| Ile | Ser | Arg | Leu | Arg | Ala | Asn | Pro | Met | Lys | Ala | Leu | Tyr | Pro | Val | Thr |
|     | 930 |     |     |     |     | 935 |     |     |     |     | 940 |     |     |     |     |
| Thr | Arg | Asn | Leu | Lys | Gln | Thr | Ala | Lys | Ser | Pro | Ala | Ser | Thr | Ala | Gly |
| 945 |     |     |     |     | 950 |     |     |     |     | 955 |     |     |     |     | 960 |
| Gly | Asp | Ser | Asp | Pro | Gly | Val | Asp | Asp | Phe | Asp | Glu | Glu | Lys | Leu | Met |
|     |     |     |     | 965 |     |     |     |     | 970 |     |     |     |     | 975 |     |
| Gln | Ala | Arg | Glu | Met | Ile | Lys | Tyr | Met | Ser | Leu | Val | Ser | Ala | Met | Glu |
|     |     |     | 980 |     |     |     |     | 985 |     |     |     |     | 990 |     |     |
| Gln | Gln | Glu | His | Lys | Ala | Met | Lys | Lys | Asn | Lys | Gly | Pro | Ala | Ile | Leu |
|     |     | 995 |     |     |     |     | 1000 |    |     |     |     | 1005 |    |     |     |
| Thr | Ser | His | Leu | Thr | Asn | Met | Ala | Leu | Arg | Arg | Arg | Gly | Pro | Lys | Tyr |
|     |     | 1010 |    |     |     |     | 1015 |    |     |     |     | 1020 |    |     |     |
| Gln | Arg | Leu | Asn | Asn | Leu | Asp | Ser | Gly | Asp | Asp | Thr | Glu | Thr | Asn | Leu |
| 1025 |   |     |     |     | 1030 |    |     |     |     | 1035 |    |     |     |     | 1040 |
| Val |

( 2 ) INFORMATION FOR SEQ ID NO:5:

( i ) SEQUENCE CHARACTERISTICS:
        ( A ) LENGTH: 980 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:5:

| Met | Ser | Ser | Gly | Cys | Arg | Ser | Val | Gly | Gly | Ser | Thr | Trp | Gly | Asn | Trp |
| --- | --- | --- | --- | --- | --- | --- | --- | --- | --- | --- | --- | --- | --- | --- | --- |
| 1 |   |     |     | 5 |     |     |     |     | 10 |    |     |     |     | 15 |     |
| Arg | Gly | Asp | Gly | Gly | Asp | Leu | Arg | Gln | Arg | Val | Leu | Ser | Pro | Val |
|     |     |     | 20 |    |     |     |     | 25 |    |     |     |     | 30 |    |
| Cys | Ser | Ala | Pro | Ala | Ala | Gly | Ser | Trp | Ile | Gly | Ser | Gln | Leu | Gly | Asn |
|     |     | 35 |    |     |     |     | 40 |    |     |     |     | 45 |    |     |     |
| Val | Gly | Asn | Leu | Leu | Ala | Thr | Pro | His | Pro | Leu | Gly | Lys | Pro | Ala | Ser |
|     |     | 50 |    |     |     |     | 55 |    |     |     |     | 60 |    |     |     |
| Ser | Arg | Val | Gly | Thr | Ile | Val | Leu | Ala | Cys | Leu | Leu | Leu | Phe | Gly | Ser |

|     |     |     |     |     |     |     |     |     |     |     |     |     |     |     |
|---|---|---|---|---|---|---|---|---|---|---|---|---|---|---|
| 65  |     |     |     | 70  |     |     |     | 75  |     |     |     |     |     | 80  |
| Cys | Val | Val | Arg | Ala | Val | Pro | Thr | Thr | Pro | Ser | Pro | Pro | Thr | Ser | Thr |
|     |     |     |     | 85  |     |     |     |     | 90  |     |     |     |     | 95  |     |
| Pro | Thr | Ser | Met | Ser | Thr | His | Ser | His | Gly | Thr | Val | Asp | Pro | Thr | Leu |
|     |     |     | 100 |     |     |     |     | 105 |     |     |     |     | 110 |     |     |
| Leu | Pro | Thr | Glu | Thr | Pro | Asp | Pro | Leu | Arg | Leu | Ala | Val | Arg | Glu | Ser |
|     |     | 115 |     |     |     |     | 120 |     |     |     |     | 125 |     |     |     |
| Gly | Ile | Leu | Ala | Glu | Asp | Gly | Asp | Phe | Tyr | Thr | Cys | Pro | Pro | Pro | Thr |
|     | 130 |     |     |     |     |     | 135 |     |     |     | 140 |     |     |     |     |
| Gly | Ser | Thr | Val | Val | Arg | Ile | Glu | Pro | Pro | Arg | Thr | Cys | Pro | Lys | Phe |
| 145 |     |     |     |     | 150 |     |     |     |     | 155 |     |     |     |     | 160 |
| Asp | Leu | Gly | Arg | Asn | Phe | Thr | Glu | Gly | Ile | Ala | Val | Ile | Phe | Lys | Glu |
|     |     |     |     | 165 |     |     |     |     | 170 |     |     |     |     | 175 |     |
| Asn | Ile | Ala | Pro | Tyr | Lys | Phe | Arg | Ala | Asn | Val | Tyr | Tyr | Lys | Asp | Ile |
|     |     |     | 180 |     |     |     |     | 185 |     |     |     |     | 190 |     |     |
| Val | Val | Thr | Arg | Val | Trp | Lys | Gly | Tyr | Ser | His | Thr | Ser | Leu | Ser | Asp |
|     |     | 195 |     |     |     |     | 200 |     |     |     |     | 205 |     |     |     |
| Arg | Tyr | Asn | Asp | Arg | Val | Pro | Val | Ser | Val | Glu | Glu | Ile | Phe | Gly | Leu |
|     | 210 |     |     |     |     | 215 |     |     |     |     | 220 |     |     |     |     |
| Ile | Asp | Ser | Lys | Gly | Lys | Cys | Ser | Ser | Lys | Ala | Glu | Tyr | Leu | Arg | Asp |
| 225 |     |     |     |     | 230 |     |     |     |     | 235 |     |     |     |     | 240 |
| Asn | Ile | Met | His | His | Ala | Tyr | His | Asp | Asp | Glu | Asp | Glu | Val | Glu | Leu |
|     |     |     |     | 245 |     |     |     |     | 250 |     |     |     |     | 255 |     |
| Asp | Leu | Cys | Arg | Pro | Ser | Leu | Gln | Leu | Arg | Gly | Ala | Arg | Ala | Trp | Gln |
|     |     |     | 260 |     |     |     |     | 265 |     |     |     |     | 270 |     |     |
| Thr | Thr | Asn | Asp | Thr | Thr | Ser | Tyr | Val | Gly | Trp | Met | Pro | Trp | Arg | His |
|     |     • | 275 |     |     |     |     | 280 |     |     |     |     | 285 |     |     |     |
| Tyr | Thr | Ser | Thr | Ser | Val | Asn | Cys | Ile | Val | Glu | Glu | Val | Glu | Ala | Arg |
|     | 290 |     |     |     |     | 295 |     |     |     |     | 300 |     |     |     |     |
| Ser | Val | Tyr | Pro | Tyr | Asp | Ser | Phe | Ala | Leu | Ser | Thr | Gly | Asp | Ile | Val |
| 305 |     |     |     |     | 310 |     |     |     |     | 315 |     |     |     |     | 320 |
| Tyr | Ala | Ser | Pro | Phe | Tyr | Gly | Leu | Arg | Ala | Ala | Ala | Arg | Ile | Glu | His |
|     |     |     |     | 325 |     |     |     |     | 330 |     |     |     |     | 335 |     |
| Asn | Ser | Tyr | Ala | Gln | Glu | Arg | Phe | Arg | Gln | Val | Glu | Gly | Tyr | Arg | Pro |
|     |     |     | 340 |     |     |     |     | 345 |     |     |     |     | 350 |     |     |
| Arg | Asp | Leu | Asp | Ser | Lys | Leu | Gln | Ala | Glu | Glu | Pro | Val | Thr | Lys | Asn |
|     |     | 355 |     |     |     |     | 360 |     |     |     |     | 365 |     |     |     |
| Phe | Ile | Thr | Thr | Pro | His | Val | Thr | Val | Ser | Trp | Asn | Trp | Thr | Glu | Lys |
|     | 370 |     |     |     |     | 375 |     |     |     |     | 380 |     |     |     |     |
| Lys | Val | Glu | Ala | Cys | Thr | Leu | Thr | Lys | Trp | Lys | Glu | Val | Asp | Glu | Leu |
| 385 |     |     |     |     | 390 |     |     |     |     | 395 |     |     |     |     | 400 |
| Val | Arg | Asp | Glu | Phe | Arg | Gly | Ser | Tyr | Arg | Phe | Thr | Ile | Arg | Ser | Ile |
|     |     |     |     | 405 |     |     |     |     | 410 |     |     |     |     | 415 |     |
| Ser | Ser | Thr | Phe | Ile | Ser | Asn | Thr | Thr | Gln | Phe | Lys | Leu | Glu | Ser | Ala |
|     |     |     | 420 |     |     |     |     | 425 |     |     |     |     | 430 |     |     |
| Pro | Leu | Thr | Glu | Cys | Val | Ser | Lys | Glu | Ala | Lys | Glu | Ala | Ile | Asp | Ser |
|     |     | 435 |     |     |     |     | 440 |     |     |     |     | 445 |     |     |     |
| Ile | Tyr | Lys | Lys | Gln | Tyr | Glu | Ser | Thr | His | Val | Phe | Ser | Gly | Asp | Val |
|     | 450 |     |     |     |     | 455 |     |     |     |     | 460 |     |     |     |     |
| Glu | Tyr | Tyr | Leu | Ala | Arg | Gly | Gly | Phe | Leu | Ile | Ala | Phe | Arg | Pro | Met |
| 465 |     |     |     |     | 470 |     |     |     |     | 475 |     |     |     |     | 480 |
| Leu | Ser | Asn | Glu | Leu | Ala | Arg | Leu | Tyr | Leu | Asn | Glu | Leu | Val | Arg | Ser |
|     |     |     |     | 485 |     |     |     |     | 490 |     |     |     |     | 495 |     |

| | | | | | | | | | | | | | | |
|---|---|---|---|---|---|---|---|---|---|---|---|---|---|---|
| Asn | Arg | Thr | Tyr | Asp | Leu | Lys | Asn | Leu | Leu | Asn | Pro | Asn | Ala | Asn | Asn |
| | | | 500 | | | | 505 | | | | | 510 | | | |
| Asn | Asn | Asn | Thr | Thr | Arg | Arg | Arg | Arg | Ser | Leu | Leu | Ser | Val | Pro | Glu |
| | | 515 | | | | 520 | | | | | 525 | | | | |
| Pro | Gln | Pro | Thr | Gln | Asp | Gly | Val | His | Arg | Glu | Gln | Ile | Leu | His | Arg |
| | 530 | | | | 535 | | | | | 540 | | | | | |
| Leu | His | Lys | Arg | Ala | Val | Glu | Ala | Thr | Ala | Gly | Thr | Asp | Ser | Ser | Asn |
| 545 | | | | | 550 | | | | | 555 | | | | | 560 |
| Val | Thr | Ala | Lys | Gln | Leu | Glu | Leu | Ile | Lys | Thr | Thr | Ser | Ser | Ile | Glu |
| | | | | 565 | | | | | 570 | | | | | 575 | |
| Phe | Ala | Met | Leu | Gln | Phe | Ala | Tyr | Asp | His | Ile | Gln | Ser | His | Val | Asn |
| | | | 580 | | | | | 585 | | | | | 590 | | |
| Glu | Met | Leu | Ser | Arg | Ile | Ala | Thr | Ala | Trp | Cys | Thr | Leu | Gln | Asn | Lys |
| | | 595 | | | | | 600 | | | | | 605 | | | |
| Glu | Arg | Thr | Leu | Trp | Asn | Glu | Met | Val | Lys | Ile | Asn | Pro | Ser | Ala | Ile |
| | 610 | | | | | 615 | | | | | 620 | | | | |
| Val | Ser | Ala | Thr | Leu | Asp | Glu | Arg | Val | Ala | Ala | Arg | Val | Leu | Gly | Asp |
| 625 | | | | | 630 | | | | | 635 | | | | | 640 |
| Val | Ile | Ala | Ile | Thr | His | Cys | Ala | Lys | Ile | Glu | Gly | Asn | Val | Tyr | Leu |
| | | | | 645 | | | | | 650 | | | | | 655 | |
| Gln | Asn | Ser | Met | Arg | Ser | Met | Asp | Ser | Asn | Thr | Cys | Tyr | Ser | Arg | Pro |
| | | | 660 | | | | | 665 | | | | | 670 | | |
| Pro | Val | Thr | Phe | Thr | Ile | Thr | Lys | Asn | Ala | Asn | Asn | Arg | Gly | Ser | Ile |
| | | 675 | | | | | 680 | | | | | 685 | | | |
| Glu | Gly | Gln | Leu | Gly | Glu | Glu | Asn | Glu | Ile | Phe | Thr | Glu | Arg | Lys | Leu |
| | 690 | | | | | 695 | | | | | 700 | | | | |
| Ile | Glu | Pro | Cys | Ala | Leu | Asn | Gln | Lys | Arg | Tyr | Phe | Lys | Phe | Gly | Lys |
| 705 | | | | | 710 | | | | | 715 | | | | | 720 |
| Glu | Tyr | Val | Tyr | Tyr | Glu | Asn | Tyr | Thr | Phe | Val | Arg | Lys | Val | Pro | Pro |
| | | | | 725 | | | | | 730 | | | | | 735 | |
| Thr | Glu | Ile | Glu | Val | Ile | Ser | Thr | Tyr | Val | Glu | Leu | Asn | Leu | Thr | Leu |
| | | | 740 | | | | | 745 | | | | | 750 | | |
| Leu | Glu | Asp | Arg | Glu | Phe | Leu | Pro | Leu | Glu | Val | Tyr | Thr | Arg | Ala | Glu |
| | | 755 | | | | | 760 | | | | | 765 | | | |
| Leu | Glu | Asp | Thr | Gly | Leu | Leu | Asp | Tyr | Ser | Glu | Ile | Gln | Arg | Arg | Asn |
| | 770 | | | | | 775 | | | | | 780 | | | | |
| Gln | Leu | His | Ala | Leu | Arg | Phe | Tyr | Asp | Ile | Asp | Ser | Val | Val | Asn | Val |
| 785 | | | | | 790 | | | | | 795 | | | | | 800 |
| Asp | Asn | Thr | Ala | Val | Ile | Met | Gln | Gly | Ile | Ala | Ser | Phe | Phe | Lys | Gly |
| | | | | 805 | | | | | 810 | | | | | 815 | |
| Leu | Gly | Lys | Val | Gly | Glu | Ala | Val | Gly | Thr | Leu | Val | Leu | Gly | Ala | Ala |
| | | | 820 | | | | | 825 | | | | | 830 | | |
| Gly | Ala | Val | Val | Ser | Thr | Val | Ser | Gly | Ile | Ala | Ser | Phe | Leu | Asn | Asn |
| | | | 835 | | | | | 840 | | | | | 845 | | |
| Pro | Phe | Gly | Gly | Leu | Ala | Ile | Gly | Leu | Leu | Val | Ile | Ala | Gly | Leu | Val |
| | 850 | | | | | 855 | | | | | 860 | | | | |
| Ala | Ala | Phe | Phe | Ala | Tyr | Arg | Tyr | Val | Met | Gln | Ile | Arg | Ser | Asn | Pro |
| 865 | | | | | 870 | | | | | 875 | | | | | 880 |
| Met | Lys | Ala | Leu | Tyr | Pro | Ile | Thr | Thr | Lys | Ala | Leu | Lys | Asn | Lys | Ala |
| | | | | 885 | | | | | 890 | | | | | 895 | |
| Lys | Thr | Ser | Tyr | Gly | Gln | Asn | Glu | Glu | Asp | Asp | Gly | Ser | Asp | Phe | Asp |
| | | | 900 | | | | | 905 | | | | | 910 | | |
| Glu | Ala | Lys | Leu | Glu | Glu | Ala | Arg | Glu | Met | Ile | Lys | Tyr | Met | Ser | Met |
| | | | 915 | | | | | 920 | | | | | 925 | | |

```
Val  Ser  Ala  Leu  Glu  Lys  Gln  Glu  Lys  Lys  Ala  Ile  Lys  Lys  Asn  Ser
     930                 935                      940

Gly  Val  Gly  Leu  Ile  Ala  Ser  Asn  Val  Ser  Lys  Leu  Ala  Leu  Arg  Arg
945                      950                      955                      960

Arg  Gly  Pro  Lys  Tyr  Thr  Arg  Leu  Gln  Gln  Asn  Asp  Thr  Met  Glu  Asn
                    965                 970                      975

Glu  Lys  Met  Val
               980
```

( 2 ) INFORMATION FOR SEQ ID NO:6:

( i ) SEQUENCE CHARACTERISTICS:
      ( A ) LENGTH: 913 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

```
Met  Pro  Ala  Gly  Gly  Gly  Leu  Trp  Arg  Gly  Pro  Arg  Gly  His  Arg  Pro
1              5                    10                      15

Gly  His  His  Gly  Gly  Ala  Gly  Leu  Gly  Arg  Leu  Trp  Pro  Ala  Pro  His
               20                   25                      30

His  Ala  Ala  Ala  Ala  Arg  Gly  Ala  Val  Ala  Leu  Ala  Leu  Leu  Leu  Leu
               35                   40                      45

Ala  Leu  Ala  Ala  Ala  Pro  Pro  Cys  Gly  Ala  Ala  Ala  Val  Thr  Arg  Ala
     50                   55                      60

Ala  Ser  Ala  Ser  Pro  Thr  Pro  Gly  Thr  Gly  Ala  Thr  Pro  Asn  Asp  Val
65                       70                      75                        80

Ser  Ala  Glu  Ala  Ser  Leu  Glu  Glu  Ile  Glu  Ala  Phe  Ser  Pro  Gly  Pro
               85                   90                      95

Ser  Glu  Ala  Pro  Asp  Gly  Glu  Tyr  Gly  Asp  Leu  Asp  Ala  Arg  Thr  Ala
               100                  105                     110

Val  Arg  Ala  Ala  Ala  Thr  Glu  Arg  Asp  Arg  Phe  Tyr  Val  Cys  Pro  Pro
          115                  120                     125

Pro  Ser  Gly  Ser  Thr  Val  Val  Arg  Leu  Glu  Pro  Glu  Gln  Ala  Cys  Pro
     130                  135                     140

Glu  Tyr  Ser  Gln  Gly  Arg  Asn  Phe  Thr  Glu  Gly  Ile  Ala  Val  Leu  Phe
145                  150                     155                          160

Lys  Glu  Asn  Ile  Ala  Pro  His  Lys  Phe  Lys  Ala  His  Ile  Tyr  Tyr  Lys
               165                  170                     175

Asn  Val  Ile  Val  Thr  Thr  Val  Trp  Ser  Gly  Ser  Thr  Tyr  Ala  Ala  Ile
               180                  185                     190

Thr  Asn  Arg  Phe  Thr  Asp  Arg  Val  Pro  Val  Pro  Val  Gln  Glu  Ile  Thr
          195                  200                     205

Asp  Val  Ile  Asp  Arg  Arg  Gly  Lys  Cys  Val  Ser  Lys  Ala  Glu  Tyr  Val
     210                  215                     220

Arg  Asn  Asn  His  Lys  Val  Thr  Ala  Phe  Asp  Arg  Asp  Glu  Asn  Pro  Val
225                  230                     235                          240

Glu  Val  Asp  Leu  Arg  Pro  Ser  Arg  Leu  Asn  Ala  Leu  Gly  Thr  Arg  Gly
               245                  250                     255

Trp  His  Thr  Thr  Asn  Asp  Thr  Tyr  Thr  Lys  Ile  Gly  Ala  Ala  Gly  Phe
               260                  265                     270

Tyr  His  Thr  Gly  Thr  Ser  Val  Asn  Cys  Ile  Val  Glu  Glu  Val  Glu  Ala
```

|   |   |   |   |   | 275 |   |   |   |   | 280 |   |   |   |   | 285 |   |   |   |   |
|---|---|---|---|---|---|---|---|---|---|---|---|---|---|---|---|---|---|---|---|

Arg Ser Val Tyr Pro Tyr Asp Ser Phe Ala Leu Ser Thr Gly Asp Ile
            290             295             300

Val Tyr Met Ser Pro Phe Tyr Gly Leu Arg Glu Gly Ala His Gly Glu
305             310             315                         320

His Ile Gly Tyr Ala Pro Gly Arg Phe Gln Gln Val Glu His Tyr Tyr
                325             330                 335

Pro Ile Asp Leu Asp Ser Arg Leu Arg Ala Ser Glu Ser Val Thr Arg
            340             345             350

Asn Phe Leu Arg Thr Pro His Phe Thr Val Ala Trp Asp Trp Ala Pro
        355             360             365

Lys Thr Arg Arg Val Cys Ser Leu Ala Lys Trp Arg Glu Ala Glu Glu
    370             375             380

Met Thr Arg Asp Glu Thr Arg Asp Gly Ser Phe Arg Phe Thr Ser Arg
385             390             395                         400

Ala Leu Gly Ala Ser Phe Val Ser Asp Val Thr Gln Leu Asp Leu Gln
                405             410             415

Arg Val His Leu Gly Asp Cys Val Leu Arg Glu Ala Ser Glu Ala Ile
            420             425             430

Asp Ala Ile Tyr Arg Arg Arg Tyr Asn Ser Thr His Val Leu Ala Gly
        435             440             445

Asp Arg Pro Glu Val Tyr Leu Ala Arg Gly Gly Phe Val Val Ala Phe
450             455             460

Arg Pro Leu Ile Ser Asn Glu Leu Ala Gln Leu Tyr Ala Arg Glu Leu
465             470             475                         480

Glu Arg Leu Gly Leu Ala Gly Val Val Gly Pro Ala Ala Pro Ala Ala
                485             490             495

Ala Arg Arg Ala Arg Arg Ser Pro Gly Pro Ala Gly Thr Pro Glu Pro
            500             505             510

Pro Ala Val Asn Gly Thr Gly His Leu Arg Ile Thr Thr Gly Ser Ala
        515             520             525

Glu Phe Ala Arg Leu Gln Phe Thr Tyr Asp His Ile Gln Ala His Val
    530             535             540

Asn Asp Met Leu Gly Arg Ile Ala Ala Ala Trp Cys Glu Leu Gln Asn
545             550             555                         560

Lys Asp Arg Thr Leu Trp Ser Glu Met Ser Arg Leu Asn Pro Ser Ala
                565             570             575

Val Ala Thr Ala Ala Leu Gly Gln Arg Val Ser Ala Arg Met Leu Gly
            580             585             590

Asp Val Met Ala Ile Ser Arg Cys Val Glu Val Arg Gly Gly Val Tyr
        595             600             605

Val Gln Asn Ser Met Arg Val Pro Gly Glu Arg Gly Thr Cys Tyr Ser
    610             615             620

Arg Pro Leu Val Thr Phe Glu His Asn Gly Thr Gly Val Ile Glu Gly
625             630             635                         640

Gln Leu Gly Asp Asp Asn Glu Leu Leu Ile Ser Arg Asp Leu Ile Glu
                645             650             655

Pro Cys Thr Gly Asn His Arg Arg Tyr Phe Lys Leu Gly Ser Gly Tyr
            660             665             670

Val Tyr Tyr Glu Asp Tyr Asn Tyr Val Arg Met Val Glu Val Pro Glu
        675             680             685

Thr Ile Ser Thr Arg Val Thr Leu Asn Leu Thr Leu Leu Glu Asp Arg
    690             695             700

```
Glu Phe Leu Pro Leu Glu Val Tyr Thr Arg Glu Glu Leu Ala Asp Thr
705                 710                 715                 720

Gly Leu Leu Asp Tyr Ser Glu Ile Gln Arg Arg Asn Gln Leu His Ala
                725                 730                 735

Leu Lys Phe Tyr Asp Ile Asp Arg Val Val Lys Val Asp His Asn Val
            740                 745                 750

Val Leu Leu Arg Gly Ile Ala Asn Phe Phe Gln Gly Leu Gly Asp Val
        755                 760                 765

Gly Ala Ala Val Gly Lys Val Val Leu Gly Ala Thr Gly Ala Val Ile
    770                 775                 780

Ser Ala Val Gly Gly Met Val Ser Phe Leu Ser Asn Pro Phe Gly Ala
785                 790                 795                 800

Leu Ala Ile Gly Leu Leu Val Leu Ala Gly Leu Val Ala Ala Phe Leu
            805                 810                 815

Ala Tyr Arg His Ile Ser Arg Leu Arg Arg Asn Pro Met Lys Ala Leu
        820                 825                 830

Tyr Pro Val Thr Thr Lys Thr Leu Lys Glu Asp Gly Val Asp Glu Gly
        835                 840                 845

Asp Val Asp Glu Ala Lys Leu Asp Gln Ala Arg Asp Met Ile Arg Tyr
    850                 855                 860

Met Ser Ile Val Ser Ala Leu Glu Gln Gln Glu His Lys Ala Arg Lys
865                 870                 875                 880

Lys Asn Ser Gly Pro Ala Leu Leu Ala Ser Arg Val Gly Ala Met Ala
                885                 890                 895

Thr Arg Arg Arg His Tyr Gln Arg Leu Glu Ser Glu Asp Pro Asp Ala
            900                 905                 910

Leu
```

( 2 ) INFORMATION FOR SEQ ID NO:7:

( i ) SEQUENCE CHARACTERISTICS:
        ( A ) LENGTH: 868 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:7:

```
Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30

His Leu Gly Asp Gly Asp Glu Ile Arg Glu Ala Ile His Lys Ser Gln
        35                  40                  45

Asp Ala Glu Thr Lys Pro Thr Phe Tyr Val Cys Pro Pro Pro Thr Gly
    50                  55                  60

Ser Thr Ile Val Arg Leu Glu Pro Thr Arg Thr Cys Pro Asp Tyr His
65                  70                  75                  80

Leu Gly Lys Asn Phe Thr Glu Gly Ile Ala Val Val Tyr Lys Glu Asn
                85                  90                  95

Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
        115                 120                 125
```

| | | | | | | | | | | | | | |
|---|---|---|---|---|---|---|---|---|---|---|---|---|---|
| Tyr | Ala | Asp | Arg | Val | Pro | Ile | Pro | Val | Ser | Glu | Ile | Thr | Asp | Thr | Ile |
| | 130 | | | | | 135 | | | | | 140 | | | | |
| Asp | Lys | Phe | Gly | Lys | Cys | Ser | Ser | Lys | Ala | Thr | Tyr | Val | Arg | Asn | Asn |
| 145 | | | | | 150 | | | | | 155 | | | | | 160 |
| His | Lys | Val | Glu | Ala | Phe | Asn | Glu | Asp | Lys | Asn | Pro | Gln | Asp | Met | Pro |
| | | | | 165 | | | | | 170 | | | | | 175 | |
| Leu | Ile | Ala | Ser | Lys | Tyr | Asn | Ser | Val | Gly | Ser | Lys | Ala | Trp | His | Thr |
| | | | | 180 | | | | | 185 | | | | | 190 | |
| Thr | Asn | Asp | Thr | Tyr | Met | Val | Ala | Gly | Thr | Pro | Gly | Thr | Tyr | Arg | Thr |
| | | | 195 | | | | 200 | | | | | 205 | | | |
| Gly | Thr | Ser | Val | Asn | Cys | Ile | Ile | Glu | Glu | Val | Glu | Ala | Arg | Ser | Ile |
| | 210 | | | | | 215 | | | | | 220 | | | | |
| Phe | Pro | Tyr | Asp | Ser | Phe | Gly | Leu | Ser | Thr | Gly | Asp | Ile | Ile | Tyr | Met |
| 225 | | | | | 230 | | | | | 235 | | | | | 240 |
| Ser | Pro | Phe | Phe | Gly | Leu | Arg | Asp | Gly | Ala | Tyr | Arg | Glu | His | Ser | Asn |
| | | | | 245 | | | | | 250 | | | | | 255 | |
| Tyr | Ala | Met | Asp | Arg | Phe | His | Gln | Phe | Glu | Gly | Tyr | Arg | Gln | Arg | Asp |
| | | | 260 | | | | 265 | | | | | 270 | | | |
| Leu | Asp | Thr | Arg | Ala | Leu | Leu | Glu | Pro | Ala | Ala | Arg | Asn | Phe | Leu | Val |
| | | 275 | | | | | 280 | | | | | 285 | | | |
| Thr | Pro | His | Leu | Thr | Val | Gly | Trp | Asn | Trp | Lys | Pro | Lys | Arg | Thr | Glu |
| | 290 | | | | | 295 | | | | | 300 | | | | |
| Val | Cys | Ser | Leu | Val | Lys | Trp | Arg | Glu | Val | Glu | Asp | Val | Val | Arg | Asp |
| 305 | | | | | 310 | | | | | 315 | | | | | 320 |
| Glu | Tyr | Ala | His | Asn | Phe | Arg | Phe | Thr | Met | Lys | Thr | Leu | Ser | Thr | Thr |
| | | | | 325 | | | | | 330 | | | | | 335 | |
| Phe | Ile | Ser | Glu | Thr | Asn | Glu | Phe | Asn | Leu | Asn | Gln | Ile | His | Leu | Ser |
| | | | | 340 | | | | | 345 | | | | | 350 | |
| Gln | Cys | Val | Lys | Glu | Glu | Ala | Arg | Ala | Ile | Ile | Asn | Arg | Ile | Tyr | Thr |
| | | | | 355 | | | | | 360 | | | | | 365 | |
| Thr | Arg | Tyr | Asn | Ser | Ser | His | Val | Arg | Thr | Gly | Asp | Ile | Gln | Thr | Tyr |
| | 370 | | | | | 375 | | | | | 380 | | | | |
| Leu | Ala | Arg | Gly | Gly | Phe | Val | Val | Val | Phe | Gln | Pro | Leu | Leu | Ser | Asn |
| 385 | | | | | 390 | | | | | 395 | | | | | 400 |
| Ser | Leu | Ala | Arg | Leu | Tyr | Leu | Gln | Glu | Leu | Val | Arg | Glu | Asn | Thr | Asn |
| | | | | 405 | | | | | 410 | | | | | 415 | |
| His | Ser | Pro | Gln | Lys | His | Pro | Thr | Arg | Asn | Thr | Arg | Ser | Arg | Arg | Ser |
| | | | | 420 | | | | | 425 | | | | | 430 | |
| Val | Pro | Val | Glu | Leu | Arg | Ala | Asn | Arg | Thr | Ile | Thr | Thr | Thr | Ser | Ser |
| | | | 435 | | | | 440 | | | | | 445 | | | |
| Val | Glu | Phe | Ala | Met | Leu | Gln | Phe | Thr | Tyr | Asp | His | Ile | Gln | Glu | His |
| | 450 | | | | | 455 | | | | | 460 | | | | |
| Val | Asn | Glu | Met | Leu | Ala | Arg | Ile | Ser | Ser | Ser | Trp | Cys | Gln | Leu | Gln |
| 465 | | | | | 470 | | | | | 475 | | | | | 480 |
| Asn | Arg | Glu | Arg | Ala | Leu | Trp | Ser | Gly | Leu | Phe | Pro | Ile | Asn | Pro | Ser |
| | | | | 485 | | | | | 490 | | | | | 495 | |
| Ala | Leu | Ala | Ser | Thr | Ile | Leu | Asp | Gln | Arg | Val | Lys | Ala | Arg | Ile | Leu |
| | | | 500 | | | | | 505 | | | | | 510 | | |
| Gly | Asp | Val | Ile | Ser | Val | Ser | Asn | Cys | Pro | Glu | Leu | Gly | Ser | Asp | Thr |
| | | 515 | | | | | 520 | | | | | 525 | | | |
| Arg | Ile | Ile | Leu | Gln | Asn | Ser | Met | Arg | Val | Ser | Gly | Ser | Thr | Thr | Arg |
| | 530 | | | | | 535 | | | | | 540 | | | | |
| Cys | Tyr | Ser | Arg | Pro | Leu | Ile | Ser | Ile | Val | Ser | Leu | Asn | Gly | Ser | Gly |
| 545 | | | | | 550 | | | | | 555 | | | | | 560 |

|     |     |     |     |     |     |     |     |     |     |     |     |     |     |     |
|---|---|---|---|---|---|---|---|---|---|---|---|---|---|---|
| Thr | Val | Glu | Gly | Gln<br>565 | Leu | Gly | Thr | Asp | Asn<br>570 | Glu | Leu | Ile | Met | Ser<br>575 | Arg |
| Asp | Leu | Leu | Glu<br>580 | Pro | Cys | Val | Ala | Asn<br>585 | His | Lys | Arg | Tyr | Phe<br>590 | Leu | Phe |
| Gly | His | His<br>595 | Tyr | Val | Tyr | Tyr | Glu<br>600 | Asp | Tyr | Arg | Tyr | Val<br>605 | Arg | Glu | Ile |
| Ala | Val<br>610 | His | Asp | Val | Gly | Met<br>615 | Ile | Ser | Thr | Tyr | Val<br>620 | Asp | Leu | Asn | Leu |
| Thr<br>625 | Leu | Leu | Lys | Asp | Arg<br>630 | Glu | Phe | Met | Pro | Leu<br>635 | Gln | Val | Tyr | Thr | Arg<br>640 |
| Asp | Glu | Leu | Arg | Asp<br>645 | Thr | Gly | Leu | Leu | Asp<br>650 | Tyr | Ser | Glu | Ile | Gln<br>655 | Arg |
| Arg | Asn | Gln | Met<br>660 | His | Ser | Leu | Arg | Phe<br>665 | Tyr | Asp | Ile | Asp | Lys<br>670 | Val | Val |
| Gln | Tyr | Asp<br>675 | Ser | Gly | Thr | Ala | Ile<br>680 | Met | Gln | Gly | Met | Ala<br>685 | Gln | Phe | Phe |
| Gln | Gly<br>690 | Leu | Gly | Thr | Ala | Gly<br>695 | Gln | Ala | Val | Gly | His<br>700 | Val | Val | Leu | Gly |
| Ala<br>705 | Thr | Gly | Ala | Leu | Leu<br>710 | Ser | Thr | Val | His | Gly<br>715 | Phe | Thr | Thr | Phe | Leu<br>720 |
| Ser | Asn | Pro | Phe | Gly<br>725 | Ala | Leu | Ala | Val | Gly<br>730 | Leu | Leu | Val | Leu | Ala<br>735 | Gly |
| Leu | Val | Ala | Ala<br>740 | Phe | Phe | Ala | Tyr | Arg<br>745 | Tyr | Val | Leu | Lys | Leu<br>750 | Lys | Thr |
| Ser | Pro | Met<br>755 | Lys | Ala | Leu | Tyr | Pro<br>760 | Leu | Thr | Thr | Lys | Gly<br>765 | Leu | Lys | Gln |
| Leu | Pro<br>770 | Glu | Gly | Met | Asp | Pro<br>775 | Phe | Ala | Glu | Lys | Pro<br>780 | Asn | Ala | Thr | Asp |
| Thr<br>785 | Pro | Ile | Glu | Glu | Ile<br>790 | Gly | Asp | Ser | Gln | Asn<br>795 | Thr | Glu | Pro | Ser | Val<br>800 |
| Asn | Ser | Gly | Phe | Asp<br>805 | Pro | Asp | Lys | Phe | Arg<br>810 | Glu | Ala | Gln | Glu | Met<br>815 | Ile |
| Lys | Tyr | Met | Thr<br>820 | Leu | Val | Ser | Ala | Ala<br>825 | Glu | Arg | Gln | Glu | Ser<br>830 | Lys | Ala |
| Arg | Lys | Lys<br>835 | Asn | Lys | Thr | Ser | Ala<br>840 | Leu | Leu | Thr | Ser | Arg<br>845 | Leu | Thr | Gly |
| Leu | Ala<br>850 | Leu | Arg | Asn | Arg | Arg<br>855 | Gly | Tyr | Ser | Arg | Val<br>860 | Arg | Thr | Glu | Asn |
| Val<br>865 | Thr | Gly | Val | | | | | | | | | | | | |

( 2 ) INFORMATION FOR SEQ ID NO:8:

( i ) SEQUENCE CHARACTERISTICS:
        ( A ) LENGTH: 903 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:8:

|     |     |     |     |     |     |     |     |     |     |     |     |     |     |     |
|---|---|---|---|---|---|---|---|---|---|---|---|---|---|---|
| Met<br>1 | His | Gln | Gly | Ala<br>5 | Pro | Ser | Trp | Gly | Arg<br>10 | Arg | Trp | Phe | Val | Val<br>15 | Trp |
| Ala | Leu | Leu | Gly | Leu | Thr | Leu | Gly | Val | Leu | Val | Ala | Ser | Ala | Ala | Pro |

|   |   |   |   |   | 20 |   |   |   |   | 25 |   |   |   |   | 30 |   |   |
|---|---|---|---|---|---|---|---|---|---|---|---|---|---|---|---|---|---|
| Ser | Ser | Pro 35 | Gly | Thr | Pro | Gly | Val 40 | Ala | Arg | Asp | Pro | Gly 45 | Gly | Glu | Arg |
| Gly | Pro 50 | Cys | His | Ser | Gly 55 | Ala | Ala | Ala | Leu | Gly 60 | Ala | Pro | Thr | Gly |
| Asp 65 | Pro | Lys | Pro | Lys 70 | Lys | Asn | Lys | Lys | Pro 75 | Lys | Asn | Pro | Thr | Pro | Pro 80 |
| Arg | Pro | Ala | Gly | Asp 85 | Asn | Ala | Thr | Val | Ala 90 | Ala | Gly | His | Ala | Thr 95 | Leu |
| Arg | Glu | His | Leu 100 | Arg | Asp | Ile | Lys | Ala 105 | Glu | Asn | Thr | Asp | Ala 110 | Asn | Phe |
| Tyr | Val | Cys 115 | Pro | Pro | Pro | Thr | Gly 120 | Ala | Thr | Val | Val | Gln 125 | Phe | Glu | Gln |
| Pro | Arg 130 | Arg | Cys | Pro | Thr | Arg 135 | Pro | Glu | Gly | Gln | Asn 140 | Tyr | Thr | Glu | Gly |
| Ile 145 | Ala | Val | Val | Phe | Lys 150 | Glu | Asn | Ile | Ala | Pro 155 | Tyr | Lys | Phe | Lys | Ala 160 |
| Thr | Met | Tyr | Tyr | Lys 165 | Asp | Val | Thr | Val | Ser 170 | Gln | Val | Trp | Phe | Gly 175 | His |
| Arg | Tyr | Ser | Gln 180 | Phe | Met | Gly | Ile | Phe 185 | Glu | Asp | Arg | Ala | Pro 190 | Val | Pro |
| Phe | Glu | Glu 195 | Val | Ile | Asp | Lys | Ile 200 | Asn | Ala | Lys | Gly | Val 205 | Cys | Arg | Ser |
| Thr | Ala 210 | Lys | Tyr | Val | Arg | Asn 215 | Asn | Leu | Glu | Thr | Thr 220 | Ala | Phe | His | Arg |
| Asp 225 | Asp | His | Glu | Thr | Asp 230 | Met | Glu | Leu | Lys | Pro 235 | Ala | Asn | Ala | Ala | Thr 240 |
| Arg | Thr | Ser | Arg | Gly 245 | Trp | His | Thr | Thr | Asp 250 | Leu | Lys | Tyr | Asn | Pro 255 | Ser |
| Arg | Val | Glu | Ala 260 | Phe | His | Arg | Tyr | Gly 265 | Thr | Thr | Val | Asn | Cys 270 | Ile | Val |
| Glu | Glu | Val 275 | Asp | Ala | Arg | Ser | Val 280 | Tyr | Pro | Tyr | Asp | Glu 285 | Phe | Val | Leu |
| Ala | Thr 290 | Gly | Asp | Phe | Val | Tyr 295 | Met | Ser | Pro | Phe | Tyr 300 | Gly | Tyr | Arg | Glu |
| Gly 305 | Ser | His | Thr | Glu | His 310 | Thr | Thr | Tyr | Ala | Ala 315 | Asp | Arg | Phe | Lys | Gln 320 |
| Val | Asp | Gly | Phe | Tyr 325 | Ala | Arg | Asp | Leu | Thr 330 | Thr | Lys | Ala | Arg | Ala 335 | Thr |
| Ala | Pro | Thr | Thr 340 | Arg | Asn | Leu | Leu | Thr 345 | Thr | Pro | Lys | Phe | Thr 350 | Val | Ala |
| Trp | Asp | Trp 355 | Val | Pro | Lys | Arg | Pro 360 | Ser | Val | Cys | Thr | Met 365 | Thr | Lys | Trp |
| Gln | Glu 370 | Val | Asp | Glu | Met | Leu 375 | Arg | Ser | Glu | Tyr | Gly 380 | Gly | Ser | Phe | Arg |
| Phe 385 | Ser | Ser | Asp | Ala | Ile 390 | Ser | Thr | Thr | Phe | Thr 395 | Thr | Asn | Leu | Thr | Glu 400 |
| Tyr | Pro | Leu | Ser | Arg 405 | Val | Asp | Leu | Gly | Asp 410 | Cys | Ile | Gly | Lys | Asp 415 | Ala |
| Arg | Asp | Ala | Met 420 | Asp | Arg | Ile | Phe | Ala 425 | Arg | Arg | Tyr | Asn | Ala 430 | Thr | His |
| Ile | Lys | Val | Gly 435 | Gln | Pro | Gln | Tyr 440 | Tyr | Leu | Ala | Asn | Gly 445 | Gly | Phe | Leu |

```
Ile Ala Tyr Gln Pro Leu Leu Ser Asn Thr Leu Ala Glu Leu Tyr Val
450                     455                 460
Arg Glu His Leu Arg Glu Gln Ser Arg Lys Pro Pro Asn Pro Thr Pro
465                 470                 475                 480
Pro Pro Pro Gly Ala Ser Ala Asn Ala Ser Val Glu Arg Ile Lys Thr
                485                 490                 495
Thr Ser Ser Ile Glu Phe Ala Arg Leu Gln Phe Thr Tyr Asn His Ile
            500                 505                 510
Gln Arg His Val Asn Asp Met Leu Gly Arg Val Ala Ile Ala Trp Cys
        515                 520                 525
Glu Leu Gln Asn His Glu Leu Thr Leu Trp Asn Glu Ala Arg Lys Leu
        530                 535                 540
Asn Pro Asn Ala Ile Ala Ser Val Thr Val Gly Arg Arg Val Ser Ala
545                 550                 555                 560
Arg Met Leu Gly Asp Val Met Ala Val Ser Thr Cys Val Pro Val Ala
                565                 570                 575
Ala Asp Asn Val Ile Val Gln Asn Ser Met Arg Ile Ser Ser Arg Pro
            580                 585                 590
Gly Ala Cys Tyr Ser Arg Pro Leu Val Ser Phe Arg Tyr Glu Asp Gln
        595                 600                 605
Gly Pro Leu Val Glu Gly Gln Leu Gly Glu Asn Asn Glu Leu Arg Leu
610                 615                 620
Thr Arg Asp Ala Ile Glu Pro Cys Thr Val Gly His Arg Arg Tyr Phe
625                 630                 635                 640
Thr Phe Gly Gly Gly Tyr Val Tyr Phe Glu Glu Tyr Ala Tyr Ser His
                645                 650                 655
Gln Leu Ser Arg Ala Asp Ile Thr Thr Val Ser Thr Phe Ile Asp Leu
        660                 665                 670
Asn Ile Thr Met Leu Glu Asp His Glu Phe Val Pro Leu Glu Val Tyr
        675                 680                 685
Thr Arg His Glu Ile Lys Asp Ser Gly Leu Leu Asp Tyr Thr Glu Val
    690                 695                 700
Gln Arg Arg Asn Gln Leu His Asp Leu Arg Phe Ala Asp Ile Asp Thr
705                 710                 715                 720
Val Ile His Ala Asp Ala Asn Ala Ala Met Phe Ala Gly Leu Gly Ala
                725                 730                 735
Phe Phe Glu Gly Met Gly Asp Leu Gly Arg Ala Val Gly Lys Val Val
            740                 745                 750
Met Gly Leu Val Gly Gly Val Val Ser Ala Val Ser Gly Val Ser Ser
        755                 760                 765
Phe Met Ser Asn Pro Phe Gly Ala Leu Ala Val Gly Leu Leu Val Leu
770                 775                 780
Ala Gly Leu Ala Ala Ala Phe Phe Ala Phe Arg Tyr Val Met Arg Leu
785                 790                 795                 800
Gln Ser Asn Pro Met Lys Ala Leu Tyr Pro Leu Thr Thr Lys Glu Leu
                805                 810                 815
Lys Asn Pro Thr Asn Pro Asp Ala Ser Gly Glu Gly Glu Glu Gly Gly
            820                 825                 830
Asp Phe Asp Glu Ala Lys Leu Ala Glu Ala Arg Glu Met Ile Arg Tyr
        835                 840                 845
Met Ala Leu Val Ser Ala Met Glu Arg Thr Glu His Lys Ala Lys Lys
850                 855                 860
Lys Gly Thr Ser Arg Leu Leu Ser Ala Lys Val Thr Asp Met Val Met
865                 870                 875                 880
```

| | | | | | | | | | | | | | | |
|---|---|---|---|---|---|---|---|---|---|---|---|---|---|---|
|Arg|Lys|Arg|Arg|Asn<br>885|Thr|Asn|Tyr|Thr|Gln<br>890|Val|Pro|Asn|Lys<br>895|Asp|Gly|
|Asp|Ala|Asp|Glu<br>900|Asp|Asp|Leu| | | | | | | | |

(2) INFORMATION FOR SEQ ID NO:9:

(i) SEQUENCE CHARACTERISTICS:
        (A) LENGTH: 906 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:9:

| | | | | | | | | | | | | | | |
|---|---|---|---|---|---|---|---|---|---|---|---|---|---|---|
|Met<br>1|Glu|Ser|Arg|Ile<br>5|Trp|Cys|Leu|Val|Val<br>10|Cys|Val|Asn|Leu|Cys<br>15|Ile|
|Val|Cys|Leu|Gly<br>20|Ala|Ala|Val|Ser|Ser<br>25|Ser|Ser|Thr|Ser|His<br>30|Ala|Thr|
|Ser|Ser|Thr<br>35|His|Asn|Gly|Ser|His<br>40|Thr|Ser|Arg|Thr|Thr<br>45|Ser|Ala|Gln|
|Thr|Arg<br>50|Ser|Val|Tyr|Ser|Gln<br>55|His|Val|Thr|Ser|Ser<br>60|Glu|Ala|Val|Ser|
|His<br>65|Arg|Ala|Asn|Glu|Thr<br>70|Ile|Tyr|Asn|Thr|Thr<br>75|Leu|Lys|Tyr|Gly|Asp<br>80|
|Val|Val|Gly|Val|Asn<br>85|Thr|Thr|Lys|Tyr|Pro<br>90|Tyr|Arg|Val|Cys|Ser<br>95|Met|
|Ala|Gln|Gly|Thr<br>100|Asp|Leu|Ile|Arg|Phe<br>105|Glu|Arg|Asn|Ile|Ile<br>110|Cys|Thr|
|Ser|Met|Lys<br>115|Pro|Ile|Asn|Glu|Asp<br>120|Leu|Asp|Glu|Gly|Ile<br>125|Met|Val|Val|
|Tyr|Lys<br>130|Arg|Asn|Ile|Val|Ala<br>135|His|Thr|Phe|Lys|Val<br>140|Arg|Val|Tyr|Gln|
|Lys<br>145|Val|Leu|Thr|Phe|Arg<br>150|Arg|Ser|Tyr|Ala|Tyr<br>155|Ile|Tyr|Thr|Thr|Tyr<br>160|
|Leu|Leu|Gly|Ser|Asn<br>165|Thr|Glu|Tyr|Val|Ala<br>170|Pro|Pro|Met|Trp|Glu<br>175|Ile|
|His|His|Ile|Asn<br>180|Lys|Phe|Ala|Gln|Cys<br>185|Tyr|Ser|Ser|Tyr|Ser<br>190|Arg|Val|
|Ile|Gly|Gly<br>195|Thr|Val|Phe|Val|Ala<br>200|Tyr|His|Arg|Asp|Ser<br>205|Tyr|Glu|Asn|
|Lys|Thr<br>210|Met|Gln|Leu|Ile|Pro<br>215|Asp|Asp|Tyr|Ser|Asn<br>220|Thr|His|Ser|Thr|
|Arg<br>225|Tyr|Val|Thr|Val|Lys<br>230|Asp|Gln|Trp|His|Ser<br>235|Arg|Gly|Ser|Thr|Trp<br>240|
|Leu|Tyr|Arg|Glu|Thr<br>245|Cys|Asn|Leu|Asn|Cys<br>250|Met|Leu|Thr|Ile|Thr<br>255|Thr|
|Ala|Arg|Ser|Lys<br>260|Tyr|Pro|Tyr|His|Phe<br>265|Phe|Ala|Thr|Ser|Thr<br>270|Gly|Asp|
|Val|Val|Tyr|Ile<br>275|Ser|Pro|Phe|Tyr|Asn<br>280|Gly|Thr|Asn|Arg|Asn<br>285|Ala|Ser|
|Tyr|Phe<br>290|Gly|Glu|Asn|Ala|Asp<br>295|Lys|Phe|Phe|Ile|Phe<br>300|Pro|Asn|Tyr|Thr|
|Ile|Val|Ser|Asp|Phe|Gly|Arg|Pro|Asn|Ala|Ala|Pro|Glu|Thr|His|Arg|

|     |     |     |     |     |     |     |     |     |     |     |     |     |     |     |     |
| --- | --- | --- | --- | --- | --- | --- | --- | --- | --- | --- | --- | --- | --- | --- | --- |
| 305 |     |     |     |     | 310 |     |     |     |     | 315 |     |     |     |     | 320 |
| Leu | Val | Ala | Phe | Leu | Glu | Arg | Ala | Asp | Ser | Val | Ile | Ser | Trp | Asp | Ile |
|     |     |     |     | 325 |     |     |     | 330 |     |     |     | 335 |     |     |     |
| Gln | Asp | Glu | Lys | Asn | Val | Thr | Cys | Gln | Leu | Thr | Phe | Trp | Glu | Ala | Ser |
|     |     |     | 340 |     |     |     |     | 345 |     |     |     |     | 350 |     |     |
| Glu | Arg | Thr | Ile | Arg | Ser | Glu | Ala | Glu | Asp | Ser | Tyr | His | Phe | Ser | Ser |
|     |     | 355 |     |     |     |     | 360 |     |     |     |     | 365 |     |     |     |
| Ala | Lys | Met | Thr | Ala | Thr | Phe | Leu | Ser | Lys | Lys | Gln | Glu | Val | Asn | Met |
|     | 370 |     |     |     |     | 375 |     |     |     |     | 380 |     |     |     |     |
| Ser | Asp | Ser | Ala | Leu | Asp | Cys | Val | Arg | Asp | Glu | Ala | Ile | Asn | Lys | Leu |
| 385 |     |     |     |     | 390 |     |     |     |     | 395 |     |     |     |     | 400 |
| Gln | Gln | Ile | Phe | Asn | Thr | Ser | Tyr | Asn | Gln | Thr | Tyr | Glu | Lys | Tyr | Gly |
|     |     |     |     | 405 |     |     |     |     | 410 |     |     |     |     | 415 |     |
| Asn | Val | Ser | Val | Phe | Glu | Thr | Ser | Gly | Gly | Leu | Val | Val | Phe | Trp | Gln |
|     |     |     | 420 |     |     |     |     | 425 |     |     |     |     | 430 |     |     |
| Gly | Ile | Lys | Gln | Lys | Ser | Leu | Val | Glu | Leu | Glu | Arg | Leu | Ala | Asn | Arg |
|     |     | 435 |     |     |     |     | 440 |     |     |     |     | 445 |     |     |     |
| Ser | Ser | Leu | Asn | Ile | Thr | His | Arg | Thr | Arg | Arg | Ser | Thr | Ser | Asp | Asn |
|     | 450 |     |     |     |     | 455 |     |     |     |     | 460 |     |     |     |     |
| Asn | Thr | Thr | His | Leu | Ser | Ser | Met | Glu | Ser | Val | His | Asn | Leu | Val | Tyr |
| 465 |     |     |     |     | 470 |     |     |     |     | 475 |     |     |     |     | 480 |
| Ala | Gln | Leu | Gln | Phe | Thr | Tyr | Asp | Thr | Leu | Arg | Gly | Tyr | Ile | Asn | Arg |
|     |     |     |     | 485 |     |     |     |     | 490 |     |     |     |     | 495 |     |
| Ala | Leu | Ala | Gln | Ile | Ala | Glu | Ala | Trp | Cys | Val | Asp | Gln | Arg | Arg | Thr |
|     |     |     | 500 |     |     |     |     | 505 |     |     |     |     | 510 |     |     |
| Leu | Glu | Val | Phe | Lys | Glu | Leu | Ser | Lys | Ile | Asn | Pro | Ser | Ala | Ile | Leu |
|     |     | 515 |     |     |     |     | 520 |     |     |     |     | 525 |     |     |     |
| Ser | Ala | Ile | Tyr | Asn | Lys | Pro | Ile | Ala | Ala | Arg | Phe | Met | Gly | Asp | Val |
|     | 530 |     |     |     |     | 535 |     |     |     |     | 540 |     |     |     |     |
| Leu | Gly | Leu | Ala | Ser | Cys | Val | Thr | Ile | Asn | Gln | Thr | Ser | Val | Lys | Val |
| 545 |     |     |     |     | 550 |     |     |     |     | 555 |     |     |     |     | 560 |
| Leu | Arg | Asp | Met | Asn | Val | Lys | Glu | Ser | Pro | Gly | Arg | Cys | Tyr | Ser | Arg |
|     |     |     |     | 565 |     |     |     |     | 570 |     |     |     |     | 575 |     |
| Pro | Val | Val | Ile | Phe | Asn | Phe | Ala | Asn | Ser | Ser | Tyr | Val | Gln | Tyr | Gly |
|     |     |     | 580 |     |     |     |     | 585 |     |     |     |     | 590 |     |     |
| Gln | Leu | Gly | Glu | Asp | Asn | Glu | Ile | Leu | Leu | Gly | Asn | His | Arg | Thr | Glu |
|     |     | 595 |     |     |     |     | 600 |     |     |     |     | 605 |     |     |     |
| Glu | Cys | Gln | Leu | Pro | Ser | Leu | Lys | Ile | Phe | Ile | Ala | Gly | Asn | Ser | Ala |
|     | 610 |     |     |     |     | 615 |     |     |     |     | 620 |     |     |     |     |
| Tyr | Glu | Tyr | Val | Asp | Tyr | Leu | Phe | Lys | Arg | Met | Ile | Asp | Leu | Ser | Ser |
| 625 |     |     |     |     | 630 |     |     |     |     | 635 |     |     |     |     | 640 |
| Ile | Ser | Thr | Val | Asp | Ser | Met | Ile | Ala | Leu | Asp | Ile | Asp | Pro | Leu | Glu |
|     |     |     |     | 645 |     |     |     |     | 650 |     |     |     |     | 655 |     |
| Asn | Thr | Asp | Phe | Arg | Val | Leu | Glu | Leu | Tyr | Ser | Gln | Lys | Glu | Leu | Arg |
|     |     |     | 660 |     |     |     |     | 665 |     |     |     |     | 670 |     |     |
| Ser | Ser | Asn | Val | Phe | Asp | Leu | Glu | Glu | Ile | Met | Arg | Glu | Phe | Asn | Ser |
|     |     | 675 |     |     |     |     | 680 |     |     |     |     | 685 |     |     |     |
| Tyr | Lys | Gln | Arg | Val | Lys | Tyr | Val | Glu | Asp | Lys | Val | Val | Asp | Pro | Leu |
|     | 690 |     |     |     |     | 695 |     |     |     |     | 700 |     |     |     |     |
| Pro | Pro | Tyr | Leu | Lys | Gly | Leu | Asp | Asp | Leu | Met | Ser | Gly | Leu | Gly | Ala |
| 705 |     |     |     |     | 710 |     |     |     |     | 715 |     |     |     |     | 720 |
| Ala | Gly | Lys | Ala | Val | Gly | Val | Ala | Ile | Gly | Ala | Val | Gly | Gly | Ala | Val |
|     |     |     |     | 725 |     |     |     |     | 730 |     |     |     |     | 735 |     |

| Ala | Ser | Val | Val | Glu | Gly | Val | Ala | Thr | Phe | Leu | Lys | Asn | Pro | Phe | Gly |
|---|---|---|---|---|---|---|---|---|---|---|---|---|---|---|---|
| | | | 740 | | | | | 745 | | | | | 750 | | |

| Ala | Phe | Thr | Ile | Ile | Leu | Val | Ala | Ile | Ala | Val | Val | Ile | Ile | Thr | Tyr |
|---|---|---|---|---|---|---|---|---|---|---|---|---|---|---|---|
| | | 755 | | | | | 760 | | | | | 765 | | | |

| Leu | Ile | Tyr | Thr | Arg | Gln | Arg | Arg | Leu | Cys | Thr | Gln | Pro | Leu | Gln | Asn |
|---|---|---|---|---|---|---|---|---|---|---|---|---|---|---|---|
| | 770 | | | | | 775 | | | | | 780 | | | | |

| Leu | Phe | Pro | Tyr | Leu | Val | Ser | Ala | Asp | Gly | Thr | Thr | Val | Thr | Ser | Gly |
|---|---|---|---|---|---|---|---|---|---|---|---|---|---|---|---|
| 785 | | | | | 790 | | | | | 795 | | | | | 800 |

| Ser | Thr | Lys | Asp | Thr | Ser | Leu | Gln | Ala | Pro | Pro | Ser | Tyr | Glu | Glu | Ser |
|---|---|---|---|---|---|---|---|---|---|---|---|---|---|---|---|
| | | | | 805 | | | | | 810 | | | | | 815 | |

| Val | Tyr | Asn | Ser | Gly | Arg | Lys | Gly | Pro | Gly | Pro | Pro | Ser | Ser | Asp | Ala |
|---|---|---|---|---|---|---|---|---|---|---|---|---|---|---|---|
| | | | 820 | | | | | 825 | | | | | 830 | | |

| Ser | Thr | Ala | Ala | Pro | Pro | Tyr | Thr | Asn | Glu | Gln | Ala | Tyr | Gln | Met | Leu |
|---|---|---|---|---|---|---|---|---|---|---|---|---|---|---|---|
| | | 835 | | | | | 840 | | | | | 845 | | | |

| Leu | Ala | Leu | Ala | Arg | Leu | Asp | Ala | Glu | Gln | Arg | Ala | Gln | Gln | Asn | Gly |
|---|---|---|---|---|---|---|---|---|---|---|---|---|---|---|---|
| | 850 | | | | | 855 | | | | | 860 | | | | |

| Thr | Asp | Ser | Leu | Asp | Gly | Gln | Thr | Gly | Thr | Gln | Asp | Lys | Gly | Gln | Lys |
|---|---|---|---|---|---|---|---|---|---|---|---|---|---|---|---|
| 865 | | | | | 870 | | | | | 875 | | | | | 880 |

| Pro | Asn | Leu | Leu | Asp | Arg | Leu | Arg | His | Arg | Lys | Asn | Gly | Tyr | Arg | His |
|---|---|---|---|---|---|---|---|---|---|---|---|---|---|---|---|
| | | | | 885 | | | | | 890 | | | | | 895 | |

| Leu | Lys | Asp | Ser | Asp | Glu | Glu | Glu | Asn | Val | | | | | | |
|---|---|---|---|---|---|---|---|---|---|---|---|---|---|---|---|
| | | | 900 | | | | | 905 | | | | | | | |

( 2 ) INFORMATION FOR SEQ ID NO:10:

( i ) SEQUENCE CHARACTERISTICS:
  ( A ) LENGTH: 857 amino acids
  ( B ) TYPE: amino acid
  ( C ) STRANDEDNESS: single
  ( D ) TOPOLOGY: linear ( i i ) MOLECULE TYPE: peptide ( v ) FRAGMENT TYPE: N-terminal ( x i ) SEQUENCE DESCRIPTION: SEQ ID NO:10:

| Met | Thr | Arg | Arg | Arg | Val | Leu | Ser | Val | Val | Val | Leu | Leu | Ala | Ala | Leu |
|---|---|---|---|---|---|---|---|---|---|---|---|---|---|---|---|
| 1 | | | | 5 | | | | | 10 | | | | | 15 | |

| Ala | Cys | Arg | Leu | Gly | Ala | Gln | Thr | Pro | Glu | Gln | Pro | Ala | Pro | Pro | Ala |
|---|---|---|---|---|---|---|---|---|---|---|---|---|---|---|---|
| | | | 20 | | | | | 25 | | | | | 30 | | |

| Thr | Thr | Val | Gln | Pro | Thr | Ala | Thr | Arg | Gln | Gln | Thr | Ser | Phe | Pro | Phe |
|---|---|---|---|---|---|---|---|---|---|---|---|---|---|---|---|
| | | 35 | | | | | 40 | | | | | 45 | | | |

| Arg | Val | Cys | Glu | Leu | Ser | Ser | His | Gly | Asp | Leu | Phe | Arg | Phe | Ser | Ser |
|---|---|---|---|---|---|---|---|---|---|---|---|---|---|---|---|
| | 50 | | | | | 55 | | | | | 60 | | | | |

| Asp | Ile | Gln | Cys | Pro | Ser | Phe | Gly | Thr | Arg | Glu | Asn | His | Thr | Glu | Gly |
|---|---|---|---|---|---|---|---|---|---|---|---|---|---|---|---|
| 65 | | | | | 70 | | | | | 75 | | | | | 80 |

| Leu | Leu | Met | Val | Phe | Lys | Asp | Asn | Ile | Ile | Pro | Tyr | Ser | Phe | Lys | Val |
|---|---|---|---|---|---|---|---|---|---|---|---|---|---|---|---|
| | | | | 85 | | | | | 90 | | | | | 95 | |

| Arg | Ser | Tyr | Thr | Lys | Ile | Val | Thr | Asn | Ile | Leu | Ile | Tyr | Asn | Gly | Trp |
|---|---|---|---|---|---|---|---|---|---|---|---|---|---|---|---|
| | | | 100 | | | | | 105 | | | | | 110 | | |

| Tyr | Ala | Asp | Ser | Val | Thr | Asn | Arg | His | Glu | Glu | Lys | Phe | Ser | Val | Asp |
|---|---|---|---|---|---|---|---|---|---|---|---|---|---|---|---|
| | | 115 | | | | | 120 | | | | | 125 | | | |

| Ser | Tyr | Glu | Thr | Asp | Gln | Met | Asp | Thr | Ile | Tyr | Gln | Cys | Tyr | Asn | Ala |
|---|---|---|---|---|---|---|---|---|---|---|---|---|---|---|---|
| | 130 | | | | | 135 | | | | | 140 | | | | |

| Val | Lys | Met | Thr | Lys | Asp | Gly | Leu | Thr | Arg | Val | Tyr | Val | Asp | Arg | Asp |
|---|---|---|---|---|---|---|---|---|---|---|---|---|---|---|---|
| 145 | | | | | 150 | | | | | 155 | | | | | 160 |

| Gly | Val | Asn | Ile | Thr | Val | Asn | Leu | Lys | Pro | Thr | Gly | Gly | Leu | Ala | Asn |
|---|---|---|---|---|---|---|---|---|---|---|---|---|---|---|---|
| | | | 165 | | | | | 170 | | | | | 175 | | |

```
Gly Val Arg Arg Tyr Ala Ser Gln Thr Glu Leu Tyr Asp Ala Pro Gly
            180                 185                 190
Trp Leu Ile Trp Thr Tyr Arg Thr Arg Thr Thr Val Asn Cys Leu Ile
            195                 200                 205
Thr Asp Met Met Ala Lys Ser Asn Ser Pro Phe Asp Phe Phe Val Thr
            210                 215                 220
Thr Thr Gly Gln Thr Val Glu Met Ser Pro Phe Tyr Asp Gly Lys Asn
225                 230                 235                 240
Lys Glu Thr Phe His Glu Arg Ala Asp Ser Phe His Val Arg Thr Asn
                245                 250                 255
Tyr Lys Ile Val Asp Tyr Asp Asn Arg Gly Thr Asn Pro Gln Gly Glu
            260                 265                 270
Arg Arg Ala Phe Leu Asp Lys Gly Thr Tyr Thr Leu Ser Trp Lys Leu
            275                 280                 285
Glu Asn Arg Thr Ala Tyr Cys Pro Leu Gln His Trp Gln Thr Phe Asp
            290                 295                 300
Ser Thr Ile Ala Thr Glu Thr Gly Lys Ser Ile His Phe Val Thr Asp
305                 310                 315                 320
Glu Gly Thr Ser Ser Phe Val Thr Asn Thr Thr Val Gly Ile Glu Leu
                325                 330                 335
Pro Asp Ala Phe Lys Cys Ile Glu Glu Gln Val Asn Lys Thr Met His
            340                 345                 350
Glu Lys Tyr Glu Ala Val Gln Asp Arg Tyr Thr Lys Gly Gln Glu Ala
            355                 360                 365
Ile Thr Tyr Phe Ile Thr Ser Gly Gly Leu Leu Leu Ala Trp Leu Pro
            370                 375                 380
Leu Thr Pro Arg Ser Leu Ala Thr Val Lys Asn Leu Thr Glu Leu Thr
385                 390                 395                 400
Thr Pro Thr Ser Ser Pro Pro Ser Ser Pro Ser Pro Pro Ala Pro Ser
                405                 410                 415
Ala Ala Arg Gly Ser Thr Pro Ala Ala Val Leu Arg Arg Arg Arg Arg
            420                 425                 430
Asp Ala Gly Asn Ala Thr Thr Pro Val Pro Pro Thr Ala Pro Gly Lys
            435                 440                 445
Ser Leu Gly Thr Leu Asn Asn Pro Ala Thr Val Gln Ile Gln Phe Ala
450                 455                 460
Tyr Asp Ser Leu Arg Arg Gln Ile Asn Arg Met Leu Gly Asp Leu Ala
465                 470                 475                 480
Arg Ala Trp Cys Leu Glu Gln Lys Arg Gln Asn Met Val Leu Arg Glu
            485                 490                 495
Leu Thr Lys Ile Asn Pro Thr Thr Val Met Ser Ser Ile Tyr Gly Lys
            500                 505                 510
Ala Val Ala Ala Lys Arg Leu Gly Asp Val Ile Ser Val Ser Gln Cys
            515                 520                 525
Val Pro Val Asn Gln Ala Thr Val Thr Leu Arg Lys Ser Met Arg Val
            530                 535                 540
Pro Gly Ser Glu Thr Met Cys Tyr Ser Arg Pro Leu Val Ser Phe Ser
545                 550                 555                 560
Phe Ile Asn Asp Thr Lys Thr Tyr Glu Gly Gln Leu Gly Thr Asp Asn
                565                 570                 575
Glu Ile Phe Leu Thr Lys Lys Met Thr Glu Val Cys Gln Ala Thr Ser
            580                 585                 590
Gln Tyr Tyr Phe Gln Ser Gly Asn Glu Ile His Val Tyr Asn Asp Tyr
```

|       |       |       |       | 595   |       |       |       | 600   |       |       |       | 605   |       |       |
|-------|-------|-------|-------|-------|-------|-------|-------|-------|-------|-------|-------|-------|-------|-------|
| His   | His   | Phe   | Lys   | Thr   | Ile   | Glu   | Leu   | Asp   | Gly   | Ile   | Ala   | Thr   | Leu   | Gln   | Thr
|       | 610   |       |       |       |       | 615   |       |       |       |       | 620   |       |       |       |
| Phe   | Ile   | Ser   | Leu   | Asn   | Thr   | Ser   | Leu   | Ile   | Glu   | Asn   | Ile   | Asp   | Phe   | Ala   | Ser
| 625   |       |       |       |       |       | 630   |       |       |       | 635   |       |       |       |       | 640
| Leu   | Glu   | Leu   | Tyr   | Ser   | Arg   | Asp   | Glu   | Gln   | Arg   | Ala   | Ser   | Asn   | Val   | Phe   | Asp
|       |       |       |       | 645   |       |       |       |       | 650   |       |       |       |       | 655   |
| Leu   | Glu   | Gly   | Ile   | Phe   | Arg   | Glu   | Tyr   | Asn   | Phe   | Gln   | Ala   | Gln   | Asn   | Ile   | Ala
|       |       |       | 660   |       |       |       |       | 665   |       |       |       |       | 670   |       |
| Gly   | Leu   | Arg   | Lys   | Asp   | Leu   | Asp   | Asn   | Ala   | Val   | Ser   | Asn   | Gly   | Arg   | Asn   | Gln
|       |       | 675   |       |       |       |       | 680   |       |       |       |       | 685   |       |       |
| Phe   | Val   | Asp   | Gly   | Leu   | Gly   | Glu   | Leu   | Met   | Asp   | Ser   | Leu   | Gly   | Ser   | Val   | Gly
|       | 690   |       |       |       |       | 695   |       |       |       |       | 700   |       |       |       |
| Gln   | Ser   | Ile   | Thr   | Asn   | Leu   | Val   | Ser   | Thr   | Val   | Gly   | Gly   | Leu   | Phe   | Ser   | Ser
| 705   |       |       |       |       | 710   |       |       |       |       | 715   |       |       |       |       | 720
| Leu   | Val   | Ser   | Gly   | Phe   | Ile   | Ser   | Phe   | Phe   | Lys   | Asn   | Pro   | Phe   | Gly   | Gly   | Met
|       |       |       |       | 725   |       |       |       |       | 730   |       |       |       |       | 735   |
| Leu   | Ile   | Leu   | Val   | Leu   | Val   | Ala   | Gly   | Val   | Val   | Ile   | Leu   | Val   | Ile   | Ser   | Leu
|       |       |       | 740   |       |       |       |       | 745   |       |       |       |       | 750   |       |
| Thr   | Arg   | Arg   | Thr   | Arg   | Gln   | Met   | Ser   | Gln   | Gln   | Pro   | Val   | Gln   | Met   | Leu   | Tyr
|       |       | 755   |       |       |       |       | 760   |       |       |       |       | 765   |       |       |
| Pro   | Gly   | Ile   | Asp   | Glu   | Leu   | Ala   | Gln   | Gln   | His   | Ala   | Ser   | Gly   | Glu   | Gly   | Pro
|       | 770   |       |       |       |       | 775   |       |       |       |       | 780   |       |       |       |
| Gly   | Ile   | Asn   | Pro   | Ile   | Ser   | Lys   | Thr   | Glu   | Leu   | Gln   | Ala   | Ile   | Met   | Leu   | Ala
| 785   |       |       |       |       | 790   |       |       |       |       | 795   |       |       |       |       | 800
| Leu   | His   | Glu   | Gln   | Asn   | Gln   | Glu   | Gln   | Lys   | Arg   | Ala   | Ala   | Gln   | Arg   | Ala   | Ala
|       |       |       |       | 805   |       |       |       |       | 810   |       |       |       |       | 815   |
| Gly   | Pro   | Ser   | Val   | Ala   | Ser   | Arg   | Ala   | Leu   | Gln   | Ala   | Ala   | Arg   | Asp   | Arg   | Phe
|       |       |       | 820   |       |       |       |       | 825   |       |       |       |       | 830   |       |
| Pro   | Gly   | Leu   | Arg   | Arg   | Arg   | Arg   | Tyr   | His   | Asp   | Pro   | Glu   | Thr   | Ala   | Ala   | Ala
|       |       |       | 835   |       |       |       |       | 840   |       |       |       |       | 845   |       |
| Leu   | Leu   | Gly   | Glu   | Ala   | Glu   | Thr   | Glu   | Phe   |       |       |       |       |       |       |
|       |       |       | 850   |       |       |       | 855   |       |       |       |       |       |       |       |

( 2 ) INFORMATION FOR SEQ ID NO:11:

( i ) SEQUENCE CHARACTERISTICS:
        ( A ) LENGTH: 2280 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
CGAGCCCTAA TTATTGGTTT GTATATGACT GTTGGAATTT GTTACATTTT TATTAAAACA      60
ATAAATTAAA TTTTTTAAAC TATATTACGG TTGTGTGTGT TTAAGTTTT AAATAAAGCA      120
ATATTTCGAA TTCACATTTA TCAAAAACAT TAAAACCCAA CACAAAAAAA TTTCTATAAT    180
CATTAAGGTA ATAAGTCAAA ATGAGTTTTA AAATTTTTA TCTAATATAT GTAATTATAA    240
TTTTTATAAA CTCGATAATA ACTTCGGCAT CTACATCCAA ACCTTCAACA CCTACCATAA    300
TTCCAACTTC AGCAAATGAA TCACCTGCTT CCATAGATAC AACTATAACA AAACCTATAT    360
CTACAGAGGC AAATAATTTA AAATCAGTAA GTACCTCAAT TAAACCACCT AAAAACTTAA    420
AAAAAAAATT ACTTAAATCT AAATGTAGAG ATAATGTTAT TTATAGGCCA TATTTAGTC    480
AATTAGAAAT TAACTGTACT ATAACTAAAA AGCAAAATTT AAGTAATCCT TTAATTGAGT    540
```

-continued

```
TATGGTTTAA AGAACTTTCT ACATATAATA AAACCAATGA AAATGTTGAA AGTTTAAAAA      600
CAGATATATC AAAAAATATT TTATTATTTT CGACAAAAAA TAATAGTGAT AACTTTTATA      660
ATGATTTTTT ATTAGGTATA CAAATCAAC  CAGTAAATTA TAAACTTTAC GGTTCCCAAT      720
TTTATGATAA TGGAAACATA TTACTAAATA TAAAGTCGGT TGACTTTAAA ACCTCTGGAA      780
TATATACTTG GAAACTATAT AATTCAAATA ATGAAAGTAT TTTTGAAACT TTTAAAATTC      840
AAGTATATGC ATATCATTCC CCAAATGTAA ACTTAAAATC AAACCCAAGT TTATATAATG      900
AAAACTACAG CGCTATTTGT ACAATAGCAA ATTACTTTCC ATTGGAATCT ACGGAAATAT      960
TTTGGTTTAA CGATGGACAA CCTATTGATA AAAATATAT  AGATGAAACT TATAGTGTAT     1020
GGATTGACGG TCTTATAACA CGCACTTCAA TATTATCCCT TCCCTTTTCC GAAGCCATGG     1080
AAAGCCCCCC CAATTTGCGA TGTAATGTTG AATGGTATAA AAATTCAAAG GCATCAAAAA     1140
AATTTCAAA  TACCGTTATT CCAAAGTTT  ACTATAAACC TTTTATATCT ATAAATTTG      1200
ATAATGGTTT AGCTATTTGT GATGCTAAAT GTGTTTCCCG TGAAAATAAT AAATTACAAT     1260
GGTTAGTTAA AGATATACCT ATAAATGGTG ATGATATTAT AAGCGGCCCC TGTTTAAACC     1320
ACCCTGGTTT GGTCAATATT CAAATAAAA  TAGATATATC GGATTATGAT GAACCTGTTA     1380
CCTATAAATG TTCAATTATT GGTTATCCAA TAATTTTTCC CAACTTTTAT GATGAAAAGG     1440
TGTTTGATGC ATCGGATGAA AATGTTAGTA AATCGATGTT AATAAGTATT ACCACAATAA     1500
TTGGTGGAGC CATTTTTGTT ATAGTATTGA TTTTTATAAC AGCTTTATGT TTTTATTGTT     1560
CAAAAAATAA TAAGATCTAA TATCAATATT TACGTAAATG GATTATATAA TGTTATATTC     1620
GTGTTATTAT GATTTATAAG TTCATCAAAT TTAAAAATTT GTATAGTATT AAGATTTTA     1680
ATAGGGGTAT CGTTTAATAT GGCTCAGTTA GTTTTAACTG ATATTCCCCT CGAAGATGTG     1740
GAAAATAAAA ATACTTCATC CGACGAAGAA ACAACTAACT TAAACCAGAA AAAATCAACA     1800
TGTCAATGTT TATGTGTTAC CCTTGGATTT TTTGCAGCTG GAATTTTATT AACCATAGCT     1860
GCAATAATTT TTACTTTTAT TTTTACAGTA CCATTAGAAA TGCTTGGATC TATTAATTGT     1920
CCTCCATCTA CATTTGGTAT TGATAATGTT TGTATCGAAC CAATAAAAAA ATCTATTAAT     1980
TCTTATTCAG AATTATCTAA AATATGTTAT GATAGATTGT CAAATCCGAT AAATCAGAGT     2040
ACTATTAACT CCTTATTAAC TGTTTTAAAT ATGTTTGCAG ATAAAAACTA TGAAAATGTT     2100
TATAATTGTA ATACAATGAG TGAAAAAACA TGTAATTCAT CAATAGCTAT TTGTCAAACT     2160
AATCATCCAC TAAGTTCATT GGGAAATTTT GTTATTAAAA TTAGAAAAAT TTTTGGGTTT     2220
AAATAATAAA TAAAATAAAT AAACATTACT TTTGTTTTT  GTCTTATTA  AACAGTTGTA    2280
```

( 2 ) INFORMATION FOR SEQ ID NO:12:

( i ) SEQUENCE CHARACTERISTICS:
        ( A ) LENGTH: 459 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Met Ser Phe Lys Asn Phe Tyr Leu Ile Tyr Val Ile Ile Ile Phe Ile
 1               5                  10                  15
Asn Ser Ile Ile Thr Ser Ala Ser Thr Ser Lys Pro Ser Thr Pro Thr
            20                  25                  30
```

| | | | | | | | | | | | | | |
|---|---|---|---|---|---|---|---|---|---|---|---|---|---|
| Ile | Ile | Pro<br>35 | Thr | Ser | Ala | Asn | Glu<br>40 | Ser | Pro | Ala | Ser | Ile<br>45 | Asp | Thr | Thr |
| Ile | Thr<br>50 | Lys | Pro | Ile | Ser<br>55 | Thr | Glu | Ala | Asn | Asn<br>60 | Leu | Lys | Ser | Val | Ser |
| Thr<br>65 | Ser | Ile | Lys | Pro | Pro<br>70 | Lys | Asn | Leu | Lys | Lys<br>75 | Lys | Leu | Leu | Lys | Ser<br>80 |
| Lys | Cys | Arg | Asp | Asn<br>85 | Val | Ile | Tyr | Arg | Pro<br>90 | Tyr | Phe | Ser | Gln | Leu<br>95 | Glu |
| Ile | Asn | Cys | Thr<br>100 | Ile | Thr | Lys | Lys | Gln<br>105 | Asn | Leu | Ser | Asn | Pro<br>110 | Leu | Ile |
| Glu | Leu | Trp<br>115 | Phe | Lys | Glu | Leu | Ser<br>120 | Thr | Tyr | Asn | Lys | Thr<br>125 | Asn | Glu | Asn |
| Val | Glu<br>130 | Ser | Leu | Lys | Thr | Asp<br>135 | Ile | Ser | Lys | Asn | Ile<br>140 | Leu | Leu | Phe | Ser |
| Thr<br>145 | Lys | Asn | Asn | Ser | Asp<br>150 | Asn | Phe | Tyr | Asn | Asp<br>155 | Phe | Leu | Leu | Gly | Ile<br>160 |
| Gln | Asn | Gln | Pro | Val<br>165 | Asn | Tyr | Lys | Leu | Tyr<br>170 | Gly | Ser | Gln | Phe | Tyr<br>175 | Asp |
| Asn | Gly | Asn | Ile<br>180 | Leu | Leu | Asn | Ile | Lys<br>185 | Ser | Val | Asp | Phe | Lys<br>190 | Thr | Ser |
| Gly | Ile | Tyr<br>195 | Thr | Trp | Lys | Leu | Tyr<br>200 | Asn | Ser | Asn | Asn | Glu<br>205 | Ser | Ile | Phe |
| Glu | Thr<br>210 | Phe | Lys | Ile | Gln | Val<br>215 | Tyr | Ala | Tyr | His | Ser<br>220 | Pro | Asn | Val | Asn |
| Leu<br>225 | Lys | Ser | Asn | Pro | Ser<br>230 | Leu | Tyr | Asn | Glu | Asn<br>235 | Tyr | Ser | Ala | Ile | Cys<br>240 |
| Thr | Ile | Ala | Asn | Tyr<br>245 | Phe | Pro | Leu | Glu | Ser<br>250 | Thr | Glu | Ile | Phe | Trp<br>255 | Phe |
| Asn | Asp | Gly | Gln<br>260 | Pro | Ile | Asp | Lys | Lys<br>265 | Tyr | Ile | Asp | Glu | Thr<br>270 | Tyr | Ser |
| Val | Trp | Ile<br>275 | Asp | Gly | Leu | Ile | Thr<br>280 | Arg | Thr | Ser | Ile | Leu<br>285 | Ser | Leu | Pro |
| Phe | Ser<br>290 | Glu | Ala | Met | Glu | Ser<br>295 | Pro | Pro | Asn | Leu | Arg<br>300 | Cys | Asn | Val | Glu |
| Trp<br>305 | Tyr | Lys | Asn | Ser | Lys<br>310 | Ala | Ser | Lys | Lys | Phe<br>315 | Ser | Asn | Thr | Val | Ile<br>320 |
| Pro | Lys | Val | Tyr | Tyr<br>325 | Lys | Pro | Phe | Ile | Ser<br>330 | Ile | Lys | Phe | Asp | Asn<br>335 | Gly |
| Leu | Ala | Ile | Cys<br>340 | Asp | Ala | Lys | Cys | Val<br>345 | Ser | Arg | Glu | Asn | Asn<br>350 | Lys | Leu |
| Gln | Trp | Leu<br>355 | Val | Lys | Asp | Ile | Pro<br>360 | Ile | Asn | Gly | Asp | Asp<br>365 | Ile | Ile | Ser |
| Gly | Pro<br>370 | Cys | Leu | Asn | His | Pro<br>375 | Gly | Leu | Val | Asn | Ile<br>380 | Gln | Asn | Lys | Ile |
| Asp<br>385 | Ile | Ser | Asp | Tyr | Asp<br>390 | Glu | Pro | Val | Thr | Tyr<br>395 | Lys | Cys | Ser | Ile | Ile<br>400 |
| Gly | Tyr | Pro | Ile | Ile<br>405 | Phe | Pro | Asn | Phe | Tyr<br>410 | Asp | Glu | Lys | Val | Phe<br>415 | Asp |
| Ala | Ser | Asp | Glu | Asn<br>420 | Val | Ser | Lys | Ser | Met<br>425 | Leu | Ile | Ser | Ile<br>430 | Thr | Thr |
| Ile | Ile | Gly | Gly<br>435 | Ala | Ile | Phe | Val<br>440 | Ile | Val | Leu | Ile | Phe<br>445 | Ile | Thr | Ala |
| Leu | Cys<br>450 | Phe | Tyr | Cys | Ser | Lys<br>455 | Asn | Asn | Lys | Ile | | | | | |

( 2 ) INFORMATION FOR SEQ ID NO:13:

( i ) SEQUENCE CHARACTERISTICS:
        ( A ) LENGTH: 175 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Met Ala Gln Leu Val Leu Thr Asp Ile Pro Leu Glu Asp Val Glu Asn
  1               5                  10                  15

Lys Asn Thr Ser Ser Asp Glu Glu Thr Thr Asn Leu Asn Gln Lys Lys
             20                  25                  30

Ser Thr Cys Gln Cys Leu Cys Val Thr Leu Gly Phe Phe Ala Ala Gly
         35                  40                  45

Ile Leu Leu Thr Ile Ala Ala Ile Ile Phe Thr Phe Ile Phe Thr Val
     50                  55                  60

Pro Leu Glu Met Leu Gly Ser Ile Asn Cys Pro Pro Ser Thr Phe Gly
 65                  70                  75                  80

Ile Asp Asn Val Cys Ile Glu Pro Ile Lys Lys Ser Ile Asn Ser Tyr
                 85                  90                  95

Ser Glu Leu Ser Lys Ile Cys Tyr Asp Arg Leu Ser Asn Pro Ile Asn
             100                 105                 110

Gln Ser Thr Ile Asn Ser Leu Leu Thr Val Leu Asn Met Phe Ala Asp
         115                 120                 125

Lys Asn Tyr Glu Asn Val Tyr Asn Cys Asn Thr Met Ser Glu Lys Thr
     130                 135                 140

Cys Asn Ser Ser Ile Ala Ile Cys Gln Thr Asn His Pro Leu Ser Ser
145                 150                 155                 160

Leu Gly Asn Phe Val Ile Lys Ile Arg Lys Ile Phe Gly Phe Lys
                 165                 170                 175
```

( 2 ) INFORMATION FOR SEQ ID NO:14:

( i ) SEQUENCE CHARACTERISTICS:
        ( A ) LENGTH: 459 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:14:

```
Met Ser Phe Lys Asn Phe Tyr Leu Ile Tyr Val Ile Ile Ile Phe Ile
  1               5                  10                  15

Asn Ser Ile Ile Thr Ser Ala Ser Thr Ser Lys Pro Ser Thr Pro Thr
             20                  25                  30

Ile Ile Pro Thr Ser Ala Asn Glu Ser Pro Ala Ser Ile Asp Thr Thr
         35                  40                  45

Ile Thr Lys Pro Ile Ser Thr Glu Ala Asn Asn Leu Lys Ser Val Ser
     50                  55                  60

Thr Ser Ile Lys Pro Pro Lys Asn Leu Lys Lys Leu Leu Lys Ser
 65                  70                  75                  80

Lys Cys Arg Asp Asn Val Ile Tyr Arg Pro Tyr Phe Ser Gln Leu Glu
```

|     |     |     |     |     | 85  |     |     |     |     | 90  |     |     |     |     | 95  |     |
| --- | --- | --- | --- | --- | --- | --- | --- | --- | --- | --- | --- | --- | --- | --- | --- | --- |
| Ile | Asn | Cys | Thr<br>100 | Ile | Thr | Lys | Lys | Gln<br>105 | Asn | Leu | Ser | Asn | Pro<br>110 | Leu | Ile |
| Glu | Leu | Trp<br>115 | Phe | Lys | Glu | Leu | Ser<br>120 | Thr | Tyr | Asn | Lys | Thr<br>125 | Asn | Glu | Asn |
| Val | Glu<br>130 | Ser | Leu | Lys | Thr | Asp<br>135 | Ile | Ser | Lys | Asn | Ile<br>140 | Leu | Leu | Phe | Ser |
| Thr<br>145 | Lys | Asn | Asn | Ser | Asp<br>150 | Asn | Phe | Tyr | Asn | Asp<br>155 | Phe | Leu | Leu | Gly | Ile<br>160 |
| Gln | Asn | Gln | Pro | Val<br>165 | Asn | Tyr | Lys | Leu | Tyr<br>170 | Gly | Ser | Gln | Phe | Tyr<br>175 | Asp |
| Asn | Gly | Asn | Ile<br>180 | Leu | Leu | Asn | Ile | Lys<br>185 | Ser | Val | Asp | Phe | Lys<br>190 | Thr | Ser |
| Gly | Ile | Tyr<br>195 | Thr | Trp | Lys | Leu | Tyr<br>200 | Asn | Ser | Asn | Asn | Glu<br>205 | Ser | Ile | Phe |
| Glu | Thr<br>210 | Phe | Lys | Ile | Gln | Val<br>215 | Tyr | Ala | Tyr | His | Ser<br>220 | Pro | Asn | Val | Asn |
| Leu<br>225 | Lys | Ser | Asn | Pro | Ser<br>230 | Leu | Tyr | Asn | Glu | Asn<br>235 | Tyr | Ser | Ala | Ile | Cys<br>240 |
| Thr | Ile | Ala | Asn | Tyr<br>245 | Phe | Pro | Leu | Glu | Ser<br>250 | Thr | Glu | Ile | Phe | Trp<br>255 | Phe |
| Asn | Asp | Gly | Gln<br>260 | Pro | Ile | Asp | Lys | Lys<br>265 | Tyr | Ile | Asp | Glu | Thr<br>270 | Tyr | Ser |
| Val | Trp | Ile<br>275 | Asp | Gly | Leu | Ile | Thr<br>280 | Arg | Thr | Ser | Ile | Leu<br>285 | Ser | Leu | Pro |
| Phe | Ser<br>290 | Glu | Ala | Met | Glu | Ser<br>295 | Pro | Pro | Asn | Leu | Arg<br>300 | Cys | Asn | Val | Glu |
| Trp<br>305 | Tyr | Lys | Asn | Ser | Lys<br>310 | Ala | Ser | Lys | Lys | Phe<br>315 | Ser | Asn | Thr | Val | Ile<br>320 |
| Pro | Lys | Val | Tyr | Tyr<br>325 | Lys | Pro | Phe | Ile | Ser<br>330 | Ile | Lys | Phe | Asp | Asn<br>335 | Gly |
| Leu | Ala | Ile | Cys<br>340 | Asp | Ala | Lys | Cys | Val<br>345 | Ser | Arg | Glu | Asn | Asn<br>350 | Lys | Leu |
| Gln | Trp | Leu<br>355 | Val | Lys | Asp | Ile | Pro<br>360 | Ile | Asn | Gly | Asp | Asp<br>365 | Ile | Ile | Ser |
| Gly | Pro<br>370 | Cys | Leu | Asn | His | Pro<br>375 | Gly | Leu | Val | Asn | Ile<br>380 | Gln | Asn | Lys | Ile |
| Asp<br>385 | Ile | Ser | Asp | Tyr | Asp<br>390 | Glu | Pro | Val | Thr | Tyr<br>395 | Lys | Cys | Ser | Ile | Ile<br>400 |
| Gly | Tyr | Pro | Ile | Ile<br>405 | Phe | Pro | Asn | Phe | Tyr<br>410 | Asp | Glu | Lys | Val | Phe<br>415 | Asp |
| Ala | Ser | Asp | Glu<br>420 | Asn | Val | Ser | Lys | Ser<br>425 | Met | Leu | Ile | Ser | Ile<br>430 | Thr | Thr |
| Ile | Ile | Gly<br>435 | Gly | Ala | Ile | Phe | Val<br>440 | Ile | Val | Leu | Ile | Phe<br>445 | Ile | Thr | Ala |
| Leu | Cys<br>450 | Phe | Tyr | Cys | Ser | Lys<br>455 | Asn | Asn | Lys | Ile |     |     |     |     |     |

( 2 ) INFORMATION FOR SEQ ID NO:15:

( i ) SEQUENCE CHARACTERISTICS:
        ( A ) LENGTH: 533 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:15:

```
Met Arg Arg Tyr Arg Met Gly Arg Gly Ile Tyr Leu Leu Tyr Ile Cys
 1               5                  10                  15
Leu Leu Tyr Thr Tyr Leu Gln Phe Gly Thr Ser Ser Thr Thr Ala Val
             20                  25                  30
Ser Ile Glu Asn Ser Asp Asn Ser Thr Ala Glu Met Leu Ser Ser Thr
             35                  40                  45
Ser Met Ser Ala Thr Thr Pro Ile Ser Gln Pro Thr Ser Pro Phe Thr
     50                  55                  60
Thr Pro Thr Arg Arg Ser Thr Asn Ile Ala Thr Ser Ser Ser Thr Thr
 65                  70                  75                  80
Gln Ala Ser Gln Pro Thr Ser Thr Leu Thr Thr Leu Thr Arg Ser Ser
                 85                  90                  95
Thr Thr Ile Ala Thr Ser Pro Ser Thr Thr Gln Ala Ala Thr Phe Ile
             100                 105                 110
Gly Ser Ser Thr Asp Ser Asn Thr Thr Leu Leu Lys Thr Thr Lys Lys
             115                 120                 125
Pro Lys Arg Lys Lys Asn Lys Asn Asn Gly Ala Arg Phe Lys Leu Asp
     130                 135                 140
Cys Gly Tyr Lys Gly Val Ile Tyr Arg Pro Tyr Phe Ser Pro Leu Gln
145                 150                 155                 160
Leu Asn Cys Thr Leu Pro Thr Glu Pro His Ile Thr Asn Pro Ile Asp
             165                 170                 175
Phe Glu Ile Trp Phe Lys Pro Arg Thr Arg Phe Gly Asp Phe Leu Gly
             180                 185                 190
Asp Lys Glu Asp Phe Val Gly Asn His Thr Arg Thr Ser Ile Leu Leu
             195                 200                 205
Phe Ser Ser Arg Asn Gly Ser Val Asn Ser Met Asp Leu Gly Asp Ala
     210                 215                 220
Thr Leu Gly Ile Leu Gln Ser Arg Ile Pro Asp Tyr Thr Leu Tyr Asn
225                 230                 235                 240
Ile Pro Ile Gln His Thr Glu Ala Met Ser Leu Gly Ile Lys Ser Val
                 245                 250                 255
Glu Ser Ala Thr Ser Gly Val Tyr Thr Trp Arg Val Tyr Gly Gly Asp
             260                 265                 270
Gly Leu Asn Lys Thr Val Leu Gly Gln Val Asn Val Ser Val Val Ala
             275                 280                 285
Tyr His Pro Pro Ser Val Asn Leu Thr Pro Arg Ala Ser Leu Phe Asn
     290                 295                 300
Lys Thr Phe Glu Ala Val Cys Ala Val Ala Asn Tyr Phe Pro Arg Ser
305                 310                 315                 320
Thr Lys Leu Thr Trp Tyr Leu Asp Gly Lys Pro Ile Glu Arg Gln Tyr
             325                 330                 335
Ile Ser Asp Thr Ala Ser Val Trp Ile Asp Gly Leu Ile Thr Arg Ser
             340                 345                 350
Ser Val Leu Ala Ile Pro Thr Thr Glu Thr Asp Ser Glu Lys Pro Asp
     355                 360                 365
Ile Arg Cys Asp Leu Glu Trp His Glu Ser Pro Val Ser Tyr Lys Arg
370                 375                 380
Phe Thr Lys Ser Val Ala Pro Asp Val Tyr Tyr Pro Pro Thr Val Ser
385                 390                 395                 400
```

```
Val Thr Phe Ala Asp Thr Arg Ala Ile Cys Asp Val Lys Cys Val Pro
            405                 410                 415

Arg Asp Gly Ile Ser Leu Met Trp Lys Ile Gly Asn Tyr His Leu Pro
            420                 425                 430

Lys Ala Met Ser Ala Asp Ile Leu Ile Thr Gly Pro Cys Ile Glu Arg
            435                 440                 445

Pro Gly Leu Val Asn Ile Gln Ser Met Cys Asp Ile Ser Glu Thr Asp
            450                 455                 460

Gly Pro Val Ser Tyr Thr Cys Gln Thr Ile Gly Tyr Pro Pro Ile Leu
465                 470                 475                 480

Pro Gly Phe Tyr Asp Thr Gln Val Tyr Asp Ala Ser Pro Glu Ile Val
                485                 490                 495

Ser Glu Ser Met Leu Val Ser Val Val Ala Val Ile Leu Gly Ala Val
            500                 505                 510

Leu Ile Thr Val Phe Ile Phe Ile Thr Ala Leu Cys Leu Tyr Tyr Ser
            515                 520                 525

His Pro Arg Arg Leu
            530
```

(2) INFORMATION FOR SEQ ID NO:16:

(i) SEQUENCE CHARACTERISTICS:
        (A) LENGTH: 468 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:16:

```
Met Trp Leu Pro Asn Leu Val Arg Phe Val Ala Val Ala Tyr Leu Ile
1               5                   10                  15

Cys Ala Gly Ala Ile Leu Thr Tyr Ala Ser Gly Ala Ser Ala Ser Ser
            20                  25                  30

Ser Gln Ser Thr Pro Ala Thr Pro Thr His Thr Thr Pro Asn Leu Thr
            35                  40                  45

Thr Ala His Gly Ala Gly Ser Asp Asn Thr Thr Asn Ala Asn Gly Thr
50                  55                  60

Glu Ser Thr His Ser His Glu Thr Thr Ile Thr Cys Thr Lys Ser Leu
65                  70                  75                  80

Ile Ser Val Pro Tyr Tyr Lys Ser Val Asp Met Asn Cys Thr Thr Ser
                85                  90                  95

Val Gly Val Asn Tyr Ser Glu Tyr Arg Leu Glu Ile Tyr Leu Asn Gln
            100                 105                 110

Arg Thr Pro Phe Ser Gly Thr Pro Pro Gly Asp Glu Glu Asn Tyr Ile
            115                 120                 125

Asn His Asn Ala Thr Lys Asp Gln Thr Leu Leu Leu Phe Ser Thr Ala
            130                 135                 140

Glu Arg Lys Lys Ser Arg Arg Gly Asp Leu Ser Val His Pro Ser Leu
145                 150                 155                 160

Lys Gly Glu Asn Tyr Arg Ala Thr Cys Val Val Ala Ser Tyr Phe Pro
                165                 170                 175

His Ser Ser Val Lys Leu Arg Trp Tyr Lys Asn Ala Arg Glu Val Asp
            180                 185                 190

Phe Thr Lys Tyr Val Thr Asn Ala Ser Ser Val Trp Val Asp Gly Leu
```

|     |     |     | 195 |     |     |     | 200 |     |     |     | 205 |     |     |     |
|-----|-----|-----|-----|-----|-----|-----|-----|-----|-----|-----|-----|-----|-----|-----|
| Ile | Thr | Arg | Ile | Ser | Thr | Val | Ser | Ile | Pro | Val | Asp | Pro | Glu | Glu |
|     | 210 |     |     |     |     | 215 |     |     |     |     | 220 |     |     |     |
| Tyr | Thr | Gly | Gln | Leu | Gly | Val | Ile | Pro | Asp | Arg | Leu | Pro | Lys | Arg | Gln |
| 225 |     |     |     |     | 230 |     |     |     |     | 235 |     |     |     |     | 240 |
| Leu | Phe | Asn | Leu | Pro | Leu | His | Thr | Glu | Gly | Gly | Thr | Lys | Phe | Pro | Leu |
|     |     |     |     | 245 |     |     |     |     | 250 |     |     |     |     | 255 |     |
| Thr | Ile | Lys | Ser | Val | Asp | Trp | Arg | Thr | Ala | Gly | Ile | Tyr | Val | Trp | Ser |
|     |     |     | 260 |     |     |     |     | 265 |     |     |     |     | 270 |     |     |
| Leu | Tyr | Ala | Lys | Asn | Gly | Thr | Leu | Val | Asn | Ser | Thr | Ser | Val | Thr | Val |
|     |     | 275 |     |     |     |     | 280 |     |     |     |     | 285 |     |     |     |
| Ser | Thr | Tyr | Asn | Ala | Pro | Leu | Leu | Pro | Ser | Leu | Arg | Cys | Ser | Ile | Asp |
|     | 290 |     |     |     |     | 295 |     |     |     |     | 300 |     |     |     |     |
| Trp | Tyr | Arg | Asp | Glu | Val | Ser | Phe | Ala | Arg | Ile | Ala | Lys | Ala | Gly | Thr |
| 305 |     |     |     |     | 310 |     |     |     |     | 315 |     |     |     |     | 320 |
| Pro | Ser | Val | Phe | Val | Ala | Pro | Thr | Val | Ser | Val | Ser | Val | Glu | Asp | Gly |
|     |     |     |     | 325 |     |     |     |     | 330 |     |     |     |     | 335 |     |
| Asp | Ala | Val | Cys | Thr | Ala | Lys | Cys | Val | Pro | Ser | Thr | Gly | Val | Phe | Val |
|     |     |     | 340 |     |     |     |     | 345 |     |     |     |     | 350 |     |     |
| Ser | Trp | Ser | Val | Asn | Asp | His | Leu | Pro | Gly | Val | Pro | Ser | Gln | Asp | Met |
|     |     | 355 |     |     |     |     | 360 |     |     |     |     | 365 |     |     |     |
| Thr | Thr | Gly | Val | Cys | Pro | Ser | His | Ser | Gly | Leu | Val | Asn | Met | Gln | Ser |
|     | 370 |     |     |     |     | 375 |     |     |     |     | 380 |     |     |     |     |
| Arg | Arg | Pro | Leu | Ser | Glu | Glu | Asn | Gly | Glu | Arg | Glu | Tyr | Ser | Cys | Ile |
| 385 |     |     |     |     | 390 |     |     |     |     | 395 |     |     |     |     | 400 |
| Ile | Glu | Gly | Tyr | Pro | Asp | Gly | Leu | Pro | Met | Phe | Ser | Asp | Thr | Val | Val |
|     |     |     |     | 405 |     |     |     |     | 410 |     |     |     |     | 415 |     |
| Tyr | Asp | Ala | Ser | Pro | Ile | Val | Glu | Asp | Arg | Pro | Val | Leu | Thr | Ser | Ile |
|     |     |     | 420 |     |     |     |     | 425 |     |     |     |     | 430 |     |     |
| Ile | Ala | Val | Thr | Cys | Gly | Ala | Ala | Ala | Leu | Ala | Leu | Val | Val | Leu | Ile |
|     |     |     | 435 |     |     |     |     | 440 |     |     |     |     | 445 |     |     |
| Thr | Ala | Val | Cys | Phe | Tyr | Cys | Ser | Lys | Pro | Ser | Gln | Ala | Pro | Tyr | Lys |
|     | 450 |     |     |     |     | 455 |     |     |     |     | 460 |     |     |     |     |
| Lys | Ser | Asp | Phe |
| 465 |     |     |     |

( 2 ) INFORMATION FOR SEQ ID NO:17:

( i ) SEQUENCE CHARACTERISTICS:
        ( A ) LENGTH: 511 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:17:

| Met | Ala | Pro | Gly | Arg | Val | Gly | Leu | Ala | Val | Val | Leu | Trp | Ser | Leu | Leu |
| 1   |     |     |     | 5   |     |     |     |     | 10  |     |     |     |     | 15  |     |
| Trp | Leu | Gly | Ala | Gly | Val | Ser | Gly | Gly | Ser | Glu | Thr | Ala | Ser | Thr | Gly |
|     |     |     |     | 20  |     |     |     |     | 25  |     |     |     |     | 30  |     |
| Pro | Thr | Ile | Thr | Ala | Gly | Ala | Val | Thr | Asn | Ala | Ser | Glu | Ala | Pro | Thr |
|     |     |     | 35  |     |     |     |     | 40  |     |     |     |     | 45  |     |     |
| Ser | Gly | Ser | Pro | Gly | Ser | Ala | Ala | Ser | Pro | Glu | Val | Thr | Pro | Thr | Ser |
|     |     | 50  |     |     |     |     | 55  |     |     |     |     | 60  |     |     |     |

```
Thr  Pro  Asn  Pro  Asn  Asn  Val  Thr  Gln  Asn  Lys  Thr  Thr  Pro  Thr  Glu
 65             70                 75                              80

Pro  Ala  Ser  Pro  Pro  Thr  Thr  Pro  Lys  Pro  Thr  Ser  Thr  Pro  Lys  Ser
                    85                      90                       95

Pro  Pro  Thr  Ser  Thr  Pro  Asp  Pro  Lys  Pro  Lys  Asn  Asn  Thr  Thr  Pro
               100                     105                      110

Ala  Lys  Ser  Gly  Arg  Pro  Thr  Lys  Pro  Pro  Gly  Pro  Val  Trp  Cys  Asp
          115                     120                    125

Arg  Arg  Asp  Pro  Leu  Ala  Arg  Tyr  Gly  Ser  Arg  Val  Gln  Ile  Arg  Cys
     130                     135                    140

Arg  Phe  Arg  Asn  Ser  Thr  Arg  Met  Glu  Phe  Arg  Leu  Gln  Ile  Trp  Arg
145                      150                     155                          160

Tyr  Ser  Met  Gly  Pro  Ser  Pro  Pro  Ile  Ala  Pro  Ala  Pro  Asp  Leu  Glu
                    165                     170                     175

Glu  Val  Leu  Thr  Asn  Ile  Thr  Ala  Pro  Pro  Gly  Gly  Leu  Leu  Val  Tyr
               180                     185                     190

Asp  Ser  Ala  Pro  Asn  Leu  Thr  Asp  Pro  His  Val  Leu  Trp  Ala  Glu  Gly
          195                     200                     205

Ala  Gly  Pro  Gly  Ala  Asp  Pro  Pro  Leu  Tyr  Ser  Val  Thr  Gly  Pro  Leu
     210                     215                     220

Pro  Thr  Gln  Arg  Leu  Ile  Ile  Gly  Glu  Val  Thr  Pro  Ala  Thr  Gln  Gly
225                      230                     235                          240

Met  Tyr  Tyr  Leu  Ala  Trp  Gly  Arg  Met  Asp  Ser  Pro  His  Glu  Tyr  Gly
                    245                     250                     255

Thr  Trp  Val  Arg  Val  Arg  Met  Phe  Arg  Pro  Pro  Ser  Leu  Thr  Leu  Gln
               260                     265                     270

Pro  His  Ala  Val  Met  Glu  Gly  Gln  Pro  Phe  Lys  Ala  Thr  Cys  Thr  Ala
          275                     280                     285

Ala  Ala  Tyr  Tyr  Pro  Arg  Asn  Pro  Val  Glu  Phe  Val  Trp  Phe  Glu  Asp
     290                     295                     300

Asp  His  Gln  Val  Phe  Asn  Pro  Gly  Gln  Ile  Asp  Thr  Gln  Thr  His  Glu
305                      310                     315                          320

His  Pro  Asp  Gly  Phe  Thr  Thr  Val  Ser  Thr  Val  Thr  Ser  Glu  Ala  Val
                    325                     330                     335

Gly  Gly  Gln  Val  Pro  Pro  Arg  Thr  Phe  Thr  Cys  Gln  Met  Thr  Trp  His
               340                     345                     350

Arg  Asp  Ser  Val  Thr  Phe  Ser  Arg  Arg  Asn  Ala  Thr  Gly  Leu  Ala  Leu
          355                     360                     365

Val  Leu  Pro  Arg  Pro  Thr  Ile  Thr  Met  Glu  Phe  Gly  Val  Arg  Ile  Val
     370                     375                     380

Val  Cys  Thr  Ala  Gly  Cys  Val  Pro  Glu  Gly  Val  Thr  Phe  Ala  Trp  Phe
385                      390                     395                          400

Leu  Gly  Asp  Asp  Pro  Ser  Pro  Ala  Ala  Lys  Ser  Ala  Val  Thr  Ala  Gln
                    405                     410                     415

Glu  Ser  Cys  Asp  His  Pro  Gly  Leu  Ala  Thr  Val  Arg  Ser  Thr  Leu  Pro
               420                     425                     430

Ile  Ser  Tyr  Asp  Tyr  Ser  Glu  Tyr  Ile  Cys  Arg  Leu  Thr  Gly  Tyr  Pro
          435                     440                     445

Ala  Gly  Ile  Pro  Val  Leu  Glu  His  His  Gly  Ser  His  Gln  Pro  Pro  Pro
     450                     455                     460

Arg  Asp  Pro  Thr  Glu  Arg  Gln  Val  Ile  Glu  Ala  Ile  Glu  Trp  Val  Gly
465                      470                     475                          480

Ile  Gly  Ile  Gly  Val  Leu  Ala  Ala  Gly  Val  Leu  Val  Thr  Ala  Ile
                    485                     490                     495
```

```
      Val  Tyr  Val  Val  Arg  Thr  Ser  Gln  Ser  Arg  Gln  Arg  His  Arg  Arg
                      500                      505                     510
```

( 2 ) INFORMATION FOR SEQ ID NO:18:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

```
GATATTTAAT  AAAACTATTA  TGAAACTTCT  TATAACTTAT  TTGTTTTTAT  TAAATGGGTT    60
GGGTTGGTTT  TAAAATTACA  TACGTGTATT  AAGAATTAAC  ATCATAAAGG  ACACACCCAT   120
GAAAAACATT  TAAATTCTAT  TAATTTGAAC  GGATTAAACA  TTTTCTCATT  TTAAGAGTTG   180
CTACGACTTT  TGATAGTAAA  ATGATTAAAC  TTCTATTTAT  CTTATTTTAT  TTTAACCCAA   240
TAACTGGATA  TAAATGGGTA  GACCCTCCTC  GTAGGTATAA  TTACACCGTT  TTAAGAATGA   300
TTCCAGATAT  TCCAAATCCA  ATGGATCCTT  CTAAAACGC   TGAAGTTCGG  TATGTAACTT   360
CTACTGACCC  ATGTGATATG  GTTGCTTTGA  TTTCTAATCC  AAATATAGAA  TCTACAATTA   420
AAACGATTCA  ATTTGTGCAA  AAGAAAAAAT  TTTACAATGC  ATCTCTTAGT  TGGTTTAAAG   480
TTGGAGATGA  TTGTACATAT  CCAATATATT  TAATTCAATA  TTTTGATTGT  GATCCTCAAA   540
GAGAATTTGG  CATATGTTTA  AAAAGATCTC  CAGATTTTTG  GAAACCATCG  TTAGTTGGTT   600
ACACATTTTT  AACTGATGAT  GAATTGGGAT  TAGTTTTAGC  TGCCCCCGCT  CCATTTAATC   660
AAGGTCAATA  TAGACGGGTT  ATTCAAATTG  AAAATGAAGT  TTTTTATACT  GATTTTATGG   720
TTCAATTACC  ACGAGAAACT  TGTTATTTTT  CTAAAGAAGA  TAAATTTGAA  CCAACTTTTA   780
TGGAATGGTG  TAAGGAATCT  AGATCTGTAG  GAGCATCAAA  AGTTGACGAT  GAACTTTTTT   840
ATCTAAATAG  AGCTGGTCCC  CAAACCCTGC  TTAAATATTA  TGTTATTAAA  GATTTTTATA   900
GACTTAACGG  TAGAGAACCT  CCAATAAAAT  TTAAAGAAGC  TCTTAGATAC  GATATACCAT   960
ATAAAGTGAA  TGATAAATTT  GATGATGAAT  TACCATCGAG  GCCACATATT  AGTAATACTA  1020
TTAATAAAAC  TATTAAAGAA  ATTGTAAATC  TTGAAGATTA  TTTTAAAAAT  ACAAATGTTA  1080
TAGATACTAC  TACCCCAACA  CCAATAAATA  ATACCCCAAA  AAATATAACC  GTGGGAATTG  1140
TTATAATTAT  ATTAATAATA  CTATTTATAA  TTGGATTTTT  TGTTTATAAA  AGACAAAAAA  1200
TATATAATAA  TTATAAAAAA  TTAACAACAA  ATGTTTAGCC  TTTATAAATT  AATTTACAGA  1260
ATAAACAACT  GGGCGGTCTT  TTGTTTAATA  AAAATTCATG  TACCTACAAC  TTTTATTCAC  1320
```

( 2 ) INFORMATION FOR SEQ ID NO:19:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:19:

```
      Met  Ile  Lys  Leu  Leu  Phe  Ile  Leu  Phe  Tyr  Phe  Asn  Pro  Ile  Thr  Gly
       1                   5                        10                       15

Tyr  Lys  Trp  Val  Asp  Pro  Pro  Arg  Arg  Tyr  Asn  Tyr  Thr  Val  Leu  Arg
```

| | | | | | | 20 | | | | 25 | | | | 30 | | | |
|---|---|---|---|---|---|---|---|---|---|---|---|---|---|---|---|---|---|
| | Met | Ile | Pro<br>35 | Asp | Ile | Pro | Asn | Pro<br>40 | Met | Asp | Pro | Ser | Lys<br>45 | Asn | Ala | Glu |
| | Val | Arg<br>50 | Tyr | Val | Thr | Ser<br>55 | Thr | Asp | Pro | Cys | Asp<br>60 | Met | Val | Ala | Leu | Ile |
| | Ser<br>65 | Asn | Pro | Asn | Ile | Glu<br>70 | Ser | Thr | Ile | Lys | Thr<br>75 | Ile | Gln | Phe | Val | Gln<br>80 |
| | Lys | Lys | Lys | Phe | Tyr<br>85 | Asn | Ala | Ser | Leu | Ser<br>90 | Trp | Phe | Lys | Val | Gly<br>95 | Asp |
| | Asp | Cys | Thr | Tyr<br>100 | Pro | Ile | Tyr | Leu | Ile<br>105 | Gln | Tyr | Phe | Asp | Cys<br>110 | Asp | Pro |
| | Gln | Arg | Glu<br>115 | Phe | Gly | Ile | Cys | Leu<br>120 | Lys | Arg | Ser | Pro | Asp<br>125 | Phe | Trp | Lys |
| | Pro | Ser | Leu<br>130 | Val | Gly | Tyr | Thr<br>135 | Phe | Leu | Thr | Asp | Asp<br>140 | Glu | Leu | Gly | Leu |
| | Val<br>145 | Leu | Ala | Ala | Pro | Ala<br>150 | Pro | Phe | Asn | Gln | Gly<br>155 | Gln | Tyr | Arg | Arg | Val<br>160 |
| | Ile | Gln | Ile | Glu | Asn<br>165 | Glu | Val | Phe | Tyr | Thr<br>170 | Asp | Phe | Met | Val | Gln<br>175 | Leu |
| | Pro | Arg | Glu | Thr<br>180 | Cys | Tyr | Phe | Ser | Lys<br>185 | Glu | Asp | Lys | Phe | Glu<br>190 | Pro | Thr |
| | Phe | Met | Glu<br>195 | Trp | Cys | Lys | Glu | Ser<br>200 | Arg | Ser | Val | Gly | Ala<br>205 | Ser | Lys | Val |
| | Asp | Asp<br>210 | Glu | Leu | Phe | Tyr | Leu<br>215 | Asn | Arg | Ala | Gly | Pro<br>220 | Gln | Thr | Leu | Leu |
| | Lys<br>225 | Tyr | Tyr | Val | Ile | Lys<br>230 | Asp | Phe | Tyr | Arg | Leu<br>235 | Asn | Gly | Arg | Glu | Pro<br>240 |
| | Pro | Ile | Lys | Phe | Lys<br>245 | Glu | Ala | Leu | Arg | Tyr<br>250 | Asp | Ile | Pro | Tyr | Lys<br>255 | Val |
| | Asn | Asp | Lys | Phe<br>260 | Asp | Asp | Glu | Leu | Pro<br>265 | Ser | Arg | Pro | His | Ile<br>270 | Ser | Asn |
| | Thr | Ile | Asn<br>275 | Lys | Thr | Ile | Lys | Glu<br>280 | Ile | Val | Asn | Leu | Glu<br>285 | Asp | Tyr | Phe |
| | Lys | Asn<br>290 | Thr | Asn | Val | Ile | Asp<br>295 | Thr | Thr | Thr | Pro | Thr<br>300 | Pro | Ile | Asn | Asn |
| | Thr<br>305 | Pro | Lys | Asn | Ile | Thr<br>310 | Val | Gly | Ile | Val | Ile<br>315 | Ile | Ile | Leu | Ile | Ile<br>320 |
| | Leu | Phe | Ile | Ile | Gly<br>325 | Phe | Phe | Val | Tyr | Lys<br>330 | Arg | Gln | Lys | Ile | Tyr<br>335 | Asn |
| | Asn | Tyr | Lys | Lys<br>340 | Leu | Thr | Thr | Asn | Val<br>345 | | | | | | | |

( 2 ) INFORMATION FOR SEQ ID NO:20:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:20:

| Met<br>1 | Ile | Lys | Leu | Leu<br>5 | Phe | Ile | Leu | Phe | Tyr<br>10 | Phe | Asn | Pro | Ile | Thr<br>15 | Gly |
|---|---|---|---|---|---|---|---|---|---|---|---|---|---|---|---|

| | | | | | | | | | | | | | | |
|---|---|---|---|---|---|---|---|---|---|---|---|---|---|---|
| Tyr | Lys | Trp | Val 20 | Asp | Pro | Pro | Arg 25 | Arg | Tyr | Asn | Tyr | Thr 30 | Val | Leu | Arg |
| Met | Ile | Pro 35 | Asp | Ile | Pro | Asn 40 | Pro | Met | Asp | Pro | Ser 45 | Lys | Asn | Ala | Glu |
| Val | Arg 50 | Tyr | Val | Thr | Ser 55 | Thr | Asp | Pro | Cys | Asp 60 | Met | Val | Ala | Leu | Ile |
| Ser 65 | Asn | Pro | Asn | Ile | Glu 70 | Ser | Thr | Ile | Lys | Thr 75 | Ile | Gln | Phe | Val | Gln 80 |
| Lys | Lys | Lys | Phe | Tyr 85 | Asn | Ala | Ser | Leu | Ser 90 | Trp | Phe | Lys | Val | Gly 95 | Asp |
| Asp | Cys | Thr | Tyr 100 | Pro | Ile | Tyr | Leu | Ile 105 | Gln | Tyr | Phe | Asp | Cys 110 | Asp | Pro |
| Gln | Arg | Glu 115 | Phe | Gly | Ile | Cys | Leu 120 | Lys | Arg | Ser | Pro | Asp 125 | Phe | Trp | Lys |
| Pro | Ser | Leu 130 | Val | Gly | Tyr | Thr 135 | Phe | Leu | Thr | Asp | Asp 140 | Glu | Leu | Gly | Leu |
| Val 145 | Leu | Ala | Ala | Pro | Ala 150 | Pro | Phe | Asn | Gln | Gly 155 | Gln | Tyr | Arg | Arg | Val 160 |
| Ile | Gln | Ile | Glu | Asn 165 | Glu | Val | Phe | Tyr | Thr 170 | Asp | Phe | Met | Val | Gln | Leu 175 |
| Pro | Arg | Glu | Thr 180 | Cys | Tyr | Phe | Ser | Lys 185 | Glu | Asp | Lys | Phe | Glu 190 | Pro | Thr |
| Phe | Met | Glu 195 | Trp | Cys | Lys | Glu | Ser 200 | Arg | Ser | Val | Gly | Ala 205 | Ser | Lys | Val |
| Asp | Asp 210 | Glu | Leu | Phe | Tyr | Leu 215 | Asn | Arg | Ala | Gly | Pro 220 | Gln | Thr | Leu | Leu |
| Lys 225 | Tyr | Tyr | Val | Ile | Lys 230 | Asp | Phe | Tyr | Arg | Leu 235 | Asn | Gly | Arg | Glu | Pro 240 |
| Pro | Ile | Lys | Phe | Lys 245 | Glu | Ala | Leu | Arg | Tyr 250 | Asp | Ile | Pro | Tyr | Lys 255 | Val |
| Asn | Asp | Lys | Phe 260 | Asp | Asp | Glu | Leu | Pro 265 | Ser | Arg | Pro | His | Ile 270 | Ser | Asn |
| Thr | Ile | Asn 275 | Lys | Thr | Ile | Lys | Glu 280 | Ile | Val | Asn | Leu | Glu 285 | Asp | Tyr | Phe |
| Lys | Asn 290 | Thr | Asn | Val | Ile | Asp 295 | Thr | Thr | Thr | Pro | Thr 300 | Pro | Ile | Asn | Asn |
| Thr 305 | Pro | Lys | Asn | Ile | Thr 310 | Val | Gly | Ile | Val | Ile 315 | Ile | Ile | Leu | Ile | Ile 320 |
| Leu | Phe | Ile | Ile | Gly 325 | Phe | Phe | Val | Tyr | Lys 330 | Arg | Gln | Lys | Ile | Tyr 335 | Asn |
| Asn | Tyr | Lys | Lys 340 | Leu | Thr | Thr | Asn | Val 345 | | | | | | | |

( 2 ) INFORMATION FOR SEQ ID NO:21:

( i ) SEQUENCE CHARACTERISTICS:
        ( A ) LENGTH: 374 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:21:

| | | | | | | | | | | | | | | |
|---|---|---|---|---|---|---|---|---|---|---|---|---|---|---|
| Met 1 | Met | Thr | Arg | Leu 5 | His | Phe | Trp | Trp | Cys 10 | Gly | Ile | Phe | Ala | Val 15 | Leu |

| | | | | | | | | | | | | | | |
|---|---|---|---|---|---|---|---|---|---|---|---|---|---|---|
| Lys | Tyr | Leu | Val 20 | Cys | Thr | Ser | Ser | Leu 25 | Thr | Thr | Thr | Pro | Lys 30 | Thr | Thr |
| Thr | Val | Tyr 35 | Val | Lys | Gly | Phe | Asn 40 | Ile | Pro | Pro | Leu | Arg 45 | Tyr | Asn | Tyr |
| Thr | Gln 50 | Ala | Arg | Ile | Val | Pro 55 | Lys | Ile | Pro | Gln | Ala 60 | Met | Asp | Pro | Lys |
| Ile 65 | Thr | Ala | Glu | Val | Arg 70 | Tyr | Val | Thr | Ser | Met 75 | Asp | Ser | Cys | Gly | Met 80 |
| Val | Ala | Leu | Ile | Ser 85 | Glu | Pro | Asp | Ile | Asp 90 | Ala | Thr | Ile | Arg | Thr 95 | Ile |
| Gln | Leu | Ser | Gln 100 | Lys | Lys | Thr | Tyr | Asn 105 | Ala | Thr | Ile | Ser | Trp 110 | Phe | Lys |
| Val | Thr | Gln 115 | Gly | Cys | Glu | Tyr | Pro 120 | Met | Phe | Leu | Met | Asp 125 | Met | Arg | Leu |
| Cys | Asp 130 | Pro | Lys | Arg | Glu | Phe 135 | Gly | Ile | Cys | Ala | Leu 140 | Arg | Ser | Pro | Ser |
| Tyr 145 | Trp | Leu | Glu | Pro | Leu 150 | Thr | Lys | Tyr | Met | Phe 155 | Leu | Thr | Asp | Asp | Glu 160 |
| Leu | Gly | Leu | Ile | Met 165 | Met | Ala | Pro | Ala | Gln 170 | Phe | Asn | Gln | Gly | Gln 175 | Tyr |
| Arg | Arg | Val | Ile 180 | Thr | Ile | Asp | Gly | Ser 185 | Met | Phe | Tyr | Thr | Asp 190 | Phe | Met |
| Val | Gln | Leu 195 | Ser | Pro | Thr | Pro | Cys 200 | Trp | Phe | Ala | Lys | Pro 205 | Asp | Arg | Tyr |
| Glu | Glu 210 | Ile | Leu | His | Glu | Trp 215 | Cys | Arg | Asn | Val | Lys 220 | Thr | Ile | Gly | Leu |
| Asp 225 | Gly | Ala | Arg | Asp | Tyr 230 | His | Tyr | Tyr | Trp | Val 235 | Pro | Tyr | Asn | Pro | Gln 240 |
| Pro | His | His | Lys | Ala 245 | Val | Leu | Leu | Tyr | Trp 250 | Tyr | Arg | Thr | His | Gly 255 | Arg |
| Glu | Pro | Pro | Val 260 | Arg | Phe | Gln | Glu | Ala 265 | Ile | Arg | Tyr | Asp | Arg 270 | Pro | Ala |
| Ile | Pro | Ser 275 | Gly | Ser | Glu | Asp | Ser 280 | Lys | Arg | Ser | Asn | Asp 285 | Ser | Arg | Gly |
| Glu | Ser 290 | Ser | Gly | Pro | Asn | Trp 295 | Ile | Asp | Ile | Glu | Asn 300 | Tyr | Thr | Pro | Lys |
| Asn 305 | Asn | Val | Pro | Ile | Ile 310 | Ile | Ser | Asp | Asp | Val 315 | Pro | Thr | Ala | Pro 320 | |
| Pro | Lys | Gly | Met | Asn 325 | Asn | Gln | Ser | Val | Val 330 | Ile | Pro | Ala | Ile | Val 335 | Leu |
| Ser | Cys | Leu | Ile 340 | Ile | Ala | Leu | Ile | Leu 345 | Gly | Val | Ile | Tyr | Tyr 350 | Ile | Leu |
| Arg | Val | Lys 355 | Arg | Ser | Arg | Ser | Thr 360 | Ala | Tyr | Gln | Gln | Leu 365 | Pro | Ile | Ile |
| His | Thr 370 | Thr | His | His | Pro | | | | | | | | | | |

( 2 ) INFORMATION FOR SEQ ID NO:22:

( i ) SEQUENCE CHARACTERISTICS:
( A ) LENGTH: 442 amino acids
( B ) TYPE: amino acid
( C ) STRANDEDNESS: single
( D ) TOPOLOGY: linear ( i i ) MOLECULE TYPE: peptide ( v ) FRAGMENT TYPE: N-terminal ( x i ) SEQUENCE DESCRIPTION: SEQ ID NO:22:

```
Met Pro Ala Val Leu Leu Val Leu Tyr Val Asn Pro Pro Ser Val
 1               5                  10                  15

Cys Ile Leu Thr Gln Lys Leu Ser Leu Gly Leu Tyr Asn Gln Trp Trp
            20                  25                  30

Arg Val Cys Arg Ser Val Pro Pro Trp Tyr Val Phe Phe Asn Lys
         35                  40                  45

Arg Ser Met Ser Thr Phe Lys Leu Met Met Asp Gly Arg Leu Val Phe
     50                  55                  60

Ala Met Ala Ile Ala Ile Leu Ser Val Val Leu Ser Cys Gly Thr Cys
 65                  70                  75                  80

Glu Lys Ala Lys Arg Ala Val Arg Gly Arg Gln Asp Arg Pro Lys Glu
                 85                  90                  95

Phe Pro Pro Pro Arg Tyr Asn Tyr Thr Ile Leu Thr Arg Tyr Asn Ala
             100                 105                 110

Thr Ala Leu Ala Ser Pro Phe Ile Asn Asp Gln Val Lys Asn Val Asp
         115                 120                 125

Leu Arg Ile Val Thr Ala Thr Arg Pro Cys Glu Met Ile Ala Leu Ile
    130                 135                 140

Ala Lys Thr Asn Ile Asp Ser Ile Leu Lys Glu Leu Ala Ala Ala Gln
145                 150                 155                 160

Lys Thr Tyr Ser Ala Arg Leu Thr Trp Phe Lys Ile Met Pro Thr Cys
                 165                 170                 175

Ala Thr Pro Ile His Asp Val Ser Tyr Met Lys Cys Asn Pro Lys Leu
             180                 185                 190

Ser Phe Ala Met Cys Asp Glu Arg Ser Asp Ile Leu Trp Gln Ala Ser
         195                 200                 205

Leu Ile Thr Met Ala Ala Glu Thr Asp Asp Glu Leu Gly Leu Val Leu
    210                 215                 220

Ala Ala Pro Ala His Ser Ala Ser Gly Leu Tyr Arg Arg Val Ile Glu
225                 230                 235                 240

Ile Asp Gly Arg Arg Ile Tyr Thr Asp Phe Ser Val Thr Ile Pro Ser
                 245                 250                 255

Glu Arg Cys Pro Ile Ala Phe Glu Leu Asn Phe Gly Asn Pro Asp Arg
             260                 265                 270

Cys Lys Thr Pro Glu Gln Tyr Ser Arg Gly Val Phe Thr Arg Arg
         275                 280                 285

Phe Leu Gly Glu Phe Asn Phe Pro Gln Gly Glu His Met Thr Trp Val
    290                 295                 300

Lys Phe Trp Phe Val Tyr Asp Gly Gly Asn Leu Pro Val Gln Phe Tyr
305                 310                 315                 320

Glu Ala Gln Ala Phe Ala Arg Pro Val Pro Pro Asp Asn His Pro Gly
                 325                 330                 335

Phe Asp Ser Val Glu Ser Glu Ile Thr Gln Asn Lys Thr Asp Pro Lys
             340                 345                 350

Pro Gly Gln Ala Asp Pro Lys Pro Asn Gln Pro Phe Lys Trp Pro Ser
         355                 360                 365

Ile Lys His Leu Val Pro Arg Leu Asp Glu Val Asp Glu Val Ile Glu
    370                 375                 380

Pro Val Thr Lys Pro Pro Lys Thr Ser Lys Ser Asn Ser Thr Phe Val
385                 390                 395                 400
```

```
       Gly  Ile  Ser  Val  Gly  Leu  Gly  Ile  Ala  Gly  Leu  Val  Leu  Val  Gly  Val
                           405                      410                     415

Ile  Leu  Tyr  Val  Cys  Leu  Arg  Arg  Lys  Lys  Glu  Leu  Lys  Val  Cys  Thr
                           420                      425                     430

Glu  Arg  Leu  Asp  Ser  Pro  Thr  Leu  Asp  Leu
                      435                      440
```

( 2 ) INFORMATION FOR SEQ ID NO:23:

( i ) SEQUENCE CHARACTERISTICS:
        ( A ) LENGTH: 393 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:23:

```
       Met  Gly  Gly  Ala  Ala  Ala  Arg  Leu  Gly  Ala  Val  Ile  Leu  Phe  Val  Val
       1                      5                      10                      15

Ile  Val  Gly  Leu  His  Gly  Val  Arg  Gly  Lys  Tyr  Ala  Leu  Ala  Asp  Ala
                           20                      25                      30

Ser  Leu  Lys  Met  Ala  Asp  Pro  Asn  Arg  Phe  Arg  Gly  Lys  Asp  Leu  Pro
                      35                      40                      45

Val  Leu  Asp  Gln  Leu  Thr  Asp  Pro  Pro  Gly  Val  Arg  Arg  Val  Tyr  His
                 50                      55                      60

Ile  Gln  Ala  Gly  Leu  Pro  Asn  Pro  Phe  Gln  Pro  Pro  Ser  Leu  Pro  Ile
       65                      70                      75                      80

Thr  Val  Tyr  Arg  Arg  Val  Glu  Arg  Ala  Cys  Arg  Ser  Val  Leu  Leu  Asn
                           85                      90                      95

Ala  Pro  Ser  Glu  Ala  Pro  Gln  Ile  Val  Arg  Gly  Ala  Ser  Glu  Asp  Val
                           100                     105                     110

Arg  Lys  Gln  Pro  Tyr  Asn  Leu  Thr  Ile  Ala  Trp  Phe  Arg  Met  Gly  Gly
                      115                     120                     125

Asn  Cys  Ala  Ile  Pro  Ile  Thr  Val  Met  Glu  Tyr  Thr  Glu  Cys  Ser  Tyr
                 130                     135                     140

Asn  Lys  Ser  Leu  Gly  Ala  Cys  Pro  Ile  Arg  Thr  Gln  Pro  Arg  Trp  Asn
       145                     150                     155                     160

Tyr  Tyr  Asp  Ser  Phe  Ser  Ala  Val  Ser  Glu  Asp  Asn  Leu  Gly  Phe  Leu
                           165                     170                     175

Met  His  Ala  Pro  Ala  Phe  Glu  Thr  Ala  Gly  Thr  Tyr  Leu  Arg  Leu  Val
                           180                     185                     190

Lys  Ile  Asn  Asp  Trp  Thr  Glu  Ile  Thr  Gln  Phe  Ile  Leu  Glu  His  Arg
                      195                     200                     205

Ala  Lys  Gly  Ser  Cys  Lys  Tyr  Thr  Leu  Pro  Leu  Arg  Ile  Pro  Pro  Ser
                 210                     215                     220

Ala  Cys  Leu  Ser  Pro  Gln  Ala  Tyr  Gln  Gln  Gly  Val  Thr  Val  Asp  Ser
       225                     230                     235                     240

Ile  Gly  Met  Leu  Pro  Arg  Phe  Ile  Pro  Glu  Asn  Gln  Arg  Thr  Val  Ala
                           245                     250                     255

Val  Tyr  Ser  Leu  Lys  Ile  Ala  Gly  Trp  His  Gly  Pro  Arg  Ala  Pro  Tyr
                           260                     265                     270

Thr  Ser  Thr  Leu  Leu  Pro  Pro  Glu  Leu  Pro  Glu  Thr  Pro  Asn  Ala  Thr
                      275                     280                     285

Gln  Pro  Glu  Leu  Ala  Pro  Glu  Asp  Pro  Glu  Asp  Ser  Ala  Leu  Leu  Glu
                 290                     295                     300
```

```
    Asp  Pro  Val  Gly  Thr  Val  Ala  Pro  Gln  Ile  Pro  Pro  Asn  Trp  His  Ile
    305                      310                      315                      320

Pro  Ser  Ile  Gln  Asp  Ala  Ala  Thr  Pro  Tyr  His  Pro  Pro  Ala  Thr  Pro
                        325                      330                      335

Asn  Asn  Met  Gly  Leu  Ile  Ala  Gly  Ala  Val  Gly  Gly  Ser  Leu  Leu  Ala
                   340                      345                      350

Ala  Leu  Val  Ile  Cys  Gly  Ile  Val  Tyr  Trp  Met  Arg  Arg  Arg  Thr  Arg
              355                      360                      365

Lys  Ala  Pro  Lys  Arg  Ile  Arg  Leu  Pro  His  Ile  Arg  Glu  Asp  Asp  Gln
         370                      375                      380

Pro  Ser  Ser  His  Gln  Pro  Leu  Phe  Tyr
    385                      390
```

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

TAATTAACTA GCTACCCGGG 20

( 2 ) INFORMATION FOR SEQ ID NO:25:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GTACATTAAT TGATCGATGG GCCCTTAA 28

( 2 ) INFORMATION FOR SEQ ID NO:26:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

AGCTTCCCGG GTAAGTAATA CGTCAAGGAG AAAACGAAAC GATCTGTAGT TAGCGGCCGC 60

CTAATTAACT AAT 73

( 2 ) INFORMATION FOR SEQ ID NO:27:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

AGGGCCCATT CATTATGCAG TTCCTCTTTT GCTTTGCTAG ACATCAATCG CCGGCGGATT 60

AATTGATTA                                                                                         69

( 2 ) INFORMATION FOR SEQ ID NO:28:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:28:

TTAGTTAATT AGGCGGCCGC                                                                             20

( 2 ) INFORMATION FOR SEQ ID NO:29:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:29:

CGATTACTAT GAAGGATCCG TT                                                                          22

( 2 ) INFORMATION FOR SEQ ID NO:30:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:30:

TAATGATACT TCCTAGGCAA                                                                             20

( 2 ) INFORMATION FOR SEQ ID NO:31:

( i ) SEQUENCE CHARACTERISTICS:
            ( A ) LENGTH: 41 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:31:

CGATTACTAG ATCTGAGCTC CCCGGGCTCG AGGGATCCGT T                                                     41

( 2 ) INFORMATION FOR SEQ ID NO:32:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:32:

TAATGATCTA GACTCGAGGG GCCCGAGCTC CCTAGGCAA                                                        39

( 2 ) INFORMATION FOR SEQ ID NO:33:

( i ) SEQUENCE CHARACTERISTICS:
   ( A ) LENGTH: 16 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:33:

GATCCGAATT CTAGCT  16

( 2 ) INFORMATION FOR SEQ ID NO:34:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:34:

GCTTAAGATC GA  12

( 2 ) INFORMATION FOR SEQ ID NO:35:

( i ) SEQUENCE CHARACTERISTICS:
      ( A ) LENGTH: 75 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:35:

TATGAGTAAC TTAACTCTTT TGTTAATTAA AAGTATATTC AAAAAATAAG TTATATAAAT  60

AGATCTGAAT TCGTT  75

( 2 ) INFORMATION FOR SEQ ID NO:36:

( i ) SEQUENCE CHARACTERISTICS:
      ( A ) LENGTH: 73 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:36:

ACTCATTGAA TTGAGAAAAC AATTAATTTT CATATAAGTT TTTTATTCAA TATATTTATC  60

TAGACTTAAG CAA  73

( 2 ) INFORMATION FOR SEQ ID NO:37:

( i ) SEQUENCE CHARACTERISTICS:
      ( A ) LENGTH: 73 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:37:

ACTCATTGAA TTGAGAAAAC AATTAATTTT CATATAAGTT TTTTATTCAA TATATTTATC  60

TAGACTTAAG CAA  73

( 2 ) INFORMATION FOR SEQ ID NO:38:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

```
ACACGAATGA  TTTTCTAAAG  TATTTGGAAA  GTTTTATAGG  TAGTTGATAG  AACAAAATAC        60

ATAATTT                                                                      67
```

( 2 ) INFORMATION FOR SEQ ID NO:39:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
TGTGCTTACT  AAAAGATTTC  ATAAACCTTT  CAAAATATCC  ATCAACTATC  T                 51
```

( 2 ) INFORMATION FOR SEQ ID NO:40:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

```
TGTAAAAATA  AATCACTTTT  TATACTAAGA  TCTCCCGGGC  TGCAGC                       46
```

( 2 ) INFORMATION FOR SEQ ID NO:41:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

```
TGTTTTATGT  ATTAAAACAT  TTTTATTTAG  TGAAAAATAT  GATTCTAGAG  GGCCCGACGT        60

CGCCGG                                                                       66
```

( 2 ) INFORMATION FOR SEQ ID NO:42:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

```
TTTCTGTATA  TTTGCACCAA  TTTAGATCTT  ACTCAAAATA  TGTAACAATA                   50
```

( 2 ) INFORMATION FOR SEQ ID NO:43:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:43:

TGTCATTTAA CACTATACTC ATATTAATAA AAATAATATT TATT  44

( 2 ) INFORMATION FOR SEQ ID NO:44:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:44:

GATCCTGAGT ACTTTGTAAT ATAATGATAT ATATTTTCAC TTTATCTCAT TTGAGAATAA  60

AAAGATCTTA GG  72

( 2 ) INFORMATION FOR SEQ ID NO:45:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:45:

GACTCATGAA ACATTATATT ACTATATATA AAAGTGAAAT AGAGTAAACT CTTATTTTTC  60

TAGAATCCTT AA  72

( 2 ) INFORMATION FOR SEQ ID NO:46:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:46:

GATCCAGATC TCCCGGGAAA AAAATTATTT AACTTTTCAT TAATAGGGAT TTGACGTATG  60

TAGCGTACTA GG  72

( 2 ) INFORMATION FOR SEQ ID NO:47:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:47:

GTCTAGAGGG CCCTTTTTTT AATAAATTGA AAAGTAATTA TCCCTAAACT GCATACTACG  60

CATGATCCTT AA  72

( 2 ) INFORMATION FOR SEQ ID NO:48:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

```
GGGAGATCTC TCGAGCTGCA GGGCGCCGGA TCCTTTTTCT                    40
```

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

```
CCCTCTAGAG AGCTCGACGT CCCGCGGCCT AGGAAAAAGA                    40
```

( 2 ) INFORMATION FOR SEQ ID NO:50:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

```
CGATATCCGT TAAGTTTGTA TCGTAATGGG CTCCAGATCT TCTACCAGGA TCCCGGTAC    59
```

( 2 ) INFORMATION FOR SEQ ID NO:51:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

```
CGGGATCCTG GTAGAAGATC TGGAGCCCAT TACGATACAA ACTTAACGGA TATCG        55
```

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

```
AATTCGAGCT CCCCGGG                                             17
```

( 2 ) INFORMATION FOR SEQ ID NO:53:

( i ) SEQUENCE CHARACTERISTICS:

5,529,780

171                                                                 172
-continued ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

CCCGGGGAGC TCG                                                                                                  13

( 2 ) INFORMATION FOR SEQ ID NO:54:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

CTTTTTATAA AAAGTTAACT ACGTAG                                                                                    26

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

GATCCTACGT AGTTAACTTT TTATAAAAAG AGCT                                                                           34

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

CTTAACTCAG CTGACTATCC                                                                                           20

( 2 ) INFORMATION FOR SEQ ID NO:57:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

TACGTAGTTA ACTTTTTATA AAAATCATAT TTTTGTAGTG GCTC                                                                 44

( 2 ) INFORMATION FOR SEQ ID NO:58:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

| AATTCAGGAT | CGTTCCTTTA | CTAGTTGAGA | TTCTCAAGGA | TGATGGGATT | TAATTTTTAT | 60 |
|---|---|---|---|---|---|---|
| AAGCTTG | | | | | | 67 |

( 2 ) INFORMATION FOR SEQ ID NO:59:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

| AATTCAAGCT | TATAAAAATT | AAATCCCATC | ATCCTTGAGA | ATCTCAACTA | GTAAAGGAAC | 60 |
|---|---|---|---|---|---|---|
| GATCCTG | | | | | | 67 |

( 2 ) INFORMATION FOR SEQ ID NO:60:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

| CTAGACACTT | TATGTTTTTT | AATATCCGGT | CTTAAAAGCT | TCCCGGGGAT | CCTTATACGG | 60 |
|---|---|---|---|---|---|---|
| GGAATAAT | | | | | | 68 |

( 2 ) INFORMATION FOR SEQ ID NO:61:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

| ATTATTCCCC | GTATAAGGAT | CCCCCGGGAA | GCTTTTAAGA | CCGGATATTA | AAAAACATAA | 60 |
|---|---|---|---|---|---|---|
| AGTGT | | | | | | 65 |

( 2 ) INFORMATION FOR SEQ ID NO:62:

( i ) SEQUENCE CHARACTERISTICS:
        ( A ) LENGTH: 3209 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:62:

| TGAATGTTAA | ATGTTATACT | TTGGATGAAG | CTATAAATAT | GCATTGGAAA | AATAATCCAT | 60 |
|---|---|---|---|---|---|---|
| TTAAAGAAAG | GATTCAAATA | CTACAAAACC | TAAGCGATAA | TATGTTAACT | AAGCTTATTC | 120 |
| TTAACGACGC | TTTAAATATA | CACAAATAAA | CATAATTTTT | GTATAACCTA | ACAAATAACT | 180 |
| AAAACATAAA | AATAATAAAA | GGAAATGTAA | TATCGTAATT | ATTTACTCA | GGAATGGGGT | 240 |

| | | | | | |
|---|---|---|---|---|---|
| TAAATATTTA | TATCACGTGT | ATATCTATAC | TGTTATCGTA | TACTCTTTAC | AATTACTATT | 300 |
| ACGAATATGC | AAGAGATAAT | AAGATTACGT | ATTTAAGAGA | ATCTTGTCAT | GATAATTGGG | 360 |
| TACGACATAG | TGATAAATGC | TATTTCGCAT | CGTTACATAA | AGTCAGTTGG | AAAGATGGAT | 420 |
| TTGACAGATG | TAACTTAATA | GGTGCAAAAA | TGTTAAATAA | CAGCATTCTA | TCGGAAGATA | 480 |
| GGATACCAGT | TATATTATAC | AAAAATCACT | GGTTGGATAA | AACAGATTCT | GCAATATTCG | 540 |
| TAAAAGATGA | AGATTACTGC | GAATTTGTAA | ACTATGACAA | TAAAAAGCCA | TTTATCTCAA | 600 |
| CGACATCGTG | TAATTCTTCC | ATGTTTTATG | TATGTGTTTC | AGATATTATG | AGATTACTAT | 660 |
| AAACTTTTTG | TATACTTATA | TTCCGTAAAC | TATATTAATC | ATGAAGAAAA | TGAAAAGTA | 720 |
| TAGAAGCTGT | TCACGAGCGG | TTGTTGAAAA | CAACAAAATT | ATACATTCAA | GATGGCTTAC | 780 |
| ATATACGTCT | GTGAGGCTAT | CATGGATAAT | GACAATGCAT | CTCTAAATAG | GTTTTTGGAC | 840 |
| AATGGATTCG | ACCCTAACAC | GGAATATGGT | ACTCTACAAT | CTCCTCTTGA | AATGGCTGTA | 900 |
| ATGTTCAAGA | ATACCGAGGC | TATAAAAATC | TTGATGAGGT | ATGGAGCTAA | ACCTGTAGTT | 960 |
| ACTGAATGCA | CAACTTCTTG | TCTGCATGAT | GCGGTGTTGA | GAGACGACTA | CAAAATAGTG | 1020 |
| AAAGATCTGT | TGAAGAATAA | CTATGTAAAC | AATGTTCTTT | ACAGCGGAGG | CTTTACTCCT | 1080 |
| TTGTGTTTGG | CAGCTTACCT | TAACAAAGTT | AATTTGGTTA | AACTTCTATT | GGCTCATTCG | 1140 |
| GCGGATGTAG | ATATTTCAAA | CACGGATCGG | TTAACTCCTC | TACATATAGC | CGTATCAAAT | 1200 |
| AAAAATTTAA | CAATGGTTAA | ACTTCTATTG | AACAAGGTG | CTGATACTGA | CTTGCTGGAT | 1260 |
| AACATGGGAC | GTACTCCTTT | AATGATCGCT | GTACAATCTG | GAAATATTGA | AATATGTAGC | 1320 |
| ACACTACTTA | AAAAAAATAA | AATGTCCAGA | ACTGGGAAAA | ATTGATCTTG | CCAGCTGTAA | 1380 |
| TTCATGGTAG | AAAAGAAGTG | CTCAGGCTAC | TTTTCAACAA | AGGAGCAGAT | GTAAACTACA | 1440 |
| TCTTTGAAAG | AAATGGAAAA | TCATATACTG | TTTTGGAATT | GATTAAAGAA | AGTTACTCTG | 1500 |
| AGACACAAAA | GAGGTAGCTG | AAGTGGTACT | CTCAAAATGC | AGAACGATGA | CTGCGAAGCA | 1560 |
| AGAAGTAGAG | AAATAACACT | TTATGACTTT | CTTAGTTGTA | GAAAGATAG | AGATATAATG | 1620 |
| ATGGTCATAA | ATAACTCTGA | TATTGCAAGT | AAATGCAATA | ATAAGTTAGA | TTTATTTAAA | 1680 |
| AGGATAGTTA | AAAATAGAAA | AAAAGAGTTA | ATTTGTAGGG | TTAAAATAAT | ACATAAGATC | 1740 |
| TTAAAATTTA | TAAATACGCA | TAATAATAAA | AATAGATTAT | ACTTATTACC | TTCAGAGATA | 1800 |
| AAATTTAAGA | TATTTACTTA | TTTAACTTAT | AAAGATCTAA | AATGCATAAT | TTCTAAATAA | 1860 |
| TGAAAAAAAA | GTACATCATG | AGCAACGCGT | TAGTATATTT | TACAATGGAG | ATTAACGCTC | 1920 |
| TATACCGTTC | TATGTTTATT | GATTCAGATG | ATGTTTTAGA | AAAGAAAGTT | ATTGAATATG | 1980 |
| AAAACTTTAA | TGAAGATGAA | GATGACGACG | ATGATTATTG | TTGTAAATCT | GTTTTAGATG | 2040 |
| AAGAAGATGA | CGCGCTAAAG | TATACTATGG | TTACAAAGTA | TAAGTCTATA | CTACTAATGG | 2100 |
| CGACTTGTGC | AAGAAGGTAT | AGTATAGTGA | AAATGTTGTT | AGATTATGAT | TATGAAAAAC | 2160 |
| CAAATAAATC | AGATCCATAT | CTAAAGGTAT | CTCCTTTGCA | CATAATTTCA | TCTATTCCTA | 2220 |
| GTTAGAATA | CTTTTCATTA | TATTTGTTTA | CAGCTGAAGA | CGAAAAAAT | ATATCGATAA | 2280 |
| TAGAAGATTA | TGTTAACTCT | GCTAATAAGA | TGAAATTGAA | TGAGTCTGTG | ATAATAGCTA | 2340 |
| TAATCAGAGA | AGTTCTAAAA | GGAAATAAAA | ATCTAACTGA | TCAGGATATA | AAACATTGG | 2400 |
| CTGATGAAAT | CAACAAGGAG | GAACTGAATA | TAGCTAAACT | ATTGTTAGAT | AGAGGGGCCA | 2460 |
| AAGTAAATTA | CAAGGATGTT | TACGGTTCTT | CAGCTCTCCA | TAGAGCTGCT | ATTGGTAGGA | 2520 |
| AACAGGATAT | GATAAAGCTG | TTAATCGATC | ATGGAGCTGA | TGTAAACTCT | TTAACTATTG | 2580 |
| CTAAAGATAA | TCTTATTAAA | AAAAAATAAT | ATCACGTTTA | GTAATATTAA | AATATATTAA | 2640 |

| | | | | | |
|---|---|---|---|---|---|
| TAACTCTATT | ACTAATAACT | CCAGTGGATA | TGAACATAAT | ACGAAGTTTA | TACATTCTCA | 2700 |
| TCAAAATCTT | ATTGACATCA | AGTTAGATTG | TGAAAATGAG | ATTATGAAAT | TAAGGAATAC | 2760 |
| AAAAATAGGA | TGTAAGAACT | TACTAGAATG | TTTTATCAAT | AATGATATGA | ATACAGTATC | 2820 |
| TAGGGCTATA | AACAATGAAA | CGATTAAAAA | TTATAAAAAT | CATTTCCCTA | TATATAATAC | 2880 |
| GCTCATAGAA | AAATTCATTT | CTGAAAGTAT | ACTAAGACAC | GAATTATTGG | ATGGAGTTAT | 2940 |
| AAATTCTTTT | CAAGGATTCA | ATAATAAATT | GCCTTACGAG | ATTCAGTACA | TTATACTGGA | 3000 |
| GAATCTTAAT | AACCATGAAC | TAAAAAAAAT | TTTAGATAAT | ATACATTAAA | AAGGTAAATA | 3060 |
| GATCATCTGT | TATTATAAGC | AAAGATGCTT | GTTGCCAATA | ATATACAACA | GGTATTTGTT | 3120 |
| TTTATTTTTA | ACTACATATT | TGATGTTCAT | TCTCTTTATA | TAGTATACAC | AGAAAATTCA | 3180 |
| TAATCCACTT | AGAATTTCTA | GTTATCTAG  |            |            |            | 3209 |

( 2 ) INFORMATION FOR SEQ ID NO:63:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

GCTTCCCGGG AATTCTAGCT AGCTAGTTT                                                  29

( 2 ) INFORMATION FOR SEQ ID NO:64:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

ACTCTCAAAA GCTTCCCGGG AATTCTAGCT AGCTAGTTTT TATAAA                    46

( 2 ) INFORMATION FOR SEQ ID NO:65:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:65:

GATCTTTATA AAAACTAGCT AGCTAGAATT CCCGGGAAGC TTTTGAGAGT             50

( 2 ) INFORMATION FOR SEQ ID NO:66:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

CTGAAATTAT TCATTATCG CGATATCCGT TAAGTTTGTA TCGTAATGGT TCCTCAGGCT        60

CTCCTGTTTG T                                                                                          7 1

( 2 ) INFORMATION FOR SEQ ID NO:67:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:67:

CATTACGATA CAAACTTAAC GGATATCGCG ATAATGAAAT AATTTCAG                                                   4 8

( 2 ) INFORMATION FOR SEQ ID NO:68:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:68:

ACCCCTTCTG GTTTTTCCGT TGTGTTTTGG GAAATTCCCT ATTTACACGA TCCCAGACAA                                      6 0

GCTTAGATCT CAG                                                                                        7 3

( 2 ) INFORMATION FOR SEQ ID NO:69:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:69:

CTGAGATCTA AGCTTGTCTG GGATCGTGTA AATAGGGAAT TTCCCAAAAC A                                               5 1

( 2 ) INFORMATION FOR SEQ ID NO:70:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:70:

CAACGGAAAA ACCAGAAGGG GTACAAACAG GAGAGCCTGA GGAAC                                                      4 5

( 2 ) INFORMATION FOR SEQ ID NO:71:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:71:

GGATCCCCGG G                                                                                          1 1

( 2 ) INFORMATION FOR SEQ ID NO:72:

( i ) SEQUENCE CHARACTERISTICS:
        ( A ) LENGTH: 3659 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:72:

| | | | | | |
|---|---|---|---|---|---|
| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAAGAAGTAC | CAGTAAAAAG | 120 |
| TGTGGCATAT | GCATAGAAGA | AATAAACAAA | AAACATATTT | CCGAACAGTA | TTTTGGAATT | 180 |
| CTCCCAAGTT | GTAAACATAT | TTTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAAA | TATTATATAA | TAGATATAAG | 360 |
| AAAATGATTT | TTACAAAAAT | ACCTATAAGA | ACAATAAAAA | TATAATTACA | TTTACGGAAA | 420 |
| ATAGCTGGTT | TTAGTTTACC | AACTTAGAGT | AATTATCATA | TTGAATCTAT | ATTGTTTTTT | 480 |
| AGTTATATAA | AAACATGATT | AGCCCCCAAT | CGGATGAAAA | TATAAAGAT | GTTGAGAATT | 540 |
| TCGAATACAA | CAAAAGAGG | AATCGTACGT | TGTCCATATC | CAAACATATA | AATAAAAATT | 600 |
| CAAAAGTAGT | ATTATACTGG | ATGTTTAGAG | ATCAACGTGT | ACAAGATAAT | TGGGCTTTAA | 660 |
| TTTACGCACA | ACGATTAGCG | TTAAAACTCA | AAATACCTCT | AAGAATATGC | TTTTGTGTCG | 720 |
| TGCCAAAATT | TCACACTACT | ACTTCTAGAC | ACTTTATGTT | TTTAATATCC | GGTCTTAAAG | 780 |
| AAGTCGCGGA | AGAATGTAAA | AGACTATGTA | TAGGGTTTTC | ATTGATATAT | GGCGTACCAA | 840 |
| AAGTAATAAT | TCCGTGTATA | GTAAAAAAAT | ACAGAGTCGG | AGTAATCATA | ACGGATTTCT | 900 |
| TTCCATTACG | TGTTCCCGAA | AGATTAATGA | AACAGACTGT | AATATCTCTT | CCAGATAACA | 960 |
| TACCTTTTAT | ACAAGTAGAC | GCTCATAATA | TAGTACCTTG | TTGGGAAGCT | TCTGATAAAG | 1020 |
| AAGAATACGG | TGCACGAACT | TTAAGAAAAA | AGATATTTGA | TAAATTATAT | GAATATATGA | 1080 |
| CAGAATTTCC | TGTTGTTCGT | AAACATCCAT | ACGGTCCATT | TTCTATATCT | ATTGCAAAAC | 1140 |
| CCAAAAATAT | ATCATTAGAC | AAGACGGTAT | TACCCGTAAA | ATGGGCAACG | CCTGGAACAA | 1200 |
| AAGCTGGAAT | AATTGTTTTA | AAAGAATTTA | TAAAAAACAG | ATTACCGTCA | TACGACGCGG | 1260 |
| ATCATAACAA | TCCTACGTGT | GACGCTTTGA | GTAACTTATC | TCCGTGGCTA | CATTTGGTC | 1320 |
| ATGTATCCGC | ACAACGTGTT | GCCTTAGAAG | TATTAAAATG | TATACGAGAA | AGCAAAAAAA | 1380 |
| ACGTTGAAAC | GTTTATAGAT | GAAATAATTG | TAAGAAGAGA | ACTATCGGAT | AATTTTTGTT | 1440 |
| ACTATAACAA | ACATTATGAT | AGTATCCAGT | CTACTCATTC | ATGGGTTAGA | AAAACATTAG | 1500 |
| AAGATCACAT | TAATGATCCT | AGAAAGTATA | TATATTCCAT | TAAACAACTC | GAAAAAGCGG | 1560 |
| AAACTCATGA | TCCTCTATGG | AACGCGTCAC | AAATGCAGAT | GGTGAGAGAA | GGAAAAATGC | 1620 |
| ATAGTTTTTT | ACGAATGTAT | TGGGCTAAGA | AGATACTTGA | ATGGACTAGA | ACACCTGAAG | 1680 |
| ACGCTTTGAG | TTATAGTATC | TATTTGAACA | ACAAGTACGA | ACTAGACGGC | ACGGATCCTA | 1740 |
| ACGGATACGT | AGGTTGTATG | TGGTCTATTT | GCGGATTACA | CGATAGAGCG | TGGAAAGCAA | 1800 |
| GACCGATATT | TGGAAAGATA | AGATATATGA | ATTATGAGAG | TTCTAAGAAG | AAATTTGATG | 1860 |
| TTGCTGTATT | TATACAGAAA | TACAATTAAG | ATAAATAATA | TACAGCATTG | TAACCATCGT | 1920 |
| CATCCGTTAT | ACGGGGAATA | ATATTACCAT | ACAGTATTAT | TAAATTTTCT | TACGAAGAAT | 1980 |
| ATAGATCGGT | ATTTATCGTT | AGTTTATTTT | ACATTTATTA | ATTAAACATG | TCTACTATTA | 2040 |

| | | | | | |
|---|---|---|---|---|---|
| CCTGTTATGG | AAATGACAAA | TTTAGTTATA | TAATTTATGA | TAAAATTAAG | ATAATAATAA | 2100 |
| TGAAATCAAA | TAATTATGTA | AATGCTACTA | GATTATGTGA | ATTACGAGGA | AGAAAGTTTA | 2160 |
| CGAACTGGAA | AAAATTAAGT | GAATCTAAAA | TATTAGTCGA | TAATGTAAAA | AAAATAAATG | 2220 |
| ATAAAACTAA | CCAGTTAAAA | ACGGATATGA | TTATATACGT | TAAGGATATT | GATCATAAAG | 2280 |
| GAAGAGATAC | TTGCGGTTAC | TATGTACACC | AAGATCTGGT | ATCTTCTATA | TCAAATTGGA | 2340 |
| TATCTCCGTT | ATTCGCCGTT | AAGGTAAATA | AAATTATTAA | CTATTATATA | TGTAATGAAT | 2400 |
| ATGATATACG | ACTTAGCGAA | ATGGAATCTG | ATATGACAGA | AGTAATAGAT | GTAGTTGATA | 2460 |
| AATTAGTAGG | AGGATACAAT | GATGAAATAG | CAGAAATAAT | ATATTTGTTT | AATAAATTTA | 2520 |
| TAGAAAAATA | TATTGCTAAC | ATATCGTTAT | CAACTGAATT | ATCTAGTATA | TTAAATAATT | 2580 |
| TTATAAATTT | TATAAATTTT | AATAAAAAAT | ACAATAACGA | CATAAAGATA | TTTAATCTTT | 2640 |
| AATTCTTGAT | CTGAAAAACA | CATCTATAAA | ACTAGATAAA | AAGTTATTCG | ATAAAGATAA | 2700 |
| TAATGAATCG | AACGATGAAA | AATTGGAAAC | AGAAGTTGAT | AAGCTAATTT | TTTTCATCTA | 2760 |
| AATAGTATTA | TTTTATTGAA | GTACGAAGTT | TTACGTTAGA | TAAATAATAA | AGGTCGATTT | 2820 |
| TTACTTTGTT | AAATATCAAA | TATGTCATTA | TCTGATAAAG | ATACAAAAAC | ACACGGTGAT | 2880 |
| TATCAACCAT | CTAACGAACA | GATATTACAA | AAAATACGTC | GGACTATGGA | AAACGAAGCT | 2940 |
| GATAGCCTCA | ATAGAAGAAG | CATTAAAGAA | ATTGTTGTAG | ATGTTATGAA | GAATTGGGAT | 3000 |
| CATCCTCAAC | GAAGAAATAG | ATAAAGTTCT | AAACTGGAAA | AATGATACAT | TAAACGATTT | 3060 |
| AGATCATCTA | AATACAGATG | ATAATATTAA | GGAAATCATA | CAATGTCTGA | TTAGAGAATT | 3120 |
| TGCGTTTAAA | AAGATCAATT | CTATTATGTA | TAGTTATGCT | ATGGTAAAAC | TCAATTCAGA | 3180 |
| TAACGAACAT | TGAAAGATAA | AATTAAGGAT | TATTTTATAG | AAACTATTCT | TAAAGACAAA | 3240 |
| CGTGGTTATA | AACAAAAGCC | ATTACCCGGA | TTGGAAACTA | AAATACTAGA | TAGTATTATA | 3300 |
| AGATTTTAAA | AACATAAAAT | TAATAGGTTT | TTATAGATTG | ACTTATTATA | TACAATATGG | 3360 |
| ATAAAAGATA | TATATCAACT | AGAAAGTTGA | ATGACGGATT | CTTAATTTTA | TATTATGATT | 3420 |
| CAATAGAAAT | TATTGTCATG | TCGTGTAATC | ATTTTATAAA | TATATCAGCG | TTACTAGCTA | 3480 |
| AGAAAAACAA | GGACTTTAAT | GAATGGCTAA | AGATAGAATC | ATTTAGAGAA | ATAATAGATA | 3540 |
| CTTTAGATAA | AATTAATTAC | GATCTAGGAC | AACGATATTG | TGAAGAACTT | ACGGCGCATC | 3600 |
| ACATTCCAGT | GTAATTATTG | AGGTCAAAGC | TAGTAACTTA | ATAGATGACA | GGACAGCTG | 3659 |

( 2 ) INFORMATION FOR SEQ ID NO:73:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:73:

TCATTATCGC GATATCCGTG TTAACTAGCT AGCTAATTTT TATTCCCGGG ATCCTTATCA    60

( 2 ) INFORMATION FOR SEQ ID NO:74:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:74:

| | | | | | |
|---|---|---|---|---|---|
| GTATAAGGAT | CCCGGGAATA | AAAATTAGCT | AGCTAGTTAA | CACGGATATC | GCGATAATGA | 60 |

( 2 ) INFORMATION FOR SEQ ID NO:75:

( i ) SEQUENCE CHARACTERISTICS:
        ( A ) LENGTH: 2356 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:75:

| | | | | | |
|---|---|---|---|---|---|
| TGTCTGGACT | AACTGATTTC | ATGGAACAAT | TTTCATCAAA | AATATCAGTT | ATACCTAGTT | 60 |
| CTACAAAGAC | AGAACTTTGA | TGTTATGTTT | GTGTTTGTAT | AGAAAATTTT | GGGATACTAA | 120 |
| CTGATATTTC | TGAATATTTC | TGAATATTTC | ATGTTACTTA | CTTACTCCTA | TCTTAGACGA | 180 |
| TAATAAAATT | CGAGGCGTAA | TATGTTTTTC | CAAATATTTG | AAATTCTTAT | ACGTATCGGC | 240 |
| GAAGAAAAGT | AACATACTAT | AAGTGTTATG | CAAGTAAGGT | ATGTTAATGA | TATTGGATTT | 300 |
| AATTTCATTG | ACAATACATA | TGTCCAAACA | TTCCACTCGT | AATTATGTAC | GGAACGACTT | 360 |
| TAGTTAAATA | CTTAGTCACA | AAAAACTTAT | GACTGTCATT | ATCTGAAAAC | GGTGATTCCC | 420 |
| ATAAATCAGA | ATACTTAATA | TTAAATAGAA | TGCTCGCTTC | TGGAGGTTTC | CGGATACTAG | 480 |
| ATAACATATC | TTCTGTATTA | TAGTTTAATT | CACTCATTTT | ATTACATAAT | ACAGTAACAT | 540 |
| CTCCCGAAAC | CAATGATGTT | ATATTAGATT | TACTTACATA | CTTCTTGTAA | CTATCATGAA | 600 |
| TACGTTTGTT | ATGATCTATA | AGAAGATGG | ATGTATATTC | TGTTCTAGAT | AGCAAGTTCT | 660 |
| TTAAGTTATT | CTTTGTCTGT | ATTACTATCA | TCGTCTTCAT | CATCGTCTAA | AGGTAGCATT | 720 |
| ATATAATAAA | TCTAATAGTT | GATTTCTCGA | TCTATCAGTA | CTCGCTTTCA | ATAACATTTT | 780 |
| TACTATAAGC | ATAATAGAAG | GCGGTGATAT | CACTATATTT | TATCGGGTA | TTCTTTTAGT | 840 |
| AATTAGTTAG | TTCGTAGAAT | TTCGTAGAGA | TAAAAGCCAA | TTTGTTGTTG | ATACTGCTTA | 900 |
| CGTTACTCAT | GTTTCTTGTT | TCTGTTAATT | AACAGGTATA | CCCTTACAAT | AAGTTTAATT | 960 |
| AACTTTTAGG | TTTTTGTGAA | GAACTTTTAG | CTTCTAGTTC | CCTTATCCAT | AATTGGGTCT | 1020 |
| TAGATCTAGA | TTCTTCCCAT | GTATAAAGGG | GGACATACCC | AAAATCTTTA | AATGCTTTGT | 1080 |
| CCGTTTCTAT | AGTAAATGTC | GTACATTCCT | TAATCAAAGT | ATAAGGATTT | AGTAAAGGCG | 1140 |
| TGTAAGAACA | AATAGGTGAT | AGTAATACTC | TTAAACCTTT | ATTAATATTA | GCGATAAACC | 1200 |
| TTAAACACCA | TAAAGGAAGA | CATGTATTCC | GTAGATCCAT | CCCTAATTGA | TTAAAGAAAT | 1260 |
| GCATGTTAAA | ATCATGATAA | TGTTCAGTAG | GAGAGGTATC | GTAACAGTAA | TACACGTTAT | 1320 |
| TGCAGAGAGG | ACTATGTTGA | CCATTTTCTA | TCATATTTCT | TGCTGCTAAA | ATATGCATCC | 1380 |
| AAGCTACGTT | TCCTGCATAG | ACTCTGCTAT | GAAATACTTT | ATCATCCGCA | TATTTATACA | 1440 |
| TTTTCCTGCT | TTTATACGAT | CTTCTGTATA | AAGTTTCTAG | TACTGGACAG | TATTCTCCGA | 1500 |
| AAACACCTAA | TGGGCGTAGC | GACAAGTGCA | TAATCTAAGT | CCTATATTAG | ACATAGTACC | 1560 |
| GTTAGCTTCT | AGTATATATT | TCTCAGATAA | CTTGTTTACT | AAGAGGATAA | GCCTCTTTAT | 1620 |
| GGTTAGATTG | ATAATACGTA | TTCTCGTTTC | CTCTTATCAT | CGCATCTCCG | GAGAAAGTTA | 1680 |
| GGACCTACCG | CAGAATAACT | ACTCGTATAT | ACTAAGACTC | TTACGCCGTT | ATACAGACAA | 1740 |
| GAATCTACTA | CGTTCTTCGT | TCCGTTGATA | TTAACGTCCA | TTATAGAGTC | GTTAGTAAAC | 1800 |
| TTACCCGCTA | CATCATTTAT | CGAAGCAATA | TGAATGACCA | CATCTGCTGA | TCTAAGCGCT | 1860 |
| TCGTCCAAAG | TACTTTTATT | TCTAACATCT | CCAATCACGG | GAACTATCTT | TATTATATTA | 1920 |

```
CATTTTTCTA  CAAGATCTAG  TAACCATTGG  TCGATTCTAA  TATCGTAAAC  ACGAACTTCT      1980

TTTTAAAGAG  GATTCGAACA  AGATAAGATT  ATTTATAATG  TGTCTACCTA  AAAATCCACA      2040

CCCTCCGGTT  ACCACGTATA  CTAGTGTACG  CATTTTGAGT  ATTAACTATA  TAAGACCAAA      2100

ATTATATTTT  CATTTTCTGT  TATATTATAC  TATATAATAA  AAACAAATAA  ATATACGAAT      2160

ATTATAAGAA  ATTTAGAACA  CGTTATTAAA  GTATTGCCTT  TTTTATTAAC  GGCGTGTTCT      2220

TGTAATTGCC  GTTAGAATA   GTCTTTATTT  ACTTTAGATA  ACTCTTCTAT  CATAACCGTC      2280

TCCTTATTCC  AATCTTCTTC  AGAAGTACAT  GAGTACTTAC  CGAAGTTTAT  CATCATAGAG      2340

ATTATATATG  AAGAAA                                                          2356
```

( 2 ) INFORMATION FOR SEQ ID NO:76:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:76:

```
GACAATCTAA  GTCCTATATT  AGAC                                                  24
```

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:77:

```
GGATTTTTAG  GTAGACAC                                                          18
```

( 2 ) INFORMATION FOR SEQ ID NO:78:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

```
TCATCGTCTT  CATCATCG                                                          18
```

( 2 ) INFORMATION FOR SEQ ID NO:79:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:79:

```
GTCTTAAACT  TATTGTAAGG  GTATACCTG                                             29
```

( 2 ) INFORMATION FOR SEQ ID NO:80:

( i ) SEQUENCE CHARACTERISTICS:
  ( A ) LENGTH: 61 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:80:

```
AACGATTAGT TAGTTACTAA AAGCTTGCTG CAGCCCGGGT TTTTTATTAG TTTAGTTAGT        60
C                                                                       61
```

( 2 ) INFORMATION FOR SEQ ID NO:81:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:81:

```
GACTAACTAA CTAATAAAAA ACCCGGGCTG CAGCAAGCTT TTTGTAACTA ACTAATCGTT        60
```

( 2 ) INFORMATION FOR SEQ ID NO:82:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:82:

```
GCACGGAACA AAGCTTATCG CGATATCCGT TAAGTTTGTA TCGTAATGCT ATCAATCACG        60
ATTCTGTTCC TGCTCATAGC AGAGGGCTCA TCTCAGAAT                              99
```

( 2 ) INFORMATION FOR SEQ ID NO:83:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:83:

```
ATTCTGAGAT GAGCCCTCTG CTATGAGCAG GAACAGAATC GTGATTGATA GCATTACGAT        60
ACAAACTTAA CGGATATCGC GATAAGCTTT GTTCCGTGC                              99
```

( 2 ) INFORMATION FOR SEQ ID NO:84:

( i ) SEQUENCE CHARACTERISTICS:
    ( A ) LENGTH: 66 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:84:

```
GAAAAATTTA AAGTCGACCT GTTTGTTGA GTTGTTTGCG TGGTAACCAA TGCAAATCTG         60
GTCACT                                                                  66
```

( 2 ) INFORMATION FOR SEQ ID NO:85:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:85:

```
TCTAGCAAGA CTGACTATTG CAAAAGAAG CACTATTTCC TCCATTACGA TACAAACTTA      60
ACGGAT                                                               66
```

( 2 ) INFORMATION FOR SEQ ID NO:86:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

```
ATCCGTTAAG TTTGTATCGT AATGGAGGAA ATAGTGCTTC TTTTTGCAAT AGTCAGTCTT      60
GCTAGAAGTG ACCAGATTTG CATTGGT                                         87
```

( 2 ) INFORMATION FOR SEQ ID NO:87:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:87:

```
TACCACGCAA ACAACTCAAC AAAACAGGTC GACTTTAAAT TTTTCTGCA                 49
```

( 2 ) INFORMATION FOR SEQ ID NO:88:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:88:

```
GTACAGGTCG ACAAGCTTCC CGGGTATCGC GATATCCGTT AAGTTTGTAT CGTAATGAAT      60
ACTCAAATTC TAATACTCAC TCTTGTGGCA GCCATTCACA CAAATGCAGA CAAAATCTGC     120
CTTGGACATC AT                                                        132
```

( 2 ) INFORMATION FOR SEQ ID NO:89:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:89:

```
ATGATGTCCA  AGGCAGATTT  TGTCTGCATT  TGTGTGAATG  GCTGCCACAA  GAGTGAGTAT         60

TAGAATTTGA  GTATTCATTA  CGATACAAAC  TTAACGGATA  TCGCGATACC  CGGGAAGCTT        120

GTCGACCTGT  AC                                                                132
```

( 2 ) INFORMATION FOR SEQ ID NO:90:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:90:

```
ATAACATGCG  GTGCACCATT  TGTATATAAG  TTAACGAATT  CCAAGTCAAG  C                  51
```

( 2 ) INFORMATION FOR SEQ ID NO:91:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:91:

```
GCTTGACTTG  GAATTCGTTA  ACTTATATAC  AAATGGTGCA  CCGCATGTTA  T                  51
```